US011565994B2

(12) United States Patent
Cole et al.

(10) Patent No.: US 11,565,994 B2
(45) Date of Patent: Jan. 31, 2023

(54) INHIBITORS OF HISTONE LYSINE SPECIFIC DEMETHYLASE (LSD1) AND HISTONE DEACETYLASES (HDACS)

(71) Applicant: The Johns Hopkins University, Baltimore, MD (US)

(72) Inventors: Philip Cole, Baltimore, MD (US);
Shonoi Ming, Baltimore, MD (US);
Polina Prusevich, Baltimore, MD (US);
Jay Kalin, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 16/892,825

(22) Filed: Jun. 4, 2020

(65) Prior Publication Data
US 2021/0009511 A1    Jan. 14, 2021

Related U.S. Application Data

(63) Continuation of application No. 15/124,208, filed as application No. PCT/US2015/019467 on Mar. 9, 2015, now abandoned.

(60) Provisional application No. 61/949,675, filed on Mar. 7, 2014.

(51) Int. Cl.
| | |
|---|---|
| C07C 243/18 | (2006.01) |
| A61K 45/06 | (2006.01) |
| A61K 31/167 | (2006.01) |
| C07C 233/29 | (2006.01) |
| C07C 259/06 | (2006.01) |
| A61K 31/137 | (2006.01) |
| A61K 31/255 | (2006.01) |
| A61K 31/325 | (2006.01) |
| A61K 31/405 | (2006.01) |
| C07C 271/02 | (2006.01) |
| C07C 309/66 | (2006.01) |
| C07D 209/18 | (2006.01) |

(52) U.S. Cl.
CPC .......... *C07C 243/18* (2013.01); *A61K 31/137* (2013.01); *A61K 31/167* (2013.01); *A61K 31/255* (2013.01); *A61K 31/325* (2013.01); *A61K 31/405* (2013.01); *A61K 45/06* (2013.01); *C07C 233/29* (2013.01); *C07C 259/06* (2013.01); *C07C 271/02* (2013.01); *C07C 309/66* (2013.01); *C07D 209/18* (2013.01); *C07C 2602/02* (2017.05)

(58) Field of Classification Search
CPC .................................................. C07C 243/18
See application file for complete search history.

(56) References Cited

U.S. PATENT DOCUMENTS

| | | | |
|---|---|---|---|
| 3,773,919 | A | 11/1973 | Boswell et al. |
| 4,485,045 | A | 11/1984 | Regen |
| 4,544,545 | A | 10/1985 | Patrick et al. |
| 6,004,984 | A | 12/1999 | Goulet et al. |
| 2007/0281934 | A1 | 12/2007 | Buggy et al. |
| 2009/0012075 | A1 | 1/2009 | Miller et al. |
| 2012/0035377 | A1 | 2/2012 | Mastroianni et al. |
| 2012/0264823 | A1 | 10/2012 | Ortega Munoz et al. |
| 2013/0267542 | A1 | 10/2013 | Chern et al. |
| 2014/0011857 | A1 | 1/2014 | Casero et al. |
| 2017/0029366 | A1 | 2/2017 | Cole et al. |

FOREIGN PATENT DOCUMENTS

| | | |
|---|---|---|
| EP | 0058481 A1 | 8/1982 |
| EP | 0102324 A2 | 3/1984 |
| EP | 0133988 A2 | 3/1985 |
| GB | 1193700 A | 6/1970 |
| WO | WO 2008/053136 A1 | 5/2008 |
| WO | WO 2012/042042 A1 | 4/2012 |

OTHER PUBLICATIONS

Cancer and Metastasis Reviews (1998), 17(1), 91-106.*
Science (1999), vol. 286, 531-537.*
Cancer [online], [retrieved on Jul. 6, 2007], Retrieved from the internet, URL http://www.nlm.nih.gov/medlineplus/cancer.html>.*
Angus-Hill et al., "T cell factor 4 functions as a tumor suppressor whose disruption modulates colon cell proliferation and tumorigenesis," Proc. Natl. Acad. Sci., 2011, 108(12):4914-9.
Apsel et al., "Targeted polypharmacology: discovery of dual inhibitors of tyrosine and phosphoinositide kinases," Nat Chem Biol, Nov. 2008;4(11):691-9.
Baraldi et al., "Design, synthesis, and biological evaluation of a second generation of pyrazolo[4,3-e]-1,2,4-triazolo[1,5-c]pyrimidines as potent and selective A2A adenosine receptor antagonists," J. Med. Chem., 1998, 41, 2126-2133.
Baron et al., "Molecular mimicry and ligand recognition in binding and catalysis by the histone demethylase LSD1-CoREST complex," Structure, 2011, 19(2):212-220.

(Continued)

*Primary Examiner* — Shawquia Jackson
(74) *Attorney, Agent, or Firm* — Casimir Jones, S.C.; Jeffrey W. Childers

(57) ABSTRACT

A series of phenelzine analogs comprising a phenelzine scaffold linked to an aromatic moiety and their use as inhibitors of lysine-specific demethylase 1 (LSD1) and/or one or more histone deacetylases (HDACs) is provided. The presently disclosed phenelzine analogs exhibit potency and selectivity for LSD1 versus MAO and LSD2 enzymes and exhibit bulk, as well as, gene specific histone methylation changes, anti-proliferative activity in several cancer cell lines, and neuroprotection in response to oxidative stress. Accordingly, the presently disclosed phenelzine analogs can be used to treat diseases, conditions, or disorders related to LSD1 and/or HDACs, including, but not limited to, cancers and neurodegenerative diseases.

7 Claims, 36 Drawing Sheets

Specification includes a Sequence Listing.

(56) References Cited

OTHER PUBLICATIONS

Beckers et al., Distinct pharmacological properties of second generation HDAC inhibitors with the benzamide or hydroxamate head group, Int J Cancer, 2007, 121, 1138-48.

Binda et al., "Biochemical, structural, and biological evaluation of tranylcypromine derivatives as inhibitors of histone demethylases LSD1 and LSD2," J. Am. Chem. Soc., 2010, 132, 6827-6833.

Blair et al., "MassSQUIRM: An assay for quantitative measurement of lysine demethylase activity," Epigenetics, 2011, 6, 490-499.

Bostrom et al., "Variants of the antibody herceptin that interact with HER2 and VEGF at the antigen binding site. Science," 2009, 323(5921):1610-4.

Bradner et al., "Chemical phylogenetics of histone deacetylases," Nat Chem Biol, 2010, 6, 238-243.

Breslow et al., "Potent cytodifferentiating agents related to hexamethylenebisacetamide," Proc. Natl. Acad. Sci., 1991, 88, 5542-6.

Calabretta et al., Sodium Cyanoborohydride Reduction of (Benzyloxycarbonyl)- and (tert -Butoxycarbonyl)hydrazones, Synthesis, 1991, 536-539.

Caramel et al., "A switch in the expression of embryonic EMT-inducers drives the development of malignant melanoma," Cancer Cell, 2013, 24(4):466-80.

Carroll et al., "Synthesis and biological evaluation of bupropion analogues as potential pharmacotherapies for cocaine addiction," J. Med. Chem., 2009, 52, 6768-6781.

Culhane et al., "A mechanism-based inactivator for histone demethylase LSD1," J. Am. Chem. Soc., 2006, 128, 4536-4537.

Culhane et al., "Comparative analysis of small molecules and histone substrate analogues as LSD1 lysine demethylase inhibitors," J. Am. Chem. Soc., 2010, 132, 3164-3176.

Culhane et al., "LSD1 and the chemistry of histone demethylation," Curr. Opin. Chem. Biol., 2007, 11, 561-568.

Dalcanale et al., "Selective Oxidation of Aldehydes to Carboxylic-Acids with Sodium-Chlorite Hydrogen-Peroxide," Journal of Organic Chemistry, 1986, 51, 567-569.

Dancy et al., "Azalysine analogues as probes for protein lysine deacetylation and demethylation," J. Am. Chem. Soc., 2012, 134, 5138-5148.

De Yebenes et al., "Continuous intracerebroventricular infusion of dopamine and dopamine agonists through a totally implanted drug delivery system in animal models of Parkinson's disease," Mov. Disord., 1987, 2:143.

Dulla et al., "Synthesis and evaluation of 3-amino/guanidine substituted phenyl oxazoles as a novel class of LSD1 inhibitors with anti-proliferative properties," Org. Biomol. Chem., 2013, 11, 3103-3107.

Eichhoff et al., "Differential LEF1 and TCF4 expression is involved in melanoma cell phenotype switching," Pigment Cell Melanoma Res, 2011, 24(4):631-42.

Epstein et al., "Biological Activity of Liposome-Encapsulated Murine Interferon γ is Mediated by a Cell Membrane Receptor," Proc. Natl. Acad. Sci., 1985, 82:3688.

Erikson et al., "Oxidative metabolism of some hydrazine derivatives by rat liver and lung tissue fractions," J Biochem Toxicol, 1986;1:41.

Fiskus et al., "Highly effective combination of LSD1 (KDM1A) antagonist and pan-histone deacetylase inhibitor against human AML cells," Leukemia, 2014, 28, 2155-64.

Forneris et al., "A highly specific mechanism of histone H3-K4 recognition by histone demethylase LSD1," J. Biol. Chem., 2006, 281, 35289-35295.

Forneris et al., "Histone demethylation catalysed by LSD1 is a flavin-dependent oxidative process," FEBS Lett, 2005, 579, 2203-2207.

Forneris et al., "Human histone demethylase LSD1 reads the histone code," J. Biol. Chem., 2005, 280, 41360-41365.

Forneris et al., "LSD1: oxidative chemistry for multifaceted functions in chromatin regulation. Trends Biochem," Science, 2008, 33, 181-189.

Forneris et al., "New roles of flavoproteins in molecular cell biology: histone demethylase LSD1 and chromatin," FEBS J., 2009, 276, 4304-4312.

Forneris et al., "Structural basis of LSD1-CoREST selectivity in histone H3 recognition," J. Biol. Chem., 2007, 282, 20070-20074.

Gaweska et al., "Use of pH and kinetic isotope effects to establish chemistry as rate-limiting in oxidation of a peptide substrate by LSD1," Biochemistry, 2009, 48, 5440-5445.

Gooden et al., "Facile synthesis of substituted trans-2-arylcyclopropylamine inhibitors of the human histone demethylase LSD1 and monoamine oxidases A and B," Bioorg. Med. Chem. Lett., 2008, 18, 3047-3051.

Guenther et al., "A core SMRT corepressor complex containing HDAC3 and TBL1, a WD40-repeat protein linked to deafness," Genes Dev, 2000, 14, 1048-57.

Hakimi et al., "A candidate X-linked mental retardation gene is a component of a new family of histone deacetylase-containing complexes," 2003, J. Biol. Chem. 278, 7234-7239.

Han et al., "Synergistic reactivation of epigenetically silenced genes by combinatorial inhibition of DNMTs and LSD1 in cancer cells," PloS One, 2013, 8, e75136.

Hazeldine et al., "Low molecular weight amidoximes that act as potent inhibitors of lysine-specific demethylase 1," J. Med. Chem., 2012, 55, 7378-7391.

Heintzman et al., "Distinct and predictive chromatin signatures of transcriptional promoters and enhancers in the human genome," Nat. Genet., 2007, 39, 311-318.

Holt et al., "A continuous spectrophotometric assay for monoamine oxidase and related enzymes in tissue homogenates," Anal. Biochem., 1997, 244, 384-392.

Huang et al., "Histone deacetylase inhibitors stimulate histone H3 lysine 4 methylation in part via transcriptional repression of histone H3 lysine 4 demethylases," Mol Pharmacol, 2011, 79, 197-206.

Huang et al., "Inhibition of lysine-specific demethylase 1 by polyamine analogues results in reexpression of aberrantly silenced genes," Proc. Natl. Acad. Sci., 2007, 104, 8023-8028.

Huang et al., "Inhibitors of histone demethylation and histone deacetylation cooperate in regulating gene expression and inhibiting growth in human breast cancer cells," Breast Cancer Res. Treat., 2012, 131, 777-789.

Huang et al., "Novel oligoamine analogues inhibit lysine-specific demethylase 1 and induce reexpression of epigenetically silenced genes," Clin. Cancer Res, 2009, 15, 7217-7228.

Humphrey et al., "Stable histone deacetylase complexes distinguished by the presence of SANT domain proteins CoREST/kiaa0071 and Mta-L1," J Biol Chem, 2001, 276, 6817-24.

Hwang et al., "Hepatic uptake and degradation of unilamellar sphingomyelin/cholesterol liposomes: A kinetic study," Proc. Natl. Acad. Sci., 1980, 77:4030-4034.

Hwang et al., "Thermodynamic characterization of the binding interaction between the histone demethylase LSD1/KDM1 and CoREST," Biochemistry, 2011, 50, 546-557.

Jin et al., "Loss of LSD1 (lysine-specific demethylase 1) suppresses growth and alters gene expression of human colon cancer cells in a p53) and DNMT1(DNA methyltransferase 1)-independent manner," Biochem. J., 2013, 449, 459-468.

Karytinos et al., "A novel mammalian flavin-dependent histone demethylase," J. Biol. Chem., 2009, 284, 17775-17782.

Kerenyi et al., "Histone demethylase Lsd1 represses hematopoietic stem and progenitor cell signatures during blood cell maturation," eLife, 2013, 2, e00633.

Kim et al., "Substrate and functional diversity of lysine acetylation revealed by a proteomics survey," Mol Cell, 2006, 23, 607-18.

Klose et al., "Regulation of histone methylation by demethylimination and demethylation," Nat. Rev. Mol. Cell Biol., 2007, 8, 307-318.

Kozikowski et al., "Searching for disease modifiers-PKC activation and HDAC inhibition—a dual drug approach to Alzheimer's disease that decreases Abeta production while blocking oxidative stress," ChemMedChem, 2009, 4, 1095-1105.

Laherty et al., "Histone deacetylases associated with the mSin3 corepressor mediate mad transcriptional repression," Cell, 1997, 89, 349-56.

(56) References Cited

OTHER PUBLICATIONS

Lakowski et al., "CoREST-like complexes regulate chromatin modification and neuronal gene expression," J Mol Neurosci, 2006, 29, 227-39.
Langer et al., "Biocompatibility of polymeric delivery systems for macromolecules," J. Biomed. Mater. Res., 1981, 15:267-277.
Langer, "Controlled release of macromolecules," Chem. Tech., 1982, 12:98-105.
Langley et al., "Pulse inhibition of histone deacetylases induces complete resistance to oxidative death in cortical neurons without toxicity and reveals a role for cytoplasmic p21(waf1/cip1) in cell cycle-independent neuroprotection," J. Neurosci, 2008, 28, 163-176.
Lee et al., "Histone H3 lysine 4 demethylation is a target of nonselective antidepressive medications," Chem. Biol., 2006, 13, 563-567.
Lee et al., "Temporary inactivation of plasma amine oxidase by alkylhydrazines. A combined enzyme/model study implicates cofactor reduction/reoxidation but cofactor deoxygenation and subsequent reoxygenation in the case of hydrazine itself," J. Org. Chem., 2001, 66, 1925-1937.
Li et al., "Characterization and prediction of lysine (K)-acetyltransferase specific acetylation sites," Mol Cell Proteomics, 2012, 11, M111 011080.
Li et al., "Fast and accurate short read alignment with Burrows-Wheeler transform. Bioinforma," Oxf. Engl., 2009, 25, 1754-1760.
Liang et al., "Distinct localization of histone H3 acetylation and H3-K4 methylation to the transcription start sites in the human genome," Proc. Natl. Acad. Sci., 2004, 101, 7357-7362.
Lim et al., "Lysine-specific demethylase 1 (LSD1) is highly expressed in ERnegative breast cancers and a biomarker predicting aggressive biology," Carcinogenesis, 2010, 31, 512-520.
Liu et al., "Inhibition of p300 impairs Foxp3(+) T regulatory cell function and promotes antitumor immunity," Nat Med, 2013, 19, 1173-7.
Lv et al., "Over-Expression of LSD1 Promotes Proliferation, Migration and Invasion in Non-25 Small Cell Lung Cancer," PLoS One, 2012, 7, e35065.
Martin et al., "Cyclin-dependent kinase inhibitor dinaciclib interacts with the acetyl-lysine recognition site of bromodomains," ACS Chem Biol., 2013, 8(11):2360-5.
Metzger et al., "LSD1 demethylates repressive histone marks to promote androgen)receptor)/ependent transcription. Nature, 2005, 437, 436-439.
Mimasu et al., "Structurally designed trans-2-phenylcyclopropylamine derivatives potently inhibit histone demethylase LSD1/KDM1," Biochemistry, 2010, 49, 6494-6503.
Mosmann, "Rapid colorimetric assay for cellular growth and survival: application to proliferation and cytotoxicity assays," J. Immunol. Methods, 1983, 65, 55-63.
Murray-Stewart et al., "The re-expression of the epigenetically silenced e-cadherin gene by a polyamine analogue lysine-specific demethylase-1 (LSD1) inhibitor in human acute myeloid leukemia cell lines," Amino Acids, 2014, 46(3):585-594.
Neelamegam et al., "Brain-Penetrant LSD1 Inhibitors Can Block Memory Consolidation," ACS Chem. Neurosci, 2012, 3, 120-128.
Nishikawa et al., "Regulatory T cells in tumor immunity," Int J Cancer, 2010, 127, 759-67.
Peng et al., "Highly Efficient N-Monomethylation of Primary Aryl Amines," Chinese Journal of Chemistry, 2009, 27, 1339-1344.
Pollock et al., "Lysine-specific histone demethylase 1 inhibitors control breast cancer proliferation in ERα-dependent and -independent manners," ACS Chem. Biol., 2012, 7, 1221-1231.
Prusevich et al., "A Selective Phenelzine Analogue Inhibitor of Histone Demethylase LSD1," ACS Chemical Biology, 2014, 9(6):1284-1293.
Ratan et al., "Oxidative stress induces apoptosis in embryonic cortical neurons," J. Neurochem, 1994, 62(1):376-379.
Robinson et al., "Integrative genomics viewer," Nat. Biotechnol, 2011, 29, 24-26.
Romeiro et al., "Discovery of LASSBio-772, a 1,3-benzodioxole N-phenylpiperazine derivative with potent alpha 1 A/D-adrenergic receptor blocking properties," Eur. J. Med. Chem., 2011, 46, 3000-3012.
Saito et al., "A synthetic inhibitor of histone deacetylase, MS-27-275, with marked in vivo antitumor activity against human tumors," Proc. Natl. Acad. Sci., 1999, 96, 4592-7.
Schmidt et al., "trans-2-Phenylcyclopropylamine is a mechanism-based inactivator of the histone demethylase LSD1," Biochemistry, 2007, 46, 4408-4416.
Shechter et al., "Extraction, purification and analysis of histones," Nat. Protoc., 2007, 2, 1445-1457.
Shen et al., "diffReps: detecting differential chromatin modification sites from ChIP-seq data with biological replicates," PloS One, 2013, 8, e65598.
Shi et al., "Histone Demethylation Mediated by the Nuclear Amine Oxidase Homolog LSD1," Cell, 2004, 119, 941-953.
Sidman et al., "Controlled release of macromolecules and pharmaceuticals from synthetic polypeptides based on glutamic acid," Biopolymers, 1983, 22:547.
Sobotka et al., "Zur Existenz des p-Idol-Ringes," Berichte Der Deutschen Chemischen Gesellschaft, 1929, p. 2191.
Song et al., "Identifying dispersed epigenomic domains from ChIP-Seq data," Bioinformatics, 2011, 27, 870-871.
Su et al., "Histone H4 acetylation dynamics determined by stable isotope labeling with amino acids in cell culture and mass spectrometry," Anal. Biochem., 2007, 363, 22-34.
Szewczuk et al., "Mechanistic Analysis of a Suicide Inactivator of Histone Demethylase LSD1," Biochemistry, 2007, 46, 6892-6902.
Takai et al., "Array-Based Approaches for the Identification of Epigenetic Silenced Tumor Suppressor Genes," Curr. Genomics, 2008, 9, 22-24.
Taylor et al., "A Convergent Synthesis of 5,10-Dideaza-5,6,7,8-Tetrahydrofolic Acid and 5,10-Dideaza-5,6,7,8-Tetrahydrohomofolic Acid—an Effective Principle for Carbonyl Group Activation," Journal of Organic Chemistry, 1990, 55, 3222-3227.
Thorvaldsóttir et al., "Integrative Genomics Viewer (IGV): high-performance genomics data visualization and exploration," Brief. Bioinform., 2013, 14, 178-192.
Tongkate et al., "Hexabromoacetone and ethyl tribromoacetate: a highly efficient reagent for bromination of alcohol," Tetrahedron Letters, 2008, 49, 1146-1148.
Tortorici et al., "Protein recognition by short peptide reversible inhibitors of the chromatin-modifying LSD1/CoREST lysine demethylase," ACS Chem. Biol., 2013, 8, 1677-1682.
Tsukada et al., "Histone demethylation by a family of JmjC domain-containing proteins," Nature, 2005, 439, 811-816.
Wang et al., "Design, synthesis, and biological evaluation of semicarbazide-sensitive amine oxidase (SSAO) inhibitors with anti-inflammatory activity," Journal of Medicinal Chemistry, 2006, 49(7):2166-73.
Wang et al., "Novel histone demethylase LSD1 inhibitors selectively target cancer cells with pluripotent stem cell properties," Cancer Res, 2011, 71, 7238-7249.
Wang et al., "Properties of purified recombinant human polyamine oxidase, PAOh1/SMO," Biochem. Biophys. Res. Commun., 2003, 304, 605-611.
Wang et al., "Small molecule epigenetic inhibitors targeted to histone lysine methyltransferases and demethylases," Q Rev Biophys, 2013, 46, 349-73.
Witter et al., "Optimization of biaryl Selective HDAC1&2 Inhibitors (SHI-1:2)," Bioorg Med Chem Lett, 2008, 18, 726-31.
Xue et al., "NURD, a novel complex with both ATP-dependent chromatin-remodeling and histone deacetylase activities," Mol Cell, 1998, 2, 851-61.
Yang et al., "Structural basis for the inhibition of the LSD1 histone demethylase by the antidepressant trans-2-phenylcyclopropylamine," Biochemistry, 2007, 46, 8058-8065.
Yang et al., "Structural basis of histone demethylation by LSD1 revealed by suicide inactivation," Nat. Struct. Mol. Biol., 2007, 14, 535-539.

(56) References Cited

OTHER PUBLICATIONS

You et al., "CoREST is an integral component of the CoREST-human histone deacetylase complex," Proc. Natl. Acad. Sci., 2001, 98, 1454-8.

Yu et al., "Bisubstrate Inhibition: Theory and application to N-acetyltransferases," Biochemistry, 2006, 45(49):14788-94.

Zhang et al., "Analysis of the NuRD subunits reveals a histone deacetylase core complex and a connection with DNA methylation," Genes Dev, 1999, 13, 1924-35.

Zhang et al., "Distribution of lysine-specific demethylase 1 in the brain of rat and its response in transient global cerebral ischemia," Neurosci. Res., 2010, 68, 66-72.

Zhang et al., "Model-based analysis of ChIP-Seq (MACS)," Genome Biol., 2008, 9, R137.

Zhang et al., "Structure-function analysis reveals a novel mechanism for regulation of histone demethylase LSD2/AOF1/KDM1b," Cell Res, 2013, 23, 225-241.

Zhu et al., "Polyamine analogs modulate gene expression by inhibiting lysine-specific demethylase 1 (LSD1) and altering chromatin structure in human breast cancer cells," Amino Acids, 2012, 42, 887-898.

International Search Report and Written Opinion for Application No. PCT/US2015/019467 dated Jun. 1, 2015 (11 pages).

European Patent Office Extended Search Report for Application No. 15758257.8 dated Sep. 15, 2017 (9 pages).

* cited by examiner

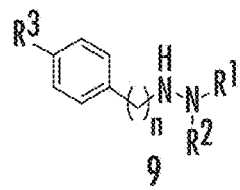 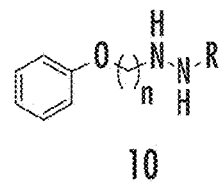

9 a  n=2, R¹=CH₃,   R²=H,      R³=H
b  n=2, R¹=CH₃,   R²=CH₃,    R³=H
c  n=3, R¹=H,     R²=H,      R³=H
d  n=3, R¹=CH₃,   R²=H,      R³=H
e  n=3, R¹=H,     R²=H,      R³=OCH₃
f  n=3, R¹=CH₃,   R²=H,      R³=OCH₃
g  n=3, R¹=COCH₃, R²=H,      R³=OCH₃
h  n=4, R¹=H,     R²=H,      R³=H

10

A  n=2, R=H
B  n=3, R=H

11

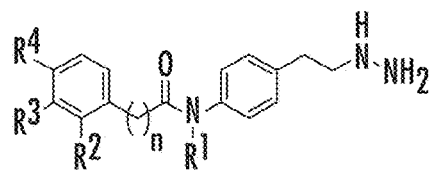

12

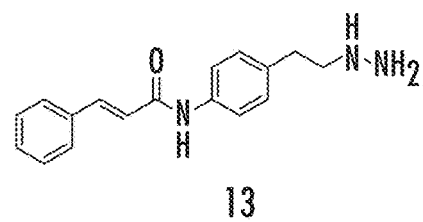

13 a  n=0, R¹=H,      R²=H,       R³=H,       R⁴=H
b  n=1, R¹=H,      R²=H,       R³=H,       R⁴=H
c  n=2, R¹=H,      R²=H,       R³=H,       R⁴=H
d  n=3, R¹=H,      R²=H,       R³=H,       R⁴=H
e  n=4, R¹=H,      R²=H,       R³=H,       R⁴=H
f  n=3, R¹=H,      R²=H,       R³=H,       R⁴=Cl
g  n=3, R¹=H,      R²=H,       R³=H,       R⁴=F
h  n=3, R¹=H,      R²=H,       R³=H,       R⁴=OMe
i  n=3, R¹=H,      R²=H,       R³=H,       R⁴=NO₂
j  n=2, R¹=H,      R²=OSO₂Me,  R³=H,       R⁴=H
k  n=2, R¹=H,      R²=H,       R³=OSO₂Me,  R⁴=H
l  n=3, R¹=CH₃,    R²=H,       R³=H,       R⁴=H
m  n=3, R¹=CH₂Ph,  R²=H,       R³=H,       R⁴=H

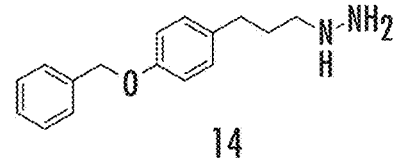

14

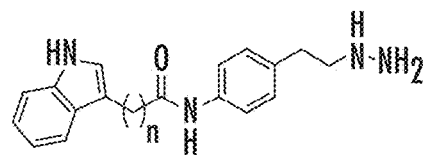

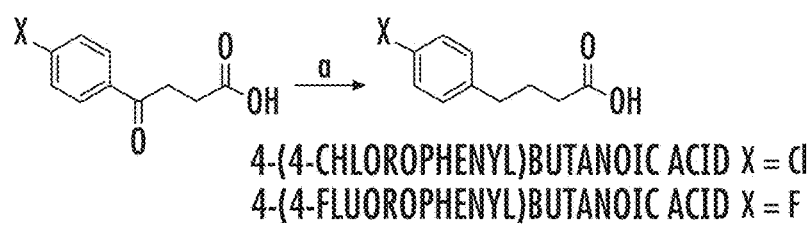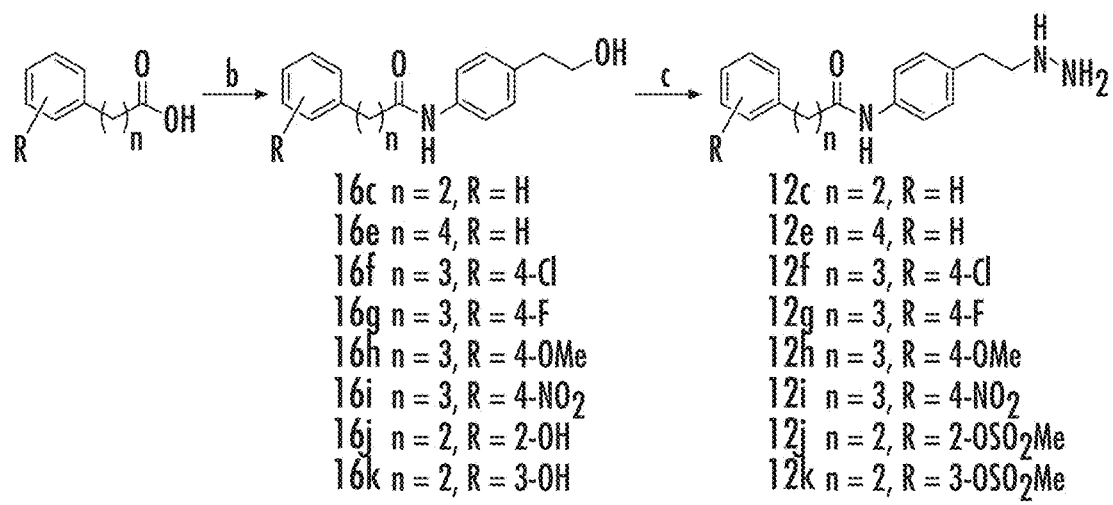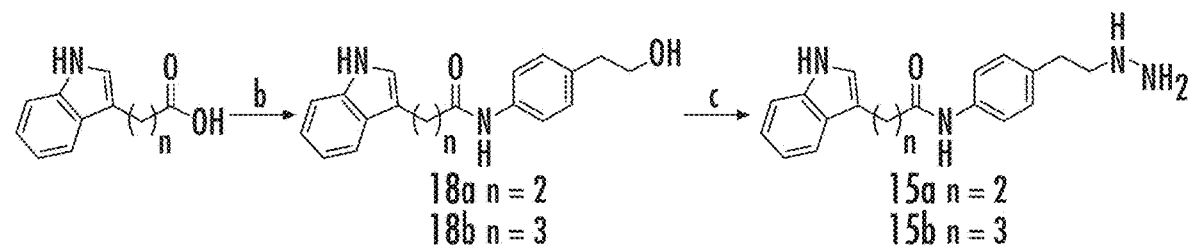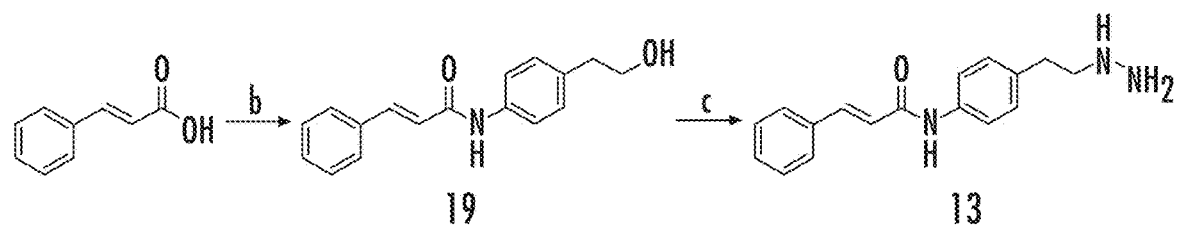
FIG. 10

| COMPOUND ID | STRUCTURE | $k_{INACT}(MIN^{-1})$ | $K_{I(INACT)}(\mu M)$ | $k_{INACT}/K_{I(INACT)}$ $(\mu M^{-1} MIN^{-1})$ |
|---|---|---|---|---|
| JK-2-29 | 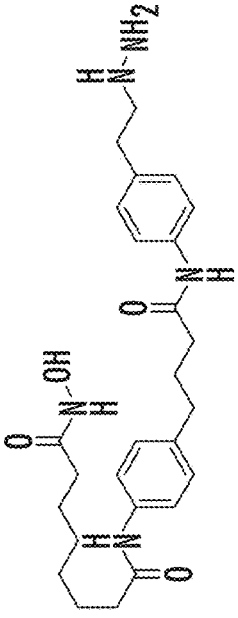 | 0.066 ± 0.015 | 0.16 ± 0.052 | 0.42 ± 0.044 |
| JK-2-50 | 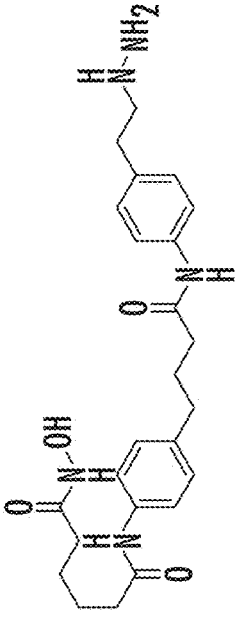 | 0.28 | 0.39 | 0.73 |
| JK-2-34 | 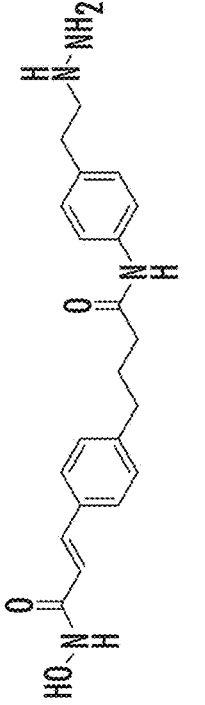 | 0.16 ± 0.010 | 0.37 ± 0.081 | 0.45 ± 0.072 |
| JK-1-68 | 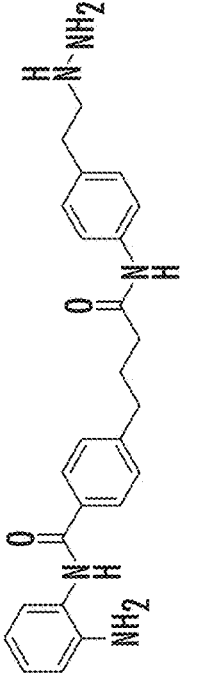 | 0.12 | 0.39 | 0.31 |
FIG. 23

INHIBITORS OF HISTONE LYSINE SPECIFIC DEMETHYLASE (LSD1) AND HISTONE DEACETYLASES (HDACS)

FEDERALLY SPONSORED RESEARCH OR DEVELOPMENT

This invention was made with government support under GM062437 awarded by the National Institutes of Health. The government has certain rights in the invention.

BACKGROUND

Reversible histone lysine methylation is a major mechanism for regulating chromatin dynamics and gene expression. Lysine-specific demethylase 1 (LSD1), the first histone demethylase identified, is responsible for oxidatively cleaving one or two methyl groups from Lys4 of histone H3 (H3K4). Culhane, J. C., and Cole, P. A. (2007). In this way, LSD1 is thought to play a role in gene silencing, since methylation of H3K4 in promoter regions is a well-established chromatin mark linked to transcriptional activation. Liang, G., et al. (2004), Heintzman, N. D., et al. (2007).

Since its discovery, LSD1 histone demethylase activity has been investigated as a pharmacologic target for cancer and other diseases. It has been found that LSD1 levels are often elevated in various cancers. Lv, T., et al. (2012), Lim, S., et al. (2010), Metzger, E., et al. (2005). Moreover, a variety of tumor suppressors that have been shown to be silenced in cancer by epigenetic mechanisms could theoretically be reactivated by LSD1 blockers, Murray-Stewart, T., et al. (2013), Huang, Y., et al. (2007), Huang, Y., et al. (2009), Jin, L., et al. (2013), as has been achieved with histone deacetylase and DNA methyltransferase inhibitors. Takai, N., and Narahara, H. (2008).

LSD1 is a 90 kDa flavin-bound enzyme that belongs to the amine oxidase protein superfamily, which uses molecular oxygen as a cosubstrate and generates hydrogen peroxide and formaldehyde as byproducts (FIG. 1A). Culhane, J. C., and Cole, P. A. (2007), Shi, Y., et al. (2004), Gaweska, H. (2009), Forneris, F. (2005). Based on its enzyme mechanism, LSD1 cannot demethylate trimethylated H3 Lys4 (H3K4Me3), but members of the iron-dependent Jmj histone demethylases are known to serve this function. Culhane, J. C., and Cole, P. A. (2007); Tsukada, Y., et al. (2005). In addition to the C-terminal amine oxidase catalytic domain, LSD1 also contains an N-terminal SWIRM domain and a 105 aa Tower domain insert, which is located in the amine oxidase domain that can bind CoREST.

In cells, LSD1 is often found in CoREST complexes that include HDAC½. Hakimi, M.-A., et al. (2003), Klose, R. J., et al. (2007), Hwang, S., et al. (2011), Baron, R., et al. (2011), Forneris, F. (2009). The LSD1 homolog, LSD2, also catalyzes demethylation of H3K4Me1 and H3K4Me2, but lacks the CoREST binding Tower domain insert, and exhibits significant sequence and local structure differences compared to LSD1. Zhang, Q. et al. (2013) Zhang, Q., et al. (2013), Karytinos, A., et al. (2009). Mechanistically and structurally, LSD1 also is related to the flavin-dependent monoamine oxidases (MAO A/B), as well as polyamine oxidase enzymes. Huang, Y., et al. (2009), Forneris, F., et al. (2009), Wang, Y., et al. (2003).

Several LSD1 demethylase inhibitors have been reported, including peptides (1,2), MAOIs and derivatives thereof (3-6), polyamines (7), and guanidine containing compounds (8) (FIG. 1B). Yang, M., et al. (2007), Culhane, J. C., et al. (2010), Dancy, B. C. R., et al. (2012), Tortorici, M., et al. (2013), Binda, C., et al. (2010), Mimasu, S, et al. (2010), Zhu, Q., et al. (2012), Wang, J., et al. (2011), Culhane, J. C., (2006), Pollock, J. A., et al. (2012), Gooden, D. M., et al. (2008) Dulla, B., et al. (2013), Hazeldine, S., et al. (2012).

One strategy that has shown promise has been the development of tranylcypromine analogs. Pollock, J. A., et al. (2012), Gooden, D. M., et al. (2008). Tranylcypromine is a classical MAO inhibitor used for the treatment of clinical depression, and is weakly potent as an LSD1 mechanism-based inactivator ($K_{i(inact)}$ 0.5 mM, $k_{(inact)}$ 0.67 min$^{-1}$). Yang, M., et al. (2007), Schmidt, D. M. Z., and McCafferty, D. G. (2007), Lee, M. G., et al. (2006). It has been shown, however, that tranylcypromine can be modified with the addition of an aryl attachment to produce more selective LSD1 inhibitors with enhanced potency. Binda, C., et al. (2010), Mimasu, S, et al. (2010). Further, phenelzine, a MAO inhibitor used to treat depression, has been shown to be more potent than tranylcypromine as an LSD1 inhibitor. Culhane, J. C., (2010)

SUMMARY

In some aspects, the presently disclosed subject matter provides a compound of Formula (I):

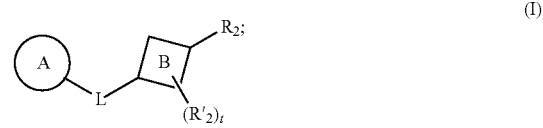

wherein:

t is an integer selected from the group consisting of 0, 1, 2, 3, and 4;

L is a linking group selected from the group consisting of —$X_1$—, —[$X_1$—C(=O)—$NR_1$]$_d$—, —[$X_1$—$NR_1$—C(=O)]$_d$—, —[C(=O)—$NR_1$—$X_1$]$_d$—, —[$NR_1$—C(=O)—$X_1$]$_d$—, —[$NR_1$—C(=O)—$NR_1$—$X_1$]$_d$—, —[$X_1$—$NR_1$—C(=O)—$NR_1$]$_d$—, —[$X_1$—O—C(=O)—$NR_1$]$_d$—, —[O—C(=O)—$NR_1$—$X_1$]—, —[$X_1$—$NR_1$—C(=O)—O]$_d$—, —[$NR_1$—C(=O)—O—$X_1$]$_d$—, —$X_1$—O—, —$X_1$—$NR_1$, —$X_1$—S—, —$X_1$—SO—, —$X_1$—$SO_2$—, —$X_1$—O—$X_1$—, —$X_1$—$NR_1$—$X_1$—, —$X_1$—S—$X_1$—, —$X_1$—SO—$X_1$—, and —$X_1$—$SO_2$—$X_1$—, wherein d is an integer selected from the group consisting of 1, 2, 3, and 4;

wherein $X_1$ is selected from the group consisting of —$(CH_2)_n$—, —[$(CH_2)_n$—CH=CH—$(CH_2)_m$]$_e$—, —[$(CH_2)_n$—C≡C—$(CH_2)_m$]$_e$—, and —$(CH_2)_m$—O—, wherein n and m are each independently an integer selected from the group consisting of 0, 1, 2, 3, 4, 5, 6, 7, 8, 9, 10, 11, 12, 13, 14, 15, 16, 17, 18, 19, and 20, e is an integer selected from the group consisting of 1, 2, 3 and 4, wherein the —$(CH_2)_n$—, —$(CH_2)_m$—, and —CH=CH— groups can optionally be substituted with a substituent selected from the group consisting of substituted or unsubstituted linear or branched alkyl, hydroxyl, alkoxyl, amino, cyano, halogen, and oxo, and wherein one or more carbon atoms of —$(CH_2)_n$— and —$(CH_2)_m$— can optionally be replaced with one or more heteroatoms selected from the group consisting of O, S, and $NR'_1$, wherein each —$(CH_2)_n$— or —$(CH_2)_m$— group can contain a cycloalkyl or cycloheteroalkyl unit;

$R_1$ and $R'_1$ are each independently selected from the group consisting of hydrogen, substituted or unsubstituted linear or branched alkyl, alkoxyl, substituted or unsubstituted cycloalkyl, substituted or unsubstituted cycloheteroalkyl, substituted or unsubstituted aryl, substituted or unsubstituted heteroaryl, substituted or unsubstituted arylalkyl, and substituted or unsubstituted heteroarylalkyl, and $R_1$ can form a ring system with ring B via a substituted or unsubstituted alkylene or heteroalkylene chain;

$R_2$ is —$(CH_2)_p$—$NR_3$—$NR_4R_5$ or —$(CH_2)_p$—$X_2$; wherein p is an integer selected from the group consisting of 0, 1, 2, 3, and 4, and wherein the —$(CH_2)_p$— group can be saturated or unsaturated or contain a cycloalkyl unit and optionally be substituted with a substituent selected from the group consisting of substituted or unsubstituted linear or branched alkyl, hydroxyl, alkoxyl, amino, cyano, halogen, and oxo, and one or more carbon atoms of —$(CH_2)_p$— can optionally be replaced with one or more heteroatoms selected from the group consisting of O, S, and $NR'_1$;

each $R'_2$ is independently selected at each occurrence from the group consisting of substituted or unsubstituted alkyl, substituted or unsubstituted cycloalkyl, substituted or unsubstituted cycloheteroalkyl, allyl, hydroxyl, alkoxyl, amino, cyano, carboxyl, halogen, nitro, oxo, —$CF_3$, substituted or unsubstituted aryl, substituted or unsubstituted heteroaryl;

$R_3$, $R_4$, and $R_5$ are each independently selected from the group consisting of hydrogen, substituted or unsubstituted linear or branched alkyl, alkoxyl, substituted or unsubstituted cycloalkyl, substituted or unsubstituted cycloheteroalkyl, substituted or unsubstituted aryl, substituted or unsubstituted heteroaryl, substituted or unsubstituted arylalkyl, and substituted or unsubstituted heteroarylalkyl, and —C(=O)—O—$R_{21}$, or $R_4$ and $R_5$ together can form a substituted or unsubstituted 4- to 6-membered cycloalkyl, and wherein $R_{24}$ is substituted or unsubstituted linear or branched alkyl;

$X_2$ is selected from the group consisting of hydroxyl, halogen, and —O—Si$(R_{21}R_{22})_2$—$R_{23}$, wherein $R_{21}$, $R_{22}$, and $R_{23}$ are each independently substituted or unsubstituted linear or branched alkyl;

A is selected from the group consisting of mono-or multicyclic substituted or unsubstituted cycloalkyl, substituted or unsubstituted cycloheteroalkyl, substituted or unsubstituted aryl, substituted or unsubstituted heteroaryl, substituted or unsubstituted arylalkyl, and substituted or unsubstituted heteroarylalkyl; B is selected from the group consisting of aryl or heteroaryl;

wherein one or more carbon atoms of ring B can be replaced with one or more heteroatoms selected from the group consisting of N, O, and S;

wherein one or both of ring structures A and B can be optionally substituted with one or more reactive groups capable of forming a prodrug;

and pharmaceutically acceptable salts, hydrates, and solvates thereof.

In particular aspects, the compound of Formula (I) has the following structure:

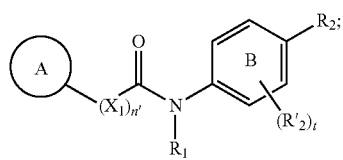

(Ia)

wherein n' is an integer selected from the group consisting of 0, 1, 2, 3, 4, 5, and 6.

In more particular aspects, the compound of Formula (Ia) has the following structure:

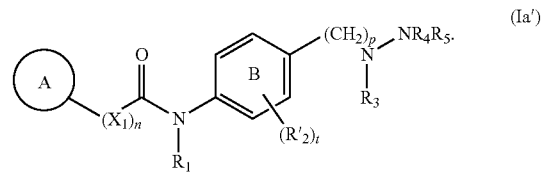

(Ia')

In other aspects, the presently disclosed subject matter provides a compound of Formula (II):

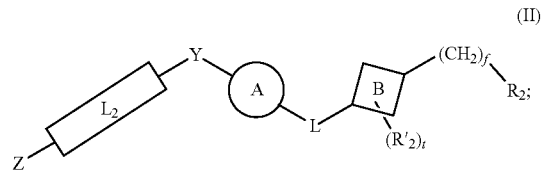

(II)

wherein:

t is an integer selected from the group consisting of 0, 1, 2, 3, and 4;

f is an integer selected from the group consisting of 0, 1, 2, 3, 4, 5, and 6;

A is selected from the group consisting of mono-or multicyclic substituted or unsubstituted cycloalkyl, substituted or unsubstituted cycloheteroalkyl, substituted or unsubstituted aryl, substituted or unsubstituted heteroaryl, substituted or unsubstituted arylalkyl, and substituted or unsubstituted heteroarylalkyl;

B is selected from the group consisting of aryl or heteroaryl;

L is a linking group selected from the group consisting of —$X_1$—, —[$X_1$—C(=O)—$NR_d$]—, —[$X_1$—$NR_1$—C(=O)]$_d$—, —[C(=O)—$NR_1$—$X_1$]$_d$—, —[$NR_1$—C(=O)—$X_1$]$_d$—, —[$NR_1$—C(=O)—$NR_1$—$X_1$]$_d$—, —[$X_1$—$NR_1$—C(=O)—$NR_1$]$_d$—, —[$X_1$—O—C(=O)—$NR_1$]$_d$—, —[O—C(=O)—$NR_1$—$X_1$]$_d$—, —[$X_1$—$NR_1$—C(=O)—O]$_d$—, —[$NR_1$—C(=O)—O—$X_1$]$_d$—, —$X_1$—O—, —$X_1$—$NR_1$, —$X_1$—S—, —$X_1$—SO—, —$X_1$—$SO_2$—, —$X_1$—O—$X_1$—, —$X_1$—$NR_1$—$X_1$—, —$X_1$—S—$X_1$—, —$X_1$—SO—$X_1$—, and —$X_1$—$SO_2$—$X_1$—, wherein d is an integer selected from the group consisting of 1, 2, 3, and 4;

wherein $X_1$ is selected from the group consisting of —$(CH_2)_n$—, —[$(CH_2)_n$—CH=CH—$(CH_2)_m$]$_e$—, —[$(CH_2)_n$—C≡C—$(CH_2)_m$]$_e$—, and —$(CH_2)_m$—O—, wherein n and m are each independently an integer selected from the group consisting of 0, 1, 2, 3, 4, 5, 6, 7, 8, 9, 10, 11, 12, 13, 14, 15, 16, 17, 18, 19, and 20, e is an integer selected from the group consisting of 1, 2, 3 and 4, wherein the —$(CH_2)_n$—, —$(CH_2)_m$—, and —CH=CH— groups can optionally be substituted with a substituent selected from the group consisting of substituted or unsubstituted linear or branched alkyl, hydroxyl, alkoxyl, amino, cyano, halogen, and oxo, and wherein one or more carbon atoms of —(CH$_2$)$_n$— and —(CH$_2$)$_m$— can optionally be replaced with one or more heteroatoms selected from the group consisting of O, S, and NR'$_1$, wherein each —(CH$_2$)$_n$— or —(CH$_2$)$_m$— group can contain a cycloalkyl or cycloheteroalkyl unit;

L$_2$ is selected from the group consisting of aryl, heteroaryl, —(CH$_2$)$_n$—, —(CH$_2$)$_n$—CH═CH(CH$_2$)$_m$—, —(CH$_2$)$_n$—C≡C—(CH$_2$)$_m$—, —(CH$_2$)$_m$—O—, wherein n and m are each independently an integer selected from the group consisting of 0, 1, 2, 3, 4, 5, and 6, wherein the —(CH$_2$)$_n$—, —(CH$_2$)$_m$—, and —CH═CH— groups can optionally be substituted with a substituent selected from the group consisting of substituted or unsubstituted linear or branched alkyl, hydroxyl, alkoxyl, amino, cyano, halogen, and oxo, and wherein one or more carbon atoms of —(CH$_2$)$_n$— and —(CH$_2$)$_m$— can optionally be replaced with one or more heteroatoms selected from the group consisting of O, S, and NR'$_1$;

R$_1$ and R'$_1$ are each independently selected from the group consisting of hydrogen, substituted or unsubstituted linear or branched alkyl, alkoxyl, substituted or unsubstituted cycloalkyl, substituted or unsubstituted cycloheteroalkyl, substituted or unsubstituted aryl, substituted or unsubstituted heteroaryl, substituted or unsubstituted arylalkyl, and substituted or unsubstituted heteroarylalkyl, and R$_1$ can form a ring system with ring B via a substituted or unsubstituted alkylene or heteroalkylene chain;

R$_2$ is —(CH$_2$)$_p$—NR$_3$NR$_4$R$_5$ or —(CH$_2$)$_p$—X$_2$; wherein p is an integer selected from the group consisting of 0, 1, 2, 3, and 4, and wherein the —(CH$_2$)$_p$— group can be saturated or unsaturated or contain a cycloalkyl unit and optionally be substituted with a substituent selected from the group consisting of substituted or unsubstituted linear or branched alkyl, hydroxyl, alkoxyl, amino, cyano, halogen, and oxo, and one or more carbon atoms of —(CH$_2$)$_p$— can optionally be replaced with one or more heteroatoms selected from the group consisting of O, S, and NR'$_1$;

each R'$_2$ is independently selected at each occurrence from the group consisting of substituted or unsubstituted alkyl, substituted or unsubstituted cycloalkyl, substituted or unsubstituted cycloheteroalkyl, allyl, hydroxyl, alkoxyl, amino, cyano, carboxyl, halogen, nitro, oxo, —CF$_3$, substituted or unsubstituted aryl, substituted or unsubstituted heteroaryl;

R$_3$, R$_4$, and R$_5$ are each independently selected from the group consisting of hydrogen, substituted or unsubstituted linear or branched alkyl, alkoxyl, substituted or unsubstituted cycloalkyl, substituted or unsubstituted cycloheteroalkyl, substituted or unsubstituted aryl, substituted or unsubstituted heteroaryl, substituted or unsubstituted arylalkyl, and substituted or unsubstituted heteroarylalkyl, and —C(═O)—O—R$_{21}$, or R$_4$ and R$_5$ together can form a substituted or unsubstituted 4- to 6-membered cycloalkyl, and wherein R$_{24}$ is substituted or unsubstituted linear or branched alkyl;

Y is selected from the group consisting of null, —N(R$^{10}$)C(═O)—, —C(═O)N(R$^{10}$)—, —N(R$^{10}$)C(═S)—, —C(═S)N(R$^{10}$)—, —SO$_2$—, —N(R$^{10}$)SO$_2$—, —N(R$^{10}$)SO$_2$N(R$^{10}$)—, —SO$_2$N(R$^{10}$)—, and —CH═CH—;

Z is selected from the group consisting of:
—C(═O)N(R$^{10}$)OH, —C(═O)OR$^{16}$, N(R$^{10}$)OH, —N(R$^{10}$)C(═O)C(R$^{11}$)$_n$S(R$^{12}$),
—B(OR$^{13}$)$_m$, —SR$^{14}$,

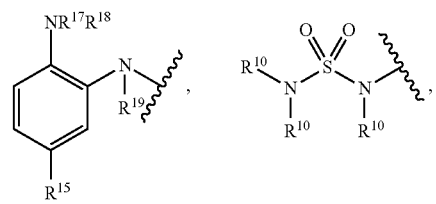

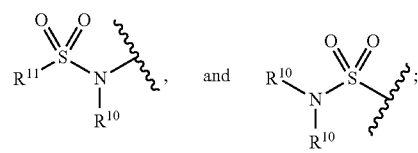

wherein R$^{10}$, R$^{11}$, R$^{12}$, R$^{13}$, R$^{14}$, and R$^{15}$ are each independently selected from the group consisting of hydrogen, substituted or unsubstituted linear or branched alkyl, alkoxyl, substituted or unsubstituted cycloalkyl, substituted or unsubstituted cycloheteroalkyl, substituted or unsubstituted aryl, substituted or unsubstituted heteroaryl, substituted or unsubstituted arylalkyl, and substituted or unsubstituted heteroarylalkyl;

R$^{16}$, R$^{17}$, R$^{18}$, and R$^{19}$ are each independently substituted or unsubstituted linear or branched alkyl;

and n and m are integers each independently selected from the group consisting of 0, 1, and 2; and pharmaceutically acceptable salts, hydrates, and solvates thereof.

In some aspects, the compound of Formula (II) has the following structure:

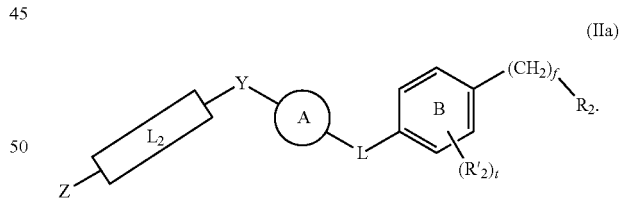

(IIa)

In other aspects, the compound of Formula (II) has the following structure:

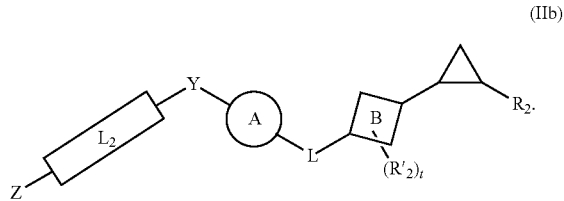

(IIb)

In yet other aspects, the compound of Formula (IIb) has the following structure:

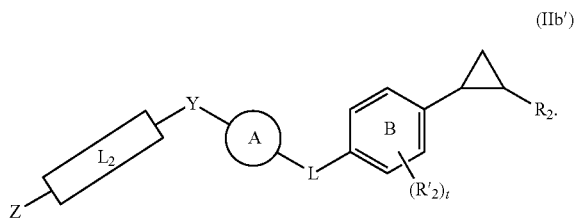

(IIb')

In other aspects, the presently disclosed subject matter provides a method for inhibiting lysine-specific demethylase 1 (LSD1) and/or one or more histone deacetylases (HDACs), the method comprising administering to a subject a compound of Formula (Ia) or a compound of Formula (II), or a pharmaceutically acceptable salt thereof, in an amount effective to inhibit LSD1 or one or more HDACs.

In yet other aspects, the presently disclosed subject matter provides a method for treating a disease, disorder, or condition associated with lysine-specific demethylase 1 (LSD1) and/or one or more histone deacetylases (HDACs), the method comprising administering to a subject in need of treatment thereof subject a compound of Formula (Ia) or Formula (II), or a pharmaceutically acceptable salt thereof, in an amount effective to inhibit LSD1 and/or one or more histone deacetylases (HDACs).

In certain aspects, the disease, disorder, or condition associated with LSD1 and/or one or more histone deacetylases (HDACs) is a cancer.

In other aspects, the disease, disorder, or condition associated with LSD1 and/or one or more histone deacetylases (HDACs) is a neurodegenerative disease.

In certain aspects, the compound of Formula (Ia) or Formula (II) is administered in combination with one or more additional therapeutic agents, wherein the one or more additional therapeutic agents has an additive or synergistic effect on cancer cell growth. In more certain aspects, the one or more additional therapeutic agents is selected from the group consisting of a histone deacetylase (HDAC) inhibitor, a DNA methyltransferase (DNMT) inhibitor, and combinations thereof.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1A:
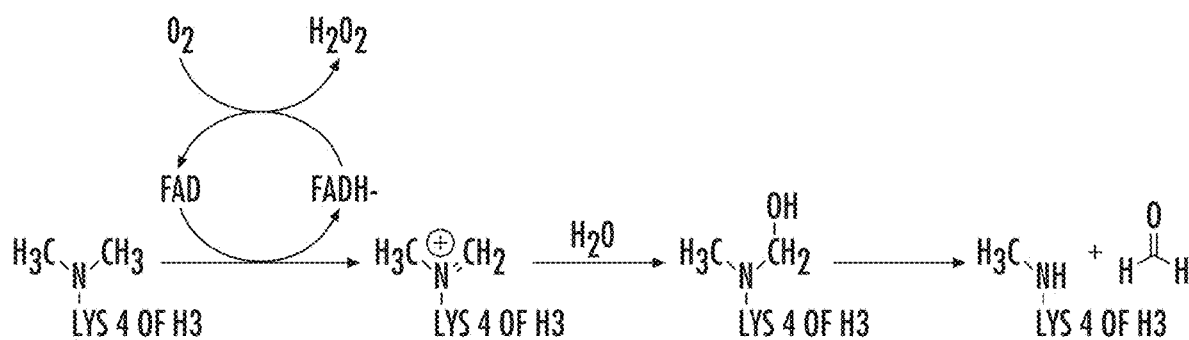
Figure 1B:
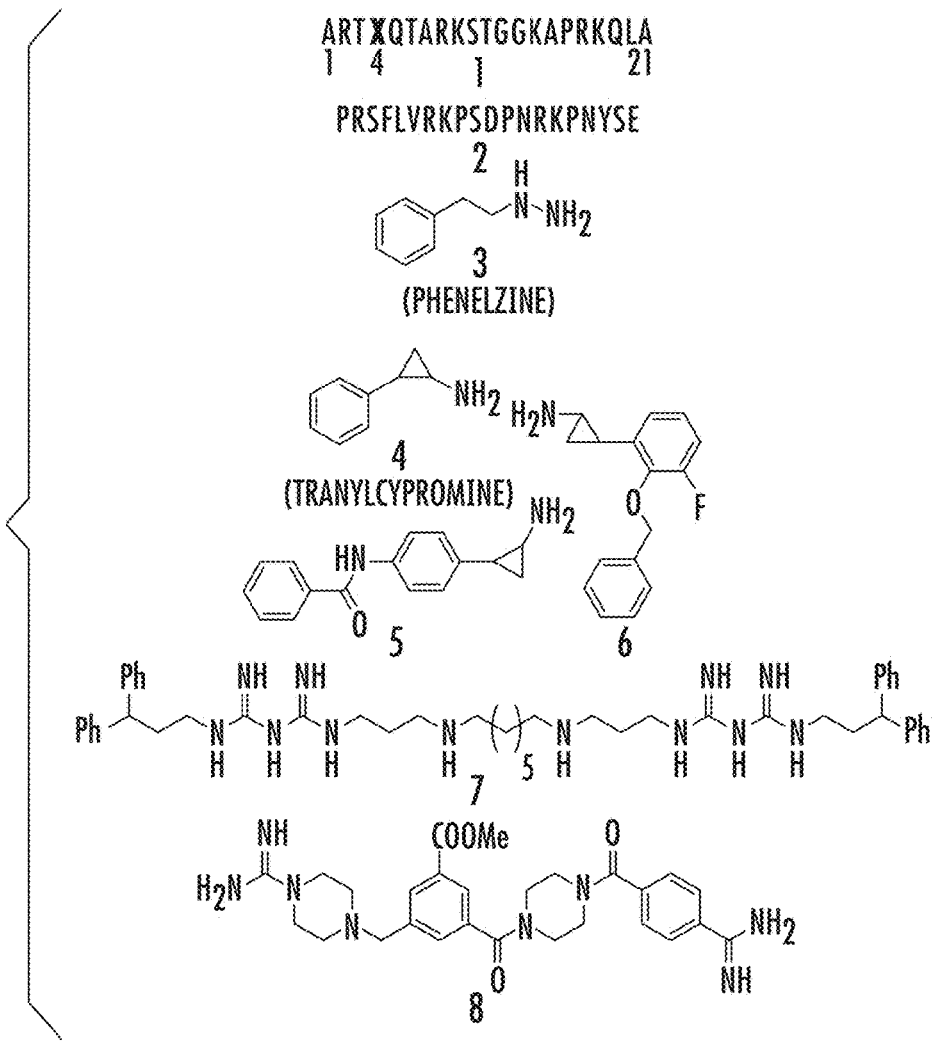
Figure 3:
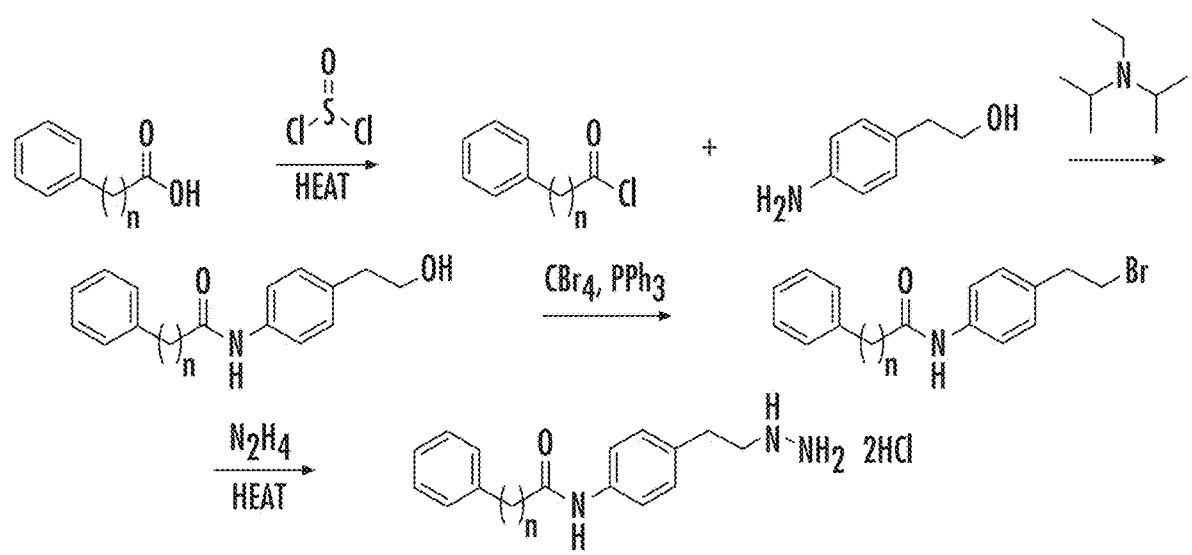
Figure 4A:
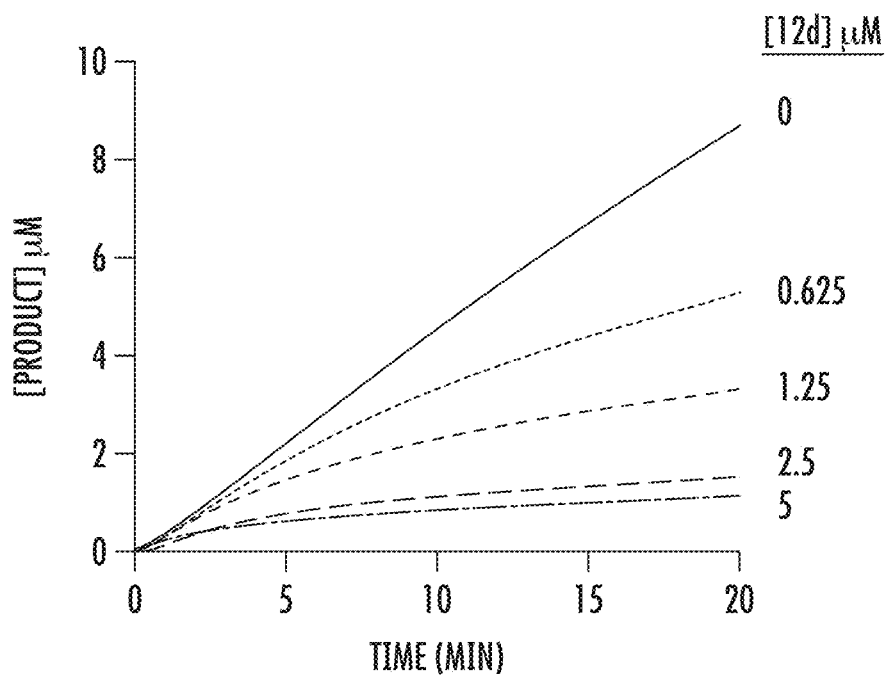
Figure 4B:
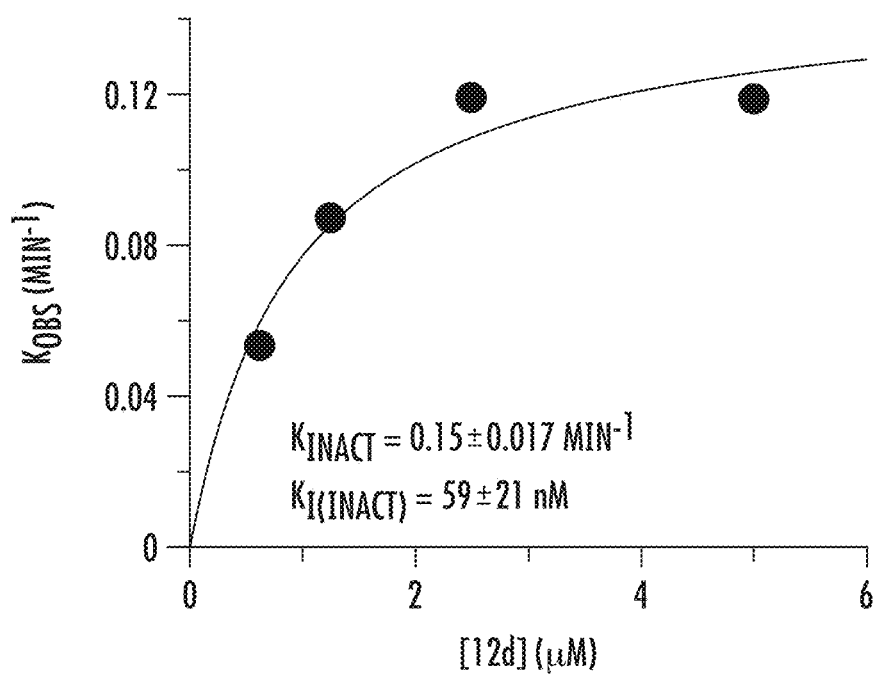
Figure 6A:
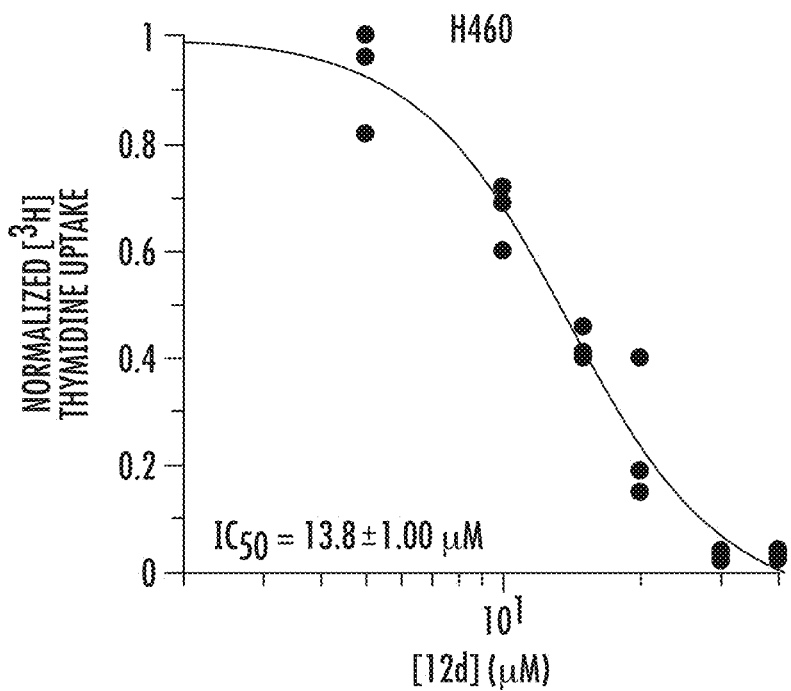
Figure 6B:
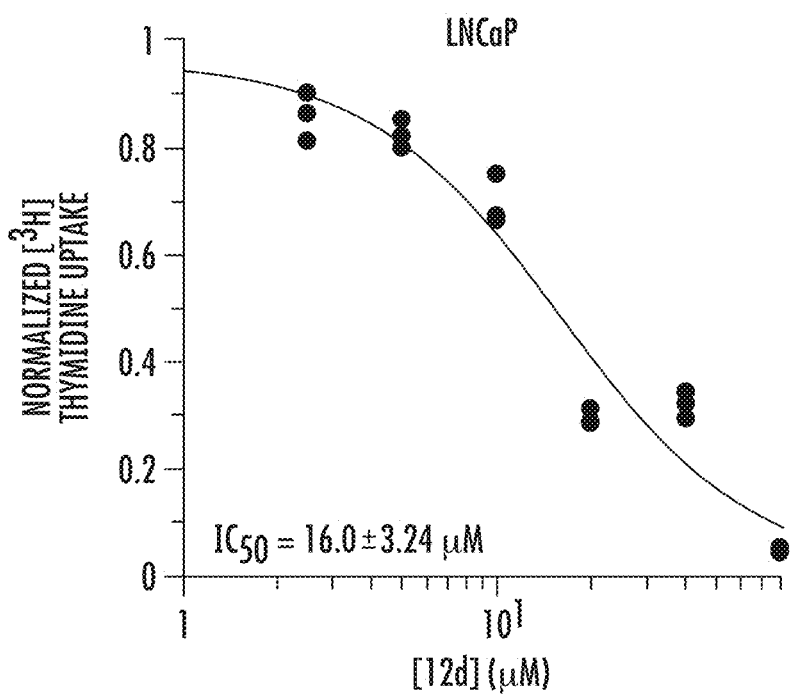
Figure 7A:
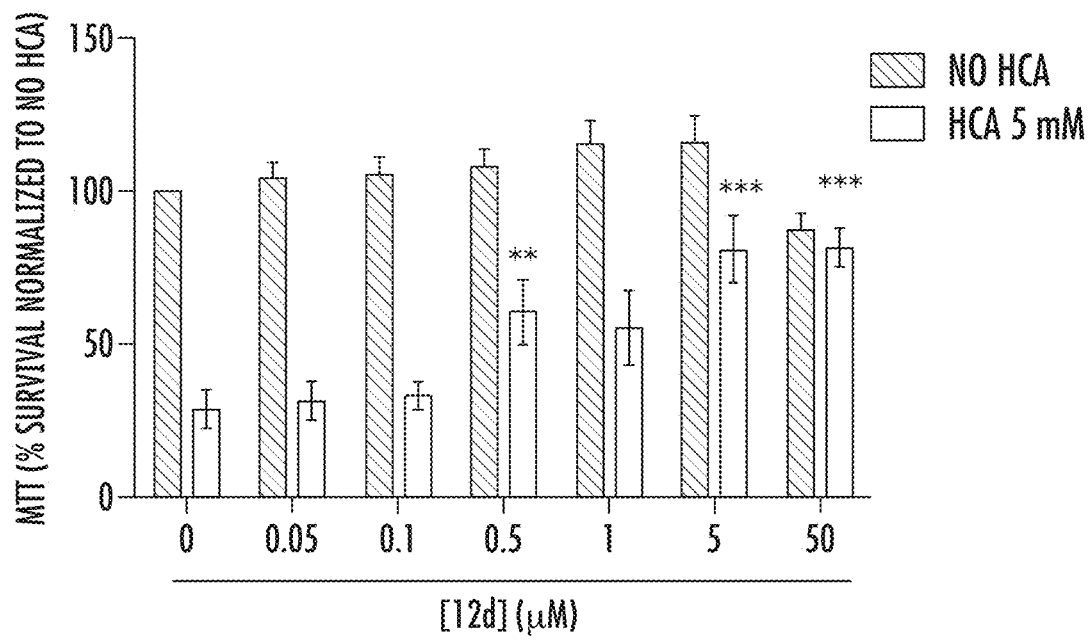
Figure 7B:
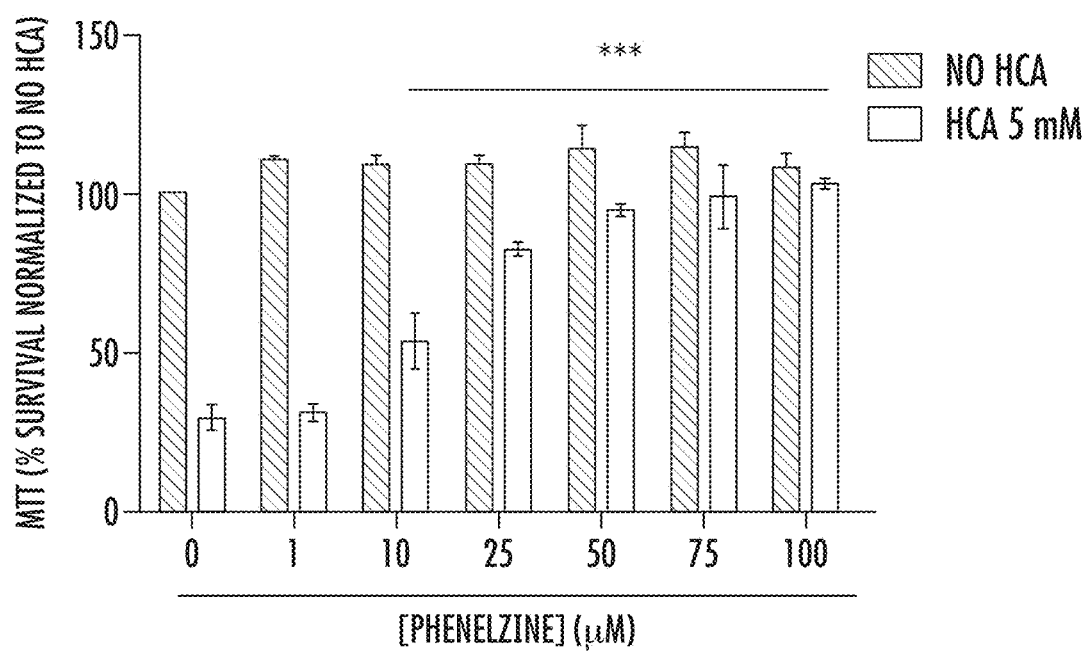
Figure 8A:
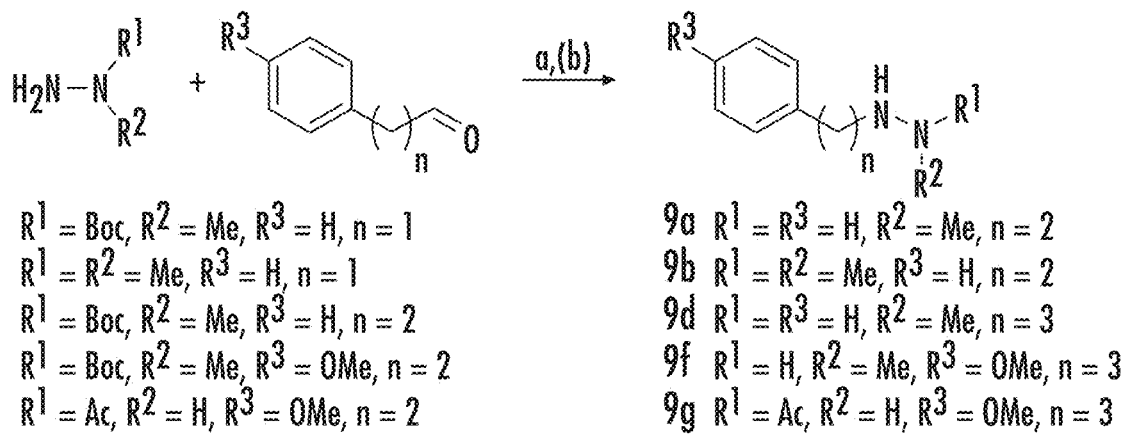
Figure 8B:
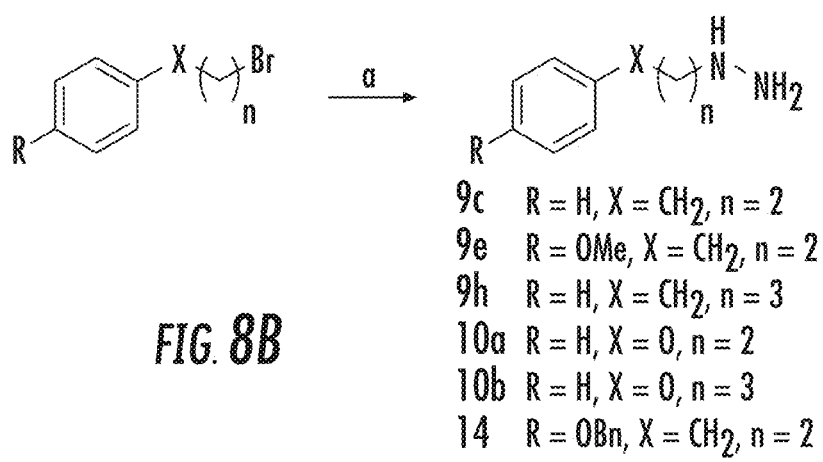
Figure 9:
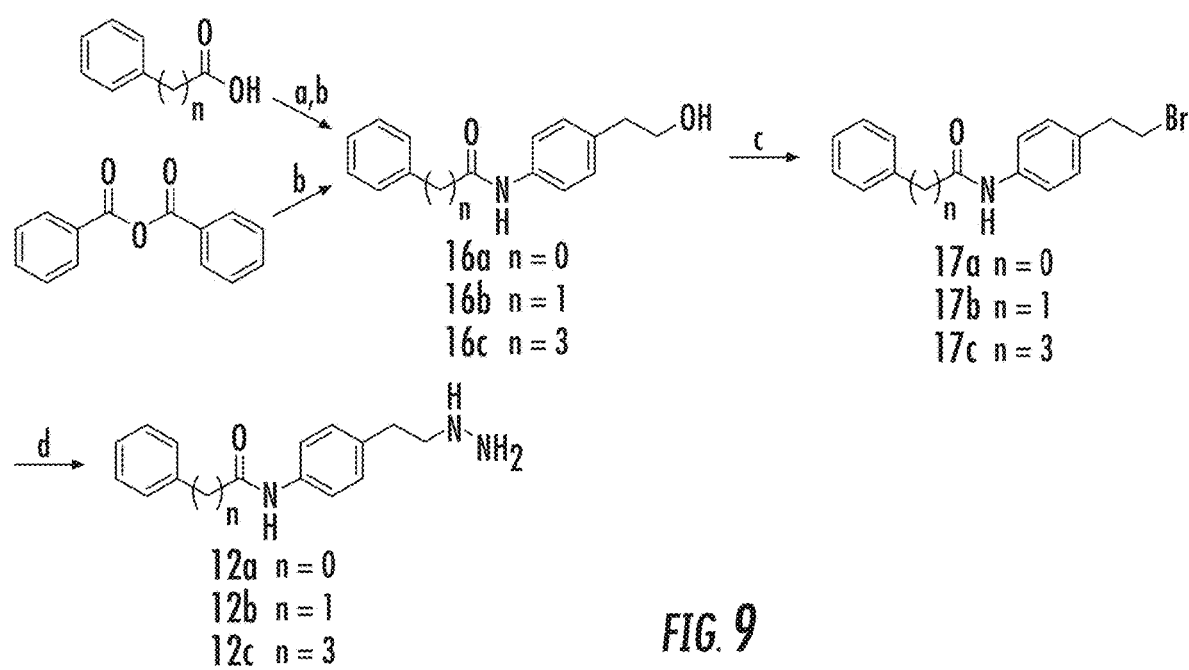
Figure 11:
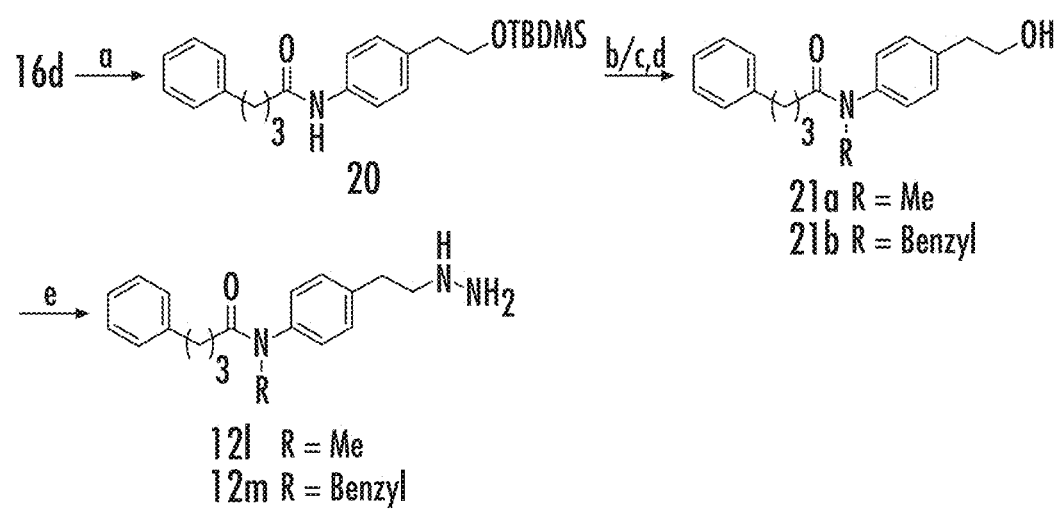
Figure 12A:
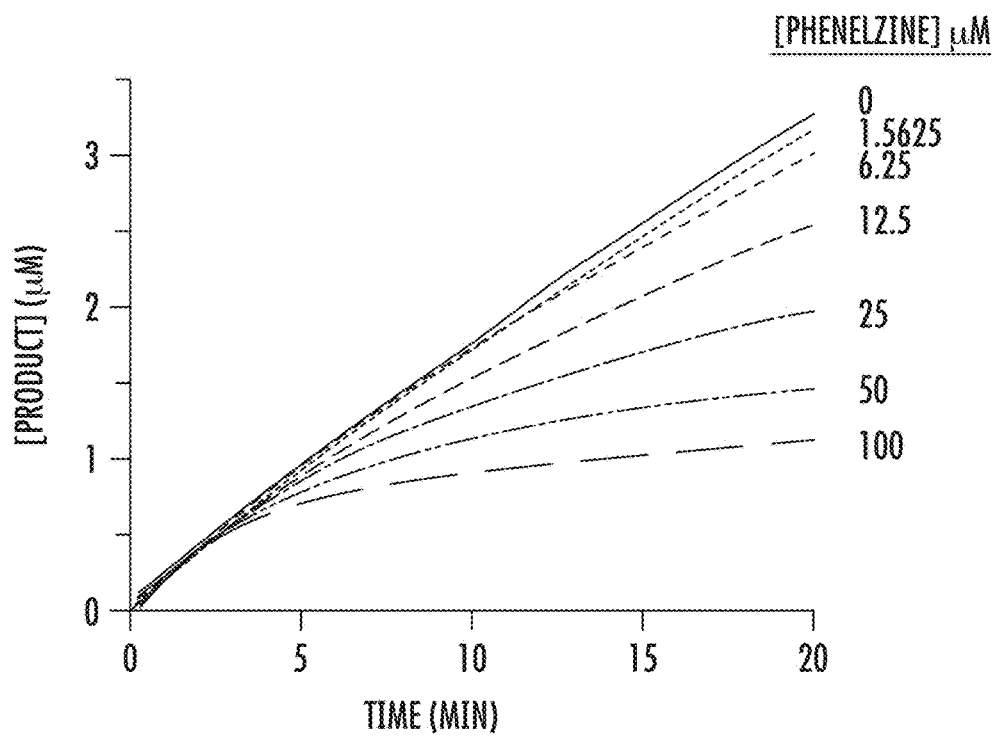
Figure 12B:
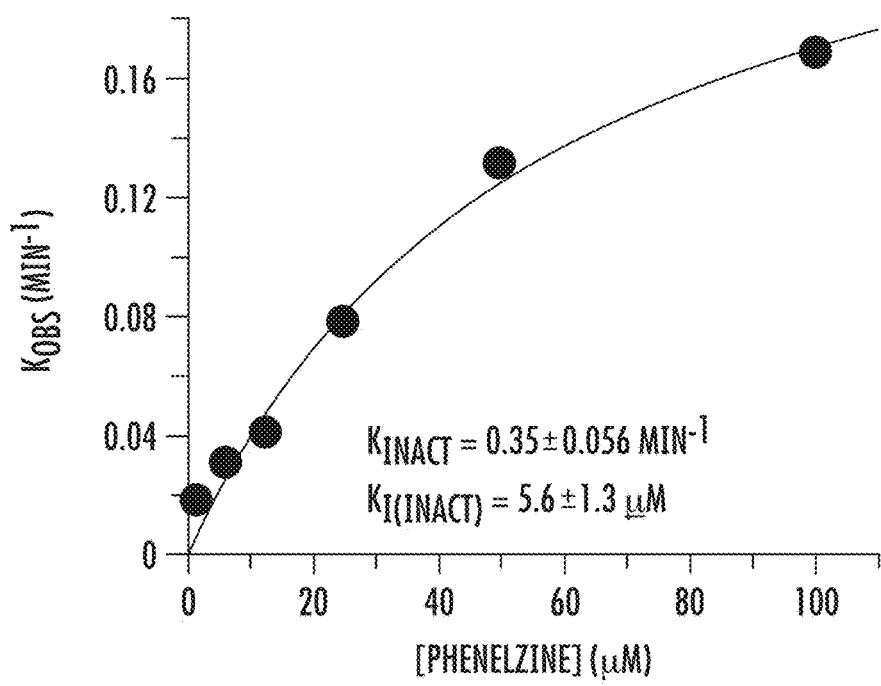
Figure 13:
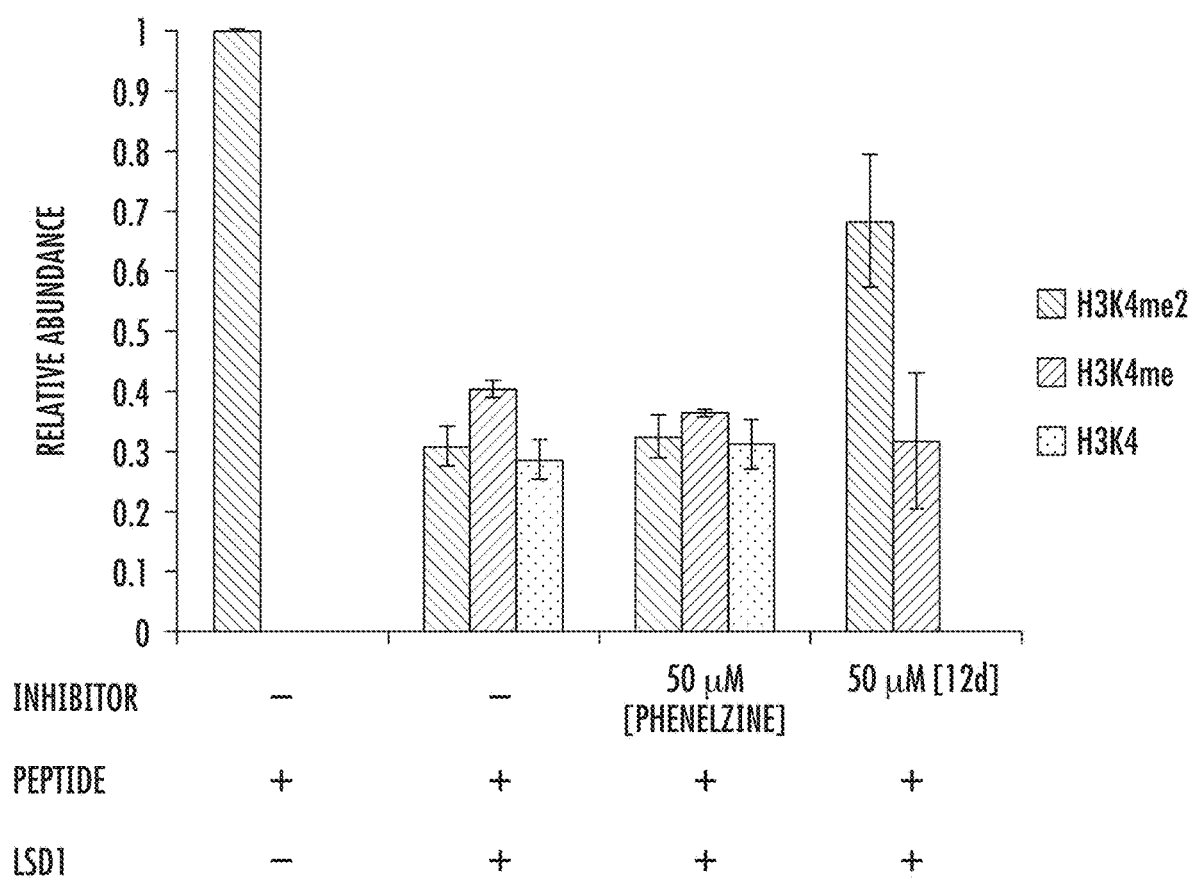
Figure 14:
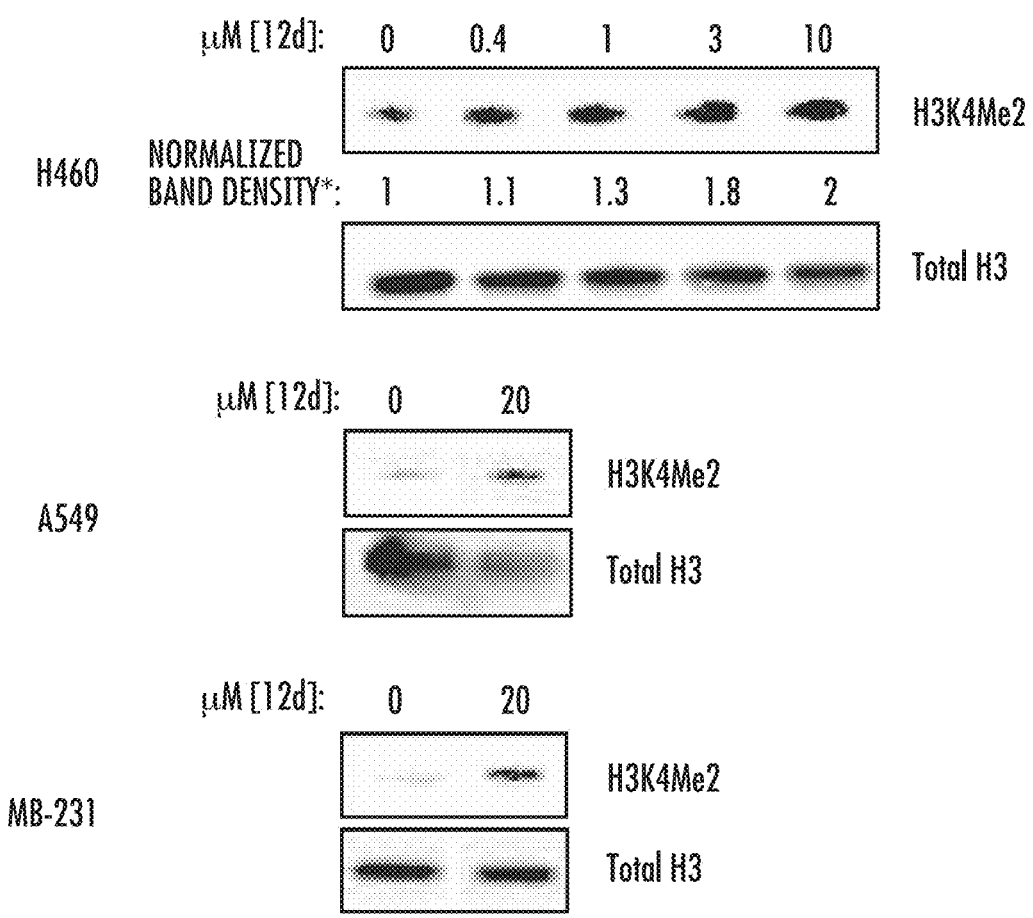
Figure 15:
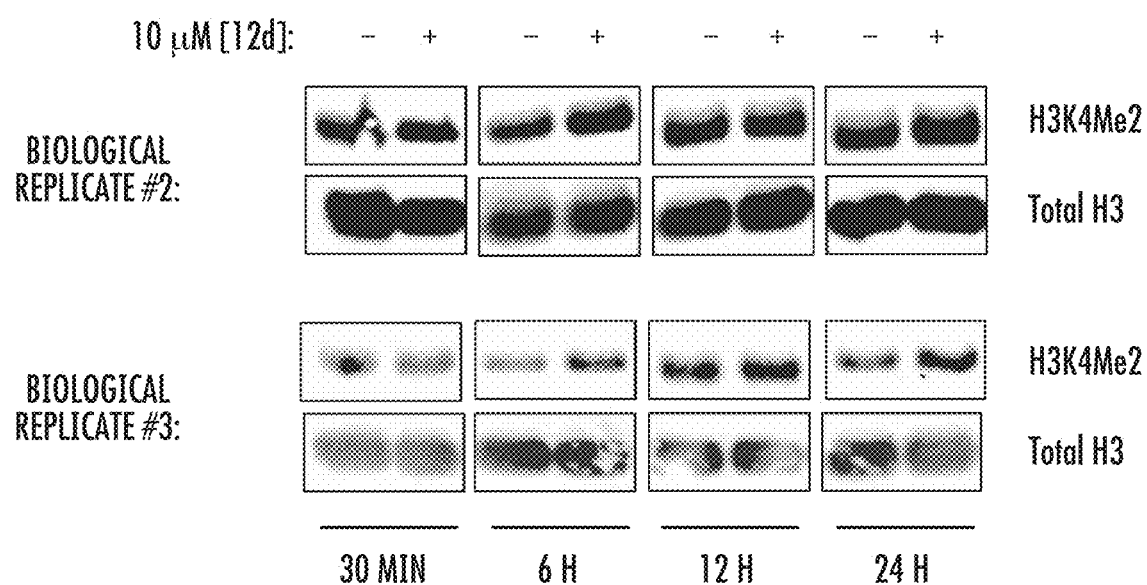
Figure 16A:
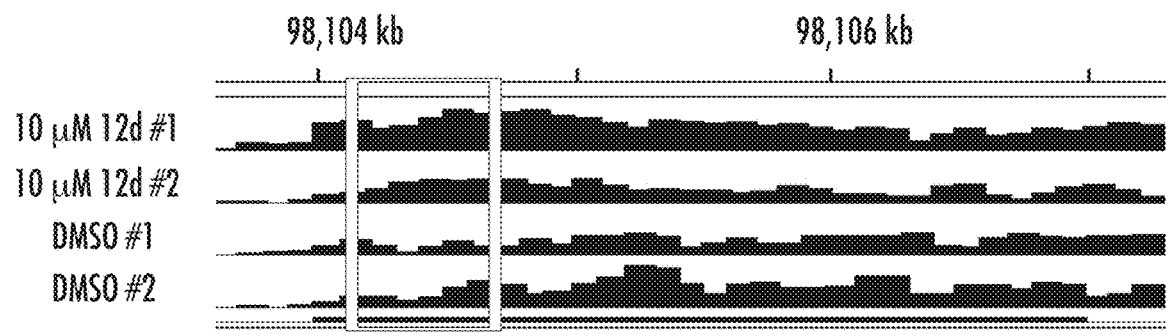
Figure 16B:
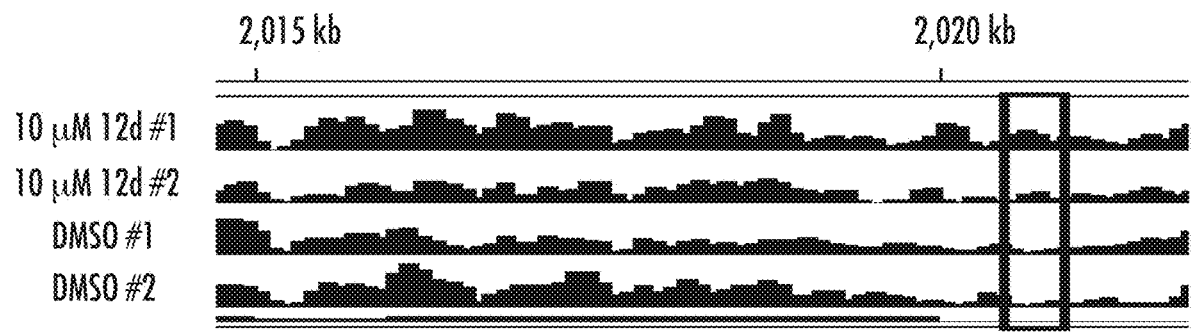
Figure 16C:
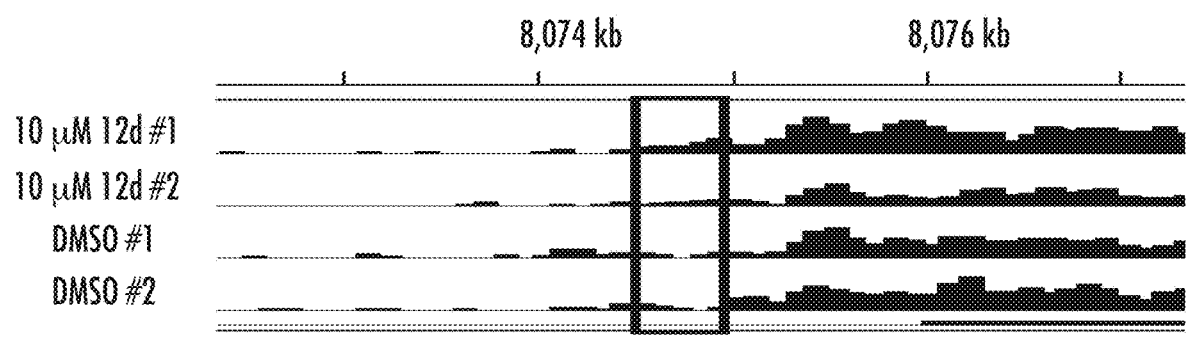
Figure 17:
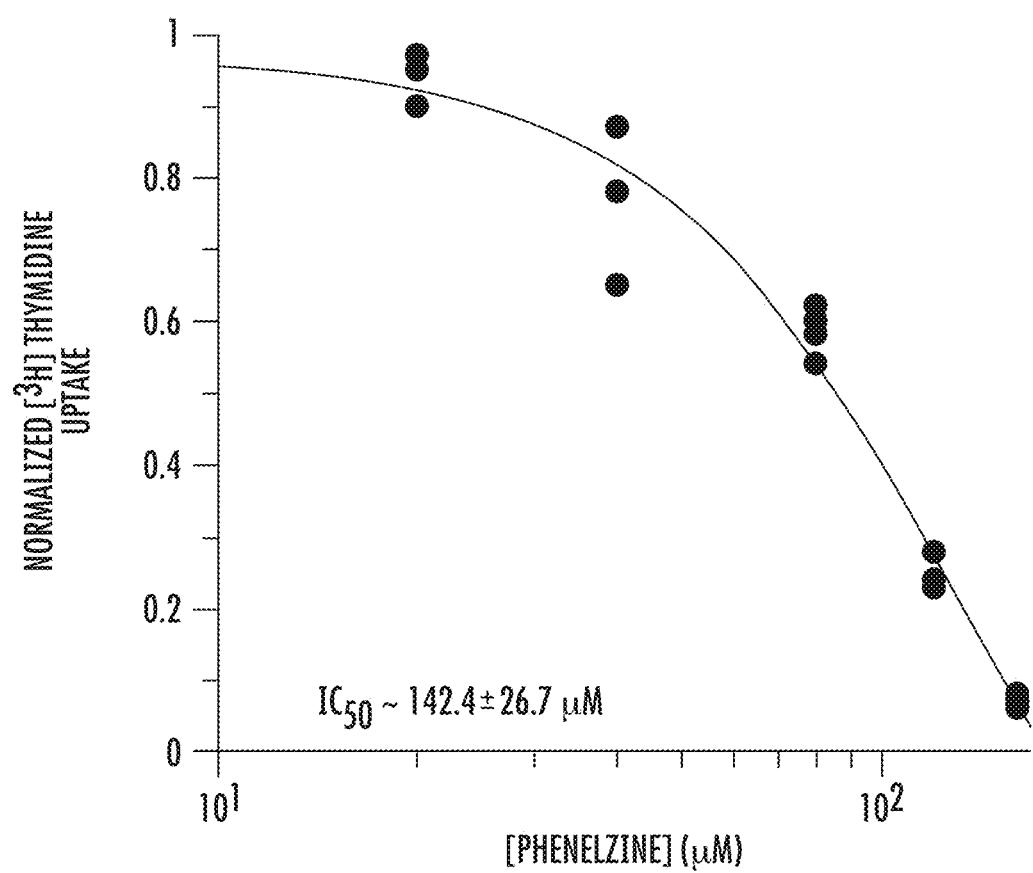
Figure 18A:
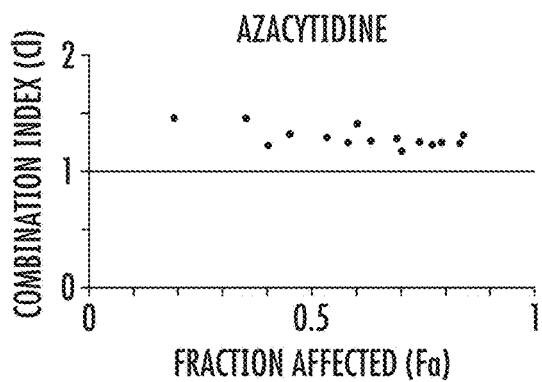
Figure 18B:
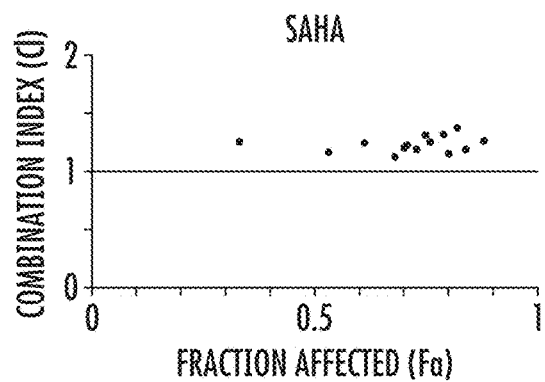
Figure 18C:
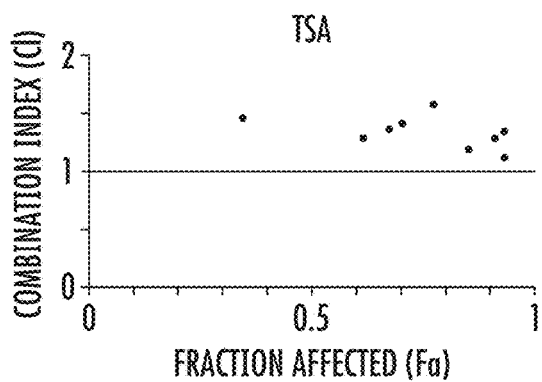
Figure 18D:
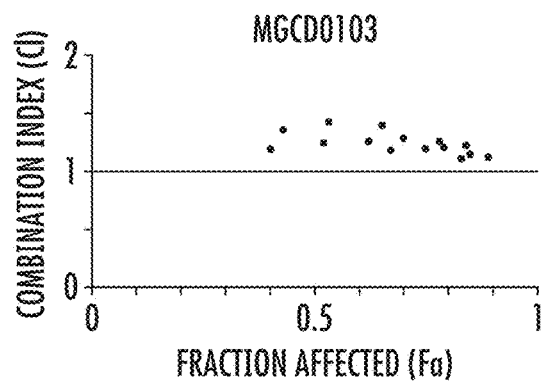
Figure 18E:
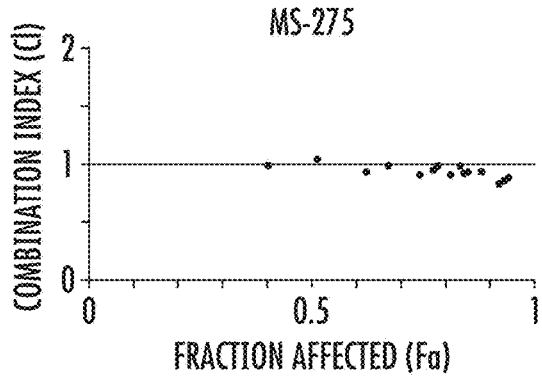
Figure 18F:
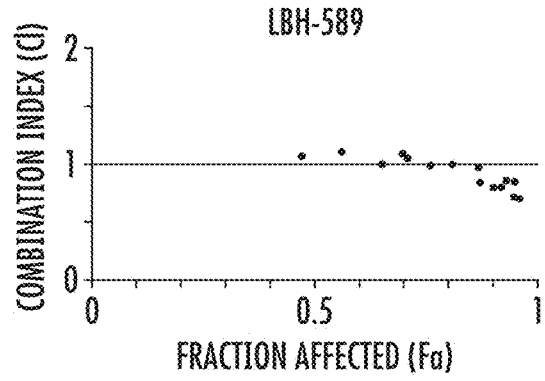
Figure 19A:
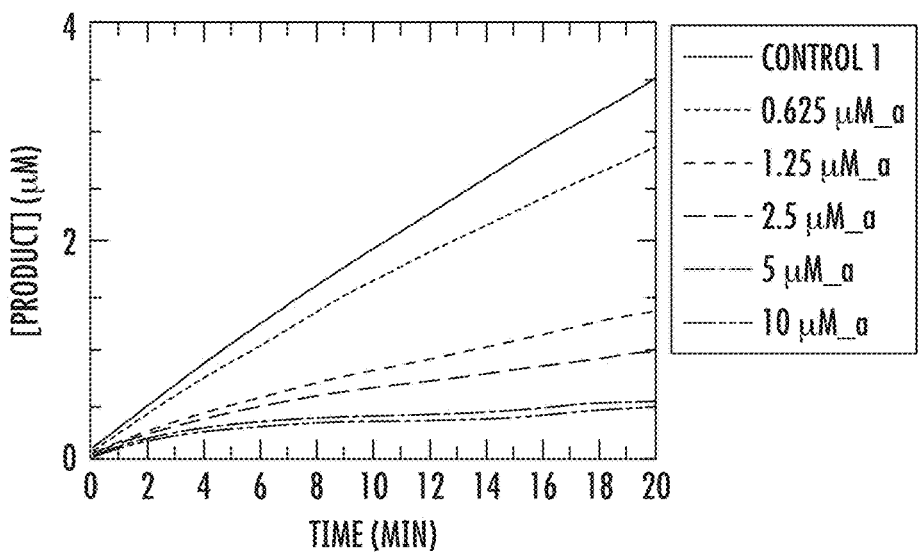
Figure 19B:
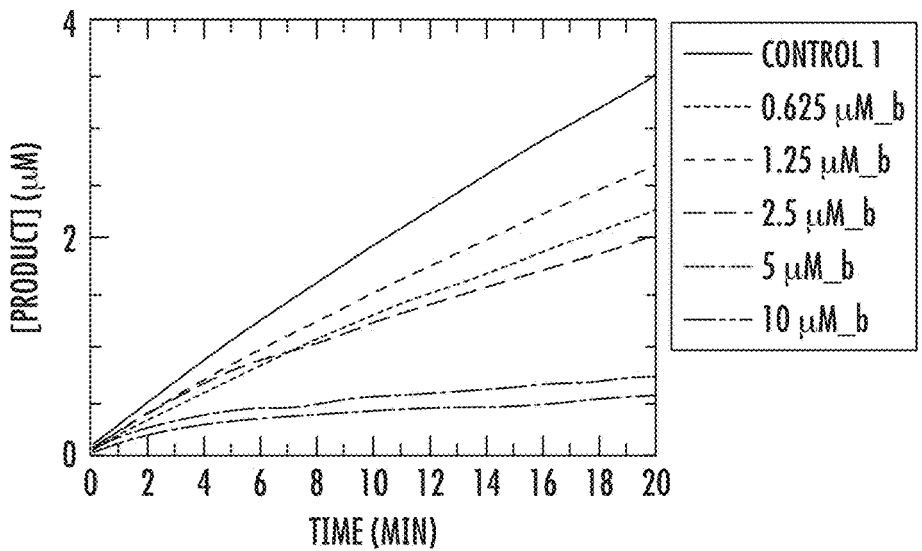
Figure 19C:
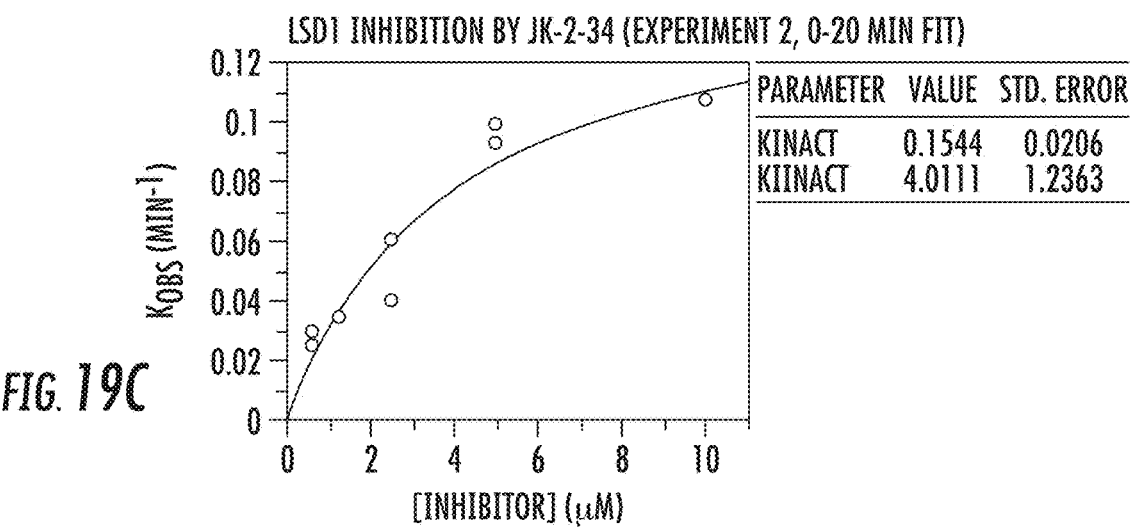
Figure 20A:
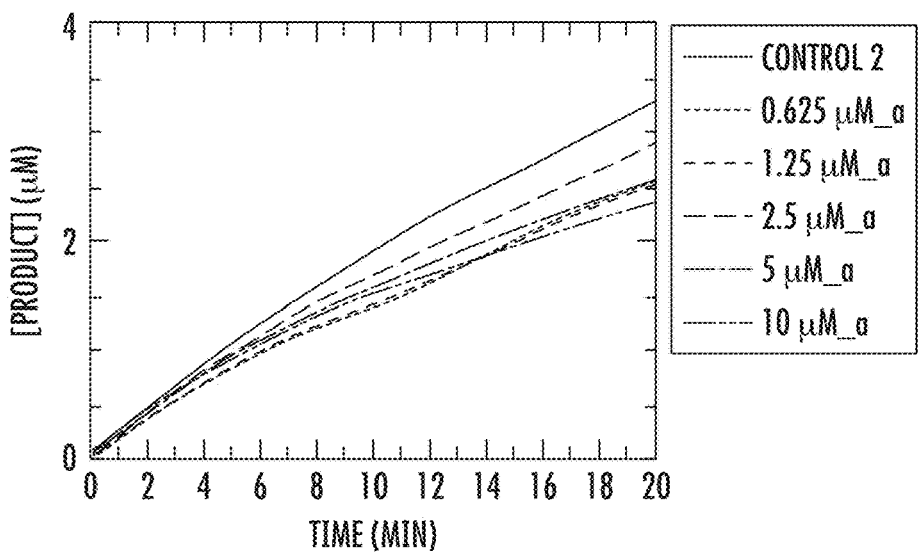
Figure 20B:
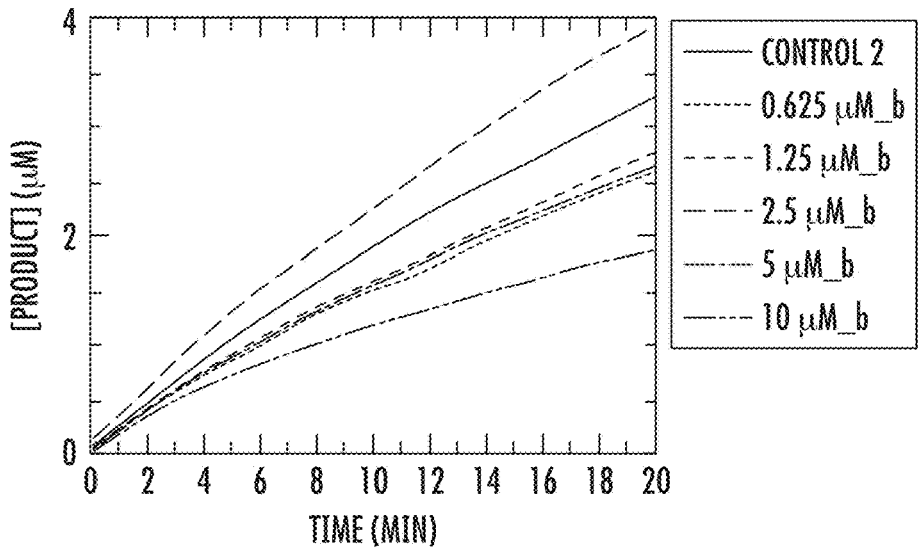
Figure 20C:
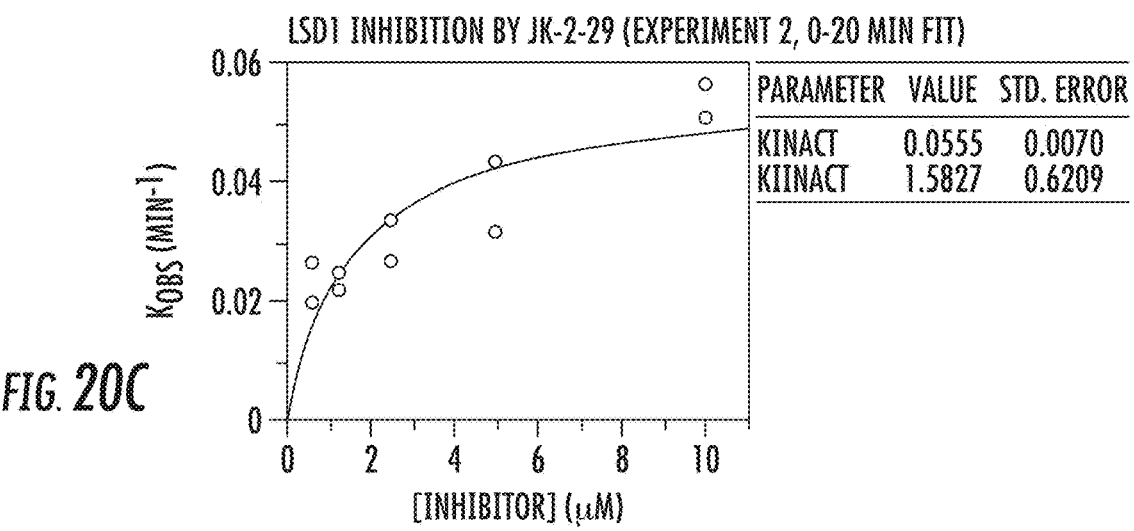
Figure 21A:
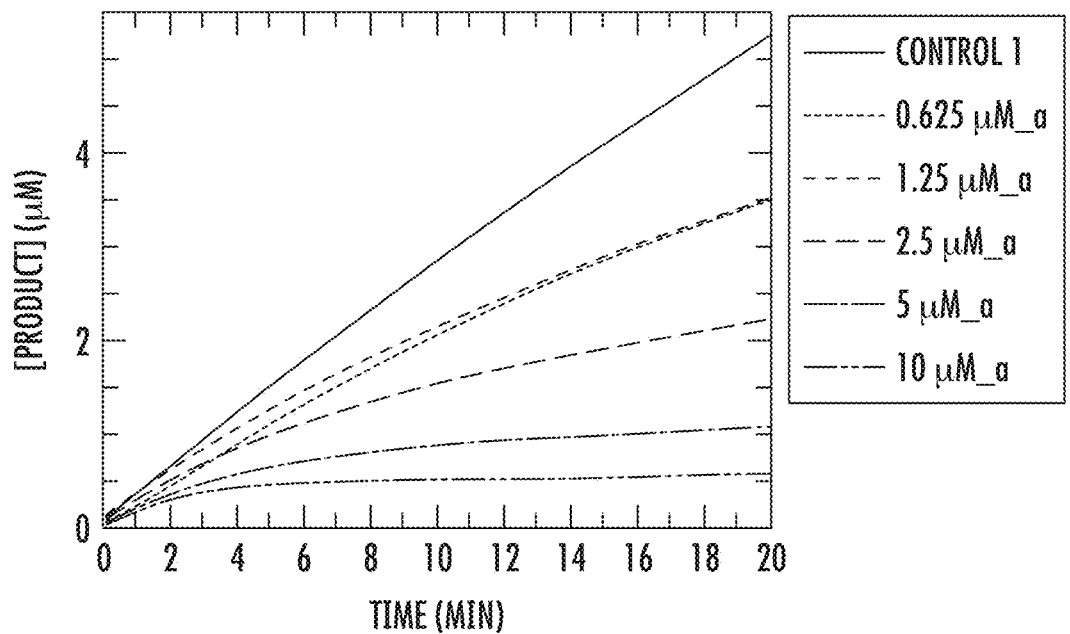
Figure 21B:
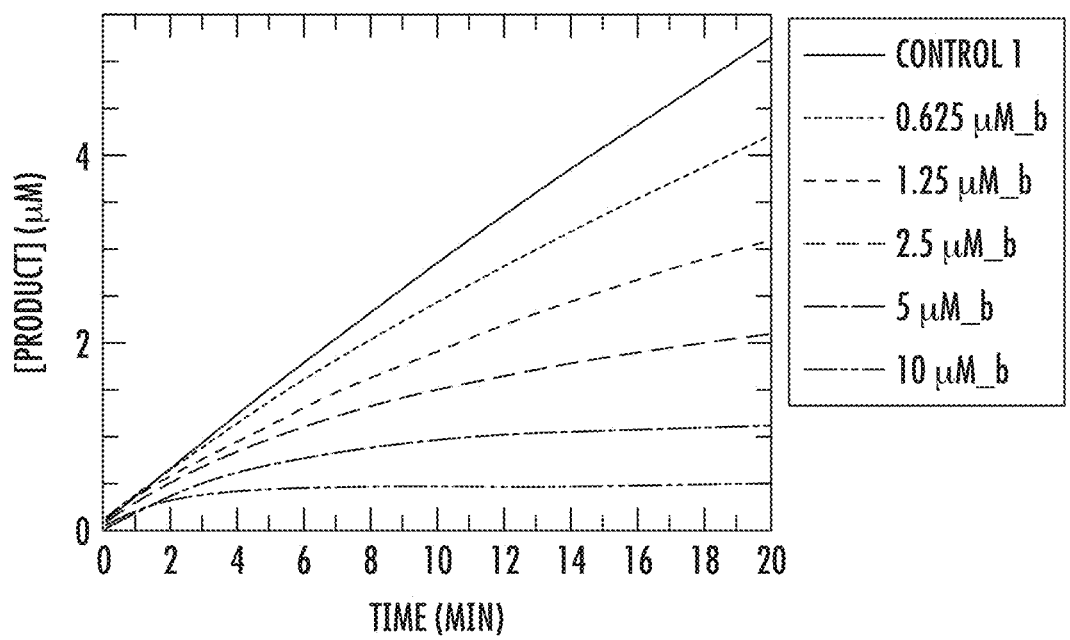
Figure 22A:
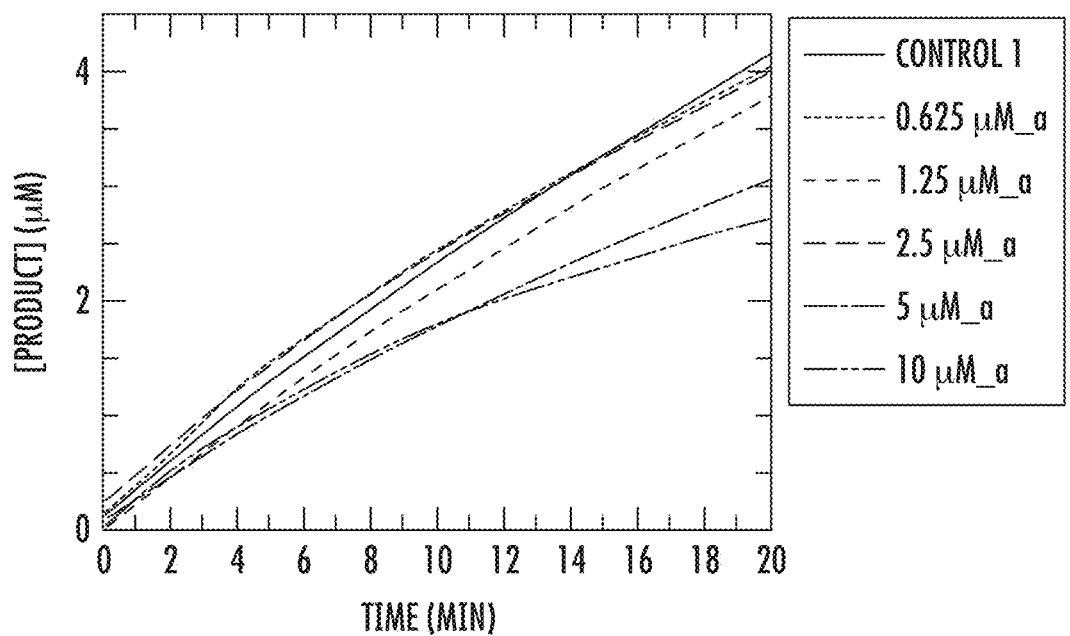
Figure 22B:
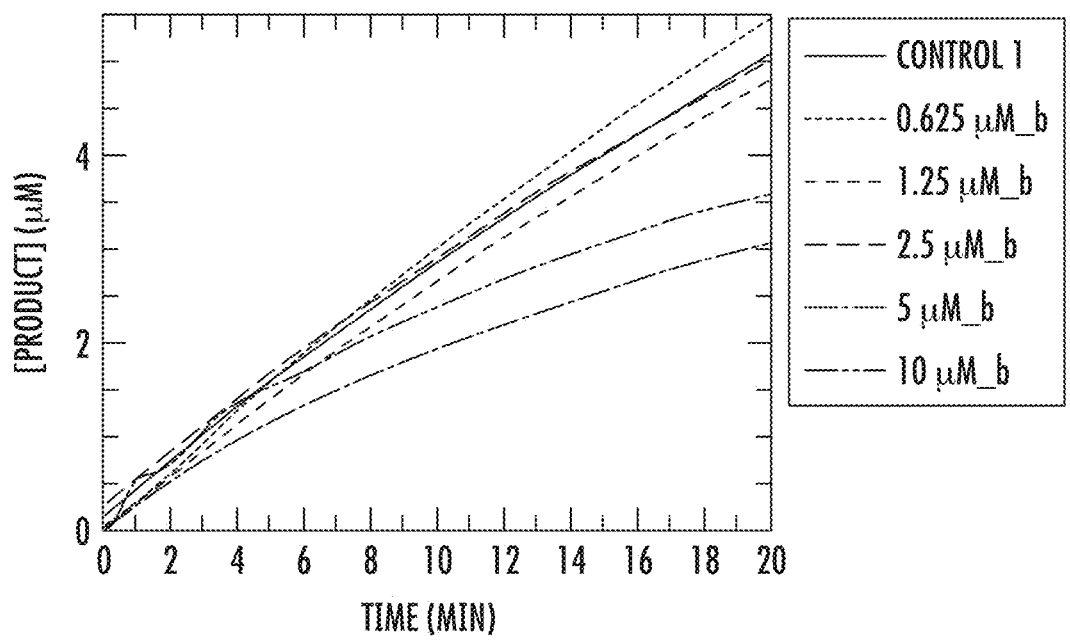
Figure 24A:
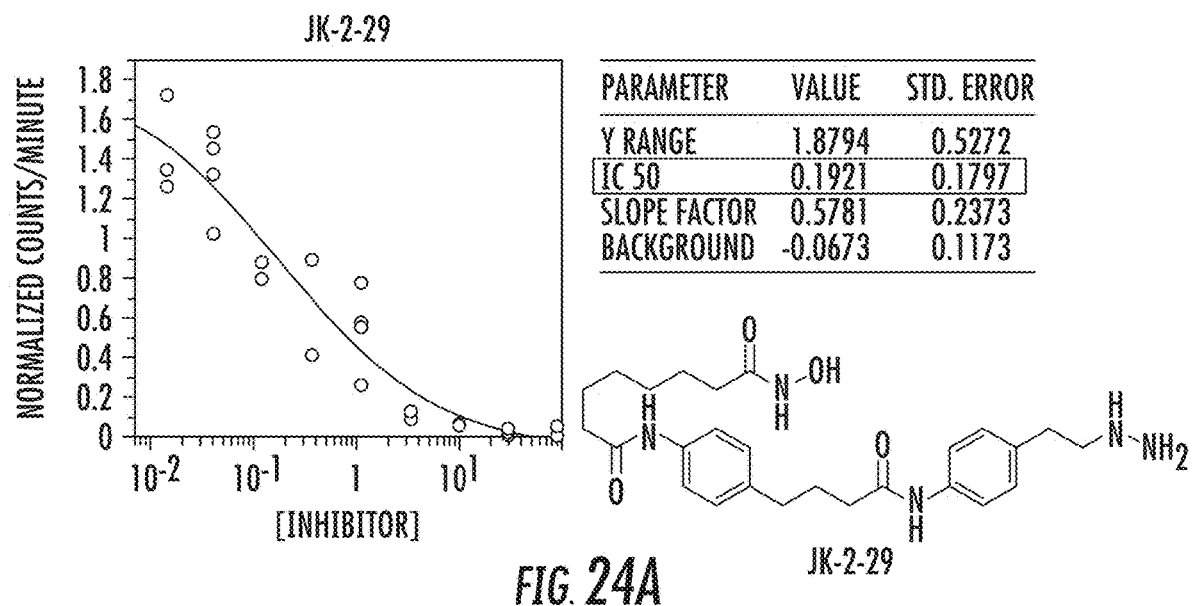
Figure 24B:
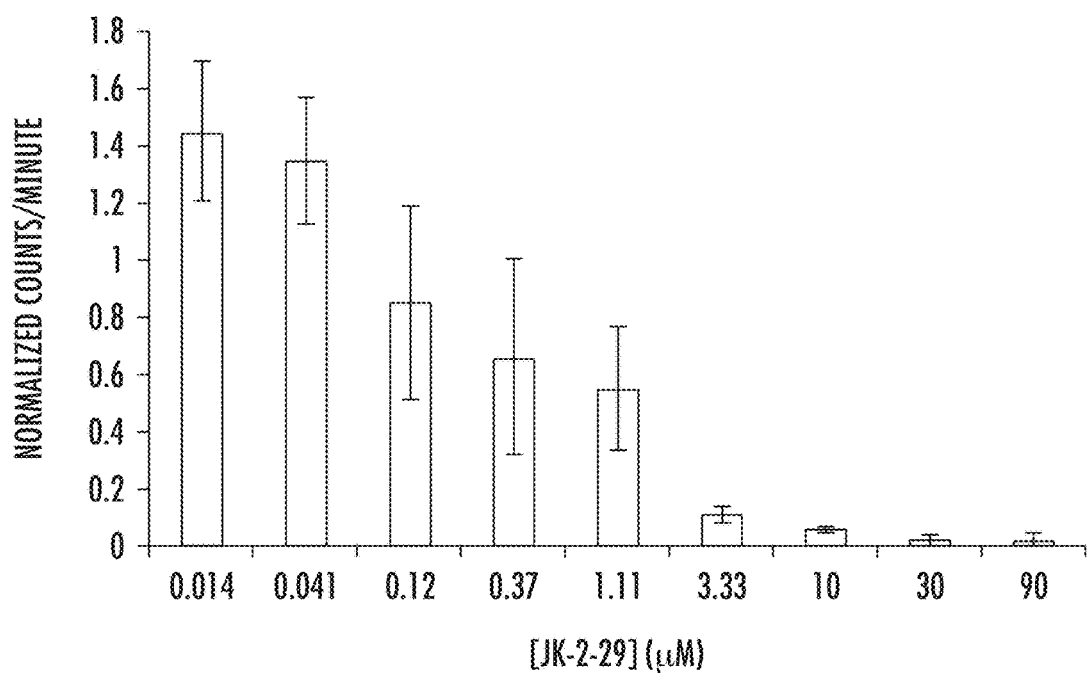
Figure 25:
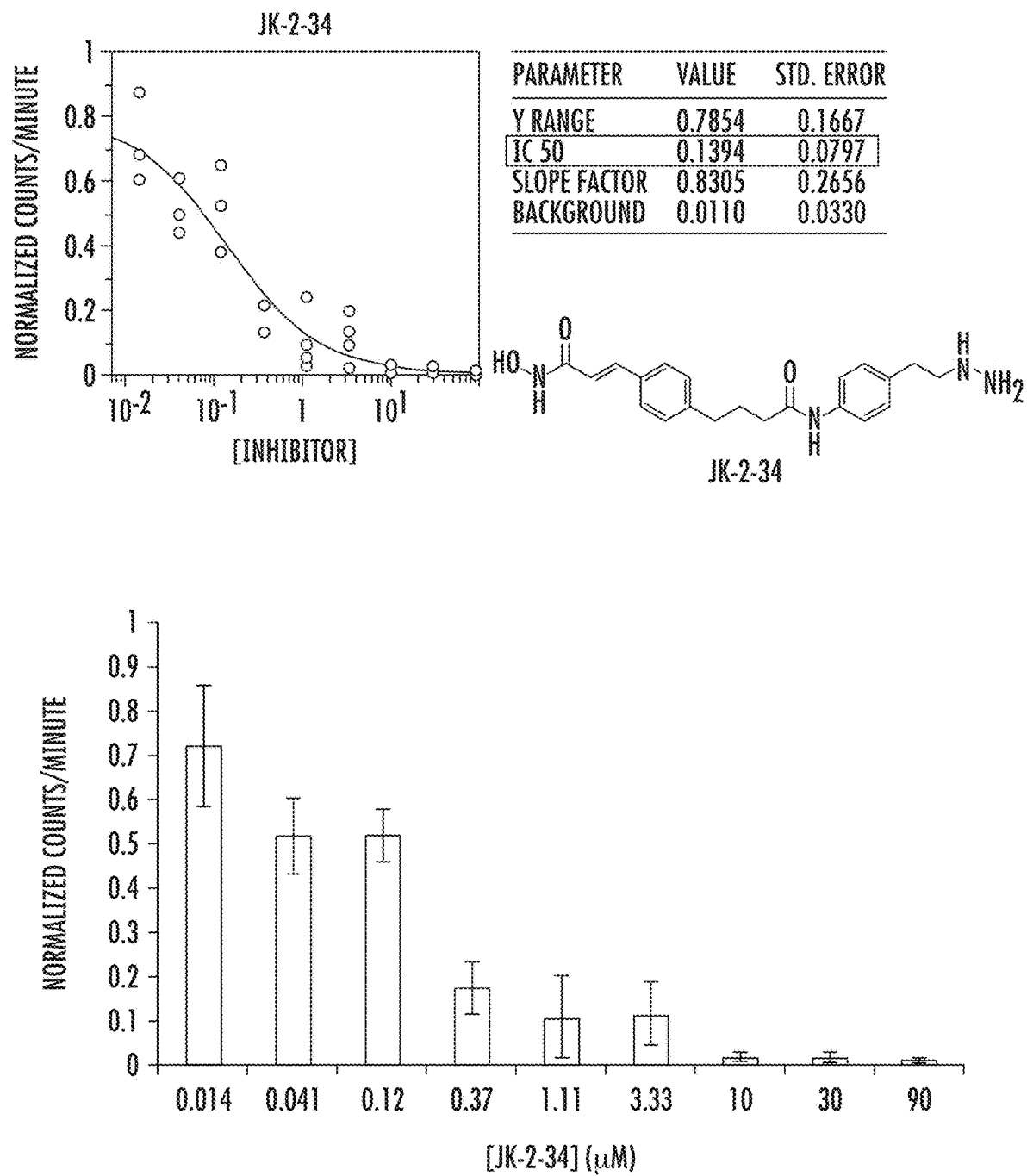
Figure 26:
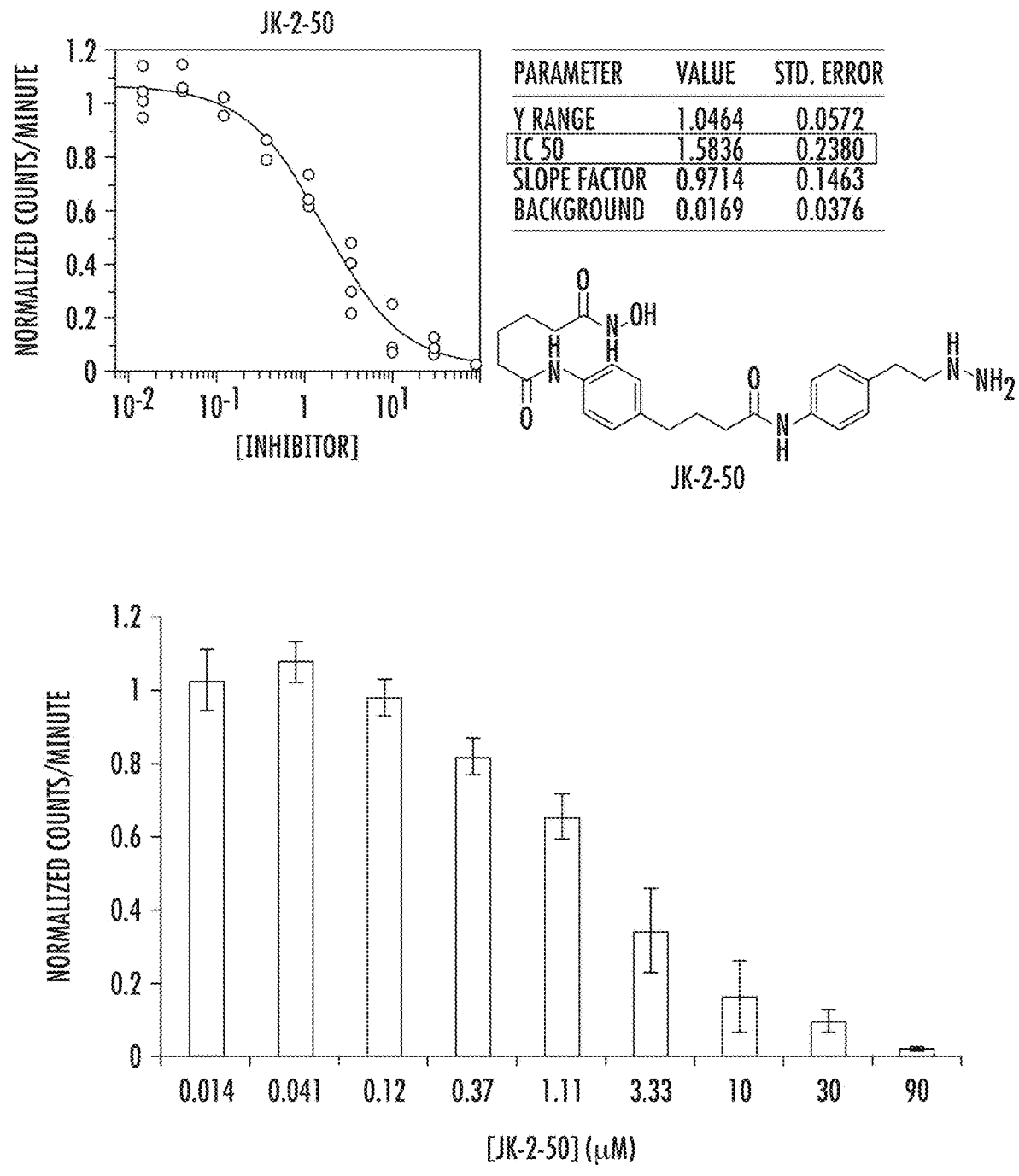
Figure 27:
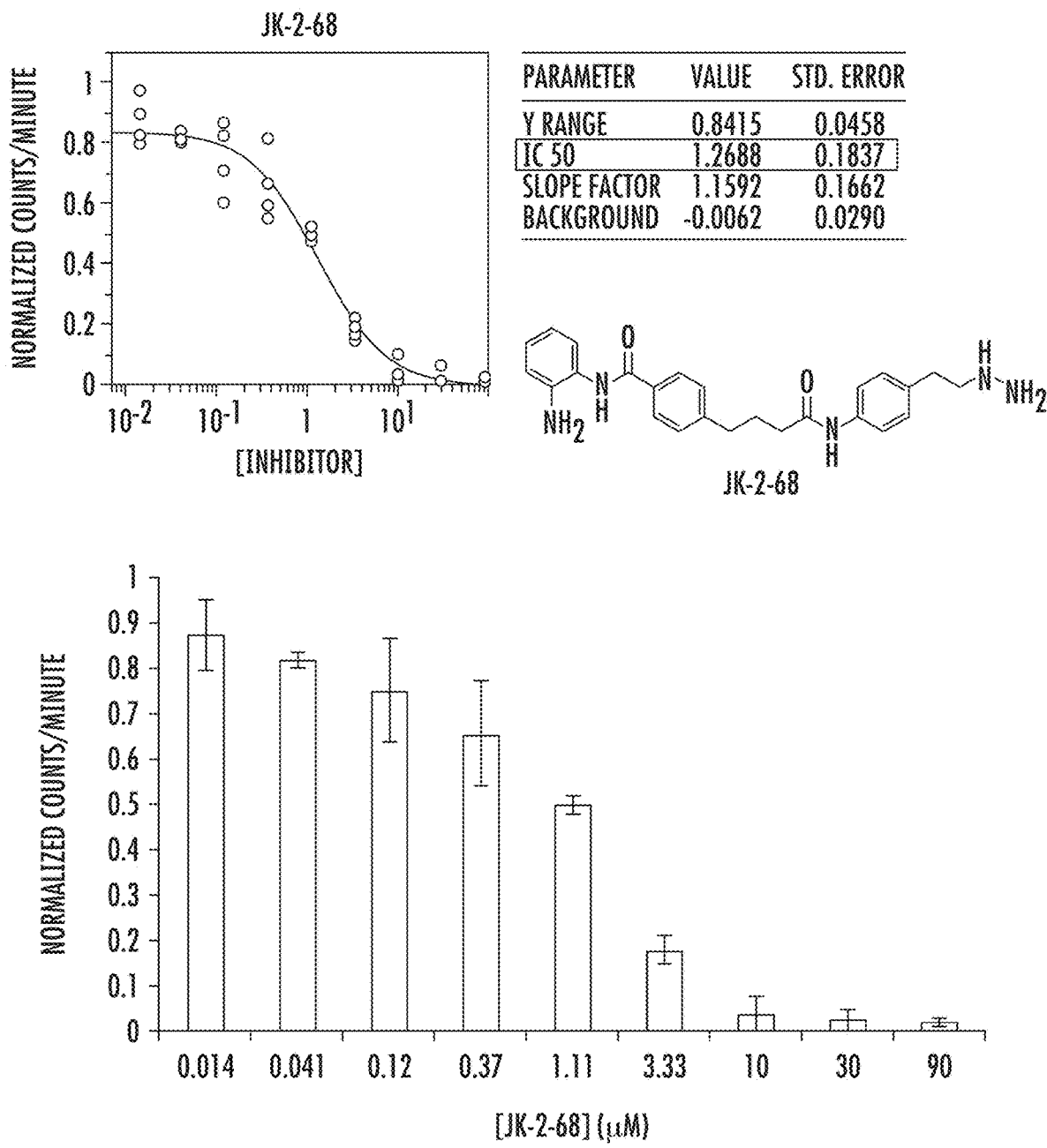
Figure 28:
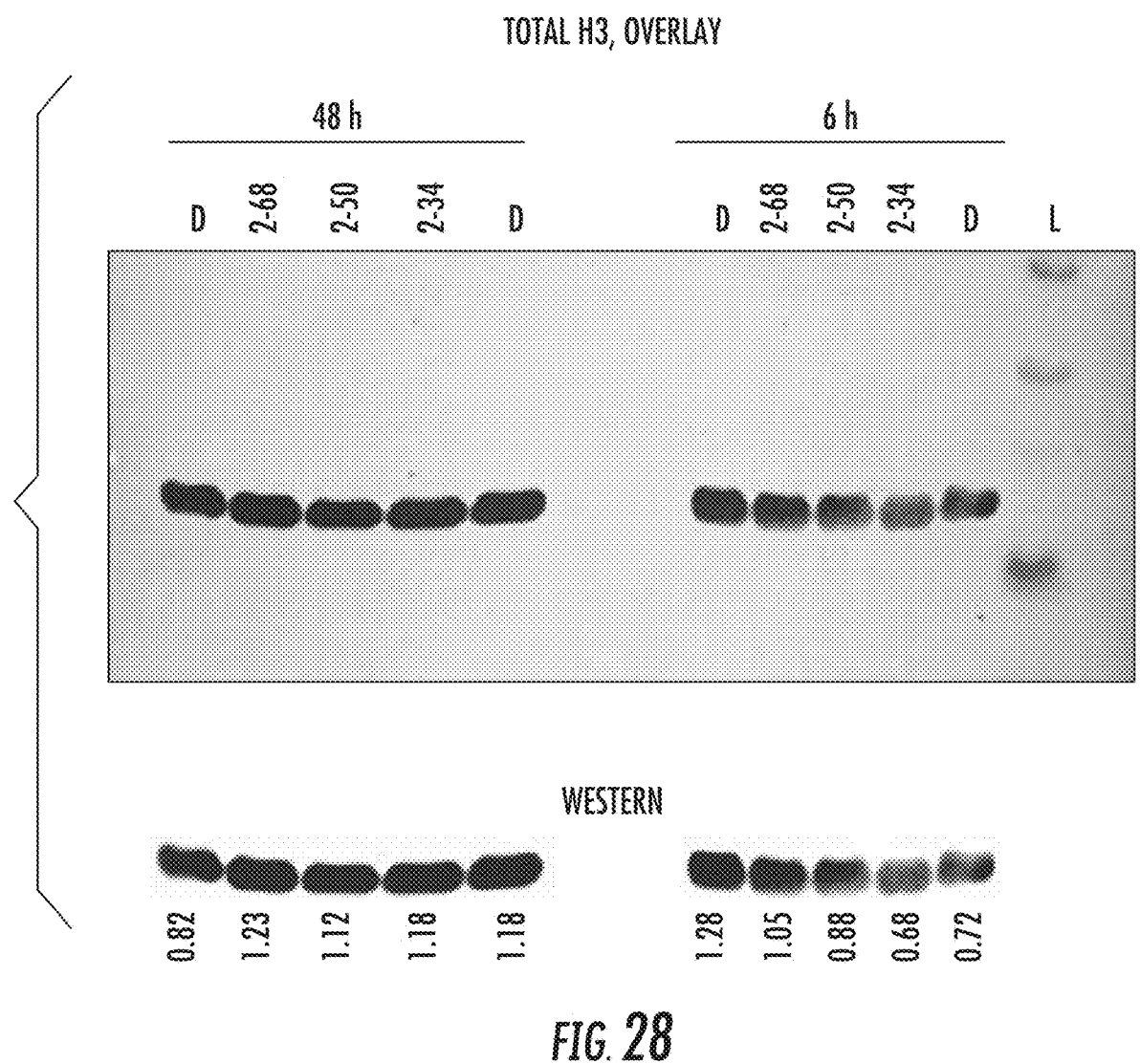
Figure 29:
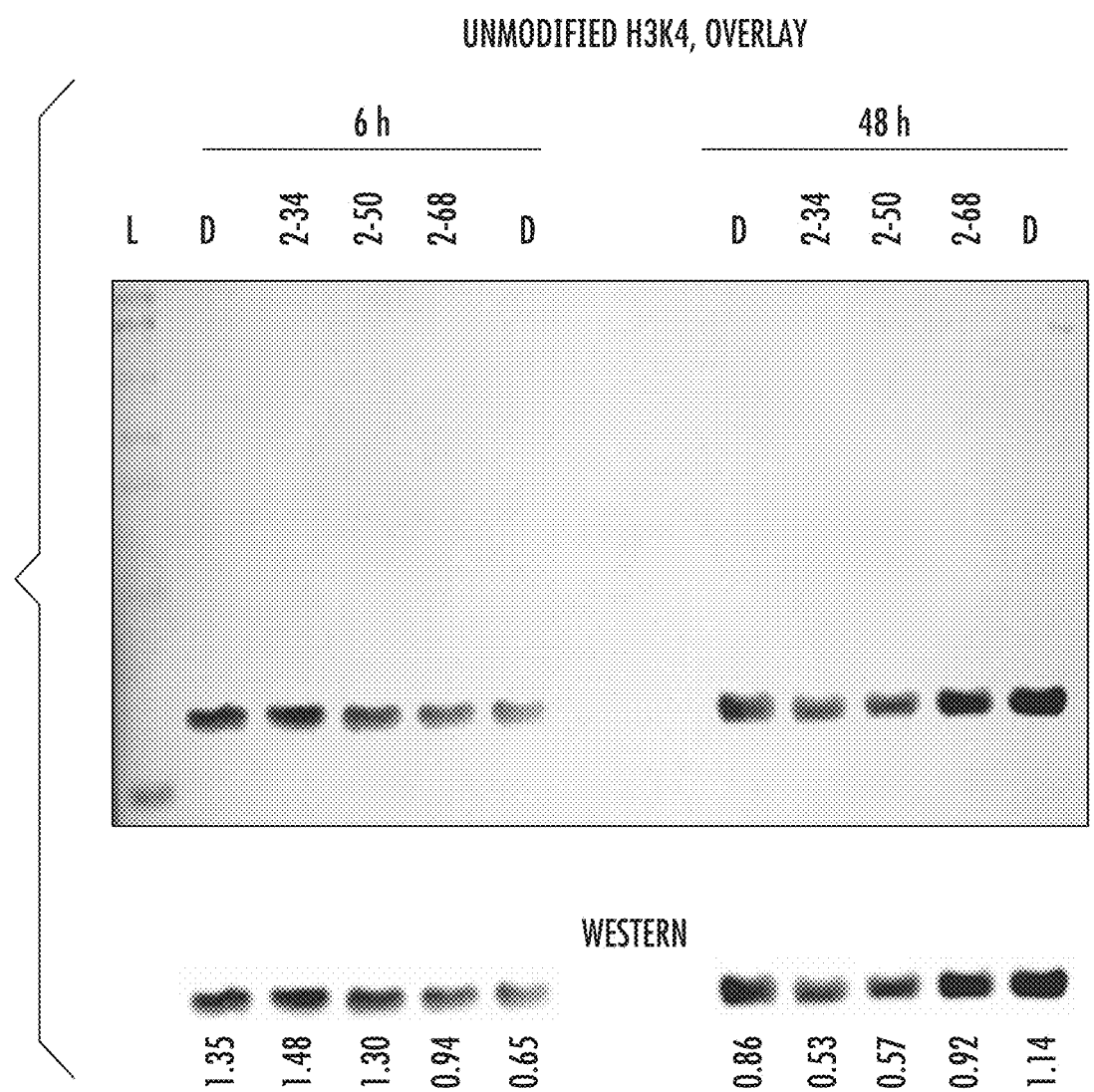
Figure 30:
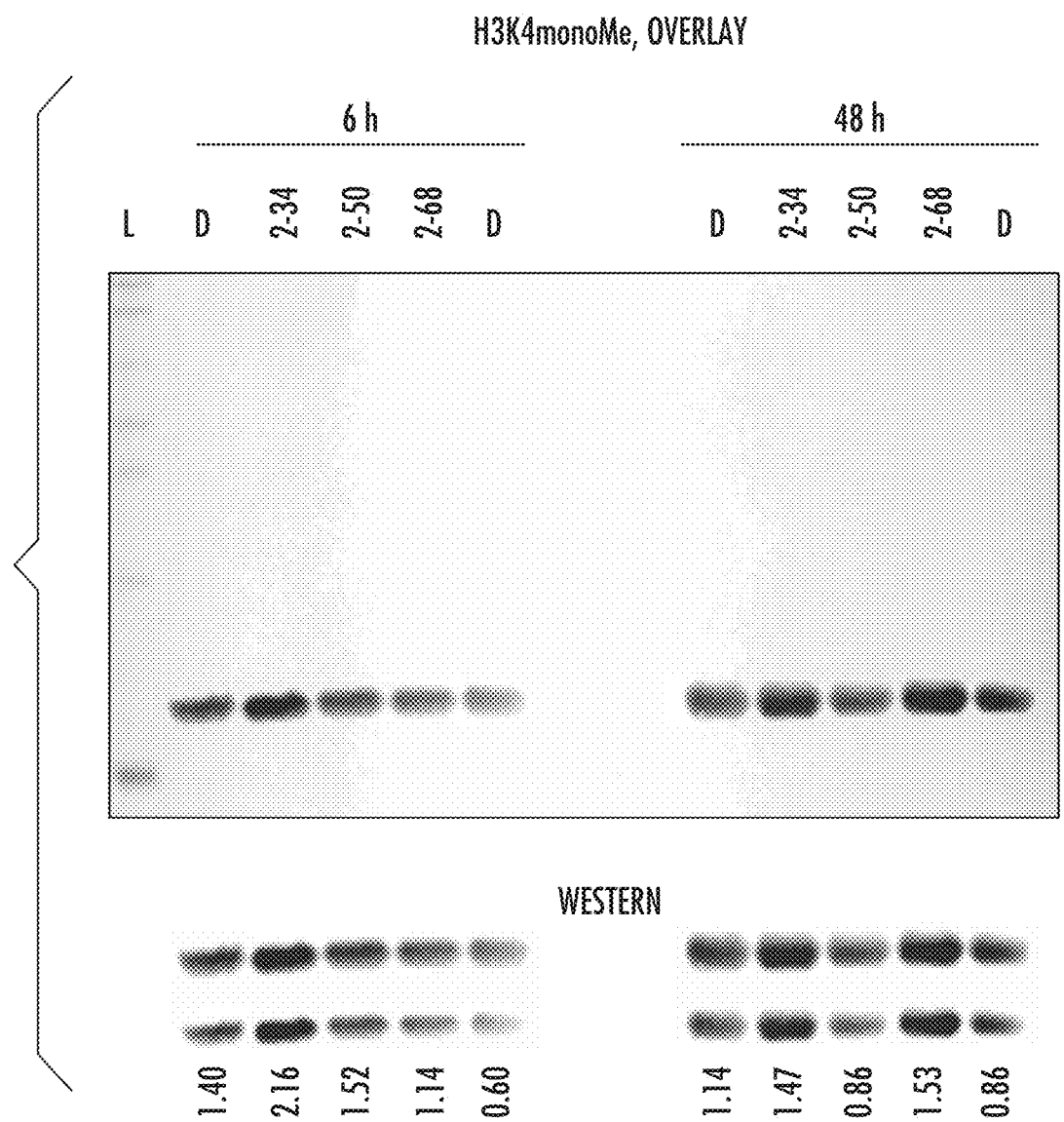
Figure 31:
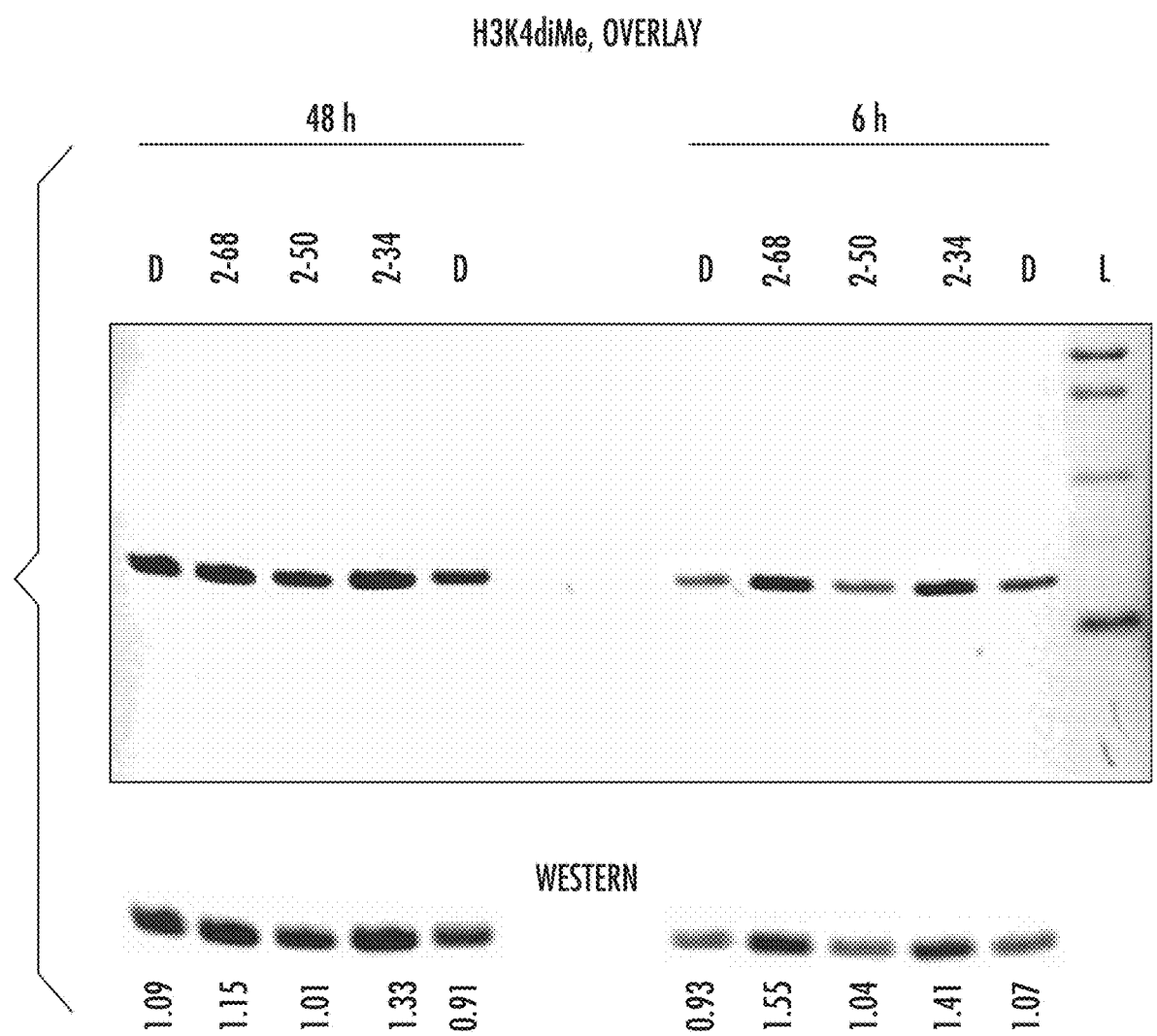
Figure 32:
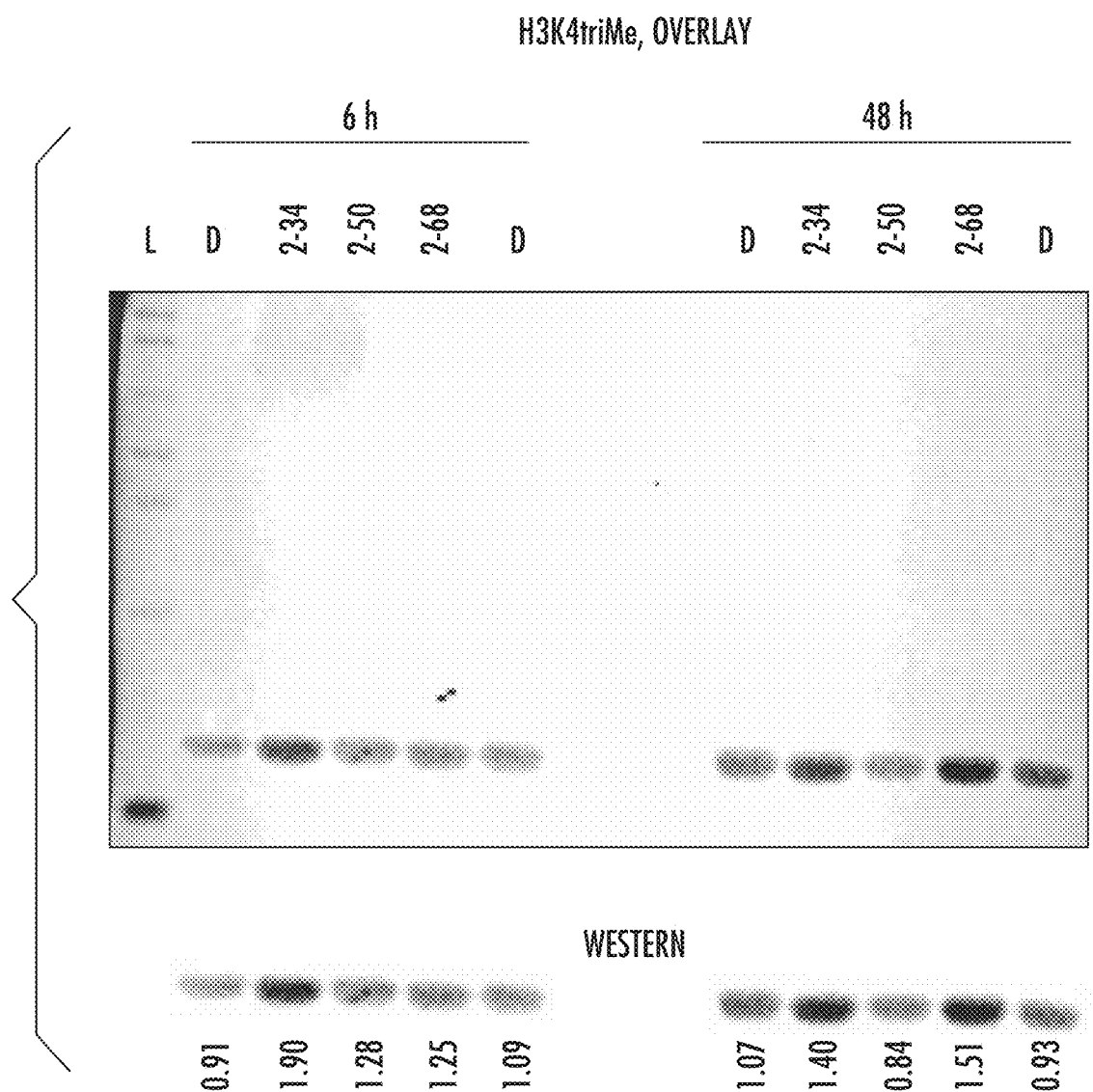
Figure 33:
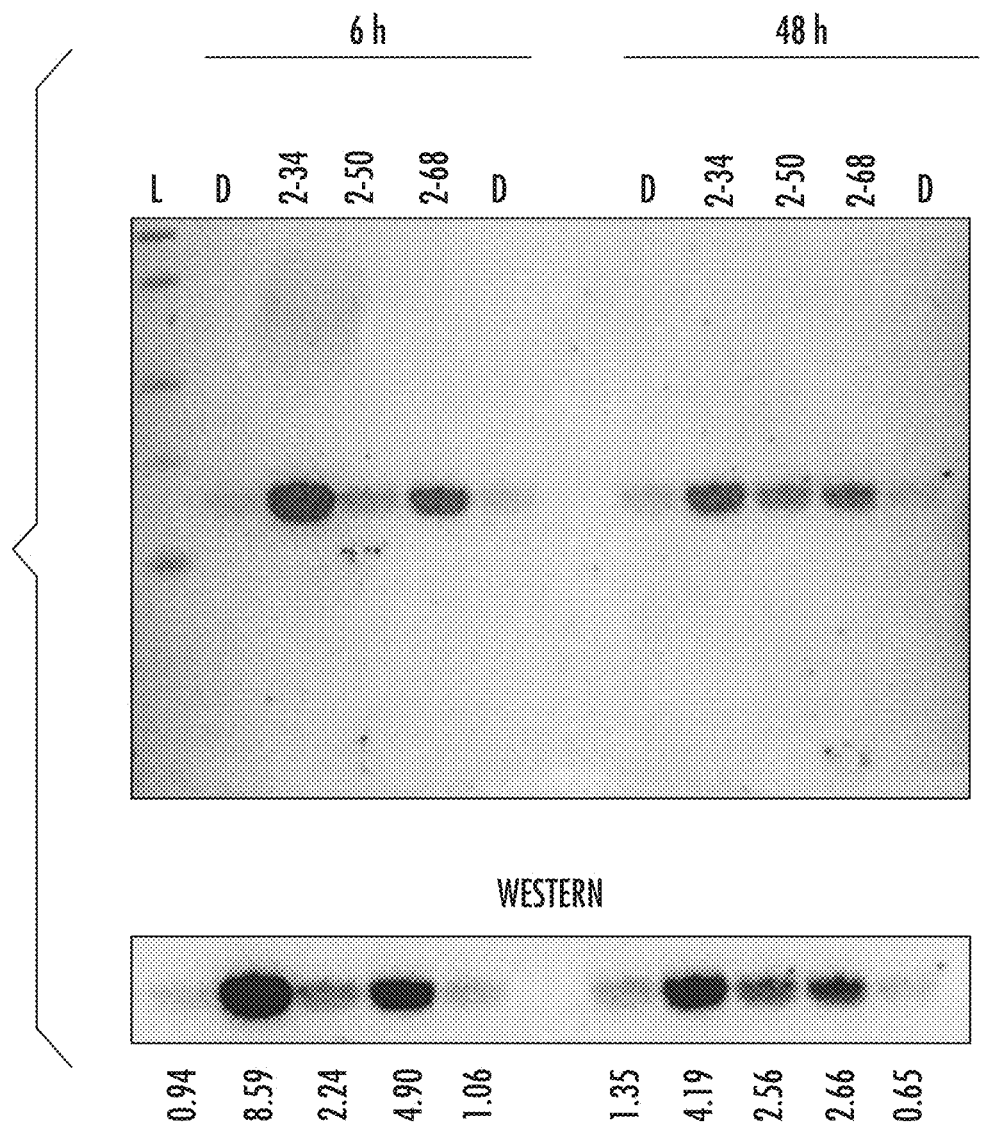
Figure 34:
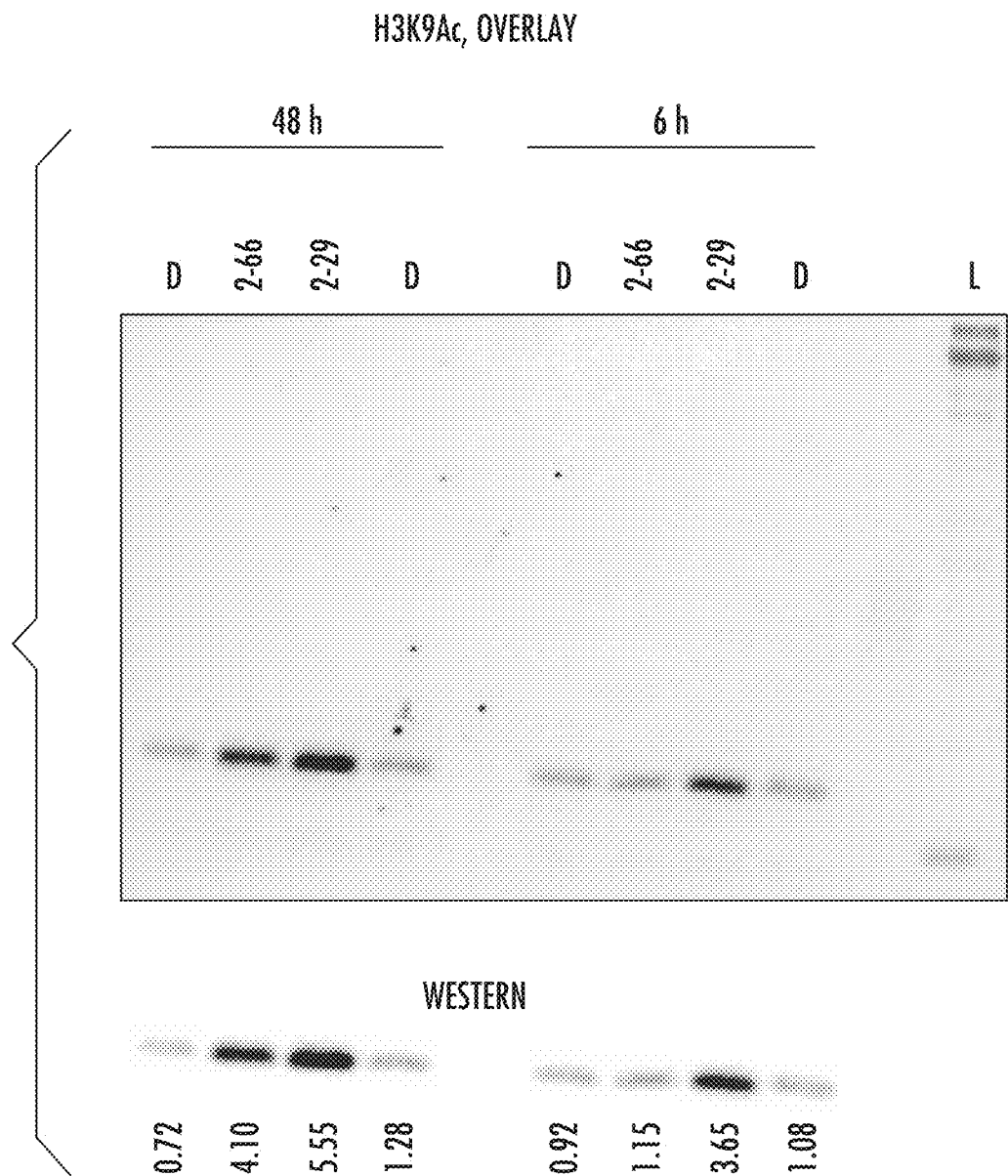
Figure 35:
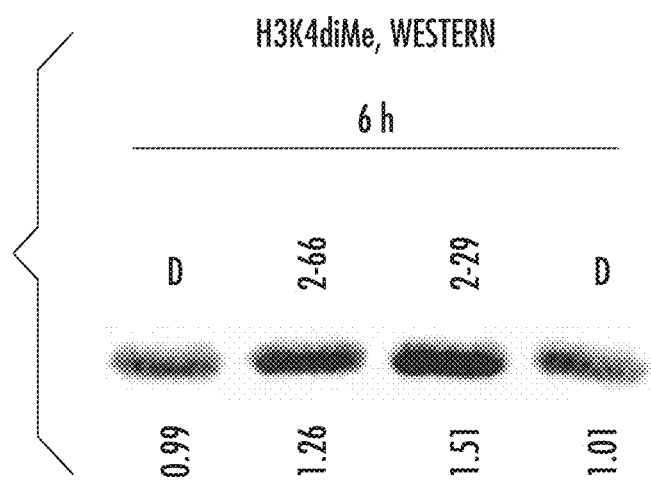
Figure 36:
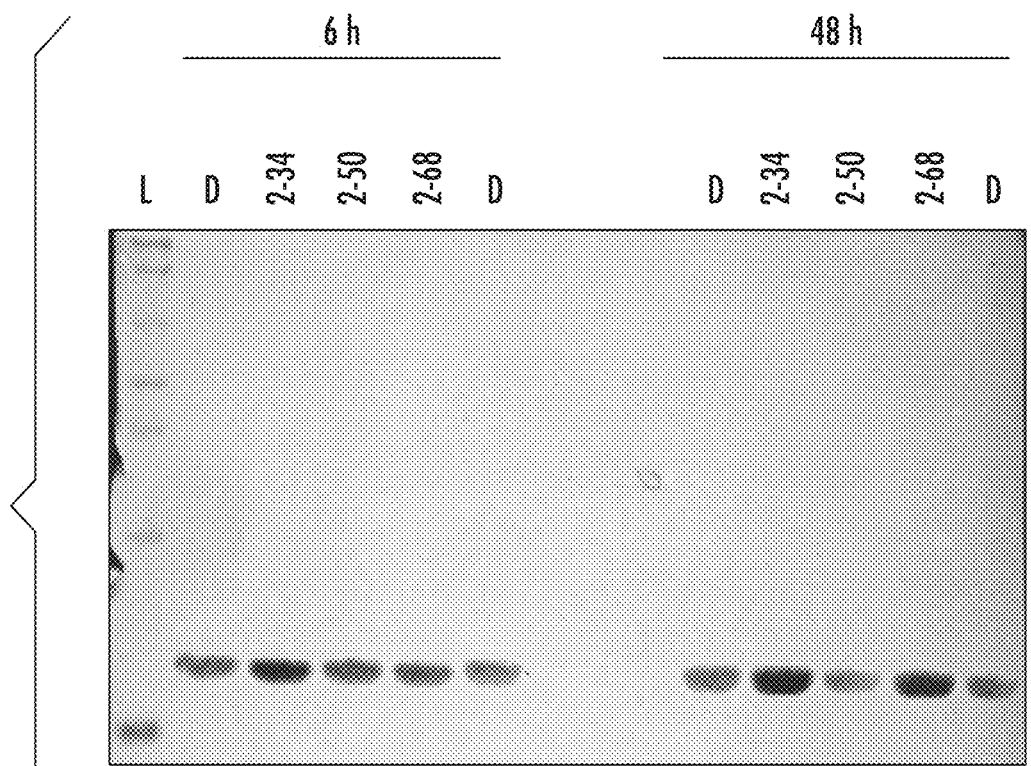

Having thus described the presently disclosed subject matter in general terms, reference will now be made to the accompanying Figures, which are not necessarily drawn to scale, and wherein:

FIGS. 1A and 1B show: (A) LSD1 demethylation mechanism; and (B) LSD1 inhibitor structures known in the art, including: (1) Histone H3-21mer peptides with various modified lysine residues, X; (2) N-terminal SNAIL1 20-mer peptide; (3) Phenelzine; (4) Tranylcypromine; (5), (6) Tranylcypromine analogs; (7) Polyamine analog; and (8) Guanidinium containing compound (Prior Art);

FIG. 2 shows representative presently disclosed phenelzine analogs tested as LSD1 inhibitors;

FIG. 3 shows the general synthesis of representative presently disclosed phenelzine analogs;

FIGS. 4A and 4B show inhibition of LSD1 by compound 12d (bizine): (A) steady-state progress curve of LSD1 inactivation by compound 12d (bizine) ranging from 0 to 5 µM; and (B) $k_{obs}$ values obtained from steady-state data plotted against inhibitor concentration to determine $k_{inact}$ and $K_{i(inact)}$ values;

FIGS. 5A-5F show LSD1 inhibition by compound 12d (bizine) in LNCaP cells. (A) Cells were treated with compound 12d (bizine) (0.4-10 µM) for 48 h and blotted against indicated proteins. (B) H3K4Me2 band density quantification plot. Statistically significant increases were observed at 3 µM and 10 µM 12d (bizine) treatment as determined by 3 biological replicates. (C) Cells were treated with compound 12d (bizine) (0.4-10 µM) for 48 h and blotted against LSD1 and actin. (D) Cells were treated with phenelzine (3-40 µM) for 48 h and blotted against H3K4Me2 and total H3. (E) Cells were treated with 10 µM compound 12d (bizine) and collected at various indicated time points and blotted against H3K4Me2 and total H3. (F) H3K4Me2 band density quantification plot normalized to vehicle at each indicated time point after 10 µM 12d (bizine) treatment. Statistically significant increases were observed at 6 h, 24 h, 48 h, 72 h, and 96 h, but not at 12 h based on 3 biological replicates;

FIGS. 6A and 6B show DNA replication dose response curves using a [$^3$H] thymidine assay in (A) H460 cells and (B) LNCaP cells after 48 h treatment with compound 12d (bizine);

FIGS. 7A and 7B demonstrate that LSD1 inhibition protects neurons against oxidative stress-mediated cell death: (A) compound 12d (bizine) and (B) phenelzine halt neuronal cell death. (Two-way ANOVA, Bonferroni post hoc test; $p<0.01$; *$p<0.0001$ compared to no HCA);

FIGS. 8A and 8B show the synthesis of representative presently disclosed LSD1 inhibitors with modifications to the alkyl chain and substitutions to the hydrazine moiety: (A) reagents and conditions: a) AcOH, NaBH$_3$CN, MeCN, 0° C. to RT, 16 h; b) HCl, EtOAc, RT, 20 min-2 h. (B) Reagents and conditions: a) N$_2$H$_4$, EtOH, 80° C., 16 h;

FIG. 9 shows the synthesis of representative presently disclosed LSD1 inhibitors with variations in the length of the alkyl chain connecting the distal phenyl moiety to the phenelzine scaffold. Reagents and conditions: a) SOCl$_2$, Et$_3$N, DCM, 0° C. to 55° C., 8 h; b) i) 2-(4-aminophenyl) ethanol, DIPEA, DCM, 0° C. to RT, 16 h; ii) NaOH, MeOH, RT, 6 h; c) PPh$_3$, CBr$_4$, DCM, RT, 6 h; d) N$_2$H$_4$, EtOH, 80° C., 1 h;

FIG. 10 shows the synthesis of representative presently disclosed LSD1 inhibitors possessing substitutions on the distal phenyl ring of 12d (bizine). Reagents and conditions: a) KOH, N$_2$H$_4$.H$_2$O, diethylene glycol, 120-130° C., 2 h; b) 2-(4-aminophenyl)ethanol, EDC, DMAP, DCM, RT, 16 h; c) i) CH$_3$SO$_2$Cl, Et$_3$N, DCM 0° C. to RT, 1-3 h; ii) N$_2$H$_4$, EtOH, 80° C., 2 h;

FIG. 11 shows the synthesis of representative presently disclosed N-substituted 12d (bizine) derivatives. Reagents and conditions: a) TBDMSCl, Et$_3$N, DMAP, DCM, RT, 2 h; b) NaH, MeI, THF, 0° C. to RT, 4 h; c) KOtBu, benzyl bromide, DCM/DMF, 0° C. to 60° C., 16 h; d) TBAF, THF, RT, 24 h; e) i) CH$_3$SO$_2$Cl, Et$_3$N, DCM, 0° C. to RT, 1-3 h; ii) N$_2$H$_4$, EtOH, 80° C., 2 h;

FIGS. 12A and 12B show inhibition of LSD1 by phenelzine: (A) steady-state progress curve of LSD1 inactivation by phenelzine ranging from 0 to 100 µM; and (B) $k_{obs}$ values obtained from steady-state data plotted against inhibitor concentration to determine $k_{inact}$ and $K_{i(inact)}$ values;

FIG. 13 shows the quantification of methylation states of H3K4 as a result of LSD1 inhibition by phenelzine or 12d (bizine) as determined by the MassSQUIRM technique;

FIG. 14 illustrates that H460, A549, and MB-231 cell lines were treated with compound 12d (bizine) (0.4-10 µM or 20 µM) for 48 h and blotted against H3K4Me2 and Total H3. *Determined using biological triplicates;

FIG. 15 shows LNCaP cells were treated with 10 µcompound 12d (bizine) for 30 min, 6 h, 12 h, and 24 h and blotted against H3K4Me2 and Total H3 (with additional two biological replicates);

FIGS. 16A-16C show representative examples of three genes' Integrative Genomics Viewer (IGV)1,2 tracks from the list of 2,432 genes identified through the ChIP-seq experiment that showed an increase in H3K4Me2 with LSD1 inhibition by 12d (bizine) (with two biological replicates): (A) RGMB (chr5:98,079,869-98,189,371); (B) SMARCA2 (chr9:1,999,116-2,177,398); and (C) ERRFI1 (chr1:7,902,135-8,201,537). Boxes mark statistically significant peak increases with 12d (bizine) treatment. Scale indicated by tick marks;

FIG. 17 shows DNA replication dose response curves using a [$^3$H] thymidine assay in H460 cells after 48 h treatment with phenelzine;

FIGS. 18A-18F show simultaneous treatment of a H460 cell line with compound 12d (bizine) and (A) azacytidine, (B) SAHA, (C) TSA, (D) MGCD0103, (E) MS-275, and (F) LBH-589 for 48 h and DNA replication was monitored using the [$^3$H] thymidine assay. Synergy was determined by CompuSyn using a non-constant ratio approach. CI>1, CI=1, or CI<1 indicates antagonism, additivity, or synergy, respectively. For example, points above, on, or under the line indicate antagonism, additivity, or synergy, respectively. $F_a$ indicates the fraction of cells affected by a given dose of drug;

FIGS. 19A-19C show (A, B) kinetic data for JK-2-34 (22) against LSD1 and (C) LSD1 inhibition by JK-2-34 (22);

FIGS. 20A-20C show (A, B) kinetic data for JK-2-29 (21) against LSD1 and (C) LSD1 inhibition by JK-2-29 (21);

FIGS. 21A and 21B show kinetic data for JK-2-50 (20) against LSD1; FIGS. 22A and 22B show kinetic data for JK-2-68 (23) against LSD1; FIG. 23 shows kinetic data for JK-2-29, JK-2-50, JK-2-34, and JK-2-68 against LSD1;

FIGS. 24A and 24B show tritiated thymidine proliferation assay for jk-2-29 in H460 cells ($IC_{50}$ reported in µM);

FIG. 25 shows tritiated thymidine proliferation assay for jk-2-34 in H460 cells ($IC_{50}$ reported in µM);

FIG. 26 shows tritiated thymidine proliferation assay for jk-2-50 in H460 cells ($IC_{50}$ reported in µM);

FIG. 27 shows tritiated thymidine proliferation assay for jk-2-68 in H460 cells ($IC_{50}$ reported in µM);

FIG. 28 shows a Western blot against total H3 for dual drugs in LNCaP cells (densitometry by ImageQuant);

FIG. 29 shows a Western blot against unmodified H3K4 for dual drugs in LNCaP cells (densitometry by ImageQuant);

FIG. 30 shows a Western blot against H3K4monoMe for dual drugs in LNCaP cells (densitometry by ImageQuant);

FIG. 31 shows a Western blot against H3K4diMe for dual drugs in LNCaP cells (densitometry by ImageQuant);

FIG. 32 shows a Western blot against H3K4triMe for dual drugs in LNCaP cells (densitometry by ImageQuant);

FIG. 33 shows a Western blot against H3K9Ac for dual drugs in LNCaP cells (densitometry by ImageQuant);

FIG. 34 shows a Western blot against H3K9Ac for dual drugs in LNCaP cells (densitometry by ImageQuant);

FIG. 35 shows a Western blot against H3K4diMe for dual drugs in LNCaP cells (densitometry by ImageQuant); and FIG. 36 shows a Western blot against H3K4diMe for dual drugs in LNCaP cells (densitometry by ImageQuant).

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

Selective Phenelzine Analog Inhibitors of Histone Demethylase LSD1

Lysine-specific demethylase 1 (LSD1) is an epigenetic enzyme that oxidatively cleaves methyl groups from monomethyl and dimethyl Lys4 of histone H3 (H3K4Me1, H3K4Me2) and can contribute to gene silencing. The presently disclosed subject matter describes the design and synthesis of analogs of a monoamine oxidase antidepressant, phenelzine, and their LSD1 inhibitory properties. In particular embodiments, the presently disclosed phenelzine analogs are potent LSD1 inhibitors in vitro and are selective versus monoamine oxidases A/B and the LSD1 homolog, LSD2. In some embodiments, the presently disclosed phenelzine analogs are effective at modulating bulk histone methylation in cancer cells. In particular embodiments, ChIP-seq experiments revealed a statistically significant overlap in the H3K4 methylation pattern of genes affected by the presently disclosed phenelzine analogs and those altered in LSD1−/− cells. In yet other embodiments, treatment of cancer cell lines, e.g., LNCaP and H460, with the presently disclosed phenelzine analogs can result in a reduction in proliferation rate, and, in some embodiments, the presently disclosed phenelzine analogs showed additive to synergistic effects on cell growth when used in combination with HDAC inhibitors. Moreover, neurons exposed to oxidative stress are protected by the presence of the presently disclosed phenelzine analogs, suggesting that the presently disclosed phenelzine analogs can be useful in treating neurodegenerative diseases.

A. Compounds of Formula (I)

In some embodiments, the presently disclosed subject matter provides a compound of Formula (I):

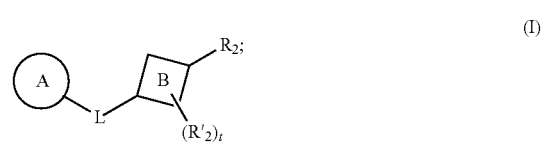

(I)

wherein:
t is an integer selected from the group consisting of 0, 1, 2, 3, and 4;
L is a linking group selected from the group consisting of —$X_1$—, —[$X_1$—C(=O)—$NR_1$]$_d$—, —[$X_1$—$NR_1$—C(=O)]$_d$—, —[C(=O)—$NR_1$—$X_1$]$_d$—, —[$NR_1$—C(=O)—$X_1$]$_d$—, —[$NR_1$—C(=O)—$NR_1$—$X_1$]$_d$—, —[$X_1$—$NR_1$—C(=O)—$NR_1$]$_d$—, —[$X_1$—O—C(=O)—$NR_1$]$_d$—, —[O—C(=O)—$NR_1$—$X_1$]$_d$—, —[$X_1$—$NR_1$—C(=O)—O]$_d$—, —[$NR_1$—C(=O)—O—$X_1$]$_d$—, —$X_1$—O—, —$X_1$—$NR_1$, —$X_1$—S—, —$X_1$—SO—, —$X_1$—$SO_2$—, —$X_1$—O—$X_1$—, —$X_1$—$NR_1$—$X_1$—, —$X_1$—S—$X_1$—, —$X_1$—SO—$X_1$—, and —$X_1$—$SO_2$—$X_1$—, wherein d is an integer selected from the group consisting of 1, 2, 3, and 4;
wherein $X_1$ is selected from the group consisting of —$(CH_2)_n$—, —[$(CH_2)_n$—CH=CH—$(CH_2)_m$]$_e$—, —[$(CH_2)_n$—C≡C—$(CH_2)_m$]$_e$—, and —$(CH_2)_m$—O—, wherein n and m are each independently an integer selected from the group consisting of 0, 1, 2, 3, 4, 5, 6, 7, 8, 9, 10, 11, 12, 13, 14, 15, 16, 17, 18, 19, and 20, e is an integer selected from the group consisting of 1, 2, 3 and 4, wherein the —$(CH_2)_n$—, —$(CH_2)_m$—, and —CH=CH— groups can optionally be substituted with a substituent selected from the group consisting of substituted or unsubstituted linear or branched alkyl, hydroxyl, alkoxyl, amino, cyano, halogen, and oxo, and wherein one or more carbon atoms of —$(CH_2)_n$— and —$(CH_2)_m$- can optionally be replaced with one or more heteroatoms selected from the group consisting of O, S, and $NR'_1$, wherein each —$(CH_2)_n$— or —$(CH_2)_m$— group can contain a cycloalkyl or cycloheteroalkyl unit;
$R_1$ and $R'_1$ are each independently selected from the group consisting of hydrogen, substituted or unsubstituted linear or branched alkyl, alkoxyl, substituted or unsubstituted cycloalkyl, substituted or unsubstituted cycloheteroalkyl, substituted or unsubstituted aryl, substituted or unsubstituted heteroaryl, substituted or unsubstituted arylalkyl, and substituted or unsubstituted heteroarylalkyl and $R_1$ can form a ring system with ring B via a substituted or unsubstituted alkylene or heteroalkylene chain;
$R_2$ is —$(CH_2)_p$—$R_3$—$NR_4R_5$ or —$(CH_2)_p$—$X_2$; wherein p is an integer selected from the group consisting of 0, 1, 2, 3, and 4, and wherein the —$(CH_2)_p$— group can be saturated or unsaturated or contain a cycloalkyl unit and optionally be substituted with a substituent selected from the group consisting of substituted or unsubstituted linear or branched alkyl, hydroxyl, alkoxyl, amino, cyano, halogen, and oxo, and one or more carbon atoms of —$(CH_2)_p$— can optionally be replaced with one or more heteroatoms selected from the group consisting of O, S, and $NR'_1$;
each $R'_2$ is independently selected at each occurrence from the group consisting of substituted or unsubstituted alkyl, substituted or unsubstituted cycloalkyl, substituted or unsubstituted cycloheteroalkyl, allyl, hydroxyl, alkoxyl, amino, cyano, carboxyl, halogen, nitro, oxo, —$CF_3$, substituted or unsubstituted aryl, substituted or unsubstituted heteroaryl;
$R_3$, $R_4$, and $R_5$ are each independently selected from the group consisting of hydrogen, substituted or unsubstituted linear or branched alkyl, alkoxyl, substituted or unsubstituted cycloalkyl, substituted or unsubstituted cycloheteroalkyl, substituted or unsubstituted aryl, substituted or unsubstituted heteroaryl, substituted or unsubstituted arylalkyl, and substituted or unsubstituted heteroarylalkyl, and —C(=O)—O—$R_{21}$, or $R_4$ and $R_5$ together can form a substituted or unsubstituted 4- to 6-membered cycloalkyl, and wherein $R_{24}$ is substituted or unsubstituted linear or branched alkyl;
$X_2$ is selected from the group consisting of hydroxyl, halogen, and —O—Si($R_{21}R_{22}$)$_2$—$R_{23}$, wherein $R_{20}$, $R_{21}$, and $R_{23}$ are each independently substituted or unsubstituted linear or branched alkyl;
A is selected from the group consisting of mono-or multicyclic substituted or unsubstituted cycloalkyl, substituted or unsubstituted cycloheteroalkyl, substituted or unsubstituted aryl, substituted or unsubstituted heteroaryl, substituted or unsubstituted arylalkyl, and substituted or unsubstituted heteroarylalkyl; B is selected from the group consisting of aryl or heteroaryl;
wherein one or more carbon atoms of ring B can be replaced with one or more heteroatoms selected from the group consisting of N, O, and S;
wherein one or both of ring structures A and B can be optionally substituted with one or more reactive groups capable of forming a prodrug;
and pharmaceutically acceptable salts, hydrates, and solvates thereof.
In particular embodiments, the compound of Formula (I) has the following structure:

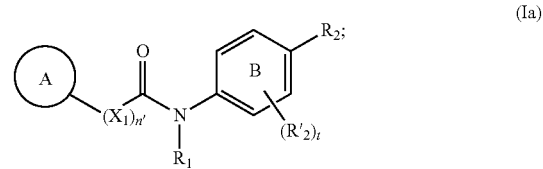

(Ia)

wherein n' is an integer selected from the group consisting of 0, 1, 2, 3, 4, 5, and 6.
In yet other embodiments, the compound of Formula (Ia) has the following structure:

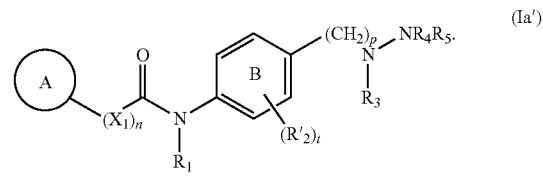

(Ia')

In yet more particular embodiments of the compounds of Formula (I), A is selected from the group consisting of:

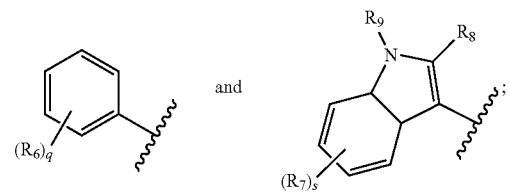

wherein q is an integer selected from the group consisting of 0, 1, 2, 3, 4, and 5; s is an integer selected from the group consisting of 0, 1, 2, 3, and 4;
$R_6$, $R_7$, and $R_8$ are each independently selected from the group consisting of hydrogen, substituted or unsubstituted linear or branched alkyl, substituted or unsubstituted alkenyl, substituted or unsubstituted alkynyl, alkoxyl, hydroxyl, halogen, nitro, cyano, oxo, amino, —CF₃, substituted or unsubstituted cycloalkyl, substituted or unsubstituted cycloheteroalkyl, substituted or unsubstituted aryl, substituted or unsubstituted heteroaryl, substituted or unsubstituted arylalkyl, and substituted or unsubstituted heteroarylalkyl, —C(═O)—R$_{10}$, and —O—SO$_2$—R$_{11}$;

wherein R$_{10}$ and R$_{11}$ are each independently selected from the group consisting of substituted or unsubstituted linear or branched alkyl, alkoxyl, —CF$_3$, substituted or unsubstituted cycloalkyl, substituted or unsubstituted cycloheteroalkyl, substituted or unsubstituted aryl, substituted or unsubstituted heteroaryl, substituted or unsubstituted arylalkyl, and substituted or unsubstituted heteroarylalkyl; and R$_9$ is selected from the group consisting of hydrogen, substituted or unsubstituted linear or branched alkyl, alkoxyl, substituted or unsubstituted cycloalkyl, substituted or unsubstituted cycloheteroalkyl, substituted or unsubstituted aryl, substituted or unsubstituted heteroaryl, substituted or unsubstituted arylalkyl, and substituted or unsubstituted heteroarylalkyl.

In yet even more embodiments, the compound of Formula (Ia') has the following structure:

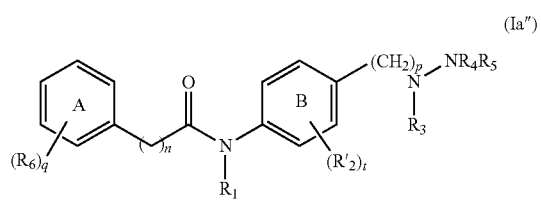
(Ia'')

In representative embodiments, the compound of Formula (I) is selected from the group consisting of:

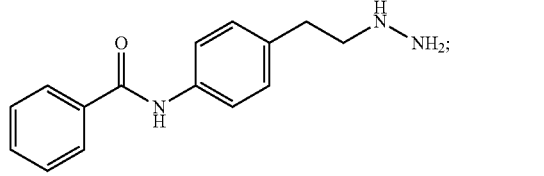
(12a)

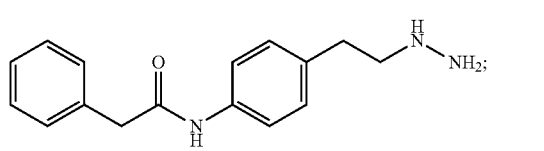
(12b)

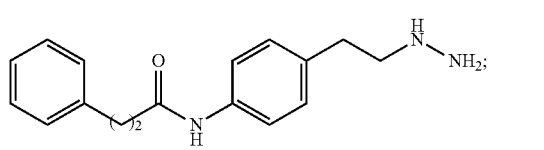
(12c)

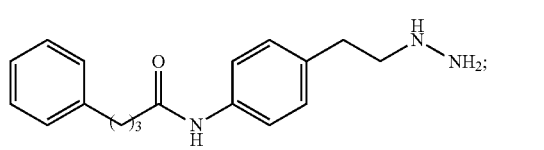
(12d)

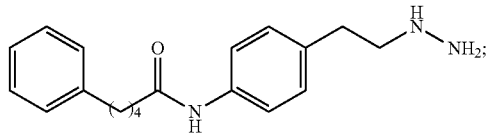
(12e)

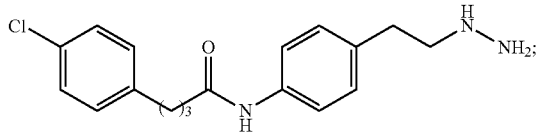
(12f)

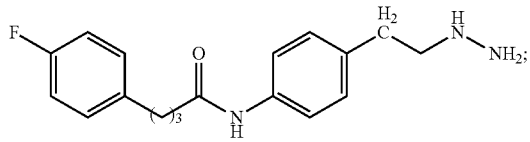
(12g)

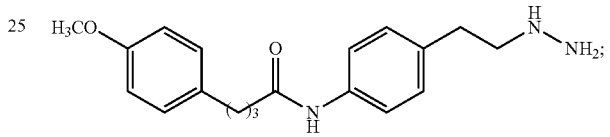
(12h)

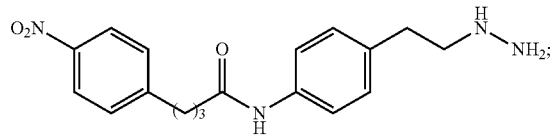
(12i)

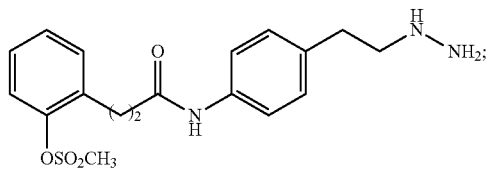
(12j)

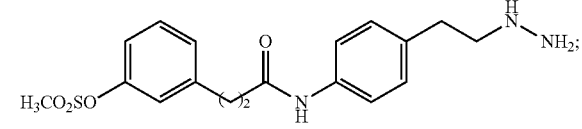
(12k)

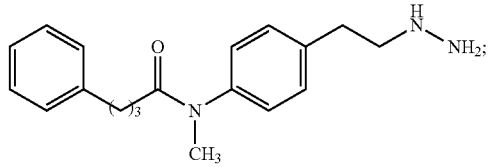
(12l)

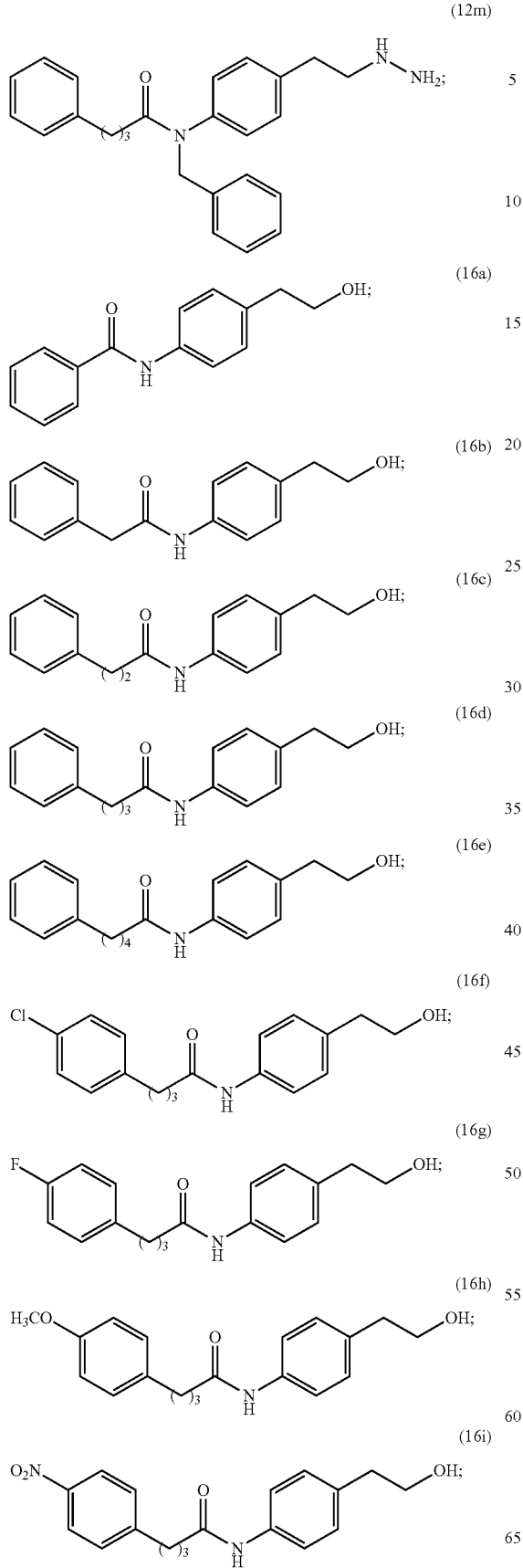
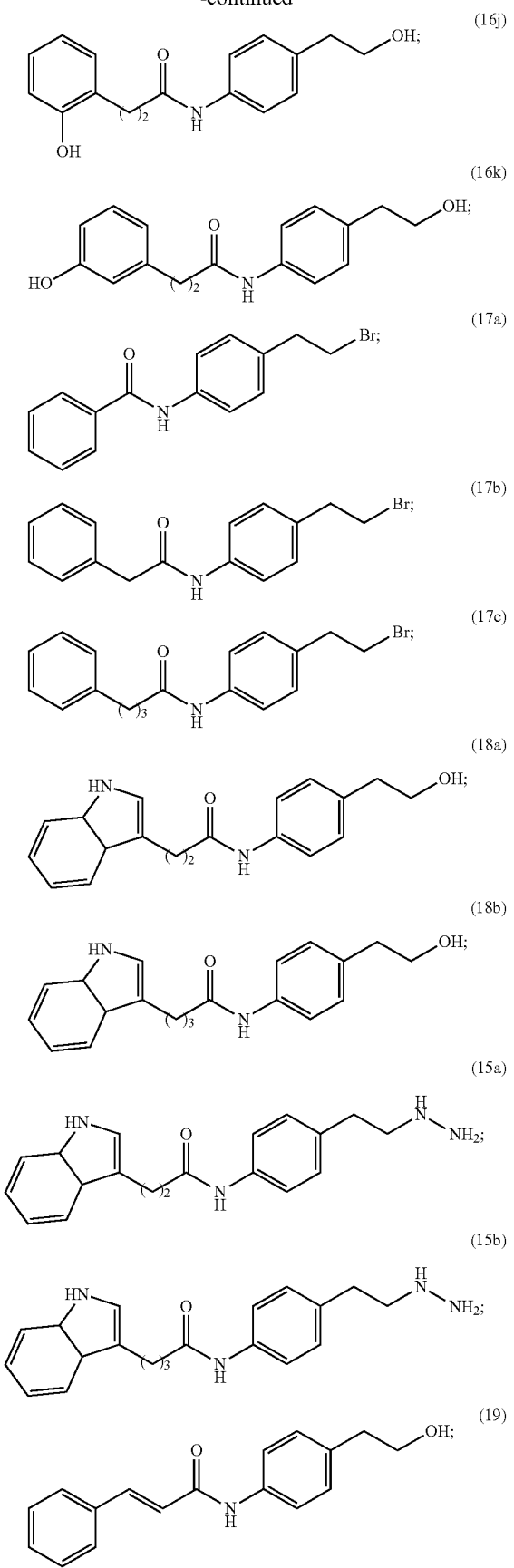

-continued

(13)
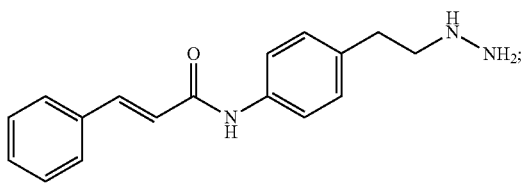

(14)
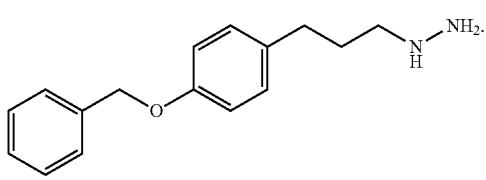

B. Compounds of Formula (II)

In other embodiments, the presently disclosed subject matter provides compounds of Formula (II), which are designed to target the CoREST complex by incorporating structural elements that inhibit both lysine specific demethylase 1 and histone deacetylase (HDAC) with a single chemical entity. Although the presently disclosed compounds of Formula (II) specifically target the class I HDACs, in particular HDAC1 and 2, the presently disclosed compounds also target the other HDAC isoforms. Structurally, the presently disclosed inhibitors have two pharmacophores incorporated into one molecule to impart the necessary dual pharmacological effect as follows:

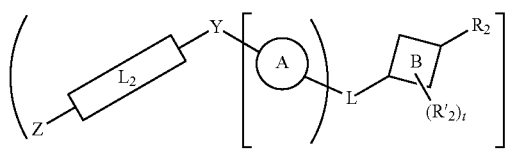

example:

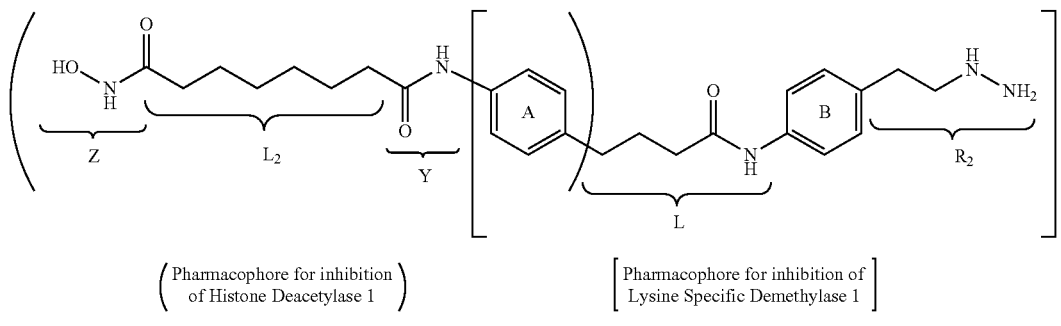

In more particular embodiments, the presently disclosed compounds of Formula (II) can be represented as follows:

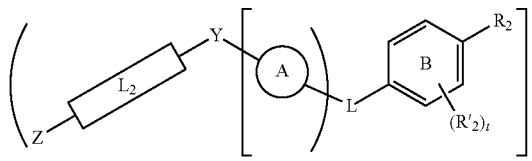

example:

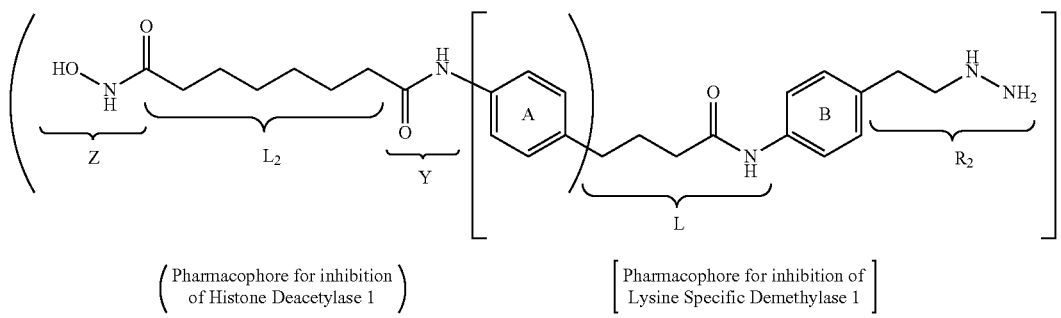

The pharmacophore for inhibiting LSD1 is as previously described herein for compounds of Formula (I) with the general structure encompassed in brackets as above. Further, the pharmacophore for inhibiting histone deacetylase includes a zinc binding group, Z, a linker, $L_2$, and a point of attachment to the LSD1 pharmacophore, Y. The canonical structure of an HDAC inhibitor comprises a zinc binding group, linker, and cap group. In the embodiments provided immediately hereinabove, ring A represents the cap group and is shared between the two pharmacophores. Ring A is as described for the LSD1 inhibitors of Formula (I).

To impart selectivity toward LSD1 over LSD2 and the structurally related MAO A/B proteins, the incorporation of linker L and ring A is required. This characteristic is unique the presently disclosed compounds of Formula (II) and distinguishes the presently disclosed compounds of Formula (II) from other dual drug approaches to inhibit the CoREST complex.

Accordingly, in some embodiments, the presently disclosed subject matter provides a compound of Formula (II):

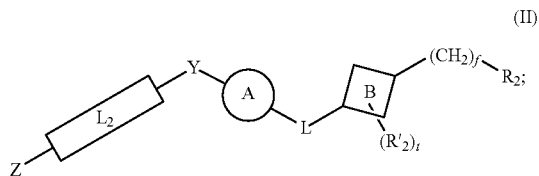

(II)

wherein:

t is an integer selected from the group consisting of 0, 1, 2, 3, and 4;

f is an integer selected from the group consisting of 0, 1, 2, 3, 4, 5, and 6;

A is selected from the group consisting of mono-or multicyclic substituted or unsubstituted cycloalkyl, substituted or unsubstituted cycloheteroalkyl, substituted or unsubstituted aryl, substituted or unsubstituted heteroaryl, substituted or unsubstituted arylalkyl, and substituted or unsubstituted heteroarylalkyl;

B is selected from the group consisting of aryl or heteroaryl;

L is a linking group selected from the group consisting of —$X_1$—, —[$X_1$—C(=O)—$NR_1$]$_d$—, —[$X_1$—$NR_1$—C(=O)]$_d$—, —[C(=O)—$NR_1$—$X_1$]$_d$—, —[$NR_1$—C(=O)—$X_1$]$_d$—, —[$NR_1$—C(=O)—$NR_1$—$X_1$]$_d$—, —[$X_1$—$NR_1$—C(=O)—$NR_1$]$_d$—, —[$X_1$—O—C(=O)—$NR_1$]$_d$—, —[O—C(=O)—$NR_1$—$X_1$]$_d$—, —[$X_1$—$NR_1$—C(=O)—O]$_d$—, —[$NR_1$—C(=O)—O—$X_1$]$_d$—, —$X_1$—O—, —$X_1$—$NR_1$, —$X_1$—S—, —$X_1$—SO—, —$X_1$—$SO_2$—, —$X_1$— O— $X_1$—, —$X_1$— $NR_1$— $X_1$—, —$X_1$— S— $X_1$—, —$X_1$—SO— $X_1$—, and —$X_1$— $SO_2$— $X_1$—, wherein d is an integer selected from the group consisting of 1, 2, 3, and 4;

wherein $X_1$ is selected from the group consisting of —(CH$_2$)$_n$—, —[(CH$_2$)$_n$—CH=CH—(CH$_2$)$_m$]$_e$—, —[(CH$_2$)$_n$—C≡C—(CH$_2$)$_m$]$_e$–, and —(CH$_2$)$_m$—O—, wherein n and m are each independently an integer selected from the group consisting of 0, 1, 2, 3, 4, 5, 6, 7, 8, 9, 10, 11, 12, 13, 14, 15, 16, 17, 18, 19, and 20, e is an integer selected from the group consisting of 1, 2, 3 and 4, wherein the —(CH$_2$)$_n$—, —(CH$_2$)$_m$—, and —CH=CH— groups can optionally be substituted with a substituent selected from the group consisting of substituted or unsubstituted linear or branched alkyl, hydroxyl, alkoxyl, amino, cyano, halogen, and oxo, and wherein one or more carbon atoms of —(CH$_2$)$_n$— and —(CH$_2$)m— can optionally be replaced with one or more heteroatoms selected from the group consisting of O, S, and NR'$_1$, wherein each —(CH$_2$)$_n$— or —(CH$_2$)$_m$— group can contain a cycloalkyl or cycloheteroalkyl unit;

$L_2$ is a linker in the HDAC inhibitor portion of the molecule and includes, but is not limited to, aryl, heteroaryl, —(CH$_2$)$_n$—, —(CH$_2$)$_n$—CH=CH—(CH$_2$)$_m$—, —(CH$_2$)$_n$—C≡C—(CH$_2$)$_m$—, —(CH$_2$)$_m$—O—,wherein n and m are each independently an integer selected from the group consisting of 0, 1, 2, 3, 4, 5, and 6, wherein the —(CH$_2$)$_n$—, —(CH$_2$)$_m$—, and —CH=CH— groups can optionally be substituted with a substituent selected from the group consisting of substituted or unsubstituted linear or branched alkyl, hydroxyl, alkoxyl, amino, cyano, halogen, and oxo, and wherein one or more carbon atoms of —(CH$_2$)$_n$— and —(CH$_2$)$_m$— can optionally be replaced with one or more heteroatoms selected from the group consisting of O, S, and NR'$_1$;

$R_1$ and R'$_1$ are each independently selected from the group consisting of hydrogen, substituted or unsubstituted linear or branched alkyl, alkoxyl, substituted or unsubstituted cycloalkyl, substituted or unsubstituted cycloheteroalkyl, substituted or unsubstituted aryl, substituted or unsubstituted heteroaryl, substituted or unsubstituted arylalkyl, and substituted or unsubstituted heteroarylalkyl, and $R_1$ can form a ring system with ring B via a substituted or unsubstituted alkylene or heteroalkylene chain;

$R_2$ is —(CH$_2$)$_p$—$NR_3$—$NR_4R_5$ or —(CH$_2$)$_p$—$X_2$; wherein p is an integer selected from the group consisting of 0, 1, 2, 3, and 4, and wherein the —(CH$_2$)$_p$— group can be saturated or unsaturated or contain a cycloalkyl unit and optionally be substituted with a substituent selected from the group consisting of substituted or unsubstituted linear or branched alkyl, hydroxyl, alkoxyl, amino, cyano, halogen, and oxo, and one or more carbon atoms of —(CH$_2$)$_p$— can optionally be replaced with one or more heteroatoms selected from the group consisting of O, S, and NR'$_1$;

each R'$_2$ is independently selected at each occurrence from the group consisting of substituted or unsubstituted alkyl, substituted or unsubstituted cycloalkyl, substituted or unsubstituted cycloheteroalkyl, allyl, hydroxyl, alkoxyl, amino, cyano, carboxyl, halogen, nitro, oxo, —CF$_3$, substituted or unsubstituted aryl, substituted or unsubstituted heteroaryl;

$R_3$, $R_4$, and $R_5$ are each independently selected from the group consisting of hydrogen, substituted or unsubstituted linear or branched alkyl, alkoxyl, substituted or unsubstituted cycloalkyl, substituted or unsubstituted cycloheteroalkyl, substituted or unsubstituted aryl, substituted or unsubstituted heteroaryl, substituted or unsubstituted arylalkyl, and substituted or unsubstituted heteroarylalkyl, and —C(=O)—O—$R_{21}$, or $R_4$ and $R_5$ together can form a substituted or unsubstituted 4- to 6-membered cycloalkyl, and wherein $R_{24}$ is substituted or unsubstituted linear or branched alkyl;

Z is a zinc binding group comprising the HDAC inhibitor portion of the molecule and includes, but is not limited to: Hydroxamic acids: —C(=O)N(R$^{10}$)OH,

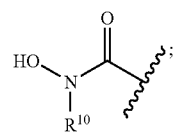

Mercaptoacetamides: —N(R$^{10}$)C(=O)C(R$^{11}$)$_n$S(R$^{12}$),

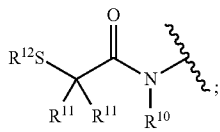

Boronic acids: —B(OR$^{13}$)$_m$;
Thiols: —SR$^{14}$;
Phenylenediamines:

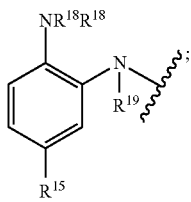

Sulfonamides:

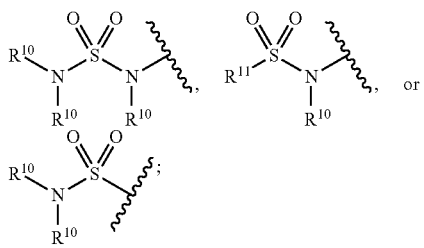

Protecting groups: C(=O)OR$^{16}$;

wherein R$^{10}$, R$^{11}$, R$^{12}$, R$^{13}$, R$^{14}$, and R$^{15}$ are each independently selected from the group consisting of hydrogen, substituted or unsubstituted linear or branched alkyl, alkoxyl, substituted or unsubstituted cycloalkyl, substituted or unsubstituted cycloheteroalkyl, substituted or unsubstituted aryl, substituted or unsubstituted heteroaryl, substituted or unsubstituted arylalkyl, and substituted or unsubstituted heteroarylalkyl;

R$^{16}$, R$^{17}$, R$^{18}$, and R$^{19}$ are each independently substituted or unsubstituted linear or branched alkyl;

and n and m are integers each independently selected from the group consisting of 0, 1, and 2; and pharmaceutically acceptable salts, hydrates, and solvates thereof.

Y connects the HDAC inhibitor pharmacophore to ring A of the LSD1 pharmacophore and includes, but is not limited to, null, —N(R$^{10}$)C(=O)—, —C(=O)N(R$^{10}$)—, —N(R$^{10}$)C(=S)—, —C(=S)N(R$^{10}$)—, —SO$_2$—, —N(R$^{10}$)SO$_2$—, —N(R$^{10}$)SO$_2$N(R$^{10}$)—, —SO$_2$N(R$^{10}$)—, and —CH=CH—; and pharmaceutically acceptable salts, hydrates, and solvates thereof.

In some embodiments, the compound of Formula (II) has the following structure:

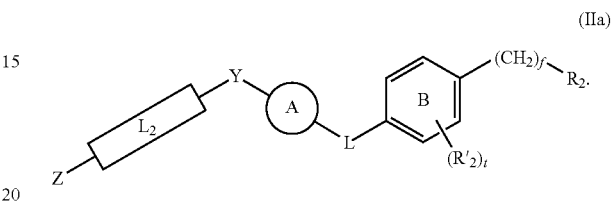

(IIa)

In other embodiments, the compound of Formula (II) has the following structure:

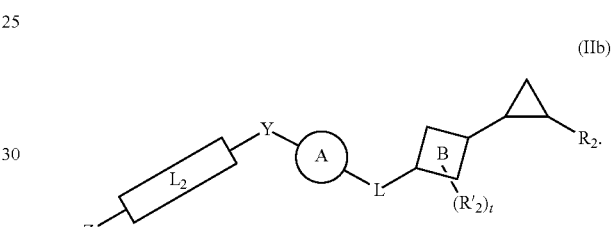

(IIb)

In yet other embodiments, the compound of Formula (IIb) has the following structure:

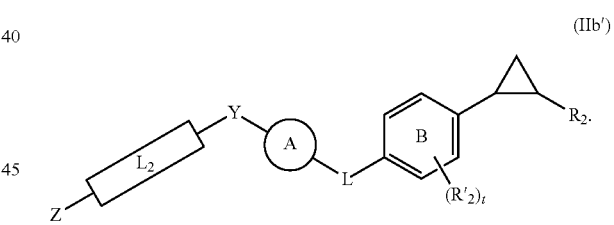

(IIb')

In certain embodiments, the compound of Formula (IIa) is selected from the group consisting of:

20

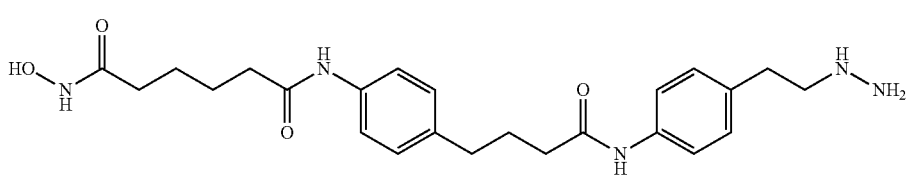

21

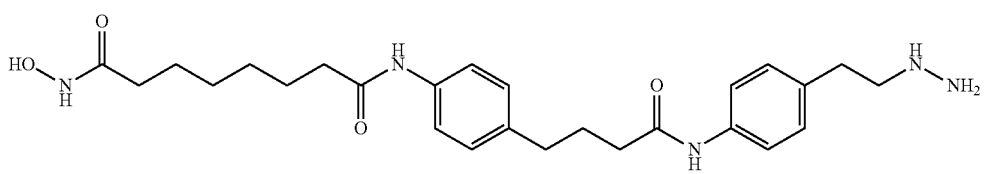

-continued
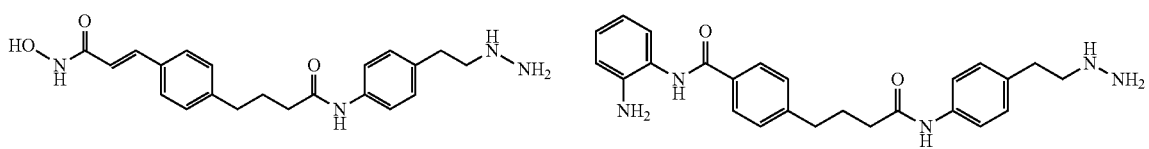
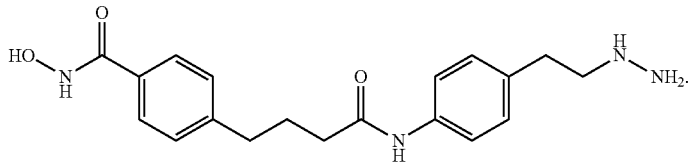
In certain embodiments of compounds of Formula (IIb'):
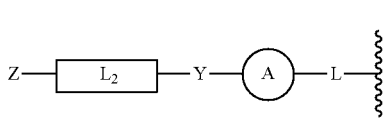
is selected from the group consisting of:
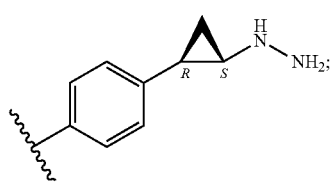
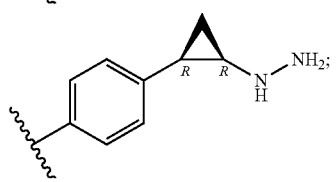
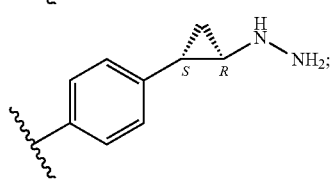
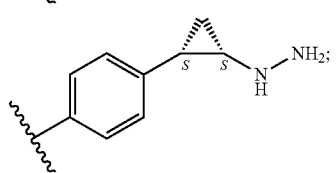
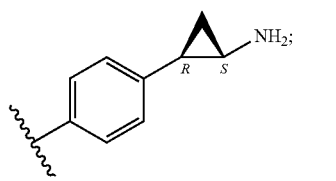
is selected from the group consisting of:
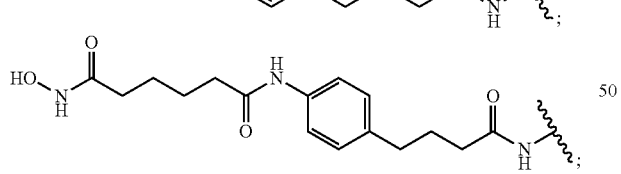
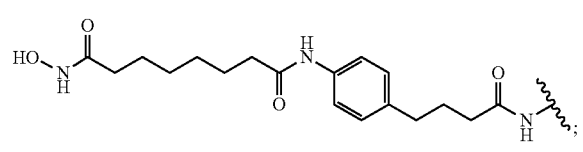
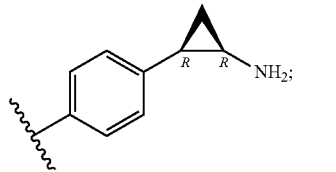
and
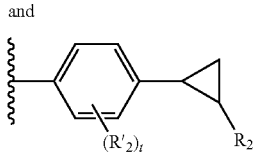
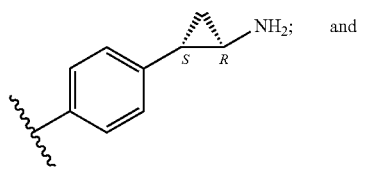
and

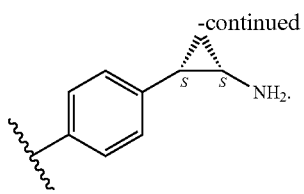

In some embodiments, the presently disclosed subject matter provides a pharmaceutical composition comprising a compound of Formula (I) or Formula (II). In some embodiments, the pharmaceutical composition further comprises one or more additional therapeutic agents. In particular embodiments, the one or more additional therapeutic agents is selected from the group consisting of a histone deacetylase (HDAC) inhibitor, a DNA methyltransferase (DNMT) inhibitor, and combinations thereof.

C. Methods of Treatment

In other embodiments, the presently disclosed subject matter provides a method for treating a disease, disorder, or condition in a subject in need thereof, the method comprising administering to the subject a therapeutically effective amount of a compound of Formula (Ia) or Formula (II), or a pharmaceutically acceptable salt thereof, thereby treating or preventing the disease, disorder, or condition:

In representative embodiments, the presently disclosed compounds of Formula (Ia) or Formula (II) inhibit lysine-specific demethylase 1 (LSD1) and/or one or more histone deacetylases (HDACs). In particular embodiments, the LSD1 and/or one or more histone deacetylases (HDACs) is involved in a biological pathway associated with a cancer or a neurodegenerative disease, disorder, or condition. Accordingly, by inhibiting LSD1 and/or one or more histone deacetylases (HDACs), the presently disclosed compounds of Formula (Ia) or Formula (II) can be used to treat a cancer or a neurodegenerative disease.

Thus, in some embodiments, the presently disclosed subject matter provides a method for inhibiting lysine-specific demethylase 1 (LSD1) and/or one or more histone deacetylases (HDACs), the method comprising administering to a subject a compound of Formula (Ia) or Formula (II), or a pharmaceutically acceptable salt thereof, in an amount effective to inhibit LSD1 and/or one or more histone deacetylases (HDACs).

As used herein, the term "inhibit" or "inhibits" means to decrease, suppress, attenuate, diminish, arrest, or stabilize the development or progression of a disease, disorder, or condition, or the activity of a biological pathway, e.g., by at least 10%, 20%, 30%, 40%, 50%, 60%, 70%, 80%, 90%, 95%, 98%, 99%, or even 100% compared to an untreated control subject, cell, or biological pathway. By the term "decrease" is meant to inhibit, suppress, attenuate, diminish, arrest, or stabilize a symptom of a neurodegenerative disease, disorder, or condition. It will be appreciated that, although not precluded, treating a disease, disorder or condition does not require that the disease, disorder, condition or symptoms associated therewith be completely eliminated.

In particular embodiments, the presently disclosed subject matter provides a method for treating a disease, disorder, or condition associated with lysine-specific demethylase 1 (LSD1) and/or one or more histone deacetylases (HDACs), the method comprising administering to a subject in need of treatment thereof subject a compound of Formula (Ia) or Formula (II), or a pharmaceutically acceptable salt thereof, in an amount effective to inhibit LSD1 and/or one or more histone deacetylases (HDACs).

In particular embodiments, the compound of Formula (Ia) is selected from the group consisting of:

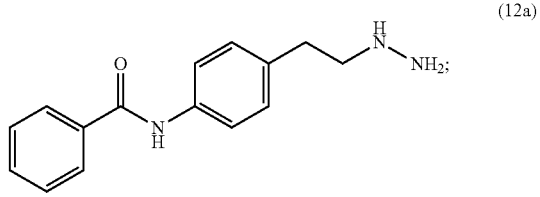

(12a)

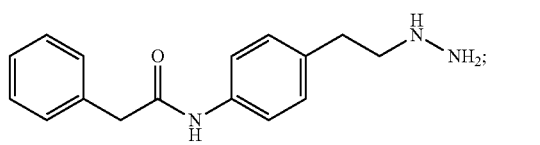

(12b)

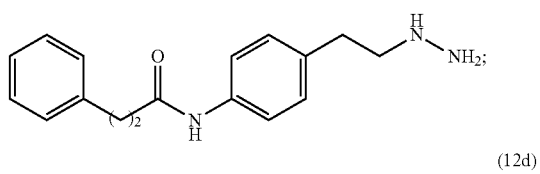

(12c)

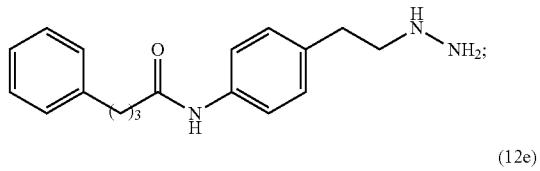

(12d)

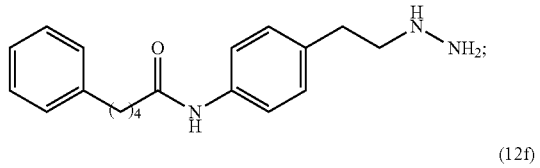

(12e)

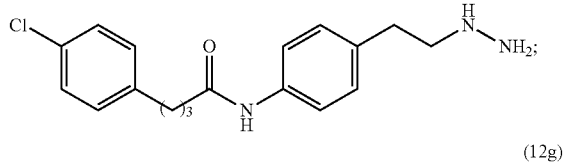

(12f)

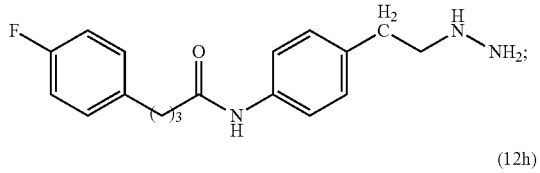

(12g)

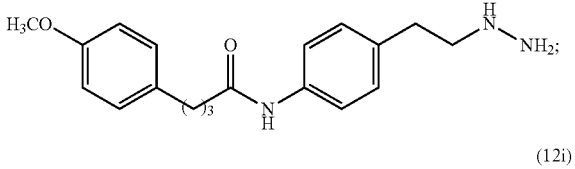

(12h)

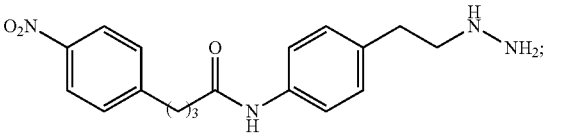

(12i)

-continued
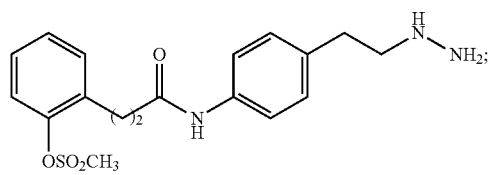
(12j)
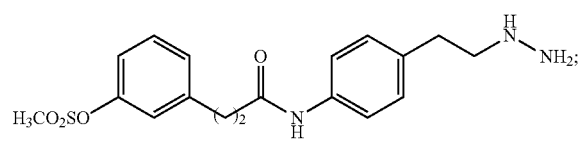
(12k)
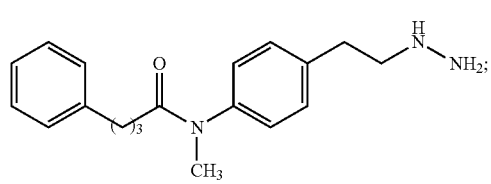
(12l)
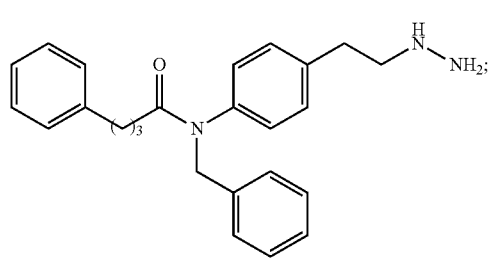
(12m)
-continued
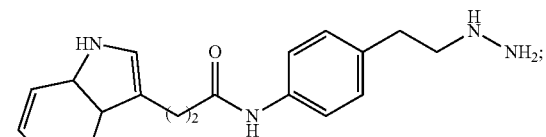
(15a)
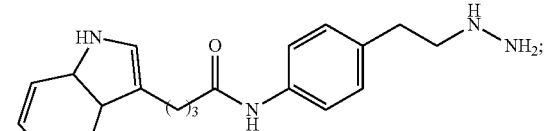
(15b)
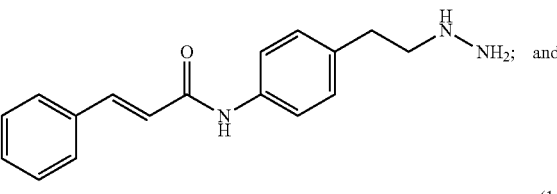
(13)
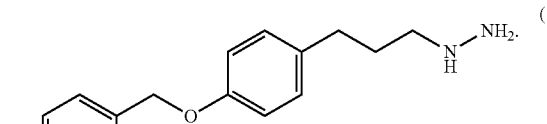
and
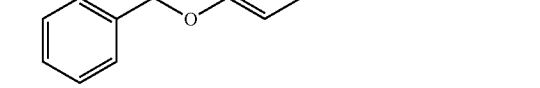
(14)
In some embodiments, the compound of Formula (II) is selected from the group consisting of:
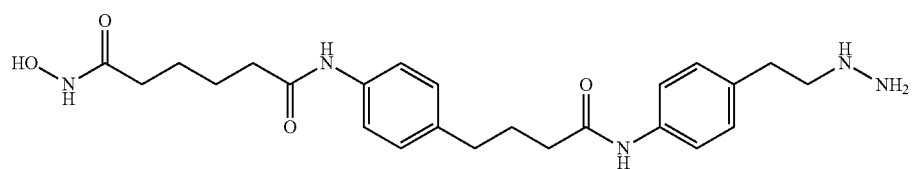
20
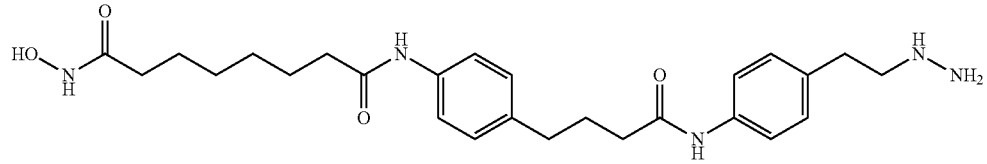
21
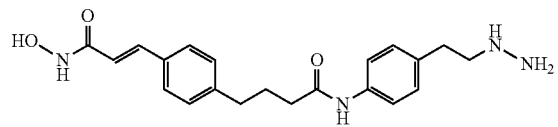
22
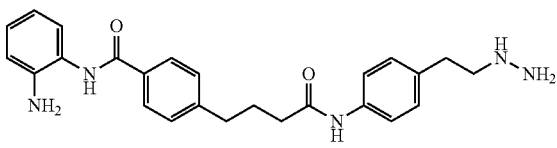
23
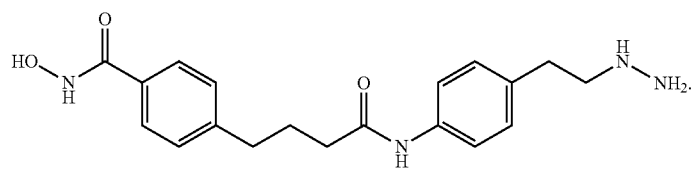
24

In yet other embodiments, the compound of Formula (II) is selected from the group consisting of:

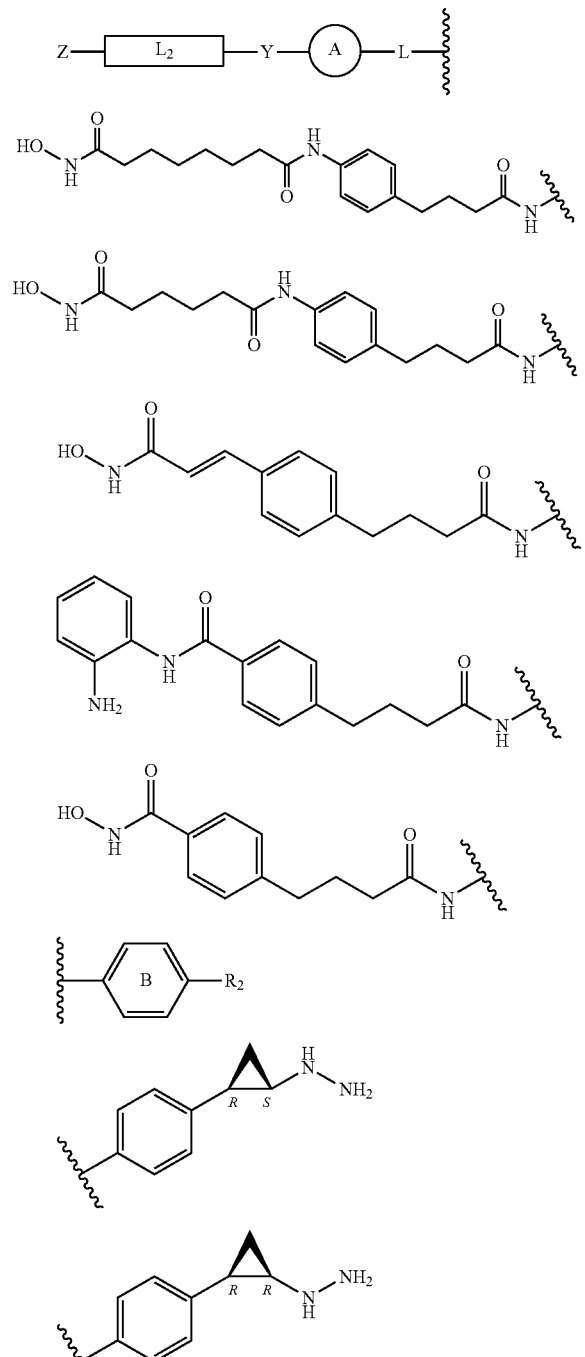

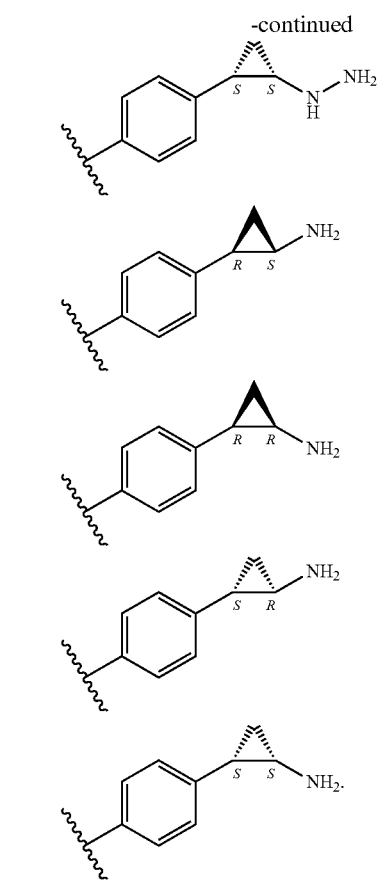

In some embodiments, the disease, disorder, or condition associated with LSD1 and/or one or more histone deacetylases (HDACs) is a cancer. In particular embodiments, the treating of the disease, disorder, or condition associated with LSD1 and/or one or more histone deacetylases (HDACs) includes activating one or more tumor suppressors silenced in cancer by an epigenetic mechanism. In other embodiments, the treating of the cancer includes modulating bulk histone methylation in one or more cancer cells. In yet other embodiments, the treating of the cancer results in a reduction in proliferation rate of one or more cancer cells.

Representative cancers include, but are not limited to, bladder, lung, non-small-cell lung cancer, breast, melanoma, colon, rectal, non-Hodgkin lymphoma, endometrial, pancreatic, kidney, prostate, leukemia, thyroid, and the like.

In some embodiments, the disease, disorder, or condition associated with LSD1 and/or one or more histone deacetylases (HDACs) is a neurodegenerative disease. In particular embodiments, the treating of the neurodegenerative disease includes protection of neurons against oxidative stress-mediated cell death.

Accordingly, in some embodiments, the subject is suffering from or susceptible to a neurodegenerative disease, disorder, or condition, such as glaucoma, e.g., a subject diagnosed as suffering from or susceptible to a neurodegenerative disease, disorder, or condition. In other embodiments, the subject has been identified (e.g., diagnosed) as suffering from or susceptible to a neurodegenerative disease, disorder, or condition (including traumatic injury) in which neuronal cell loss is implicated, or in which damage to neurites is involved, and for which treatment or prophylaxis is desired.

In other embodiments, the neurodegenerative disease, disorder, or condition is or is associated with a disease, disorder, or condition of the nervous system selected from the group consisting of amyotrophic lateral sclerosis (ALS), trigeminal neuralgia, glossopharyngeal neuralgia, Bell's Palsy, myasthenia gravis, muscular dystrophy, progressive muscular atrophy, primary lateral sclerosis (PLS), pseudobulbar palsy, progressive bulbar palsy, spinal muscular atrophy, inherited muscular atrophy, invertebrate disk syndromes, cervical spondylosis, plexus disorders, thoracic outlet destruction syndromes, peripheral neuropathies, prophyria, Alzheimer's disease, Huntington's disease, Parkinson's disease, Parkinson's-plus diseases, multiple system atrophy, progressive supranuclear palsy, corticobasal degeneration, dementia with Lewy bodies, frontotemporal dementia, demyelinating diseases, Guillain-Barre syndrome, multiple sclerosis, Charcot-Marie-Tooth disease, prion diseases, Creutzfeldt-Jakob disease, Gerstmann-Straussler-Scheinker syndrome (GSS), fatal familial insomnia (FFI), bovine spongiform encephalopathy (BSE), Pick's disease, epilepsy, AIDS dementrial complex, alcoholism, Alexander's disease, Alper's disease, ataxia telangiectasia, Batten disease, Canavan disease, Cockayne syndrome, diabetic neuropathy, frontotemporal lobar degeneration, HIV-associated dementia, Kennedy's disease, Krabbe's disease, neuroborreliosis, Machado-Joseph disease (Spinocerebellar ataxia type 3), wet or dry macular degeneration, Niemann Pick disease, Pelizaeus-Merzbacher Disease, photoreceptor degenerative diseases, Refsum's disease, Sandhoff s disease, Schilder's disease, subacute combined degeneration of spinal cord secondary to pernicious anemia, Spielmeyer-Vogt-Sjogren-Batten disease (also known as Batten disease), spinocerebellar ataxia (multiple types with varying characteristics), Steele-Richardson-Olszewski disease, and tabes dorsalis.

In yet other embodiments, the neurodegenerative disease, disorder, or condition comprises one or more conditions that are secondary to a disease, disorder, condition, or therapy having a primary effect outside of the nervous system selected from the group consisting of: peripheral neuropathy or neuralgia caused by diabetes, cancer, AIDS, hepatitis, kidney dysfunction, Colorado tick fever, diphtheria, HIV infection, leprosy, Lyme disease, polyarteritis nodosa, rheumatoid arthritis, sarcoidosis, Sjogren syndrome, syphilis, systemic lupus erythematosus, and amyloidosis.

In other embodiments, the neurodegenerative disease, disorder, or condition is associated with pain selected from the group consisting of chronic pain, fibromyalgia, spinal pain, carpel tunnel syndrome, pain from cancer, arthritis, sciatica, headaches, pain from surgery, muscle spasms, back pain, visceral pain, pain from injury, dental pain, neuralgia, such as neurogenic or neuropathic pain, nerve inflammation or damage, shingles, herniated disc, a torn ligament, and diabetes.

In further embodiments, the neurodegenerative disease, disorder, or condition is associated with one or more injuries to the nervous system. In particular embodiments, the one or more injuries to the nervous system is related to nerve damage caused by exposure to one or more agents selected from the group consisting of toxic compounds, heavy metals, industrial solvents, drugs, chemotherapeutic agents, dapsone, HIV medications, cholesterol lowering drugs, heart or blood pressure medications, and metronidazole.

In more particular embodiments, the one or more injuries to the nervous system is related to nerve damage caused by one or more conditions selected from the group consisting of burn, wound, surgery, accidents, ischemia, prolonged exposure to cold temperature, stroke, intracranial hemorrhage, and cerebral hemorrhage.

In yet other embodiments, the neurodegenerative disease, disorder, or condition comprises a psychiatric disorder. In particular embodiments, the psychiatric disorder is selected from the group consisting of schizophrenia, delusional disorder, schizoaffective disorder, schizopheniform, shared psychotic disorder, psychosis, paranoid personality disorder, schizoid personality disorder, borderline personality disorder, anti-social personality disorder, narcissistic personality disorder, obsessive-compulsive disorder, delirium, dementia, mood disorders, bipolar disorder, depression, stress disorder, panic disorder, agoraphobia, social phobia, post-traumatic stress disorder, anxiety disorder, and impulse control disorders.

In some embodiments, the method promotes or stimulates neurite growth or regeneration from one or more neuronal cells.

In further embodiments, the method comprises treating one or more neuronal cells in preparation for a nerve transplantation procedure. In particular embodiments, the treating is before, during, or after the transplantation procedure.

In other embodiments, the method treats or prevents a neuronal cell loss in the subject. In yet other embodiments, the method prevents neuronal cell death in the subject. In some embodiments, the method prevents apoptosis of one or more neuronal axons in the subject.

In certain embodiments of the above aspects, the cell is a mammalian cell, more preferably a human cell.

In some embodiments, the presently disclosed methods produce at least about a 10%, 15%, 20%, 25%, 30%, 35%, 40%, 45%, 50%, 55%, 60%, 65%, 70%, 75%, 80%, 85%, 90%, 95%, or even 100% decrease in cell loss or loss of function relative to cell survival or cell function measured in absence of the tested compound, i.e., a control sample, in an assay. In other embodiments, the compounds and amounts for use in the presently disclosed therapeutic methods produce at least about 10% to 15% increase in neuron count, neuron function, neurite count, neurite total length, or neurite average length relative to absence of the tested compound in an assay.

In any of the above-described methods, the administering of a compound of Formula (Ia) or Formula (II) can result in at least about a 10%, 15%, 20%, 25%, 30%, 35%, 40%, 45%, 50%, 55%, 60%, 65%, 70%, 75%, 80%, 85%, 90%, 95%, or even 100% decrease in one or more (e.g., 1, 2, 3, 4, 5, 6, 7, 8, 9, or 10) symptoms of a disease, disorder, or condition of the nervous system; a condition of the nervous system that is secondary to a disease, disorder, condition, or therapy having a primary effect outside of the nervous system; injury to the nervous system caused by physical, mechanical, or chemical trauma; pain; ocular-related neurodegeneration; memory loss; or psychiatric disorder, compared to a subject that is not administered the one or more of the agents described herein.

In any of the above-described methods, the administering of a compound of Formula (Ia) or Formula (II) results in at least about a 10%, 15%, 20%, 25%, 30%, 35%, 40%, 45%, 50%, 55%, 60%, 65%, 70%, 75%, 80%, 85%, 90%, 95%, or even 100% decrease in the likelihood of developing a disease, disorder, or condition of the nervous system; condition of the nervous system that is secondary to a disease, disorder, condition, or therapy having a primary effect outside of the nervous system; injury to the nervous system caused by physical, mechanical, or chemical trauma; pain;

ocular-related neurodegeneration; memory loss; or psychiatric disorder, compared to a control population of subjects that are not administered a compound of Formula (Ia) or Formula (II).

The administration of one or more agent as described herein may result in at least about a 10%, 15%, 20%, 25%, 30%, 35%, 40%, 45%, 50%, 55%, 60%, 65%, 70%, 75%, 80%, 85%, 90%, 95%, or even 100% decrease in the number of neurons (or neuron bodies, axons, or dendrites thereof) that degenerate in a neuron population or in a subject compared to the number of neurons (or neuron bodies, axons, or dendrites thereof) that degenerate in neuron population or in a subject that is not administered the one or more of the agents described herein.

The above-listed terms also include in vitro and ex vivo methods. For example, in certain embodiments, the presently disclosed methods are applicable to cell culture techniques wherein it is desirable to prevent neuronal cell death or loss of neuronal function.

As used herein, the terms "treat," treating," "treatment," and the like, are meant to decrease, suppress, attenuate, diminish, arrest, the underlying cause of a disease, disorder, or condition, or to stabilize the development or progression of a disease, disorder, condition, and/or symptoms associated therewith. The terms "treat," "treating," "treatment," and the like, as used herein can refer to curative therapy, prophylactic therapy, and preventative therapy. The treatment, administration, or therapy can be consecutive or intermittent. Consecutive treatment, administration, or therapy refers to treatment on at least a daily basis without interruption in treatment by one or more days. Intermittent treatment or administration, or treatment or administration in an intermittent fashion, refers to treatment that is not consecutive, but rather cyclic in nature. Treatment according to the presently disclosed methods can result in complete relief or cure from a disease, disorder, or condition, or partial amelioration of one or more symptoms of the disease, disease, or condition, and can be temporary or permanent. The term "treatment" also is intended to encompass prophylaxis, therapy and cure.

As used herein, the terms "prevent," "preventing," "prevention," "prophylactic treatment" and the like refer to reducing the probability of developing a disease, disorder, or condition in a subject, who does not have, but is at risk of or susceptible to developing a disease, disorder, or condition. Thus, in some embodiments, an agent can be administered prophylactically to prevent the onset of a disease, disorder, or condition, or to prevent the recurrence of a disease, disorder, or condition.

By "agent" is meant a compound of Formula (Ia) or Formula (II) or another agent, e.g., a peptide, nucleic acid molecule, or other small molecule compound administered in combination with a compound of Formula (Ia) or Formula (II). More generally, the term "therapeutic agent" means a substance that has the potential of affecting the function of an organism. Such an agent may be, for example, a naturally occurring, semi-synthetic, or synthetic agent. For example, the therapeutic agent may be a drug that targets a specific function of an organism. A therapeutic agent also may be a nutrient. A therapeutic agent may decrease, suppress, attenuate, diminish, arrest, or stabilize the development or progression of disease, disorder, or condition in a host organism.

The term "administering" as used herein refers to contacting a cell or portion thereof with a compound of Formula (Ia) or Formula (II). This term includes administration of the presently disclosed compounds to a subject in which the cell or portion thereof is present, as well as introducing the presently disclosed compounds into a medium in which a cell or portion thereof is cultured.

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing disease, disorder, condition or the prophylactic treatment for preventing the onset of a disease, disorder, or condition or an animal subject for medical, veterinary purposes, or developmental purposes. Suitable animal subjects include mammals including, but not limited to, primates, e.g., humans, monkeys, apes, gibbons, chimpanzees, orangutans, macaques and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, guinea pigs, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a disease, disorder, or condition. Thus, the terms "subject" and "patient" are used interchangeably herein. Subjects also include animal disease models (e.g., rats or mice used in experiments).

D. Pharmaceutical Compositions

The presently disclosed pharmaceutical compositions and formulations include pharmaceutical compositions of compounds of Formula (Ia) or Formula (II), alone or in combination with one or more additional therapeutic agents, in admixture with a physiologically compatible carrier, which can be administered to a subject, for example, a human subject, for therapeutic or prophylactic treatment. As used herein, "physiologically compatible carrier" refers to a physiologically acceptable diluent including, but not limited to water, phosphate buffered saline, or saline, and, in some embodiments, can include an adjuvant. Acceptable carriers, excipients, or stabilizers are nontoxic to recipients at the dosages and concentrations employed, and can include buffers such as phosphate, citrate, and other organic acids; antioxidants including ascorbic acid, BHA, and BHT; low molecular weight (less than about 10 residues) polypeptides; proteins, such as serum albumin, gelatin or immunoglobulins; hydrophilic polymers, such as polyvinylpyrrolidone, amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counter-ions such as sodium; and/or nonionic surfactants such as Tween, Pluronics, or PEG. Adjuvants suitable for use with the presently disclosed compositions include adjuvants known in the art including, but not limited to, incomplete Freund's adjuvant, aluminum phosphate, aluminum hydroxide, and alum.

Compositions to be used for in vivo administration must be sterile, which can be achieved by filtration through sterile filtration membranes, prior to or following lyophilization and reconstitution. Therapeutic compositions may be placed into a container having a sterile access port, for example, an intravenous solution bag or vial having a stopper pierceable by a hypodermic injection needle.

One of skill in the art will recognize that the pharmaceutical compositions include the pharmaceutically acceptable salts of the compounds described above. The term "pharmaceutically acceptable salts" is meant to include salts of active compounds, which are prepared with relatively non-toxic acids or bases, depending on the particular substituent moieties found on the compounds described herein.

When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include alkali or alkaline earth metal salts including, but not limited to, sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine and the like.

When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids including, but not limited to, hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids, such as acetic (acetates), propionic (propionates), isobutyric (isobutyrates), maleic (maleates), malonic, benzoic (benzoates), succinic (succinates), suberic, fumaric (fumarates), lactic (lactates), mandelic (mandelates), phthalic (phthalates), benzenesulfonic (benzosulfonates), p-tolylsulfonic, citric (citrates), tartaric (tartrates, e.g., (+)-tartrates, (−)-tartrates or mixtures thereof including racemic mixtures), methanesulfonic, and the like. Other pharmaceutically acceptable salts, include, but are not limited to, besylate, bicarbonate, bitartrate, bromide, calcium edetate, carnsylate, carbonate, edetate, edisylate, estolate, esylate, gluceptate, gluconate, glutamate, glycollylarsanilate, hexylresorcinate, hydrabamine, hydroxynaphthoate, iodide, isethionate, lactobionate, malate, mesylate, mucate, napsylate, nitrate, pamoate (embonate), pantothenate, phosphate/diphosphate, polygalacturonate, salicylate, stearate, subacetate, sulfate, tannate, and teoclate, also are included.

Also included are salts of amino acids, such as arginate and the like, and salts of organic acids, such as, glucuronic or galactunoric acids, and the like. See, for example, Berge et al, "Pharmaceutical Salts", Journal of Pharmaceutical Science, 1977, 66, 1-19. Some compounds of the present disclosure can contain both basic and acidic functionalities, which allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties. For example, salts tend to be more soluble in aqueous or other protonic solvents than are the corresponding free base forms.

In particular embodiments, the pharmaceutically acceptable salt of a compound of Formula (Ia) or Formula (II) is selected from the group consisting of HCl, a sulfonate, a sulfate, phosphate, a malonate, a succinate, a fumarate, a maleate, a tartrate, a 3-sulfopropanoic acid salt, and a citrate.

Certain compounds of the present disclosure can exist in unsolvated forms, as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

In addition to salt forms, the present disclosure provides compounds that can be in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

E. Combination Therapies

In some embodiments of the presently disclosed methods, the compound of Formula (Ia) or Formula (II) is administered in combination with one or more additional therapeutic agents. In particular embodiments, the administration of the combination of a compound of Formula (Ia) or Formula (II) with one or more additional therapeutic agents has an additive or synergistic effect on cancer cell growth. In yet more particular embodiments, the one or more additional therapeutic agents is selected from the group consisting of a histone deacetylase (HDAC), a DNA methyltransferase (DNMT) inhibitor, and combinations thereof. In certain embodiments, the one or more additional therapeutic agents is selected from the group consisting of azacytidine, SAHA, TSA, MGCD0103, MS-275, and LBH-589.

In further embodiments, the one or more additional therapeutic agents is an anti-neoplastic agent. Typically, any anti-neoplastic agent that has activity versus a susceptible tumor being treated may be co-administered in the treatment of cancer in the present invention. Examples of such agents can be found in Cancer Principles and Practice of Oncology by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Typical anti-neoplastic agents useful in the present invention include, but are not limited to, anti-microtubule agents such as diterpenoids and vinca alkaloids; platinum coordination complexes; alkylating agents such as nitrogen mustards, oxazaphosphorines, alkyl sulfonates, nitrosoureas, and triazenes; antibiotic agents such as anthracycline, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; signal transduction pathway inhibitors; non-receptor tyrosine kinase angiogenesis inhibitors; immunotherapeutic agents; proapoptotic agents; cell cycle signaling inhibitors; proteasome inhibitors; and inhibitors of cancer metabolism.

Examples of a further active ingredient or ingredients (anti-neoplastic agent) for use in combination or co-administered with the presently invented combinations are chemotherapeutic agents.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids.

Diterpenoids, which are derived from natural sources, are phase specific anticancer agents that operate at the $G_2/M$ phases of the cell cycle. It is believed that the diterpenoids stabilize the (β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5, 20-epoxy-1,2a,4,7,10,13a-hexa-hydroxy-tax-11-en-9-one 4, 10-diacetate 2-benzoate 13-ester with (2R,3S)—N-benzoyl-3-phenylisoserine; is a natural diterpene product isolated from the Pacific yew tree Taxus brevifolia and is commercially available as an injectable solution TAXOL®. It is a member of the taxane family of terpenes. It was first isolated in 1971 by Wani et al. J. Am. Chem, Soc, 93:2325. 1971), who characterized its structure by chemical and X-ray crystallographic methods. One mechanism for its activity relates to paclitaxel's capacity to bind tubulin, thereby inhibiting cancer cell growth. Schiff et al., Proc. Natl, Acad, Sci. USA, 77: 1561-1565 (1980); Schiff et al., Nature, 277:665-667 (1979); Kumar, J. Biol, Chem, 256: 10435-10441 (1981). For a review of synthesis and anticancer activity of some paclitaxel derivatives see: D. G. I. Kingston et al., Studies in Organic Chemistry vol. 26, entitled "New trends in Natural Products Chemistry 1986", Attaur-Rahman, P. W. Le Quesne, Eds. (Elsevier, Amsterdam, 1986) pp 219-235.

Paclitaxel has been approved for clinical use in the treatment of refractory ovarian cancer in the United States (Markman et al., Yale Journal of Biology and Medicine, 64:583, 1991; McGuire et al., Ann. Intern, Med., 111:273, 1989) and for the treatment of breast cancer (Holmes et al., J. Nat. Cancer Inst., 83:1797,1991.) It is a potential candidate for treatment of neoplasms in the skin (Einzig et. al., Proc. Am. Soc. Clin. Oncol., 20:46) and head and neck carcinomas (Forastire et. al., Sem. Oncol., 20:56, 1990). The compound also shows potential for the treatment of polycystic kidney disease (Woo et. al., Nature, 368:750. 1994), lung cancer and malaria. Treatment of patients with paclitaxel results in bone marrow suppression (multiple cell lineages, Ignoff, R. J. et. al, Cancer Chemotherapy Pocket Guide, 1998) related to the duration of dosing above a threshold concentration (50 nM) (Kearns, C M. et. al., Seminars in Oncology, 3(6) p.16-23, 1995).

Docetaxel, (2R,3S)—N-carboxy-3-phenylisoserine,N-tert-butyl ester, 13-ester with 5-20-epoxy-1,2a,4,7,10,13a-hexahydroxytax-11-en-9-one 4-acetate 2-benzoate, trihydrate; is commercially available as an injectable solution as TAXOTERE®.

Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree. The dose limiting toxicity of docetaxel is neutropenia.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELBAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosuppression and gastrointestinal mucositis effects occur.

Vinorelbine, 3', 4'-didehydro-4'-deoxy-C'-norvincaleukoblastine [R—(R*,R*)—2,3-dihydroxybutanedioate (1:2) (salt)], commercially available as an injectable solution of vinorelbine tartrate (NAVELBINE®), is a semisynthetic vinca alkaloid. Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum coordination complexes are non-phase specific anti-cancer agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, cisplatin and carboplatin.

Cisplatin, cis-diamminedichloroplatinum, is commercially available as PLATINOL® as an injectable solution. Cisplatin is primarily indicated in the treatment of metastatic testicular and ovarian cancer and advanced bladder cancer. The primary dose limiting side effects of cisplatin are nephrotoxicity, which may be controlled by hydration and diuresis, and ototoxicity.

Carboplatin, platinum, diammine [1,1-cyclobutane-dicarboxylate(2-)-0,0'], is commercially available as PARAPLATIN® as an injectable solution. Carboplatin is primarily indicated in the first and second line treatment of advanced ovarian carcinoma. Bone marrow suppression is the dose limiting toxicity of carboplatin.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias. Alopecia, nausea, vomiting and leukopenia are the most common dose limiting side effects of cyclophosphamide.

Melphalan, 4-[bis(2-chloroethyl)amino]-L-phenylalanine, is commercially available as an injectable solution or tablets as ALKERAN®. Melphalan is indicated for the palliative treatment of multiple myeloma and non-resectable epithelial carcinoma of the ovary. Bone marrow suppression is the most common dose limiting side effect of melphalan.

Chlorambucil, 4[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease. Bone marrow suppression is the most common dose limiting side effect of chlorambucil.

Busulfan, 1,4-butanediol dimethanesulfonate, is commercially available as MYLERAN® TABLETS. Busulfan is indicated for the palliative treatment of chronic myelogenous leukemia. Bone marrow suppression is the most common dose limiting side effects of busulfan.

Carmustine, 1,3[bis(2-chloroethyl)-1-nitrosourea, is commercially available as single vials of lyophilized material as BiCNU®. Carmustine is indicated for the palliative treatment as a single agent or in combination with other agents for brain tumors, multiple myeloma, Hodgkin's disease, and non-Hodgkin's lymphomas. Delayed myelosuppression is the most common dose limiting side effects of carmustine.

Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease. Nausea, vomiting, and anorexia are the most common dose limiting side effects of dacarbazine.

Antibiotic anti-neoplastics are non-phase specific agents, which bind or intercalate with DNA. Typically, such action results in stable DNA complexes or strand breakage, which disrupts ordinary function of the nucleic acids, leading to cell death. Examples of antibiotic anti-neoplastic agents include, but are not limited to, actinomycins such as dactinomycin, anthrocyclins such as daunorubicin and doxorubicin; and bleomycins.

Dactinomycin, also known as Actinomycin D, is commercially available in injectable form as COSMEGEN®. Dactinomycin is indicated for the treatment of Wilm's tumor and rhabdomyosarcoma. Nausea, vomiting, and anorexia are the most common dose limiting side effects of dactinomycin.

Daunorubicin, (8S-cis-)-8-acetyl-10-[(3-amino-2,3,6-trideoxy-a-L-lyxo-hexopyranosyl)oxy]-7,8,9,10-tetrahydro-6,8,11-trihydroxy-1-methoxy-5, 12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma. Myelosuppression is the most common dose limiting side effect of daunorubicin.

Doxorubicin, (8S, 10S)-10-[(3-amino-2,3,6-trideoxy-a-L-lyxo-hexopyranosyl)oxy]-8-glycoloyl, 7,8,9,10-tetrahydro-6,8,9,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas. Myelosuppression is the most common dose limiting side effect of doxorubicin.

Bleomycin, a mixture of cytotoxic glycopeptide antibiotics isolated from a strain of *Streptomyces verticillus*, is commercially available as BLENOXANE®. Bleomycin is indicated as a palliative treatment, as a single agent or in combination with other agents, of squamous cell carcinoma, lymphomas, and testicular carcinomas. Pulmonary and cutaneous toxicities are the most common dose limiting side effects of bleomycin.

Topoisomerase II inhibitors include, but are not limited to, epipodophyllotoxins. Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epipodophyllotoxin 9[4,6-0-(R)-ethylidene-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers. Myelosuppression is the most common side effect of etoposide. The incidence of leucopenia tends to be more severe than thrombocytopenia.

Teniposide, 4'-demethyl-epipodophyllotoxin 9[4,6-0-(R)-thenylidene-D-glucopyranoside], is commercially available as an injectable solution as VUMON® and is commonly known as VM-26. Teniposide is indicated as a single agent or in combination with other chemotherapy agents in the treatment of acute leukemia in children. Myelosuppression is the most common dose limiting side effect of teniposide. Teniposide can induce both leucopenia and thrombocytopenia.

Antimetabolite neoplastic agents are phase specific anti-neoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mecaptopurine, thioguanine, and gemcitabine.

5-fluorouracil, 5-fluoro-2,4-(1H,3H) pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Myelosuppression and mucositis are dose limiting side effects of 5-fluorouracil. Other fluoropyrimidine analogs include 5-fluoro deoxyuridine (floxuridine) and 5-fluorodeoxyuridine monophosphate.

Cytarabine, 4-amino-1-D-arabinofuranosyl-2 (1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2', 2'-difluorodeoxycytidine (gemcitabine). Cytarabine induces leucopenia, thrombocytopenia, and mucositis.

Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. Myelosuppression and gastrointestinal mucositis are expected side effects of mercaptopurine at high doses. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Myelosuppression, including leucopenia, thrombocytopenia, and anemia, is the most common dose limiting side effect of thioguanine administration. However, gastrointestinal side effects occur and can be dose limiting. Other purine analogs include pentostatin, erythrohydroxynonyladenine, fludarabine phosphate, and cladribine.

Gemcitabine, 2'-deoxy-2', 2'-difluorocytidine monohydrochloride 03-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer. Myelosuppression, including leucopenia, thrombocytopenia, and anemia, is the most common dose limiting side effect of gemcitabine administration.

Methotrexate, N-[4[[(2,4-diamino-6-pteridinyl) methyl]methylamino] benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder. Myelosuppression (leucopenia, thrombocytopenia, and anemia) and mucositis are expected side effect of methotrexate administration. Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below.

Irinotecan HCl, (4S)-4,11-diethyl-4-hydroxy-9-[(4-piperidinopiperidino) carbonyloxy]-1H-pyrano[3', 4', 6,7]indolizino[1,2-b]quinoline-3,14(4H,12H)-dione hydrochloride, is commercially available as the injectable solution CAMPTOSAR®. Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I:DNA:irintecan or SN-38 ternary complex with replication enzymes. Irinotecan is indicated for treatment of metastatic cancer of the colon or rectum. The dose limiting side effects of irinotecan HCl are myelosuppression, including neutropenia, and GI effects, including diarrhea.

Topotecan HCl, (S)-10-[(dimethylamino)methyl]-4-ethyl-4,9-dihydroxy-1H-pyrano[3', 4', 6,7]indolizino[1,2-b] quinoline-3, 14-(4H, 12H)-dione monohydrochloride, is commercially available as the injectable solution HYCAMTIN®. Topotecan is a derivative of camptothecin which binds to the topoisomerase I-DNA complex and prevents religation of singles strand breaks caused by Topoisomerase I in response to torsional strain of the DNA molecule. Topotecan is indicated for second line treatment of metastatic carcinoma of the ovary and small cell lung cancer. The dose limiting side effect of topotecan HCl is myelosuppression, primarily neutropenia.

Also of interest, is the camptothecin derivative of Formula A following, including the racemic mixture (R,S) form as well as the R and S enantiomers:

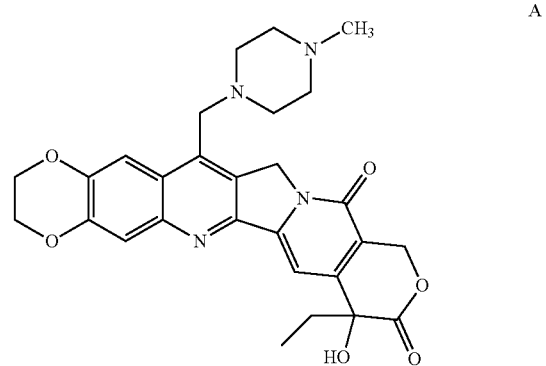 [SMILES: CCC1(O)C(=O)OCc2c1cc1n(c2=O)Cc2c-1nc1cc3c(cc1c2CN1CCN(C)CC1)OCCO3]

A known by the chemical name "7-(4-methylpiperazino-methylene)-10,11-ethylenedioxy-20(R,S)-camptothecin (racemic mixture) or "7-(4-methylpiperazino-methylene)-10,11-ethylenedioxy-20(R)-camptothecin (R enantiomer) or "7-(4-methylpiperazino-methylene)-10,11-ethylenedioxy-20(S)-camptothecin (S enantiomer). Such compounds, as well as related compounds are described, including methods of making, in U.S. Pat. Nos. 6,063,923; 5,342,947; 5,559,235; 5,491,237 and pending U.S. patent application Ser. No. 08/977,217 filed Nov. 24, 1997.

Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, adrenocorticosteroids such as prednisone and prednisolone which are useful in the treatment of malignant lymphoma and acute leukemia in children; aminoglutethimide and other aromatase inhibitors such as anastrozole, letrazole, vorazole, and exemestane useful in the treatment of adrenocortical carcinoma and hormone dependent breast carcinoma containing estrogen receptors; progestins such as megestrol acetate useful in the treatment of hormone dependent breast cancer and endometrial carcinoma; estrogens, androgens, and anti-androgens such as flutamide, nilutamide, bicalutamide, cyproterone acetate and 5a-reductases such as finasteride and dutasteride, useful in the treatment of prostatic carcinoma and benign prostatic hypertrophy; anti-estrogens such as tamoxifen, toremifene, raloxifene, droloxifene, iodoxyfene, as well as selective estrogen receptor modulators (SERMS) such those described in U.S. Pat. Nos. 5,681,835, 5,877,219, and 6,207,716, useful in the treatment of hormone dependent breast carcinoma and other susceptible cancers; and gonadotropin-releasing hormone (GnRH) and analogues thereof which stimulate the release of leutinizing hormone (LH) and/or follicle stimulating hormone (FSH)

for the treatment prostatic carcinoma, for instance, LHRH agonists and antagagonists such as goserelin acetate and luprolide.

Signal transduction pathway inhibitors are those inhibitors, which block or inhibit a chemical process which evokes an intracellular change. As used herein this change is cell proliferation or differentiation. Signal tranduction inhibitors useful in the present invention include inhibitors of receptor tyrosine kinases, non-receptor tyrosine kinases, SH2/SH3 domain blockers, serine/threonine kinases, phosphotidylinositol-3 kinases, myoinositol signaling, and Ras oncogenes.

Several protein tyrosine kinases catalyse the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are generally termed growth factor receptors. Inappropriate or uncontrolled activation of many of these kinases, i.e., aberrant kinase growth factor receptor activity, for example by over-expression or mutation, has been shown to result in uncontrolled cell growth.

Accordingly, the aberrant activity of such kinases has been linked to malignant tissue growth. Consequently, inhibitors of such kinases could provide cancer treatment methods. Growth factor receptors include, for example, epidermal growth factor receptor (EGFr), platelet derived growth factor receptor (PDGFr), erbB2, erbB4, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. Several inhibitors of growth receptors are under development and include ligand antagonists, antibodies, tyrosine kinase inhibitors and antisense oligonucleotides. Growth factor receptors and agents that inhibit growth factor receptor function are described, for instance, in Kath, John C, Exp. Opin. Ther. Patents (2000) 10(6):803-818; Shawver et al DDT Vol 2, No. 2 February 1997; and Lofts, F. J. et al, "Growth factor receptors as targets", New Molecular Targets for Cancer Chemotherapy, ed. Workman, Paul and Kerr, David, CRC press 1994, London.

Suitably, the pharmaceutically active compounds of the invention are used in combination with a VEGFR inhibitor, suitably 5-[[4-[(2,3-dimethyl-2H-indazol-6-yl)methylamino]-2-pyrimidinyl]amino]-2-methylbenzenesulfonamide, or a pharmaceutically acceptable salt, suitably the monohydrochloride salt thereof, which is disclosed and claimed in in International Application No. PCT/USO1/49367, having an International filing date of Dec. 19, 2001, International Publication Number WO02/059110 and an International Publication date of Aug. 1, 2002, the entire disclosure of which is hereby incorporated by reference, and which is the compound of Example 69. 5-[[4-[(2,3-dimethyl-2H-indazol-6-yl)methylamino]-2-pyrimidinyl]amino]-2-methylbenzenesulfonamide can be prepared as described in International Application No. PCT/USO1/49367.

Suitably, 5-[[4-[(2,3-dimethyl-2H-indazol-6-yl)methylamino]-2-pyrimidinyl]amino]-2-methylbenzenesulfonamide is in the form of a monohydrochloride salt. This salt form can be prepared by one of skill in the art from the description in International Application No. PCT/USO1/49367, having an International filing date of Dec. 19, 2001.

5-[[4-[(2,3-dimethyl-2H-indazol-6-yl)methylamino]-2-pyrimidinyl]amino]-2-methylbenzenesulfonamide is sold commercially as the monohydrochloride salt and is known by the generic name pazopanib and the trade name Votrient®.

Pazopanib is implicated in the treatment of cancer and ocular diseases/angiogenesis. Suitably the present invention relates to the treatment of cancer and ocular diseases/angiogenesis, suitably age-related macular degeneration, which method comprises the administration of one or more of the presently disclosed compounds alone or in combination with pazopanib.

Tyrosine kinases, which are not growth factor receptor kinases are termed nonreceptor tyrosine kinases. Non-receptor tyrosine kinases for use in the present invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such nonreceptor kinases and agents which inhibit non-receptor tyrosine kinase function are described in Sinh, S. and Corey, S. J., (1999) Journal of Hematotherapy and Stem Cell Research 8 (5): 465-80; and Bolen, J. B., Brugge, J. S., (1997) Annual review of Immunology. 15: 371-404.

SH2/SH3 domain blockers are agents that disrupt SH2 or SH3 domain binding in a variety of enzymes or adaptor proteins including, PI3-K p85 subunit, Src family kinases, adaptor molecules (She, Crk, Nek, Grb2) and Ras-GAP. SH2/SH3 domains as targets for anti-cancer drugs are discussed in Smithgall, T. E. (1995), Journal of Pharmacological and Toxicological Methods. 34(3) 125-32.

Inhibitors of Serine/Threonine Kinases including MAP kinase cascade blockers which include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta). IkB kinase family (IKKa, IKKb), PKB family kinases, akt kinase family members, PDK1 and TGF beta receptor kinases. Such Serine/Threonine kinases and inhibitors thereof are described in Yamamoto, T., Taya, S., Kaibuchi, K., (1999), Journal of Biochemistry. 126 (5) 799-803; Brodt, P, Samani, A., and Navab, R. (2000), Biochemical Pharmacology, 60. 1101-1107; Massague, J., Weis-Garcia, F. (1996) Cancer Surveys. 27:41-64; Philip, P. A., and Harris, A. L. (1995), Cancer Treatment and Research. 78: 3-27, Lackey, K. et al Bioorganic and Medicinal Chemistry Letters, (10), 2000, 223-226; U.S. Pat. No. 6,268,391; Pearce, L. R et al. Nature Reviews Molecular Cell Biology (2010) 11, 9-22; and Martinez-Iacaci, L., et al, Int. J. Cancer (2000), 88(1), 44-52.

Suitably, the pharmaceutically active compounds of the invention are used in combination with a B-Raf inhibitor. Suitably, N-{3-[5-(2-Amino-4-pyrimidinyl)-2-(1,1-dimethylethyl)-1,3-thiazol-4-yl]-2-fluorophenyl}-2,6-difluorobenzenesulfonamide, or a pharmaceutically acceptable salt thereof, which is disclosed and claimed, in International Application No. PCT/US2009/042682, having an International filing date of May 4, 2009, the entire disclosure of which is hereby incorporated by reference. N-{3-[5-(2-Amino-4-pyrimidinyl)-2-(1,1-dimethylethyl)-1,3-thiazol-4- yl]-2-fluorophenyl}-2,6-difluorobenzenesulfonamide can be prepared as described in International Application No. PCT/US2009/042682.

Suitably, the pharmaceutically active compounds of the invention are used in combination with an Akt inhibitor. Suitably, N-{(1,S)-2-amino-1-[(3-fluorophenyl)methyl]ethyl}-5-chloro-4-(4-chloro-1-methyl-1H-pyrazol-5-yl)-2-thiophenecarboxamide or a pharmaceutically acceptable salt thereof, which is disclosed and claimed in International Application No. PCT/US2008/053269, having an International filing date of Feb. 7, 2008; International Publication Number WO 2008/098104 and an International Publication date of Aug. 14, 2008, the entire disclosure of which is hereby incorporated by reference. N-{(1,S)-2-amino-1-[(3-fluorophenyl)methyl]ethyl}-5-chloro-4-(4-chloro-1-methyl-1H-pyrazol-5-yl)-2-thiophenecarboxamide is the compound of example 96 and can be prepared as described in International Application No. PCT/US2008/053269. Suitably, N-{(1S)-2-amino-1-[(3-fluorophenyl)methyl]ethyl}-5-chloro-4-(4-chloro-1-methyl-1H-pyrazol-5-yl)-2-thiophenecarboxamide is in the form of a hydrochloride salt. The salt form can be prepared by one of skill in the art from the description in International Application No. PCT/US2010/022323, having an International filing date of Jan. 28, 2010.

Also of interest in the present invention are Myo-inositol signaling inhibitors such as phospholipase C blockers and Myoinositol analogues. Such signal inhibitors are described in Powis, G., and Kozikowski A., (1994) New Molecular Targets for Cancer Chemotherapy ed., Paul Workman and David Kerr, CRC press 1994, London.

Another group of signal transduction pathway inhibitors are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block ras activation in cells containing wild type mutant ras, thereby acting as antiproliferation agents. Ras oncogene inhibition is discussed in Scharovsky, O. G., Rozados, V. R., Gervasoni, S. I. Matar, P. (2000), Journal of Biomedical Science. 7(4) 292-8; Ashby, M. N. (1998), Current Opinion in Lipidology. 9 (2) 99-102; and BioChim. Biophys. Acta, (19899) 1423(3): 19-30.

As mentioned above, antibody antagonists to receptor kinase ligand binding may also serve as signal transduction inhibitors. This group of signal transduction pathway inhibitors includes the use of humanized antibodies to the extracellular ligand binding domain of receptor tyrosine kinases. For example Imclone C225 EGFR specific antibody (see Green, M. C. et al, Monoclonal Antibody Therapy for Solid Tumors, Cancer Treat. Rev., (2000), 26(4), 269-286); Herceptin® erbB2 antibody (see Tyrosine Kinase Signalling in Breast cancenerbB Family Receptor Tyrosine Kniases, Breast cancer Res., 2000, 2(3), 176-183); and 2CB VEGFR2 specific antibody (see Brekken, R. A. et al, Selective Inhibition of VEGFR2 Activity by a monoclonal Anti-VEGF antibody blocks tumor growth in mice, Cancer Res. (2000) 60, 5117-5124).

Non-receptor kinase angiogenesis inhibitors may also be useful in the present invention. Inhibitors of angiogenesis related VEGFR and TIE2 are discussed above in regard to signal transduction inhibitors (both receptors are receptor tyrosine kinases). Angiogenesis in general is linked to erbB2/EGFR signaling since inhibitors of erbB2 and EGFR have been shown to inhibit angiogenesis, primarily VEGF expression.

Accordingly, non-receptor tyrosine kinase inhibitors may be used in combination with the compounds of the present invention. For example, anti-VEGF antibodies, which do not recognize VEGFR (the receptor tyrosine kinase), but bind to the ligand; small molecule inhibitors of integrin (alpha$_v$ beta$_3$) that will inhibit angiogenesis; endostatin and angiostatin (non-RTK) may also prove useful in combination with the disclosed compounds. (See Bruns C J et al (2000), Cancer Res., 60: 2926-2935; Schreiber A B, Winkler M E, and Derynck R. (1986), Science, 232: 1250-1253; Yen L et al. (2000), Oncogene 19: 3460-3469).

Agents used in immunotherapeutic regimens may also be useful in combination with the presently disclosed compounds. There are a number of immunologic strategies to generate an immune response. These strategies are generally in the realm of tumor vaccinations. The efficacy of immunologic approaches may be greatly enhanced through combined inhibition of signaling pathways using a small molecule inhibitor. Discussion of the immunologic/tumor vaccine approach against erbB2/EGFR are found in Reilly R T et al. (2000), Cancer Res. 60: 3569-3576; and Chen Y, Hu D, Eling D J, Robbins J, and Kipps T J. (1998), Cancer Res. 58: 1965-1971.

Agents used in proapoptotic regimens (e.g., bcl-2 antisense oligonucleotides) may also be used in the combination of the present invention. Members of the Bcl-2 family of proteins block apoptosis. Upregulation of bcl-2 has therefore been linked to chemoresistance. Studies have shown that the epidermal growth factor (EGF) stimulates anti-apoptotic members of the bcl-2 family (i.e., mcl-1). Therefore, strategies designed to downregulate the expression of bcl-2 in tumors have demonstrated clinical benefit and are now in Phase II/III trials, namely Genta's G3139 bcl-2 antisense oligonucleotide. Such proapoptotic strategies using the antisense oligonucleotide strategy for bcl-2 are discussed in Water J S et al. (2000), J. Clin. Oncol. 18: 1812-1823; and Kitada S et al. (1994), Antisense Res. Dev. 4: 71-79.

Cell cycle signalling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signalling are under development. For instance, examples of cyclin dependent kinases, including CDK2, CDK4, and CDK6 and inhibitors for the same are described in, for instance, Rosania et al, Exp. Opin. Ther. Patents (2000) 10(2):215-230. Further, p21WAF1/CIP1 has been described as a potent and universal inhibitor of cyclin-dependent kinases (Cdks) (Ball et al., Progress in Cell Cycle Res., 3: 125 (1997)).

Compounds that are known to induce expression of p21WAF1/CIP1 have been implicated in the suppression of cell proliferation and as having tumor suppressing activity (Richon et al., Proc. Nat Acad. Sci. U.S.A. 97(18): 10014-10019 (2000)), and are included as cell cycle signaling inhibitors.

Further, modulators of the Retinoid Acid Receptor have been used to treat leukemias. The pathology of the leukemia is associated with the abnormal accumulation of immature progenitor cells that are sensitive to retinoc acid therapy. The majority of cases of acute promyelocytic leukemia (APL), also called acute myeloid leukemia subtype M3, involve a chromosomal translocation of chromosomes 15 and 17 that causes genetic fusion of the retinoic acid receptor (RAR) gene to the promyelocytic leukemia (PML) gene. This fusion PML-RAR protein is responsible for preventing immature myeloid cells from differentiating into more mature cells. This block in differentiation is and subsequent accumulation of less differentiated cells is thought to cause leukemia. ATRA, Tretinoin, acts on PML-RAR to lift this block, causing the immature promyelocytes to differentiate to normal mature blood cells thus decreasing promyelocytes and promoting a population of terminally differentiated cells with a restricted lifespan. Talazorole is an experimental drug in the same class as Tretinoin.

Accordingly, depending on the particular disease, disorder, or condition to be treated or prevented, additional therapeutic agents, which are normally administered to treat or prevent that condition, may be administered in combination with the compounds of this disclosure. These additional agents may be administered separately, as part of a multiple dosage regimen, from the composition comprising a compound of Formula (Ia) or Formula (II). Alternatively, these agents may be part of a single dosage form, mixed together with the compound of Formula (Ia) or Formula (II) in a single composition.

By "in combination with" is meant the administration of a compound of Formula (Ia) or Formula (II) with one or more therapeutic agents either simultaneously, sequentially, or a combination thereof. Therefore, a cell or a subject administered a combination of a compound of Formula (Ia) or Formula (II) can receive a compound of Formula (Ia) or Formula (II) and one or more therapeutic agents at the same time (i.e., simultaneously) or at different times (i.e., sequentially, in either order, on the same day or on different days), so long as the effect of the combination of both agents is achieved in the cell or the subject. When administered sequentially, the agents can be administered within 1, 5, 10, 30, 60, 120, 180, 240 minutes or longer of one another. In other embodiments, agents administered sequentially, can be administered within 1, 5, 10, 15, 20 or more days of one another. Where the compound of Formula (Ia) or Formula (II) and one or more therapeutic agents are administered simultaneously, they can be administered to the cell or administered to the subject as separate pharmaceutical compositions, each comprising either a compound of Formula (Ia) or Formula (II) or one or more therapeutic agents, or they can contact the cell as a single composition or be administered to a subject as a single pharmaceutical composition comprising both agents.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times. In such combination therapies, the therapeutic effect of the first administered compound is not diminished by the sequential, simultaneous or separate administration of the subsequent compound(s).

A compound of Formula (Ia) or Formula (II) can be used in therapy in combination with one or more other compounds used to treat a neurodegenerative disease, disorder, or condition. For example, a compound of Formula (Ia) or Formula (II) can be co-administered in combination with one or more other compounds, for example, at a ratio in the range of 1:1-1:5-5:1, 1:1-1:10-10:1, 1:1-1:25-25:1, 1:1-1:100-100:1, 1:1-1:1000-1000:1 or 1:1-1:10,000-10,000:1, and the like.

The presently disclosed compounds of Formula (Ia) or Formula (II) can be optionally combined with or administered in concert with each other or other agents known to be useful in the treatment of the relevant disease, disorder, or condition. The combination therapies can involve concurrent or sequential administration, by the same or different routes, as determined to be appropriate by those of skill in the art. The presently disclosed subject matter also includes pharmaceutical compositions and kits including combinations as described herein.

In other embodiments, the presently disclosed subject matter includes a combination therapy of administering a compound of Formula (Ia) or Formula (II) in combination with surgery, e.g., surgical relief of intraocular pressure, e.g., via trabeculectomy, laser trabeculoplasty, or drainage implants, and the like.

F. Dosage and Mode of Administration

The presently disclosed pharmaceutical compositions can be administered using a variety of methods known in the art depending on the subject and the particular disease, disorder, or condition being treated. The administering can be carried out by, for example, intravenous infusion; injection by intravenous, intraperitoneal, intracerebral, intramuscular, intraocular, intraarterial or intralesional routes; or topical or ocular application.

More particularly, as described herein, the presently disclosed compounds can be administered to a subject for therapy by any suitable route of administration, including orally, nasally, transmucosally, ocularly, rectally, intravaginally, parenterally, including intramuscular, subcutaneous, intramedullary injections, as well as intrathecal, direct intraventricular, intravenous, intra-articullar, intra-sternal, intra-synovial, intra-hepatic, intralesional, intracranial, intraperitoneal, intranasal, or intraocular injections, intracisternally, topically, as by powders, ointments or drops (including eyedrops), including buccally and sublingually, transdermally, through an inhalation spray, or other modes of delivery known in the art. For example, for ocular administration, an eyedrop formulation can include an effective concentration of a compound of Formula (Ia) or Formula (II) together with other components, such as buffers, wetting agents and the like. Intravitreal injection also may be employed to administer a presently disclosed compound to the eye.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

The phrases "parenteral administration" and "administered parenterally" as used herein mean modes of administration other than enteral and topical administration, usually by injection, and includes, without limitation, intravenous, intramuscular, intarterial, intrathecal, intracapsular, intraorbital, intraocular, intracardiac, intradermal, intraperitoneal, transtracheal, subcutaneous, subcuticular, intraarticular, subcapsular, subarachnoid, intraspinal and intrasternal injection and infusion.

For intracerebral use, the compounds can be administered continuously by infusion into the fluid reservoirs of the CNS, although bolus injection may be acceptable. The presently disclosed compounds can be administered into the ventricles of the brain or otherwise introduced into the CNS or spinal fluid. Administration can be performed by use of an indwelling catheter and a continuous administration means such as a pump, or it can be administered by implantation, e.g., intracerebral implantation of a sustained-release vehicle. More specifically, the presently disclosed compounds can be injected through chronically implanted cannulas or chronically infused with the help of osmotic minipumps. Subcutaneous pumps are available that deliver proteins through a small tubing to the cerebral ventricles. Highly sophisticated pumps can be refilled through the skin and their delivery rate can be set without surgical intervention. Examples of suitable administration protocols and delivery systems involving a subcutaneous pump device or continuous intracerebroventricular infusion through a totally implanted drug delivery system are those used for the administration of dopamine, dopamine agonists, and cholinergic agonists to Alzheimer's disease patients and animal models for Parkinson's disease, as described by Harbaugh, J. Neural Transm. Suppl. 24:271, 1987; and DeYebenes et al., Mov. Disord. 2: 143, 1987.

The presently disclosed pharmaceutical compositions can be manufactured in a manner known in the art, e.g. by means of conventional mixing, dissolving, granulating, drageemaking, levitating, emulsifying, encapsulating, entrapping or lyophilizing processes.

More particularly, pharmaceutical compositions for oral use can be obtained through combination of active compounds with a solid excipient, optionally grinding a resulting mixture, and processing the mixture of granules, after adding suitable auxiliaries, if desired, to obtain tablets or dragee cores. Suitable excipients include, but are not limited to, carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethyl cellulose; and gums including arabic and tragacanth; and proteins, such as gelatin and collagen; and polyvinylpyrrolidone (PVP:povidone). If desired, disintegrating or solubilizing agents, such as cross-linked polyvinyl pyrrolidone, agar, alginic acid, or a salt thereof, such as sodium alginate, also can be added to the compositions.

Dragee cores are provided with suitable coatings, such as concentrated sugar solutions, which also can contain gum arabic, talc, polyvinylpyrrolidone, carbopol gel, polyethylene glycol (PEG), and/or titanium dioxide, lacquer solutions, and suitable organic solvents or solvent mixtures. Dyestuffs or pigments can be added to the tablets or dragee coatings for product identification or to characterize the quantity of active compound, e.g., dosage, or different combinations of active compound doses.

Pharmaceutical compositions suitable for oral administration include push-fit capsules made of gelatin, as well as soft, sealed capsules made of gelatin and a coating, e.g., a plasticizer, such as glycerol or sorbitol. The push-fit capsules can contain active ingredients admixed with a filler or binder, such as lactose or starches, lubricants, such as talc or magnesium stearate, and, optionally, stabilizers. In soft capsules, the active compounds can be dissolved or suspended in suitable liquids, such as fatty oils, liquid paraffin, or liquid polyethylene glycols (PEGs), with or without stabilizers. Stabilizers can be added as warranted.

In some embodiments, the presently disclosed pharmaceutical compositions can be administered by rechargeable or biodegradable devices. For example, a variety of slow-release polymeric devices have been developed and tested in vivo for the controlled delivery of drugs, including proteinacious biopharmaceuticals. Suitable examples of sustained release preparations include semipermeable polymer matrices in the form of shaped articles, e.g., films or microcapsules. Sustained release matrices include polyesters, hydrogels, polylactides (U.S. Pat. No. 3,773,919; EP 58,481), copolymers of L-glutamic acid and gamma ethyl-L-glutamate (Sidman et al., Biopolymers 22:547, 1983), poly (2-hydroxyethyl-methacrylate) (Langer et al., J. Biomed. Mater. Res. 15:167, 1981; Langer, Chem. Tech. 12:98, 1982), ethylene vinyl acetate (Langer et al., Id), or poly-D-(−)-3-hydroxybutyric acid (EP 133,988A). Sustained release compositions also include liposomally entrapped compounds, which can be prepared by methods known per se (Epstein et al., Proc. Natl. Acad. Sci. U.S.A. 82:3688, 1985; Hwang et al., Proc. Natl. Acad. Sci. U.S.A. 77:4030, 1980; U.S. Pat. Nos. 4,485,045 and 4,544,545; and EP 102,324A). Ordinarily, the liposomes are of the small (about 200-800 Angstroms) unilamelar type in which the lipid content is greater than about 30 mol % cholesterol, the selected proportion being adjusted for the optimal therapy. Such materials can comprise an implant, for example, for sustained release of the presently disclosed compounds, which, in some embodiments, can be implanted at a particular, pre-determined target site.

Pharmaceutical compositions for parenteral administration include aqueous solutions of active compounds. For injection, the presently disclosed pharmaceutical compositions can be formulated in aqueous solutions, for example, in some embodiments, in physiologically compatible buffers, such as Hank's solution, Ringer' solution, or physiologically buffered saline. Aqueous injection suspensions can contain substances that increase the viscosity of the suspension, such as sodium carboxymethyl cellulose, sorbitol, or dextran. Additionally, suspensions of the active compounds or vehicles include fatty oils, such as sesame oil, or synthetic fatty acid esters, such as ethyl oleate or triglycerides, or liposomes. Optionally, the suspension also can contain suitable stabilizers or agents that increase the solubility of the compounds to allow for the preparation of highly concentrated solutions.

For nasal or transmucosal administration generally, penetrants appropriate to the particular barrier to be permeated are used in the formulation. Such penetrants are generally known in the art.

For inhalation delivery, the agents of the disclosure also can be formulated by methods known to those of skill in the art, and may include, for example, but not limited to, examples of solubilizing, diluting, or dispersing substances such as, saline, preservatives, such as benzyl alcohol, absorption promoters, and fluorocarbons.

Additional ingredients can be added to compositions for topical administration, as long as such ingredients are pharmaceutically acceptable and not deleterious to the epithelial cells or their function. Further, such additional ingredients should not adversely affect the epithelial penetration efficiency of the composition, and should not cause deterioration in the stability of the composition. For example, fragrances, opacifiers, antioxidants, gelling agents, stabilizers, surfactants, emollients, coloring agents, preservatives, buffering agents, and the like can be present. The pH of the presently disclosed topical composition can be adjusted to a physiologically acceptable range of from about 6.0 to about 9.0 by adding buffering agents thereto such that the composition is physiologically compatible with a subject's skin.

In other embodiments, the pharmaceutical composition can be a lyophilized powder, optionally including additives, such as 1 mM-50 mM histidine, 0.1%-2% sucrose, 2%-7% mannitol at a pH range of 4.5 to 5.5 that is combined with buffer prior to use.

Regardless of the route of administration selected, the presently disclosed compounds, which may be used in a suitable hydrated form, and/or the pharmaceutical compositions are formulated into pharmaceutically acceptable dosage forms such as described below or by other conventional methods known to those of skill in the art.

The term "effective amount," as in "a therapeutically effective amount," of a therapeutic agent refers to the amount of the agent necessary to elicit the desired biological response. As will be appreciated by those of ordinary skill in this art, the effective amount of an agent may vary depending on such factors as the desired biological endpoint, the agent to be delivered, the composition of the pharmaceutical composition, the target tissue or cell, and the like. More particularly, the term "effective amount" refers to an amount sufficient to produce the desired effect, e.g., to reduce or ameliorate the severity, duration, progression, or onset of a disease, disorder, or condition (e.g., a disease, condition, or disorder related to loss of neuronal cells or cell function), or one or more symptoms thereof; prevent the advancement of a disease, disorder, or condition, cause the regression of a disease, disorder, or condition; prevent the recurrence, development, onset or progression of a symptom associated with a disease, disorder, or condition, or enhance or improve the prophylactic or therapeutic effect(s) of another therapy.

Actual dosage levels of the active ingredients in the presently disclosed pharmaceutical compositions can be varied so as to obtain an amount of the active ingredient that is effective to achieve the desired therapeutic response for a particular subject, composition, route of administration, and disease, disorder, or condition without being toxic to the subject. The selected dosage level will depend on a variety of factors including the activity of the particular compound employed, or salt thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of Formula (Ia) or Formula (II) employed in the pharmaceutical composition at levels lower than that required to achieve the desired therapeutic effect and gradually increase the dosage until the desired effect is achieved. Accordingly, the dosage range for administration will be adjusted by the physician as necessary. It will be appreciated that an amount of a compound required for achieving the desired biological may be different from the amount of compound effective for another purpose.

In general, a suitable daily dose of a compound of Formula (Ia) or Formula (II) will be that amount of the compound that is the lowest dose effective to produce a therapeutic effect. Such an effective dose will generally depend upon the factors described above. Generally, doses of the compounds of Formula (Ia) or Formula (II) will range from about 0.0001 to about 1000 mg per kilogram of body weight of the subject per day. In certain embodiments, the dosage is between about 1 µg/kg and about 500 mg/kg, more preferably between about 0.01 mg/kg and about 50 mg/kg. For example, in certain embodiments, a dose can be about 1, 5, 10, 15, 20, or 40 mg/kg/day.

If desired, the effective daily dose of the active compound can be administered as two, three, four, five, six or more sub-doses administered separately at appropriate intervals throughout the day, optionally, in unit dosage forms.

G. Kits or Pharmaceutical Systems

The presently disclosed compounds and compositions can be assembled into kits or pharmaceutical systems for use in treating or preventing neurodegenerative diseases, disorders, or conditions. In some embodiments, the presently disclosed kits or pharmaceutical systems include a compound of Formula (Ia) or Formula (II), or pharmaceutically acceptable salts thereof. In particular embodiments, the compounds of Formula (Ia) or Formula (II), or a pharmaceutically acceptable salt thereof, are in unit dosage form. In further embodiments, the compound of Formula (Ia) or Formula (II), or a pharmaceutically acceptable salt, can be present together with a pharmaceutically acceptable solvent, carrier, excipient, or the like, as described herein.

In some embodiments, the presently disclosed kits comprise one or more containers, including, but not limited to a vial, tube, ampule, bottle and the like, for containing the compound. The one or more containers also can be carried within a suitable carrier, such as a box, carton, tube or the like. Such containers can be made of plastic, glass, laminated paper, metal foil, or other materials suitable for holding medicaments.

In some embodiments, the container can hold a composition that is by itself or when combined with another composition effective for treating or preventing the condition and may have a sterile access port (for example the container may be an intravenous solution bag or a vial having a stopper pierceable by a hypodermic injection needle). Alternatively, or additionally, the article of manufacture may further include a second (or third) container including a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The presently disclosed kits or pharmaceutical systems also can include associated instructions for using the compounds for treating or preventing a neurodegenerative disease, disorder, or condition. In some embodiments, the instructions include one or more of the following: a description of the active compound; a dosage schedule and administration for treating or preventing a neurodegenerative disease, disorder, or condition; precautions; warnings; indications; counter-indications; overdosage information; adverse reactions; animal pharmacology; clinical studies; and references. The instructions can be printed directly on a container (when present), as a label applied to the container, as a separate sheet, pamphlet, card, or folder supplied in or with the container.

H. Chemical Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to compounds of Formula (I) or Formula (II) are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted, for example, with fluorine at one or more positions).

Where substituent groups or linking groups are specified by their conventional chemical formulae, written from left to right, they equally encompass the chemically identical substituents that would result from writing the structure from right to left, e.g., —CH$_2$O— is equivalent to —OCH$_2$—; —C(=O)O— is equivalent to —OC(=O)—; —OC(=O)NR— is equivalent to —NRC(=O)O—, and the like.

When the term "independently selected" is used, the substituents being referred to (e.g., R groups, such as groups R$_1$, R$_2$, and the like, or variables, such as "m" and "n"), can be identical or different. For example, both R$_1$ and R$_2$ can be substituted alkyls, or R$_1$ can be hydrogen and R$_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, iso-propyl, cyclopropyl, allyl, vinyl, n-butyl, tert-butyl, ethynyl, cyclohexyl, methoxy, diethylamino, and the like.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., C$_1$-C$_{10}$ means one to ten carbons). In particular embodiments, the term "alkyl" refers to C$_{1-20}$ inclusive, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, iso-pentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a C$_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to C$_{1-8}$ straight-chain alkyls. In other embodiments, "alkyl" refers, in particular, to C$_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "heteroalkyl," by itself or in combination with another term, means, unless otherwise stated, a stable straight or branched chain, or cyclic hydrocarbon group, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_{2S}$—S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH₂—NH—OCH₃ and —CH₂—O—Si(CH₃)₃.

As described above, heteroalkyl groups, as used herein, include those groups that are attached to the remainder of the molecule through a heteroatom, such as —C(O)R', —C(O)NR', —NR'R", —OR', —SR, and/or —SO₂R'. Where "heteroalkyl" is recited, followed by recitations of specific heteroalkyl groups, such as —NR'R or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl, and fused ring systems, such as dihydro- and tetrahydronaphthalene, and the like.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of nitrogen (N), oxygen (O), sulfur (S), phosphorus (P), and silicon (Si), and optionally can include one or more double bonds.

The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocyclic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl."

More particularly, the term "alkenyl" as used herein refers to a monovalent group derived from a $C_{1-20}$ inclusive straight or branched hydrocarbon moiety having at least one carbon-carbon double bond by the removal of a single hydrogen atom. Alkenyl groups include, for example, ethenyl (i.e., vinyl), propenyl, butenyl, 1-methyl-2-buten-1-yl, pentenyl, hexenyl, octenyl, and butadienyl.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched $C_{1-20}$ hydrocarbon of a designed number of carbon atoms containing at least one carbon-carbon triple bond. Examples of "alkynyl" include ethynyl, 2-propynyl (propargyl), 1-propynyl, pentynyl, hexynyl, heptynyl, and allenyl groups, and the like.

The term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—CH₂—); ethylene (—CH₂—CH₂—); propylene (—(CH₂)₃—); cyclohexylene (—C₆H₁₀—); —CH=CH—CH=CH—; CH=CH—CH₂—; —CH₂CH₂CH₂CH₂—, —CH₂CH=CHCH₂—, —CH₂CsCCH₂—, —CH₂CH₂CH (CH₂CH₂CH₃)C H₂—, —(CH₂)$_q$—N(R)—(CH₂)$_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxy (—O—CH₂—O—); and ethylenedioxyl (—O—(CH$_2$)$_2$—O—). An alkylene group can have about 2 to about 3 carbon atoms and can further have 6-20 carbons. Typically, an alkyl (or alkylene) group will have from 1 to 24 carbon atoms, with those groups having 10 or fewer carbon atoms being some embodiments of the present disclosure. A "lower alkyl" or "lower alkylene" is a shorter chain alkyl or alkylene group, generally having eight or fewer carbon atoms.

The term "heteroalkylene" by itself or as part of another substituent means a divalent group derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—, The term "aryl" means, unless otherwise stated, an aromatic hydrocarbon substituent that can be a single ring or multiple rings (such as from 1 to 3 rings), which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent forms of aryl and heteroaryl, respectively.

For brevity, the term "aryl" when used in combination with other terms (e.g., aryloxo, arylthioxo, arylalkyl) includes both aryl and heteroaryl rings as defined above. Thus, the terms "arylalkyl" and "heteroarylalkyl" are meant to include those groups in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g. "3 to 7 membered"), the term "member" refers to a carbon or heteroatom.

Further, a structure represented generally by the formula:

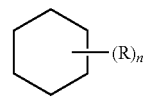

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

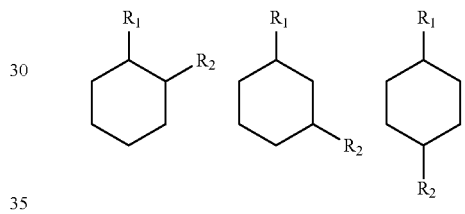

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

The symbol ⌇ denotes the point of attachment of a moiety to the remainder of the molecule.

When a named atom of an aromatic ring or a heterocyclic aromatic ring is defined as being "absent," the named atom is replaced by a direct bond.

Each of above terms (e.g., "alkyl," "heteroalkyl," "cycloalkyl, and "heterocycloalkyl", "aryl," "heteroaryl," "phosphonate," and "sulfonate" as well as their divalent derivatives) are meant to include both substituted and unsubstituted forms of the indicated group. Optional substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R''', —OC(O)R', —C(O)R', —CO$_2$R', —C(O)NR'R", —OC(O)NR'R", —NR"C(O)R', —NR'—C(O)NR"R''', —NR"C(O)OR', —NR—C(NR'R")=NR''', —S(O)R', —S(O)$_2$R', —S(O)$_2$NR'R", —NRSO$_2$R', —CN and —NO$_2$ in a number ranging from zero to (2m'+1), where m' is the total number of carbon atoms in such groups. R', R'', R''' and R'''' each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen. When a compound of the disclosure includes more than one R group, for example, each of the R groups is independently selected as are each R', R'', R''' and R'''' groups when more than one of these groups is present. When R' and R'' are attached to the same nitrogen atom, they can be combined with the nitrogen atom to form a 4-, 5-, 6-, or 7-membered ring. For example, —NR'R'' is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for alkyl groups above, exemplary substituents for aryl and heteroaryl groups (as well as their divalent derivatives) are varied and are selected from, for example: halogen, —OR', —NR'R'', —SR', -halogen, —SiR'R''R''', —OC(O)R', —C(O)R', —CO$_2$R', —C(O)NR'R'', —OC(O)NR'R'', —NR''C(O)R', —NR'—C(O)NR''R''', —NR''C(O)OR', —NR—C(NR'R''R''')=NR'''', —NR—C(NR'R'')=NR'''—S(O)R', —S(O)$_2$R', —S(O)$_2$NR'R'', —NRSO$_2$R', —CN and —NO$_2$, —R', —N$_3$, —CH(Ph)$_2$, fluoro(C$_1$-C$_4$)alkoxo, and fluoro (C$_1$-C$_4$)alkyl, in a number ranging from zero to the total number of open valences on aromatic ring system; and where R', R'', R''' and R'''' may be independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R'', R''' and R'''' groups when more than one of these groups is present.

Two of the substituents on adjacent atoms of aryl or heteroaryl ring may optionally form a ring of the formula —T—C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula —A—(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4.

One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C''R''')$_d$—, where s and d are independently integers of from 0 to 3, and X' is —O—, —NR'—, —S—, —S(O)—, —S(O)$_2$—, or —S(O)$_2$NR'—. The substituents R, R', R'' and R''' may be independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "acyl" refers to an organic acid group wherein the —OH of the carboxyl group has been replaced with another substituent and has the general formula RC(=O)—, wherein R is an alkyl, alkenyl, alkynyl, aryl, carbocylic, heterocyclic, or aromatic heterocyclic group as defined herein). As such, the term "acyl" specifically includes arylacyl groups, such as an acetylfuran and a phenacyl group. Specific examples of acyl groups include acetyl and benzoyl.

The terms "alkoxyl" or "alkoxy" are used interchangeably herein and refer to a saturated (i.e., alkyl—O—) or unsaturated (i.e., alkenyl—O— and alkynyl—O—) group attached to the parent molecular moiety through an oxygen atom, wherein the terms "alkyl," "alkenyl," and "alkynyl" are as previously described and can include C$_{1-20}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, t-butoxyl, and n-pentoxyl, neopentoxyl, n-hexoxyl, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an amide group of the formula —CONH$_2$. "Alkylcarbamoyl" refers to a R'RN—CO— group wherein one of R and R' is hydrogen and the other of R and R' is alkyl and/or substituted alkyl as previously described. "Dialkylcarbamoyl" refers to a R'RN'CO' group wherein each of R and R' is independently alkyl and/or substituted alkyl as previously described.

The term carbonyldioxyl, as used herein, refers to a carbonate group of the formula —O—CO—OR.

"Acyloxyl" refers to an acyl-O— group wherein acyl is as previously described. The term "amino" refers to the —NH$_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R", wherein R' and R" are each independently selected from the group consisting of alkyl groups. The term trialkylamino refers to a group having the structure —NR'R"R'", wherein R', R", and R'" are each independently selected from the group consisting of alkyl groups. Additionally, R', R", and/or R'" taken together may optionally be —$(CH_2)_k$— where k is an integer from 2 to 6. Examples include, but are not limited to, methylamino, dimethylamino, ethylamino, diethylamino, diethylaminocarbonyl, methylethylamino, iso-propylamino, piperidino, trimethylamino, and propylamino.

The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —(C═O)— group.

The term "carboxyl" refers to the —COOH group. Such groups also are referred to herein as a "carboxylic acid" moiety.

The terms "halo," "halide," or "halogen" as used herein refer to fluoro, chloro, bromo, and iodo groups. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "hydroxyl" refers to the —OH group.

The term "hydroxyalkyl" refers to an alkyl group substituted with an —OH group.

The term "mercapto" refers to the —SH group.

The term "oxo" as used herein means an oxygen atom that is double bonded to a carbon atom or to another element.

The term "nitro" refers to the —$NO_2$ group.

The term "thio" refers to a compound described previously herein wherein a carbon or oxygen atom is replaced by a sulfur atom.

The term "sulfate" refers to the —$SO_4$ group.

The term "sulfonate" refers to the —$OSO_2$—R group.

The term thiohydroxyl or thiol, as used herein, refers to a group of the formula —SH.

The term ureido refers to a urea group of the formula —NH—CO—$NH_2$.

Unless otherwise explicitly defined, a "substituent group," as used herein, includes a functional group selected from one or more of the following moieties, which are defined herein:

(A) —OH, —$NH_2$, —SH, —CN, —$CF_3$, —$NO_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "lower substituent" or "lower substituent group," as used herein means a group selected from all of the substituents described hereinabove for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

A "size-limited substituent" or "size-limited substituent group," as used herein means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

Throughout the specification and claims, a given chemical formula or name shall encompass all tautomers, congeners, and optical- and stereoisomers, as well as racemic mixtures where such isomers and mixtures exist.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those which are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefenic bonds or other centers of geometric asymmetry, and unless specified otherwise, it is intended that the compounds include both E and Z geometric isomers.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C-$ or $^{14}C$-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium ($^{3}H$), iodine-125 ($^{125}I$) or carbon-14 ($^{14}C$). All isotopic variations of the compounds of the present disclosure, whether radioactive or not, are encompassed within the scope of the present disclosure.

The term "protecting group" refers to chemical moieties that block some or all reactive moieties of a compound and prevent such moieties from participating in chemical reactions until the protective group is removed, for example, those moieties listed and described in T. W. Greene, P. G. M. Wuts, Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, without limitation, methyl, ethyl, and acetyl in the presence of amines blocked with acid labile groups such as tert-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(O)— catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups include, but are not limited to the following moieties:

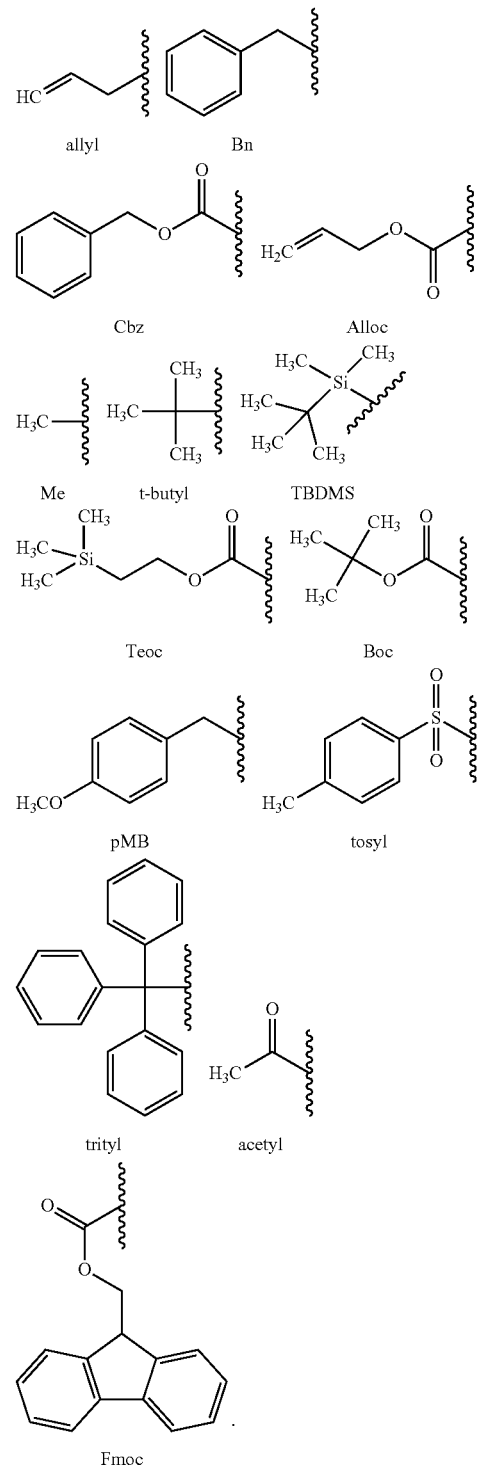

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Methods

GST-LSD1 Enzymatic Assays. GST-LSD1 production from an *E. coli* expression system followed by purification using glutathione affinity chromatography were performed as previously described. Zhang, Y. Z., et al. (2010), Szewczuk, L. M., et al. (2007). Rate measurements were performed using a peroxidase-coupled assay as previously described. Forneris, F., et al. (2005). To determine LSD1 activity, 100 µL reactions were initiated by the addition of 2 µL of GST-LSD1 (to obtain 96-154 nM GST-LSD1 final concentration) to reaction mixtures consisting of 50 mM HEPES buffer (pH 7.5), 0.1 mM 4-aminoantipyrine, 1 mM 3,5-dichloro-2-hydroxybenzenesulfonic acid, 0.04 mg/mL horseradish peroxidase (Worthington Biochemical Corporation), and appropriate concentration of buffered substrate (dimethyl-Lys-4 $H_3$-21, ARTKme2QTARKSTGGKAPRKQLA, synthesized and purified as described previously. Culhane, J. C., et al. (2006)). Absorbance changes were measured at 515 nm using a Beckman Instruments DU series 600 spectrophotometer equipped with a thermostatted cell holder (T=25° C.), and product formation was calculated using the extinction coefficient of 26,000 $M^{-1}$. Under these conditions, GST-LSD1 displayed a $k_{cat}$ of approximately 3 $min^{-1}$ and a $K_m$ for dimethyl-Lys-4 H3-21 of approximately 40 µM, but the specific parameters were measured for each batch and used for inhibitor parameter calculations. For inhibition studies, phenelzine analog compounds were dissolved in dimethylsulfoxide (DMSO) to make 5 mM stock solutions that were diluted into reactions at appropriate concentrations. Reactions were run at similar conditions as previously stated with 60-300 µM dimethyl-Lys-4 H3-21 substrate. Progress curves conducted for 20 min were then fit to the following eq 1:

$$\text{Product} = (v_o/k_{obs})(1 - e^{-k^{obs}t}) \quad \text{eq. 1}$$

The Kitz and Wilson method was then used to analyze the $k_{obs}$ values to obtain $k_{inact}$ and $K_{i(inact)}$ values with the following eq 2:

$$k_{obs} = (k_{inact} * [I])/(K_{i(inact)} + [I]) \quad \text{eq. 2}$$

The following Cheng-Prusoff equation, eq 3, was then used to a extrapolate the $K_{i(inact)}$ value to zero substrate:

$$K_i^{app} = K_i * (1 + S/K_m) \quad \text{eq. 3}$$

Each experiment was repeated at least two independent times and repeat measured values were typically within 20% of each other.

MAO-A/B Activity and Inhibition Assays. MAO-A was purchased from Sigma (product number: M 7316). MAO-B was purchased from Sigma (product number: M 7441). MAO-A/B activity was measured spectrophotometrically using a peroxidase-coupled assay as previously described. Forneris, F., et al. (2005). 100 µL reactions were initiated by the addition of 2 µL of MAO-A/B (to obtain 100-200 nM final concentration for MAO-A and 0.837 µM final concentration for MAO-B) to reaction mixtures consisting of 50 mM HEPES buffer (pH 7.5), 0.1 mM 4-aminoantipyrine, 1 mM 3,5-dichloro-2-hydroxybenzenesulfonic acid, 0.04 mg/mL horseradish peroxidase (Worthington Biochemical Corporation), and appropriate concentration of buffered substrate (tyramine). Absorbance changes were measured at 515 nm using a Beckman Instruments DU series 600 spectrophotometer equipped with a thermostatted cell holder (T=25° C.), and product formation was calculated using the extinction coefficient of 26,000 $M^{-1}$.

Under these conditions, MAO-A displayed a $k_{cat}$ of 3±0.1 $min^{-1}$ and a $K_m$ for tyramine of 26±3 µM. MAO-B displayed a $k_{cat}$ of 0.2±0.02 min−1 and a $K_m$ for tyramine of 94±26.0 µM. For inhibitor studies, phenelzine analog compounds were dissolved in dimethylsulfoxide (DMSO) to make 5 mM stock solutions that were diluted into reactions at appropriate concentrations. Reactions were run at similar conditions as previously stated with 125 µM tyramine substrate for MAO-A and with 125-1,000 µM tyramine substrate for MAO-B. Progress curves were then fit accordingly to eqs 1-3 as previously stated. Each experiment was repeated at least two independent times and repeat measured values were typically within 20% of each other.

Cell Culture. LNCaP, H460, and A549 cells were maintained in RPMI 1640+GlutaMAX (Invitrogen 61870-036) supplemented with 10% fetal bovine serum (FBS, Gibco 10437-028) and 1 unit/mL penicillin, 1 µg/mL streptomycin (Gibco 15140-122). MB-231 cells were maintained in DMEM (Gibco 11965) supplemented with 10% FBS and 1 unit/mL penicillin, 1 µg/mL streptomycin, and 292 µg/mL L-glutamine (Corning 30-009-C1). All cells were grown at 37° C. in 5%/95% $CO_2$/air.

Western Blot. Cells were seeded in 150×25 mm plastic tissue culture dishes (Corning 430599). Cells were treated at approximately 70% confluency with phenelzine analogs (>97% purity as determined by NMR) or vehicle in serum-free media for 48 h. Whole-cell extracts were isolated using RIPA buffer (Sigma R0278) and 1×protease inhibitor cocktail (Roche, 11836170001). Histone extracts were isolated as described previously. Shechter, D., et al. (2007). Concentration of whole cell lysates and histone extracts were determined using a Micro BCA Protein Assay Kit (Thermo Scientific, #23235). Proteins were resolved by 10-12% NuPAGE Novex Bis-Tris gels (Invitrogen) and transferred to nitrocellulose membranes (Invitrogen) by iBlot. Data are presented from one representative experiment. Each experiment was repeated at least three independent times with nearly identical results.

Oxidative Toxicity and Neuron Viability Assays. Immature primary cortical neurons were obtained from fetal Sprague Dawley rats at embryonic day 17 (E17) as previously described, Ratan, R. R., et al. (1994), and plated at a density of 106 cells/mL in 96-well plates for the viability experiments. The next day cells were rinsed and then placed in medium containing 5 mM HCA. In the dose-curve experiments, increasing concentrations of 12d (bizine) (>97% purity as determined by NMR) or phenelzine were added at the time of homocysteic acid (HCA) treatment. The next day, cell viability was assessed by the MTT assay (Promega). Mosmann, T. (1983). The two-way ANOVA followed by the Bonferroni posttest was used to measure statistical significance. p<0.05 was considered to be statistically significant. Each bar represents four different rat cultures. The use of animals and procedures were approved by the Institutional Animal Care and Use Committees of Weill Medical College of Cornell University.

Example 2

Results and Discussion

A series of phenelzine analogs were synthesized exploring hydrazine modifications, variations in alkyl chain length and rigidity, phenyl replacement, and phenyl ring substitution (compounds 9-15, FIG. 2). Synthetic routes generally involved late stage hydrazine introduction by converting a terminal alkyl hydroxy group to either the corresponding bromide or mesylate followed by hydrazine displacement reactions as exemplified in FIG. 3 (additional detailed routes are shown in FIGS. 8-11). Compounds were assayed for their ability to inhibit recombinantly purified GST-LSD1 using a dimethyl-Lys4 histone H3-21mer peptide substrate by monitoring peroxide formation via a colorimetric peroxidase assay. Holt, A., et al. (1997).

TABLE 1

Kinetics of phenelzine analog LSD1 inhibitors.

| Inhibitor | $K_{i(inact)}$ (µm) | $k_{(inact)}$ (min$^{-1}$) | $k_{(inact)}/K_{i(inact)}$ (µM$^{-1}$min$^{-1}$) | $IC_{50}$ (µM) |
|---|---|---|---|---|
| phenelzine | 5.6 ± 1.3 | 0.35 ± 0.056 | 0.063 ± 0.018 | N/A |
| 9a | N/A | N/A | N/A | 85.00 |
| 9b | N/A | N/A | N/A | >100.0 |
| 9c | 5.0 ± 1.1 | 0.32 ± 0.010 | 0.064 ± 0.014 | N/A |
| 9d | N/A | N/A | N/A | 46.74 |
| 9e | 8.0 ± 3.5 | 0.15 ± 0.023 | 0.019 ± 0.0087 | N/A |
| 9f | N/A | N/A | N/A | >100.0 |
| 9g | N/A | N/A | N/A | N/A |
| 9h | 22 ± 3.0 | 0.12 ± 0.01 | 0.0055 ± 0.00087 | N/A |
| 10a | 44 ± 9.7 | 0.15 ± 0.010 | 0.0034 ± 0.00079 | N/A |
| 10b | 12 ± 2.1 | 0.22 ± 0.020 | 0.018 ± 0.0036 | N/A |
| 11 | N/A | N/A | N/A | >100.0 |
| 12a | 0.28 ± 0.11 | 0.19 ± 0.036 | 0.70 ± 0.31 | N/A |
| 12b | 0.37 ± 0.033 | 0.20 ± 0.0087 | 0.54 ± 0.054 | N/A |
| 12c | 0.26 ± 0.058 | 0.24 ± 0.022 | 0.92 ± 0.22 | N/A |
| 12d | 0.059 ± 0.021 | 0.15 ± 0.017 | 2.5 ± 0.96 | N/A |
| 12e | 0.26 ± 0.11 | 0.22 ± 0.038 | 0.86 ± 0.39 | N/A |
| 12f | 0.156 ± 0.047 | 0.17 ± 0.018 | 1.1 ± 0.35 | N/A |
| 12g | 0.138 ± 0.0.48 | 0.17 ± 0.020 | 1.2 ± 0.44 | N/A |
| 12h | 0.207 ± 0.089 | 0.26 ± 0.042 | 1.2 ± 0.57 | N/A |
| 12i | 0.282 ± 0.076 | 0.21 ± 0.024 | 0.74 ± 0.22 | N/A |
| 12j | 0.204 ± 0.098 | 0.18 ± 0.034 | 0.88 ± 0.46 | N/A |
| 12k | 0.223 ± 0.064 | 0.17 ± 0.020 | 0.76 ± 0.24 | N/A |
| 12l | 2.0 ± 0.73 | 0.24 ± 0.033 | 0.12 ± 0.045 | N/A |
| 12m | 1.6 ± 0.49 | 0.22 ± 0.025 | 0.14 ± 0.044 | N/A |
| 13 | 0.10 ± 0.039 | 0.17 ± 0.21 | 1.7 ± 0.68 | N/A |
| 14 | 0.90 ± 0.45 | 0.18 ± 0.038 | 0.20 ± 0.11 | N/A |
| 15a | 0.21 ± 0.076 | 0.21 ± 0.030 | 1.0 ± 0.41 | N/A |
| 15b | 0.10 ± 0.035 | 0.17 ± 0.019 | 1.7 ± 0.60 | N/A |

These results (Table 1) showed that adjusting the alkyl chain length (9c, 9h, 10a-b) could lead to modest increases or decreases in LSD1 inhibitory potency compared with phenelzine ($K_{i(inact)}$ 5.6 µM, $k_{(inact)}$ 0.35 min$^{-1}$) (FIG. 12), whereas methyl or acetyl substitutions on the hydrazine (9a, b, d, f, g) negated LSD1 inhibitory action. Additionally, morpholine replacement of the phenyl ring (11) was not compatible with LSD1 inhibition. Furthermore, incorporation of a methoxy substituent at the 4-position of the phenyl ring of phenelzine made little difference (9e).

In contrast, LSD1 inhibitory potency enhancements were achieved by linking aryl groups through various tethers to the phenelzine scaffold (12-15). This trend was loosely related to the previously reported results with tranylcypromine analog 5. Binda, C., et al. (2010). Compounds 12a-e showed that amino-phenelzine fused to phenylalkanoic acids via an amide spacer were improved LSD1 inhibitors compared to phenelzine itself. Of this set, compound 12d containing the propanyl spacer was the most potent LSD1 inhibitor with a k(inact) of 0.15 min$^{-1}$ and a Ki(inact) of 59 nM (FIG. 4A-B).

Alternatives to the alkanoic spacers in 12 including an alkenoic acid spacer (13) and an alkyl ether spacer (14) led to reduced LSD1 inhibitory potency. Replacing the ethanyl tether with a trans-ethenyl group, however, resulted in improved inhibitor potency as can be seen by comparing 12c with 13. Terminal aryl substitutions in the context of the ethanyl and the propanyl spacer represented in 12f-k generally had similar LSD1 potency as that of 12d, suggesting that substitutions at this position are well tolerated. Of note, N-substitution of the amide linker attachment present in 12l-m greatly attenuated LSD1 inhibition relative to 12d, potentially highlighting the importance of the amide NH group in hydrogen bonding to the LSD1 active site. Interestingly, replacement of the terminal phenyl group in 12c-d with an indole group to generate 15a-b largely preserved LSD1 inhibitory potency.

Figure 5A:
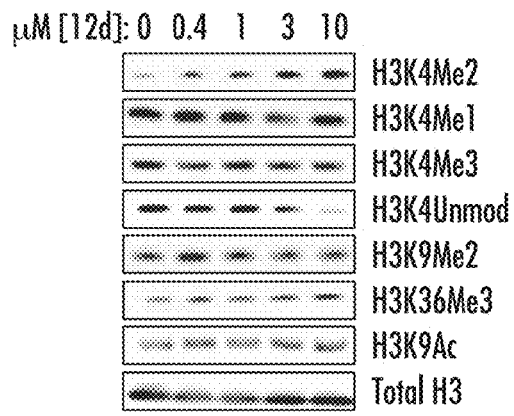
Figure 5B:
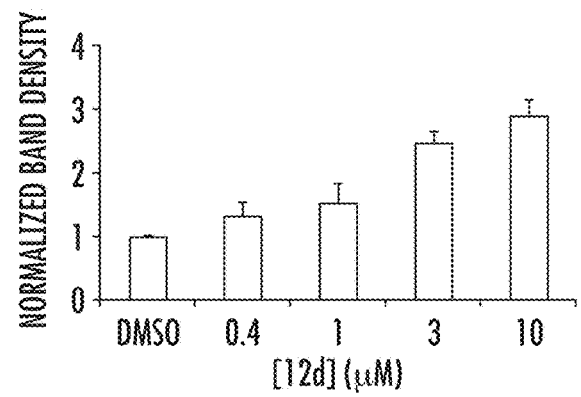
Figure 5C:
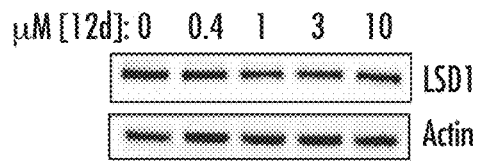
Figure 5D:
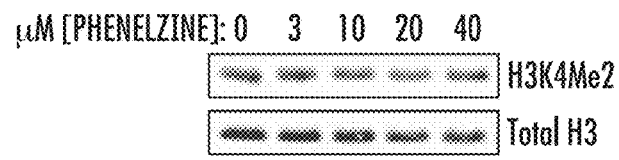

To confirm the LSD1 inhibition peroxidase assay results obtained with 12d, we turned to a recently developed isotope-based mass spectrometric assay, MassSQUIRM, to directly and quantitatively assess 12d effects on Lys4-methylation. Blair, L. P., (2011). This assay is conducted for an extended time period utilizing a high LSD1 concentration, with conditions where LSD1-catalyzed demethylation of the H3-21-K4Me2 substrate nears completion, resulting in extensive conversion of the substrate to mono- and unmethylated H3-21. As reported previously, greater than 10 mM phenelzine is needed to extinguish LSD1 activity under MassSQUIRM conditions. Blair, L. P., (2011). Thus, 50 µM each of phenelzine and analog 12d were compared in an identical LSD1 inhibition MassSQUIRM assay. Results showed that 50 µM phenelzine had a negligible impact on LSD1 inhibition, whereas the same concentration of 12d led to very substantial LSD1 inhibition, with the unreacted dimethyl-peptide remaining as the major species at the conclusion of the experiment (FIG. 13). These experiments corroborate the findings with the spectrophotometric peroxidase assay that showed that 12d was a far more potent LSD1 inhibitor than phenelzine. To assess the relative selectivity of 12d, counter screen enzyme assays were carried out versus MAO A, MAO B, and LSD2. Based on k(inact)/Ki(inact) measure of inactivation efficiency, 12d is 23-fold selective for inhibiting LSD1 versus MAO A, 63-fold selective versus MAO B, and >100-fold versus LSD2 (Table 2). In contrast, phenelzine preferentially inhibits MAO A and is equipotent in blocking MAO B compared with LSD1. These results support the potential utility of 12d as a selective pharmacologic probe for cellular LSD1 histone demethylase activity.

increase in cellular global H3K4Me2 levels after treatment with bizine is a primary effect that is consistent with prior studies with less selective LSD1 inhibitors and genetic LSD1 alterations. Huang, Y., et al. (2007), Binda, C., et al. (2010), Pollock, J. A., et al. (2012). In the presently disclosed experiments with LNCaP cells, however, the MAO inhibitorphenelzine, which is approximately 100-fold weaker LSD1 inhibitor than bizine, did not induce H3K4Me2 changes at concentrations up to 40 µM (FIG. 5D). This observation is consistent with the hypothesis that the Western blot effects related to bizine are mediated through LSD1 inhibition.

Figure 5E:
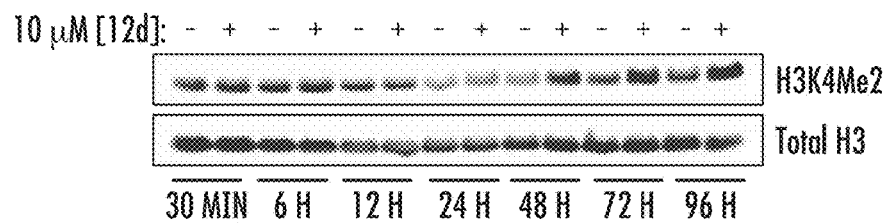
Figure 5F:
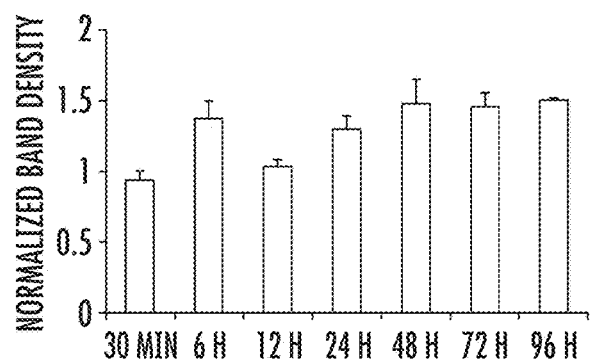

The effects of bizine on histone K4 methylation were further examined by assaying additional cancer cell lines (FIG. 14). With the lung cancer line H460, there were comparable dose-response effects of bizine on H3K4Me2 levels. The lung cancer line A549 and the breast cancer line MB-231 also showed increases in H3K4Me2 in response to bizine, but a higher concentration (20 µM) was required for reproducible effects. The kinetics of bizine effects on H3 methylation in the LNCaP cell line also were measured. This time course experiment revealed that changes in H3K4Me2 could be detected within 6 h of compound exposure and effects can be observed up to 96 h (FIG. 5E-F). There was, however, a reproducible drop in H3K4Me2 at 12 h, which suggests a somewhat complex dynamic process involving competing waves of lysine methyltransferase and demethylase action (FIG. 15). It seems that cellular turnover of H3K4-methylation, however, can be a relatively rapid process, on a time scale that is commensurate with many protein acetylation events. Su, X., et al. (2007).

To examine the effect of LSD1 inhibition on chromatin H3 Lys-methylation with individual gene resolution, a ChIP-seq experiment in was carried out in LNCaP cells treated for 48 hours with bizine. Differential peaks between samples with two biological replicates were identified by diffReps. Shen et al. (2013).

TABLE 2

Phenelzine and 12d (bizine) selectivity profile for LSD1 vs. MAO-A, MAO-B, and LSD2.

| Enzyme Tested | Inhibitor | $K_{i(inact)}$ (µM) | $k_{(inact)}$ (min$^{-1}$) | $k_{(inact)}/K_{i(inact)}$ (µM$^{-1}$min$^{-1}$) | Selectivity for LSD1 vs. Enzyme Tested |
|---|---|---|---|---|---|
| MAO-A | phenelzine | 0.82 ± 0.47 | 0.24 ± 0.057 | 0.29 ± 0.18 | 0.217 |
|  | 12d | 2.6 ± 2.3 | 0.30 ± 0.11 | 0.11 ± 0.11 | 22.7 |
| MAO-B | phenelzine | 3.9 ± 1.7 | 0.20 ± 0.040 | 0.051 ± 0.025 | 1.24 |
|  | 12d | 6.5 ± 4.6 | 0.26 ± 0.14 | 0.040 ± 0.036 | 62.5 |
| LSD2 | phenelzine | N/A | N/A | N/A | N/A |
|  | 12d | N/A | N/A | N/A | >100 |

Compound 12d Effects on Cellular H3K4 Methylation

The ability of compound 12d (hereafter referred to as "bizine") to induce bulk histone H3-Lys4 methylation was assessed using Western blots in the prostate cancer LNCaP cell line with histone H3 methylation-state specific antibodies. As can be seen, after 48 h treatment with bizine, there was a dose-dependent increase in H3K4Me2 signal (FIG. 5A-B). The EC50 of this bizine effect was approximately 2 µM. There were no significant reproducible changes in H3K4Me1, H3K4Me3, unmethylated H3K4 or other histone H3 marks examined including H3K9Me2, H3K9Ac, and H3K36Me3 (FIG. 5A). Furthermore, there was no discernible effect of bizine on LSD1 protein levels (FIG. 5C). The In total, 17,542 differential H3K4Me2 peaks were obtained between cells treated with 10 µM compound bizine versus vehicle (data not shown). Among those, 10,874 peaks were found to be unregulated (cut off p-value: p<0.0001) with LSD1 inhibition. Out of those peaks, there were 2,432 genes identified that showed an increase in H3K4Me2 with LSD1 inhibition near the genes' promoter regions (see FIG. 16). Furthermore, gene ontology (GO) analysis of these 2,432 genes revealed many processes related to LSD1 function (data not shown).

After culling the list to exclude microRNA and non-standard gene names from the 2,432 gene list, the remaining 1,767 genes were compared to the 1,587 genes identified in a ChIP-seq experiment that used an LSD1−/−hematopoietic cell line, which also analyzed H3K4Me2 increases at gene promoters. Kerenyi, M. A., et al. (2013). There were 146 genes (p-value=0.0028) that overlapped in the chemical inhibition and LSD1 knockout experiments. This result indicated the presence of a statistically significant overlap in genes affected despite the different LSD1 inhibition methods and cell lines used. GO analysis performed on the 146 genes showed that gene regulation was one of the top five statistically significant processes affected (Supplemental Table 5). Of note, many (26) (p-value=5.80E-9) of the 146 overlapped genes (data not shown) are established or proposed to be tumor suppressors, consistent with the proposal that LSD1 inhibitors might have anti-cancer applications.

Bizine Anti-Proliferation Effects

The effects of bizine on cell proliferation using a $^3$H-thymidine incorporation assay were examined as a measure of the rate of DNA synthesis. These studies revealed that bizine can slow cellular proliferation rate with an $IC_{50}$ of 14 µM and 16 µM in treated H460 and LNCaP cancer cell lines, respectively (FIGS. 6A-B). These IC50's are considerably higher than the EC50's for Western blot changes in H3K4Me2. These findings raised concerns about the mechanistic basis of the LNCaP anti-proliferative effects by bizine. To further address this issue, the impact of phenelzine on LNCaP cell proliferation was tested. There was less than a 50% reduction in $^3$H-thymidine incorporation in LNCaP cells after 48 h with 80 µM phenelzine (FIG. 17), indicating that MAO inhibition by bizine does not primarily contribute to its cell growth inhibitory effects. These experiments suggest that LSD1 inhibition by bizine likely contributes to LNCaP growth inhibition, and perhaps that nearly complete LSD1 inhibition at concentrations well above the bizine Western blot $EC_{50}$ are necessary for reducing cell growth.

As LSD1 is an enzyme implicated in gene silencing, it is plausible that LSD1 inhibitors combined with histone deacetylase (HDAC) or DNA methyltransferase (DNMT) inhibitors might result in additive or synergistic effects. This concept has been evaluated previously with LSD1 inhibitors that have low selectivity and potency, but nevertheless show additivity and synergy with various HDAC and DNMT inhibitors. Han, H., et al. (2013); Huang, Y., et al. (2012).

Bizine was examined in binary combinations with one DNMT inhibitor, azacytidine, as well as five HDAC inhibitors, SAHA, TSA, MGCD0103, MS-275, and LBH-589, using $^3$H-thymidine incorporation in LNCaP cells after 48 h treatment. The Combination Index (CI) was calculated for each inhibitor pair. Chou, T. C., and Talalay, P. (1984). Unexpectedly, four of the agents, azacytidine, SAHA, TSA, and MGCD0103, when combined with bizine, exhibited moderate antagonism, CI>1, on LNCaP cell inhibition at all ratios of the two agents examined (FIGS. 18A-F). In contrast, MS-275 and LBH-589, in combination with bizine, showed additive to synergistic effects on LNCaP cell inhibition, with the most synergy observed at the highest concentrations of compounds employed. These results reveal that in LNCaP cells, dual LSD1/HDAC inhibition may be promising, provided a suitable combination of inhibitors is identified that may reflect the precise specificities of the compounds involved.

LSD1 Inhibition and Neuroprotection

HDAC inhibition has previously been reported to protect against oxidative stress in neurons subjected to homocysteic acid (HCA) treatment, which induces glutathione depletion. Langley, B., et al., (2008); Kozikowski, A. P., et al. (2009). Accordingly, it was explored whether bizine might confer neuroprotection against HCA-induced oxidative stress. Indeed, 0.5 µM bizine led to significantly enhanced survival of neurons after HCA-treatment in a dose-dependent fashion (FIG. 7). This level of neuroprotection was comparable to the effect of 10 µM phenelzine, consistent with the greater potency of bizine versus phenelzine as an LSD1 inhibitor. These results suggest that LSD1 might serve as an attractive target to treat or protect against neurologic disease, such as stroke, which can be placed in the context of prior work that investigated LSD1 functions in the brain. Neelamegam, R., et al. (2012); Zhang, Y.-Z., et al., (2010).

Conclusion

The presently disclosed subject matter describes a potent and selective LSD1 inhibitor, bizine, derived from the MAO inhibitor, phenelzine. Structure-activity-relationships demonstrate the key roles of the hydrazine functionality, the secondary amide linker, and the second aryl group in achieving potent LSD1 inhibition. Compound bizine shows potent action in cancer cells as demonstrated by modulating histone H3K4 methylation and exhibiting moderate anti-proliferative properties. Interestingly, some HDAC inhibitors show additive to synergistic effects in combination with bizine in reducing LNCaP cell growth, whereas other HDAC inhibitors and azacytidine did not. A potentially promising direction is the application of LSD1 inhibition in neuroprotection against oxidative stress. In conclusion, it is thought that bizine should be a useful probe in the continuing functional evaluation of LSD1's demethylase activity in physiologic and pathophysiologic conditions.

Example 3

Synthesis of Representative Compounds

Overview of the Synthetic Schemes. The presently disclosed compounds were synthesized from commercially available or readily prepared starting materials. A series of compounds containing substitutions to the hydrazine moiety was prepared via reductive amination with commercially available aldehydes and either substituted or protected hydrazines. Calabretta, R., et al. (1991).

Subsequent deprotection of the hydrazine was carried out in the presence of hydrochloric acid as necessary to yield compounds 9a-b, 9d, and 9f-g, which were isolated as free bases or as dihydrochloride salts (FIG. 8). Additionally, phenelzine derivatives possessing heteroatom substitutions in the alkyl chain and variations in the overall chain length, as well as substitutions to the para position of the phenyl ring, were easily prepared in one step from commercially available starting materials (FIG. 9). Nucleophilic substitution of various alkyl bromides with excess anhydrous hydrazine resulted in the desired compounds 9c, 9e, 9h, 10a-b, and 14. Lee, Y., et al. (2001); Baraldi, P. G., et al. (1998).

Further, a series of compounds with larger hydrophobic groups attached to the para position of the phenyl ring of phenelzine was prepared (Scheme 2). Excess benzoic anhydride was treated directly with 2-(4-aminophenyl)ethanol resulting in acylation of the aryl amine and aliphatic alcohol. Alternatively, an excess amount of various phenyl alkyl substituted acids differing in alkyl linker length were converted to acid chlorides using thionyl chloride and then treated with 2-(4-aminophenyl)ethanol which yielded diacylated products similar to those obtained from the anhydride reaction. The esters were subsequently saponified with sodium hydroxide to provide the desired alcohols 16a-b and 16d. The Appel reaction was employed using triphenylphosphine and carbon tetrabromide to convert the alcohols to their respective alkyl bromides 17a-c. Then, the alkyl bromides were treated with excess anhydrous hydrazine to produce the desired final products 12a-b and 12d, which were isolated as hydrochloride salts as described in detail in the experimental section.

Additional variations in the alkyl linker and substitutions to the phenyl ring distal to the hydrazine of 12d were also explored. 4-(4-Chlorophenyl)butanoic acid and 4-(4-fluorophenyl)butanoic acid were obtained from their respective keto acids via a Wolff-Kishner reduction (Scheme 3). Carroll, F. I., et al. (2009).

Amide bond formation was achieved using standard carbodiimide coupling conditions to generate intermediate alcohols 16c, 16e-k, 18a-b, and 19 from the respective acid and 2-(4-aminophenyl)ethanol. Subsequent conversion to the mesylate, Romeiro, L. A. S., et al., (2011), followed by nucleophilic substitution with excess anhydrous hydrazine yielded the desired products which were isolated as either sulfate or oxalate salts 12c, 12e-k, 15a-b, and 13 as indicated in the experimental section (FIG. 10).

Preparation of N-substituted amides was achieved by first protecting the alcohol of 16d as a silyl ether, Walsh, T., et al. (1999), to generate common intermediate 20. Substitution of the amide nitrogen with methyl iodide or benzyl chloride using either sodium hydride, Peng, Y., et al. (2009), or potassium tert-butoxide as the base, respectively, followed by deprotection in the presence of TBAF, Davies, S., et al. (2008), resulted in the generation of intermediate alcohols 21a-b. Alcohol to hydrazine conversion was carried out as previously described and the final products were isolated as oxalate salts 12l-m (FIG. 11).

General. NMR spectra were recorded on either a Bruker 400 MHz ($^1$H, 400 MHz; $^{13}$C, 101 MHz), a Varian 400 MHz ($^1$H, 400 MHz), or a Bruker 500 MHz ($^1$H, 500 MHz; $^{13}$C, 125 MHz) spectrometer. Chemical shifts (δ) are expressed in parts per million relative to internal tetramethylsilane; coupling constants (J) are in hertz (Hz). The following abbreviations were used to describe multiplicity: br (broad), s (singlet), d (doublet), t(triplet), quin (quintet), m (multiplet), dd (double doublet), td (triple doublet), dt (double triplet). NMR spectra were processed using ACD/NMR Processor Academic Addition, version 12.01 (Advanced Chemistry Development, Inc., Toronto, Ontario, Canada, 2013). When DMSO-$d_6$ was used as the sole NMR solvent, the hydrazine protons were visible; however, the peaks were very broad and could not be accurately integrated. High resolution ESI/APCI spectra were recorded on either an Agilent LCTOF instrument at the Mass Spectrometry Facility of the University of California, Riverside (NSF grant CHE-0541848) or a Shimadzu IT-TOF instrument at the Research Resources Center Mass Spectrometry Facility of the University of Illinois at Chicago. Solvents were purchased from Aldrich as anhydrous and used as received. Starting materials and reagents were purchased from commercial sources and also were used as received. Reaction progress was monitored by thin layer chromatography (TLC) using pre-coated, glass supported silica gel plates (Sigma-Aldrich F254, 60 Å pore size, 250 μM thickness).

General Procedure A for hydrazine displacement reactions. Under argon, to a stirred solution of the appropriate alkyl bromide (1 mol equiv) in EtOH (1-3 mL/mmol) in a round-bottomed flask was added hydrazine (4-23 mol equiv). The mixture was refluxed overnight after which the volatiles were removed in vacuo and the residual product was dissolved in 1 N NaOH (10 mL). The aqueous layer was extracted with DCM (3×15 mL) and the combined organic layers were dried in vacuo. The residue was dissolved in MeOH (1-2 mL/mmol) and a 6 N HCl solution (0.3-0.4 mL/mmol) was added while stirring. After 20 min, the volatiles were removed in vacuo, and the desired product was purified via recrystallization from MeOH/Et$_2$O.

General Procedure B for reductive hydrazination. Under nitrogen and on ice, the appropriate aldehyde (1 mol equiv) was dissolved in MeOH (10 mL/mmol) in a round bottomed flask. To this stirred solution was added 1-boc-1-methylhydrazine (1 mol equiv) dropwise. The ice bath was removed after 30 min, and the reaction was left to stir for 2 h. After cooling the reaction on ice, sodium cyanoborohydride (1.75 mol equiv) was slowly added along with acetic acid (150 μL/mmol, 1.5% v/v). EtOH was then removed in vacuo and either saturated sodium bicarbonate or 1 N NaOH (5 mL/mmol) was added. The aqueous layer was extracted with EtOAc (3×15 mL) and dried in vacuo. The product was then purified via flash chromatography (SiO$_2$, 75-90% hexanes/EtOAc). The base was dissolved in EtOAc (0.5 mL/mmol) and a 6 N HCl solution (0.5 mL/mmol) was added while stirring the solution on ice. After 2 h, the reaction was concentrated in vacuo and filtered. The resulting precipitate was washed with cold EtOAc to yield the desired product.

General Procedure C for hydrazine displacement reactions. Under nitrogen, the appropriate alkyl bromide (1 mol equiv) was dissolved in EtOH (3 mL/mmol) in a roundbottomed flask. To this stirred solution was added anhydrous hydrazine (20 mol equiv) dropwise. The solution was then heated to reflux for 0.5-1.75 h with monitoring by TLC. After cooling, EtOH was removed in vacuo and 1 N NaOH (80 mL) was added. The aqueous layer was extracted with DCM (3×80 mL) and dried in vacuo. The base was then dissolved in MeOH (10 mL) and 6 N HCl (2.5-3.5 mL/mmol) was added dropwise while stirring the solution on ice. The solution was left to stir on ice for 10-15 min after which the precipitate was filtered and washed with cold Et$_2$O to yield the desired product.

General Procedure D for amide coupling. The appropriate acid (1 mol equiv) was dissolved in DCM (10 mL, 0.25 mL/mmol). The stirred solution was then placed in an ice bath and thionyl chloride (5 mol equiv) was slowly added. After the addition was complete, the resulting solution was stirred on ice for 10 min and then transferred to an oil bath and heated to 55° C. The solution was then stirred for 7.25-7.50 h and monitored by TLC. The solution was then cooled to RT and dried to furnish the appropriate acid chloride. While drying the acid chloride, 2-(4-aminophenyl)ethanol (2.00 g, 14.6 mmol) was placed under nitrogen and dissolved in DCM (20 mL). The stirred solution was placed on ice and N,N-diisopropylethylamine (18 mL, 102.1 mmol) was slowly added followed by the slow addition of the solid dried acid chloride. After the addition was complete, the resulting solution was stirred overnight and allowed to warm to RT. DCM (100 mL) was added and the organic phase was washed with 1 N HCl (100 mL), saturated sodium bicarbonate (100 mL), brine (100 mL), and dried in vacuo. The solid was then dissolved in MeOH (100 mL) at RT and to this stirred solution, 1 N NaOH (20-50 mL) was added in portions. Stirring was continued for 6 h and the reaction was monitored by TLC. After completion, the solution was concentrated in vacuo and EtOAc (100 mL) was added. The organic layer was washed with 1 N HCl (100 mL), saturated sodium bicarbonate (2×100 mL), brine (100 mL), and then dried to furnish the crude product, which was further purified by flash chromatography (SiO$_2$, 50% hexanes/EtOAc) to yield the desired product.

General Procedure E for bromination. Under nitrogen, the appropriate alcohol (1 mol equiv) was dissolved in DCM (8-20 mL/mmol) in a round-bottomed flask. To this stirred solution was added triphenylphosphine (2 mol equiv) and carbon tetrabromide (2 mol equiv). The resulting solution was stirred for 6 h and monitored by TLC. Upon completion, the solution was concentrated in vacuo to give the crude product, which was further purified by flash chromatography (SiO$_2$, 20-25% hexanes/EtOAc) to furnish the desired product.

General Procedure F for amide coupling. The appropriate acid, 2-(4-aminophenyl)ethanol (1 mol equiv), EDC (1.2 mol equiv), and DMAP (0.1 mol equiv) were placed in a round-bottomed flask under argon at 0° C. and dissolved in anhydrous DCM (2 mL/mmol). The reaction mixture was allowed to warm to RT and stirred overnight (approximately 16 h). Then, the reaction was poured into H$_2$O (20 mL) and the pH was adjusted to approximately 4 with an aqueous solution of 1 N HCl. The organic layer was isolated and the aqueous layer was further extracted with DCM (2×20 mL). The combined organic extracts were washed with 1 N HCl (15 mL) and brine (15 mL), dried over anhydrous Na$_2$SO$_4$, filtered, and concentrated in vacuo. The desired product was purified via recrystallization from EtOAc unless otherwise stated.

General Procedure G mesylate formation and hydrazine displacement reactions. The respective alcohol and triethylamine (1.2 mol equiv) were dissolved in anhydrous DCM (4 mL/mmol) under argon and cooled to 0° C. in an ice bath. Then, methanesulfonyl chloride (1.1 mol equiv) was dissolved in anhydrous DCM (1 mL/mmol) and added dropwise. The reaction was stirred for 1 h at 0° C. and then allowed to warm to RT and stirred for an additional 1-3 h or until complete as evidenced by TLC. The reaction was then slowly poured into an aqueous solution of 0.5 N HCl (approximately 10 mL), DCM was added (10 mL), and the organic layer isolated. The aqueous layer was further extracted with DCM (2×15 mL). The combined organic extracts were washed with brine (15 mL), dried with anhydrous Na$_2$SO$_4$, filtered, and concentrated in vacuo. The residue obtained was placed under argon, taken up in 95% EtOH (4 mL), and cooled to 0° C. in an ice bath. Hydrazine (20 mol equiv) was dissolved in 95% EtOH (1 mL) and added dropwise to the reaction at 0° C. The reaction was allowed to warm to RT and then heated at reflux (approximately 80° C.) for 2 h. After the reaction was complete as evidenced by TLC, it was cooled to RT and treated with a 1 N aqueous solution of NaOH (80 mL). DCM (15 mL) was added and the organic layer was isolated. The aqueous layer was further extracted with DCM (2×15 mL) and then the combined organic extracts were washed with brine (20 mL), dried with anhydrous Na$_2$SO$_4$, filtered, and concentrated in vacuo. See individual compounds for salt formation and purification.

General Procedure H for sulfate salt formation. The crude hydrazine was dissolved in MeOH (10 mL/mmol) and cooled to 0° C. in an ice bath. Concentrated H$_2$SO$_4$ (0.55 mL/mmol) was added dropwise to the solution and stirring was continued for 30 min at 0° C. The resulting precipitate was isolated by filtration, washed with cold MeOH (2 mL), and dried under vacuum. Et$_2$O can be added dropwise to facilitate precipitation of the desired product.

General procedure I for oxalate salt formation. Oxalic acid (0.90 g, 10 mmol) was dissolved in MeOH (9 mL) and cooled to 0° C. in an ice bath. Then, the crude hydrazide was dissolved in MeOH (1 mL) and added dropwise to the solution of oxalic acid at 0° C. Stirring was continued for 30 min after which Et$_2$O was added dropwise to facilitate precipitation of the desired product. The resulting precipitate was isolated by filtration, washed with cold MeOH (2 mL), and dried under vacuum.

1-Methyl-2-(2-phenylethyl)hydrazine dihydrochloride (9a): To a stirred solution of phenylacetaldehyde (200 µL, 1.7 mmol) in anhydrous CH$_3$CN (10 mL) in a roundbottomed flask at 0° C. was added t-butyl 1-methylcarboxylate (0.25 g, 1.7 mmol), followed by the addition of acetic acid (0.15 mL, 1.5% v/v). The reaction mixture was allowed to warm to RT and stirred for 2 h. Then, sodium cyanoborohydride (193 mg, 3.1 mmol) was added at 0° C. and stirring was continued overnight at RT. After completion, the volatiles were removed in vacuo and the desired compound was purified via flash chromatography (SiO$_2$, 75% hexanes/EtOAc) to yield a colorless oil (168 mg, 67%). $^1$H NMR (400 MHz, CDCl$_3$): δ 7.30 (m, 5H), 3.10 (m, 5H), 2.82 (t, J=8 Hz, 2H), 1.50 (s, 9H). This compound was taken up in EtOAc (1 mL) and to it was added a 6 M solution of aqueous HCl (1 mL) at RT. The reaction was stirred for 2 h and then the volatiles were removed in vacuo and the desired product was isolated as a white solid (137 mg, 92%). $^1$H NMR (400 MHz, MeOD): δ 7.27 (m, 5H), 3.23 (m, 2H), 2.89 (t, J=7.7 Hz, 2H), 2.79 (s, 3H). $^{13}$C NMR (125 MHz, DMSO-d$_6$): δ 138.55, 128.59, 128.40, 126.31, 48.62, 33.97, 32.41.

1,1-Dimethyl-2-(2-phenylethyl)hydrazine (9b): To a stirred solution of phenylacetaldehyde (0.20 mL, 1.7 mmol) in anhydrous CH$_3$CN (10 mL) in a roundbottomed flask at 0° C. was added N,N-dimethylhydrazine (143 µL, 1.88 mmol), followed by the addition of acetic acid (0.15 mL, 1.5% v/v). The reaction mixture was allowed to warm to RT and stirred for 2 h. Then, sodium cyanoborohydride (193 mg, 3.1 mmol) was added at 0° C. and stirring was continued overnight at RT. After completion, the volatiles were removed in vacuo and the desired product was purified via flash chromatography (SiO$_2$, 2:1 hexanes/EtOAc) and isolated as a colorless oil (100 mg, 36%). $^1$H NMR (500 MHz, MeOD): δ 7.27 (m, 4H), 7.20 (m, 1H), 3.17 (t, J=7.5 Hz, 2H), 2.83 (s, 6H), 2.75 (t, J=7.5 Hz, 2H). $^{13}$C NMR (125 MHz, MeOD): δ 140.45, 129.89, 129.67, 127.59, 51.72, 46.09, 35.12. ESI-LRMS: [M+H]+=m/z 165.2.

(3-Phenylpropyl)hydrazine dihydrochloride (9c): The title compound was synthesized from 3-phenylpropyl bromide (380 µL, 2.51 mmol) according to general procedure A and isolated as a white solid (0.256 g, 68%). $^1$H NMR (400 MHz, MeOD): δ 7.24 (m, 5H), 3.05 (m, 2H), 2.72 (t, J=7.6 Hz, 2H), 1.97 (quin, J=7.7 Hz, 2H). $^{13}$C NMR (125 MHz, MeOD): δ 142.00, 129.74, 129.55, 127.46, 52.22, 33.71, 28.04.

1-Methyl-2-(3-phenylpropyl)hydrazine dihydrochloride (9d): The title compound was synthesized from hydrocinnamaldehyde (263 µL, 2 mmol) according to general procedure B and isolated as a white powder (0.056 g, 12%). $^1$H NMR (400 MHz, MeOD): δ 7.22 (m, 5H), 3.01 (t, J=7.6 Hz, 2H), 2.76 (s, 3H), 2.71 (t, J=7.6 Hz, 2H), 1.92 (quin, J=7.8 Hz, 2H). $^{13}$C NMR (101 MHz, MeOD): δ 142.36, 129.67, 129.56, 127.32, 49.11, 35.56, 33.88, 29.20. ESI-HRMS: calcd. for C10H16N2: [M+H]+=m/z 165.1391, found: [M+H]+=m/z 165.1386.

[3-(4-Methoxyphenyl)propyl]hydrazine dihydrochloride (9e): The title compound was synthesized from 1-(3-bromopropyl)-4-methoxybenzene (524 µL, 3 mmol) according to general procedure A and isolated as a white powder (0.052 g, 7.2%). $^1$H NMR (400 MHz, MeOD): δ 7.14 (m, 2H), 6.85 (m, 2H), 3.75 (s, 3H), 3.04 (t, J=7.8 Hz, 2H), 2.65 (t, J=7.6 Hz, 2H), 1.94 (quin, J=7.6 Hz, 2H).

1-[3-(4-Methoxyphenyl)propyl]-2-methylhydrazine dihydrochloride (9f): The title compound was synthesized from 3-(4-methoxyphenyl)propionaldehyde (317 μL, 2 mmol) according to general procedure B and isolated as a white powder (0.217 g, 56%). $^1$H NMR (500 MHz, MeOD): δ 7.13 (d, J=8.6 Hz, 2H), 6.85 (d, J=8.6 Hz, 2H), 3.76 (s, 3H), 2.98 (m, 2H), 2.75 (s, 3H), 2.66 (t, J=7.5 Hz, 2H), 1.88 (quin, J=7.5 Hz, 2H). $^{13}$C NMR (125, MHz, DMSO-d$_6$): δ 157.49, 133.00, 129.20, 113.75, 54.97, 46.77, 34.08, 31.32, 27.70. ESI-HRMS: calcd. for C11H18N2O: [M+H]+=m/z 195.1496, found: [M+H]+=m/z 195.1492.

N'-[3-(4-Methoxyphenyl)propyl]acetohydrazine (9g): Under nitrogen on ice, acetylhydrazide (593 mg, 8 mmol) was dissolved in MeOH (20 mL) and 3-(4-methoxyphenyl) propionaldehyde (0.317 mL, 2 mmol) was slowly added. The ice bath was removed after 30 min, and the reaction was left to stir for 2 h. Volatiles were removed in vacuo and saturated sodium bicarbonate (10 mL) was added. The product was extracted with EtOAc (3×15 mL) and dried in vacuo. The product was then purified via flash chromatography (2% MeOH/DCM) to yield the intermediate (0.107 g, 24%) as a white powder. Under nitrogen, the intermediate (0.107 g, 0.49 mmol) was dissolved in MeOH (10 mL). Sodium cyanoborohydride (220 mg, 3.5 mmol) was slowly added along with acetic acid (300 μL, 1.5% v/v). The reaction was left to stir overnight. MeOH was then removed in vacuo and saturated sodium bicarbonate (10 mL) was added. The product was extracted with EtOAc (3×15 mL) and dried in vacuo. Purification via flash chromatography (SiO$_2$, 2% MeOH/DCM) yielded the desired product as a white powder (0.095 g, 88%). $^1$H NMR (500 MHz, MeOD): δ 7.10 (d, J=8.6 Hz, 2H), 6.81 (d, J=8.6 Hz, 2H), 3.75 (s, 3H), 2.76 (t, J=7.2 Hz, 2H), 2.60 (t, J=7.6 Hz, 2H), 1.89 (s, 3H), 1.75 (quin, J=7.4 Hz, 2H). $^{13}$C NMR (125 MHz, MeOD): δ 171.61, 159.50, 135.35, 130.46, 114.92, 55.78, 52.21, 33.43, 30.95, 20.74. ESI-HRMS: calcd. for C12H18N2O2: [M+H]+=m/z 223.1437, found: [M+H]+=m/z 223.1441.

(4-Phenylbutyl)hydrazine dihydrochloride (9h): The title compound was synthesized from 4-bromobutyl benzene (1.00 mL, 5.70 mmol) according to general procedure A and isolated as a white solid (0.640 g, 45%). $^1$H NMR (400 MHz, MeOD): δ 7.20 (m, 5H), 3.05 (m, 2H), 2.67 (t, J=7.3 Hz, 2H), 1.69 (m, 4H).

(2-Phenoxyethyl)hydrazine dihydrochloride (10a): The title compound was synthesized from beta-bromophenetole (0.500 g, 2.49 mmol) according to general procedure A and isolated as an off-white solid (0.136 g, 36%). $^1$H NMR (400 MHz, MeOD): δ 7.30 (dd, J1=8.8 Hz, J2=7.4 Hz, 2H), 6.98 (m, 3H), 4.24 (t, J=5.0 Hz, 2H), 3.43 (t, J=4.4 Hz, 2H). $^{13}$C NMR (125 MHz, CDCl$_3$/MeOD): δ 157.60, 129.46, 121.64, 114.45, 62.68, 49.74.

(3-Phenoxypropyl)hydrazine dihydrochloride (10b): The title compound was synthesized from beta-bromopropyl phenoxy ether (366 μL, 2.32 mmol) according to general procedure A and isolated as an off-white solid (0.179 g, 46%). $^1$H NMR (400 MHz, MeOD): 7.27 (t, J=8.0 Hz, 2H), 6.94 (m, 3H), 4.10 (t, J=5.8 Hz, 2H), 3.26 (t, J=7.2 Hz, 2H), 2.14 (quin, J=7.0 Hz, 2H). $^{13}$C NMR (125 MHz, MeOD): δ 160.12, 130.66, 122.25, 115.67, 66.28, 50.30, 26.63.

{3-[4-(Benxyloxy)phenyl]propyl}hydrazine (14): The title compound was synthesized from 1-(3-bromopropyl)-4-(phenylmethoxy)-benzene (400 mg, 1.30 mmol) according to general procedure C and isolated as a white powder (0.152 g, 34%). $^1$H NMR (400 MHz, DMSO-d$_6$): δ 7.37 (m, 5H), 7.12 (d, J=8.3 Hz, 2H), 6.93 (dd, J1=8.6 Hz, J2=3.0 Hz, 2H), 5.06 (s, 2H), 2.87 (t, J=7.3 Hz, 2H), 2.56 (t, J=7.3 Hz, 2H), 1.83 (quin, J=7.1 Hz, 2H). $^{13}$C NMR (101 MHz, DMSO-d$_6$): δ 156.68, 137.26, 133.11, 129.31, 128.46, 127.81, 127.69, 114.72, 69.16, 49.83, 31.16, 26.63. ESI-HRMS: calcd. for C16H20N2O: [M+H]+=m/z 257.1654, found: [M+H]+=m/z 257.1648.

4-(3-Hydrazinylpropyl) morpholine (11): Purchased from ChemBridge Screening Library (Catalog #9195784).

N-[4-(2-Hydroxyethyl)phenyl]benzamide (16a): Under nitrogen, 2-(4-aminophenyl)ethanol (2.00 g, 15.0 mmol) was dissolved in DCM (20 mL). The stirred solution was placed on ice and N,N-diisopropylethylamine (22.9 mL, 131 mmol) was slowly added followed by the slow addition of benzoic anhydride (14.8 g, 66.0 mmol). After the addition was complete, the solution was stirred overnight and allowed to warm to RT. DCM (100 mL) was added to this solution and the organic phase was washed with 1 N HCl (100 mL), saturated sodium bicarbonate (100 mL), brine (100 mL), and dried in vacuo. The intermediate was then dissolved in MeOH (100 mL). To this stirred solution, 1 N NaOH (50 mL) was added in portions. The resulting solution was stirred at RT for 6 h and monitored by TLC. The solution was then concentrated in vacuo and EtOAc (100 mL) was added. The organic layer was washed with 1 N HCl (100 mL), saturated sodium bicarbonate (2×100 mL), brine (100 mL), and then dried to furnish the crude product, which was further purified via flash chromatography (SiO$_2$, 50% hexanes/EtOAc) to yield the title compound as an off-white solid (0.600 g, 17%). $^1$H NMR (400 MHz, MeOD): δ 7.92 (m, 2H), 7.54 (m, 5H), 7.24 (m, 2H), 3.75 (t, J=7.1 Hz, 2H), 2.82 (t, J=7.1 Hz, 2H).

N-[4-(2-Hydroxyethyl)phenyl]-2-phenylacetamide (16b): The title compound was synthesized from phenylacetic acid (5.95 g, 43.7 mmol) according to general procedure D and isolated as an off-white solid (3.20 g, 86%). $^1$H NMR (400 MHz, CDCl$_3$): δ 7.41 (m, 2H), 7.35 (m, 5H), 7.15 (d, J=8.6 Hz, 2H), 7.09 (s, 1H), 3.81 (t, J=6.6 Hz, 2H), 3.74 (s, 2H), 2.81 (t, J=6.4 Hz, 2H).

N-[4-(2-Hydroxyethyl)phenyl]-4-phenylbutanamide (16d): The title compound was synthesized from 4-phenylbutyric acid (7.18 g, 43.7 mmol) according to general procedure D and isolated to furnish the pure product as an off-white solid (6.20 g, 49%). $^1$H NMR (400 MHz, CDCl$_3$): δ 7.61 (s, 1H), 7.41 (d, J=8.6 Hz, 2H), 7.29 (m, 2H), 7.21 (m, 3H), 7.13 (d, J=8.3 Hz, 2H), 3.79 (t, J=6.6 Hz, 2H), 2.80 (t, J=6.6 Hz, 2H), 2.69 (t, J=7.5 Hz, 2H), 2.32 (t, J=7.5 Hz, 2H), 2.04 (quin, J=7.5 Hz, 2H).

N-[4-(2-Bromoethyl)phenyl]benzamide (17a): The title compound was synthesized from N-[4-(2-Hydroxyethyl) phenyl]benzamide 16a (0.600 g, 2.49 mmol) according to general procedure E and isolated to furnish the final product as an off-white solid (0.600 g, 79%). $^1$H NMR (400 MHz, CDCl$_3$): δ 7.98 (s, 1H), 7.86 (dd, J1=8.2 Hz, J2=1.1 Hz, 2H), 7.61 (d, J=8.6 Hz, 2H), 7.50 (m, 3H), 7.21 (d, J=8.3 Hz, 2H), 3.56 (t, J=7.5 Hz, 2H), 3.15 (t, J=7.5 Hz, 2H). $^{13}$C NMR (101 MHz, CDCl$_3$): δ 165.76, 136.69, 135.06, 134.82, 131.81, 129.26, 128.72, 126.98, 120.44, 38.74, 33.04.

N-[4-(2-Bromoethyl)phenyl]-2-phenylacetamide (17b): The title compound was synthesized from N-[4-(2-Hydroxyethyl)phenyl]-2-phenylacetamide 16b (0.750 g, 2.93 mmol) according to general procedure E and isolated to furnish the desired product as a an off-white solid (0.500 g, 49%). $^1$H NMR (400 MHz, CDCl$_3$): δ 7.36 (m, 8H), 7.12 (d, J=8.3 Hz, 2H), 3.72 (s, 2H), 3.52 (t, J=7.5 Hz, 2H), 3.11 (t, J=7.6 Hz, 2H). $^{13}$C NMR (101 MHz, CDCl$_3$): δ 169.12, 136.38, 134.93, 134.34, 129.44, 129.15, 129.10, 127.61, 120.04, 44.68, 38.63, 33.03. ESI-HRMS: calcd. for C16H16NOBr: [M+H]+=m/z 318.0497, found: [M+H]+=m/z 318.0488.

N-[4-(2-Bromoethyl)phenyl]-4-phenylbutanamide (17c): The title compound was synthesized from N-[4-(2-Hydroxyethyl)phenyl]-4-phenylbutanamide 16d (0.700 g, 2.47 mmol) according to general procedure E and isolated to furnish the pure product as a an off-white solid (0.500 g, 58%). $^1$H NMR (400 MHz, CDCl$_3$): δ 7.46 (d, J=8.3 Hz, 2H), 7.31 (m, 3H), 7.20 (m, 5H), 3.54 (t, J=7.6 Hz, 2H), 3.12 (t, J=7.6 Hz, 2H), 2.71 (t, J=7.5 Hz, 2H), 2.34 (t, J=7.6 Hz, 2H), 2.07 (quin, J=7.5 Hz, 2H). $^{13}$C NMR (101 MHz, CDCl$_3$): δ 170.98, 141.26, 136.63, 134.68, 129.16, 128.46, 128.40, 126.01, 119.99, 38.69, 36.66, 34.99, 33.04, 26.81. ESI-HRMS: calcd. for C18H20NOBr: [M+H]+=m/z 346.0808, found: [M+H]+=m/z 346.0801.

N-[4-(2-Hydrazinylethyl)phenyl]benzamide dihydrochloride (12a): The title compound was synthesized from N-[4-(2-Bromoethyl)phenyl]benzamide 17a (0.400 g, 1.31 mmol) according to general procedure C and isolated to yield the product as a white powder (0.370 g, 91%). $^1$H NMR (400 MHz, DMSO-d$_6$): δ 10.32, (s, 1H), 7.97 (dd, J1=8.5 Hz, J2=1.1 Hz, 2H), 7.74 (d, J=8.6 Hz, 2H), 7.54 (m, 3H), 7.20 (d, J=8.3 Hz, 2H), 3.13 (t, J=7.6 Hz, 2H), 2.85 (t, J=7.3 Hz, 2H). $^{13}$C NMR (101 MHz, DMSO-d$_6$): δ 165.53, 137.74, 134.95, 133.26, 131.65, 128.80, 128.46, 127.78, 120.68, 51.37, 30.85. ESI-HRMS: calcd. for C15H17N3O: [M+H]+=m/z 256.1447, found: [M+H]+=m/z 256.1444.

N-[4-(2-Hydrazinylethyl)phenyl]-2-phenylacetamide dihydrochloride (12b): The title compound was synthesized from N-[4-(2-Bromoethyl)phenyl]-2-phenylacetamide 17b (0.400 g, 1.16 mmol) according to general procedure C and isolated to yield the product as a white powder (0.188 g, 51%). $^1$H NMR (400 MHz, DMSO-d$_6$): δ 10.37 (s, 1H), 7.57 (d, J=8.3 Hz, 2H), 7.32 (m, 4H), 7.24 (m, 1H), 7.14 (d, J=8.6 Hz, 2H), 3.64 (s, 2H), 3.07 (t, J=7.6 Hz, 2H), 2.79 (t, J=7.6 Hz, 2H). $^{13}$C NMR (101 MHz, MeOD): δ 172.37, 138.22, 137.00, 136.84, 130.26, 130.15, 129.72, 128.08, 121.69, 57.22, 44.79, 34.39. ESI-HRMS: calcd. for C16H19N3O: [M+H]+=m/z 270.1605, found: [M+H]+=m/z 270.1601.

N-[4-(2-Hydrazinylethyl)phenyl]-4-phenylbutanamide dihydrochloride (12d): Under nitrogen, N-[4-(2-Bromoethyl)phenyl]-4-phenylbutanamide 17c (0.400 g, 1.15 mmol) was dissolved in EtOH (4 mL). To this stirred solution was added anhydrous hydrazine (0.720 mL, 23.1 mmol) dropwise. The solution was then refluxed for 1 h and monitored by TLC. After cooling, EtOH was removed and 1 N NaOH (80 mL) was added. The aqueous layer was extracted with DCM (3×80 mL) and dried in vacuo. The hydrazine free base was then dissolved in MeOH (10 mL) and 6 M HCl (2 mL) was added dropwise while stirring the solution on ice. The solution was left to stir on ice for 10 min after which Et$_2$O (5 mL) was added and the reaction was concentrated in vacuo to yield a precipitate that was filtered and washed with cold Et$_2$O. The precipitate was dried to yield the product as a light yellow powder (0.132 g, 33%). $^1$H NMR (400 MHz, DMSOd$_6$): δ 9.89 (s, 1H), 7.53 (d, J=8.5 Hz, 2H), 7.29 (m, 2H), 7.19 (m, 3H), 7.14 (d, J=8.5 Hz, 2H), 3.07 (t, J=7.8 Hz, 2H), 2.78 (t, J=7.9 Hz, 2H), 2.61 (t, J=7.6 Hz, 2H), 2.31 (t, J=7.5 Hz, 2H), 1.88 (quin, J=7.5 Hz, 2H). $^{13}$C NMR (101 MHz, DMSO-d$_6$): δ 170.94, 141.76, 137.90, 132.41, 128.78, 128.39, 128.38, 125.85, 119.29, 51.42, 35.79, 34.70, 30.79, 26.92. ESI-HRMS: calcd. for C18H23N3O: [M+H]+=m/z 298.1913, found: [M+H]+=m/z 298.1914.

4-(4-Chlorophenyl)butanoic acid: 4-(4-Chlorophenyl)-4-oxobutanoic acid (1.06 g, 5 mmol) and KOH (85% by wt., 0.79 g, 12 mmol) were placed in a round-bottomed flask fitted with a Dean-Stark apparatus and a reflux condenser and suspended in diethylene glycol (10 mL) at RT. Then, hydrazine monohydrate (50% by wt., 1.20 g, 12 mmol) was added slowly to the reaction at RT after which it was heated to 120-130° C. for 2 h. The reaction became homogenous after heating for approximately 45 min. After 2 h, the temperature was increased to 180-200° C. and the reaction stirred for an additional 3 h to remove residual hydrazine and water via the Dean-Stark trap. The reaction was then cooled to RT, diluted with H$_2$O (10 mL), and poured into a 2.5 N aqueous solution of HCl (20 mL). The suspension was cooled in an ice bath and the resulting precipitate was isolated by filtration. To remove residual diethylene glycol, the solid was dissolved in a saturated aqueous solution of K$_2$CO$_3$ (20 mL), diluted with H$_2$O (20 mL), and poured into a 2.5 N aqueous solution of HCl (20 mL). The suspension was again cooled in an ice bath and the precipitate isolated by filtration, washed with cold H$_2$O (2×15 mL), and dried under vacuum. The title compound was isolated as a white solid (0.89 g, 89%). $^1$H NMR (500 MHz, DMSO-d$_6$): δ 12.06 (br, 1H), 7.32 (d, J=8.5 Hz, 2H), 7.21 (d, J=8.5 Hz, 2H), 2.57 (t, J=7.4 Hz, 2H), 2.20 (t, J=7.3 Hz, 2H), 1.77 (q, J=7.5 Hz, 2H). $^{13}$C NMR (125 MHz, DMSO-d$_6$): δ 174.16, 140.57, 130.41, 130.17, 128.20, 33.63, 32.95, 26.11. ESI-LRMS: [M–H]–=m/z 284.3. ESI-HRMS: calcd. for C10H11ClO2: [M–H]–=m/z 197.0375, found: [M–H]–=m/z 197.0379.

4-(4-Fluorophenyl)butanoic acid: 4-(4-Fluorophenyl)-4-oxobutanoic acid (0.98 g, 5 mmol) and KOH (85% by wt., 0.79 g, 12 mmol) were placed in a round-bottomed flask fitted with a Dean-Stark apparatus and a reflux condenser and suspended in diethylene glycol (10 mL) at RT. Then, hydrazine monohydrate (50% by wt., 1.20 g, 12 mmol) was added slowly to the reaction at RT after which it was heated to 120-130° C. for 2 h. The reaction became homogenous after heating for approximately 45 min. After 2 h, the temperature was increased to 180-200° C. and the reaction stirred for an additional 3 h to remove residual hydrazine and water via the Dean-Stark trap. The reaction was then cooled to RT, diluted with H$_2$O (10 mL), and poured into a 2.5 N aqueous solution of HCl (20 mL). The organic products were extracted with EtOAc (3×15 mL), washed with brine (10 mL), dried with anhydrous Na$_2$SO$_4$, filtered, and concentrated in vacuo. Purification by column chromatography (30-50% EtOAc/hexanes) afforded the desired product as a clear, viscous oil (0.32 g, 35%). $^1$H NMR (500 MHz, CDCl$_3$): δ 11.50 (br, 1H), 7.16 (m, 2H), 7.00 (m, 2H), 2.67 (t, J=7.6 Hz, 2H), 2.40 (t, J=7.4 Hz, 2H), 1.97 (quin, J=7.5 Hz, 2H). $^{13}$C NMR (125 MHz, CDCl$_3$): δ 180.16, 161.34 (d, J=243.4 Hz), 136.74, 129.76 (d, J=7.3 Hz), 115.09 (d, J=20.9 Hz), 34.09, 33.20, 26.24.

N-[4-(2-Hydroxyethyl)phenyl]-3-phenylpropanamide (16c): The title compound was synthesized from 3-phenylpropanoic acid (1.50 g, 10 mmol) according to general procedure F and isolated as a white solid (2.36 g, 88%). $^1$H NMR (500 MHz, DMSO-d$_6$): δ 9.80 (s, 1H), 7.46 (d, J=8.5 Hz, 2H), 7.27 (m, 4H), 7.18 (m, 1H), 7.11 (d, J=8.5 Hz, 2H), 4.59 (t, J=5.2 Hz, 1H), 3.55 (td, J1=7.1 Hz, J2=5.3 Hz, 2H), 2.90 (t, J=7.6 Hz, 2H), 2.65 (t, J=7.2 Hz, 2H), 2.60 (t, J=7.7 Hz, 2H). $^{13}$C NMR (125 MHz, DMSO-d$_6$): δ 170.08, 141.19, 137.12, 134.08, 128.95, 128.27, 128.21, 125.89, 118.99, 62.24, 38.45, 37.88, 30.85. ESI-HRMS: calcd. for C17H19NO2: [M+H]+=m/z 270.1489, found: [M+H]+=m/z 270.1501.

N-[4-(2-Hydroxyethyl)phenyl]-5-phenylpentanamide (16e): The title compound was synthesized from 5-phenylpentanoic acid (0.89 g, 5 mmol) according to general procedure F. Purification by recrystallization from EtOAc facilitated by the dropwise addition of hexanes afforded the desired product as a white, crystalline solid (1.12 g, 75%). $^1$H NMR (500 MHz, CDCl$_3$): δ 7.44 (d, J=8.3 Hz, 2H), 7.36

(s, 1H), 7.30 (m, 2H), 7.19 (m, 4H), 3.84 (t, J=6.4 Hz, 2H), 2.84 (t, J=6.5 Hz, 2H), 2.67 (t, J=7.4 Hz, 2H), 2.37 (t, J=7.2 Hz, 2H), 1.79 (m, 2H), 1.72 (m, 2H), 1.65 (br, 1H). $^{13}$C NMR (125 MHz, CDCl$_3$): δ 171.21, 142.07, 136.28, 134.41, 129.45, 128.36, 128.31, 125.78, 120.19, 63.57, 38.53, 37.48, 35.65, 30.97, 25.22. ESI-HRMS: calcd. for C19H23NO2: [M+H]+=m/z 298.1802, found: [M+H]+=m/z 298.1807.

4-(4-Chlorophenyl)-N-[4-(2-hydroxyethyl)phenyl]butanamide (16f): The title compound was synthesized from 4-(4-chlorophenyl)butanoic acid (0.57 g, 3 mmol) according to general procedure F. Purification by recrystallization from EtOAc facilitated by the dropwise addition of hexanes afforded the desired product as a white solid (0.89 g, 93%). $^1$H NMR (500 MHz, DMSO-d$_6$): δ 9.78 (s, 1H), 7.47 (d, J=8.5H, 2H), 7.33 (m, 2H), 7.24 (d, J=8.3 Hz, 2H), 7.11 (d, J=8.5 Hz, 2H), 4.59 (t, J=5.2 Hz, 1H), 3.55 (td, J1=7.1 Hz, J2=5.3 Hz, 2H), 2.65 (t, J=7.2 Hz, 2H), 2.61 (t, J=7.6 Hz, 2H), 2.28 (t, J=7.5 Hz, 2H), 1.87 (q, J=7.5 Hz, 2H). $^{13}$C NMR (125 MHz, DMSO-d$_6$): δ 170.56, 140.68, 137.20, 134.02, 130.37, 130.21, 128.92, 128.18, 119.01, 62.27, 38.46, 35.52, 33.82, 26.57. ESI-HRMS: calcd. for C18H20ClNO2: [M+H]+=m/z 318.1255, found: [M+H]+=m/z 318.1268.

4-(4-Fluorophenyl)-N-[4-(2-hydroxyethyl)phenyl]butanamide (16g): The title compound was synthesized from 4-(4-fluorophenyl)butanoic acid (0.32 g, 1.8 mmol) according to general procedure F and isolated as a white solid (0.53 g, 94%). $^1$H NMR (500 MHz, DMSO-d$_6$): δ 9.77 (s, 1H), 7.47 (d, J=8.3 Hz, 2H), 7.24 (m, 2H), 7.10 (m, 4H), 4.59 (t, J=5.2 Hz, 1H), 3.55 (td, J1=7.1 Hz, J2=5.3 Hz, 2H), 2.65 (t, J=7.2 Hz, 2H), 2.60 (t, J=7.5 Hz, 2H), 2.28 (t, J=7.5 Hz, 2H), 1.86 (quin, J=7.5 Hz, 2H). $^{13}$C NMR (125 MHz, DMSO-d$_6$): δ 170.61, 160.60 (d, J=241.6 Hz), 137.76 (d, J=2.7 Hz), 137.20, 134.03, 130.02 (d, J=8.2 Hz), 128.92, 119.01, 114.91 (d, J=20.9 Hz), 62.27, 38.46, 35.58, 33.70, 26.83. ESI-HRMS: calcd. for C18H20FNO2: [M+H]+=m/z 302.1551, found: [M+H]+=m/z 302.1559.

N-[4-(2-Hydroxyethyl)phenyl]-4-(4-methoxyphenyl)butanamide (16h): The title compound was synthesized from 4-(4-methoxyphenyl)butanoic acid (0.58 g, 3 mmol) according to general procedure F. Purification by column chromatography (SiO$_2$, 25-75% EtOAc/hexanes) afforded the desired product as a white solid (0.74 g, 79%). $^1$H NMR (500 MHz, CDCl$_3$): δ 7.42 (m, 3H), 7.15 (d, J=8.3 Hz, 2H), 7.10 (d, J=8.6 Hz, 2H), 6.83 (d, J=8.5 Hz, 2H), 3.81 (t, J=6.5 Hz, 2H), 3.78 (s, 3H), 2.81 (t, J=6.5 Hz, 2H), 2.64 (t, J=7.4 Hz, 2H), 2.31 (t, J=7.5 Hz, 2H), 2.02 (quin, J=7.4 Hz, 2H), 1.76 (s, 1H). $^{13}$C NMR (125 MHz, CDCl$_3$): δ 171.17, 157.84, 136.26, 134.42, 133.34, 129.43, 129.35, 120.18, 113.80, 63.53, 55.22, 38.52, 36.59, 34.10, 27.07. ESI-HRMS: calcd. for C19H23NO3: [M+H]+=m/z 314.1751, found: [M+H]+=m/z 314.1763.

N-[4-(2-Hydroxyethyl)phenyl]-4-(4-nitrophenyl)butanamide (16i): The title compound was synthesized from 4-(4-nitrophenyl)butanoic acid (1.05 g, 5 mmol) according to general procedure F and isolated as a white solid (1.49 g, 90%). $^1$H NMR (500 MHz, DMSO-d$_6$): δ 9.79 (s, 1H), 8.16 (d, J=8.8 Hz, 2H), 7.51 (d, J=8.8 Hz, 2H), 7.46 (d, J=8.5 Hz, 2H), 7.11 (d, J=8.6 Hz, 2H), 4.60 (br, 1H), 3.55 (m, 2H), 2.76 (t, J=7.6 Hz, 2H), 2.65 (t, J=7.2 Hz, 2H), 2.31 (t, J=7.4 Hz, 2H), 1.93 (quin, J=7.5 Hz, 2H). $^{13}$C NMR (125 MHz, DMSO-d$_6$): δ 170.44, 150.23, 145.87, 137.16, 134.09, 129.67, 128.95, 123.45, 119.04, 62.29, 38.47, 35.48, 34.35, 26.20. ESI-HRMS: calcd. for C18H20N2O4: [M+H]+=m/z 329.1496, found: [M+H]+=m/z 329.1501.

N-[4-(2-Hydroxyethyl)phenyl]-3-(2-hydroxyphenyl)propanamide (16j): The title compound was synthesized from 3-(2-hydroxyphenyl)propanoic acid (0.83 g, 5 mmol) according to general procedure F and isolated as a white solid (1.43 g, 82%). $^1$H NMR (500 MHz, DMSO-d$_6$): δ 9.78 (s, 1H), 9.32 (s, 1H), 7.47 (d, J=8.5 Hz, 2H), 7.11 (d, J=8.5 Hz, 2H), 7.08 (dd, J=7.4 Hz, 1.4 Hz, 1H), 7.00 (td, J=7.7 Hz, 1.7 Hz, 1H), 6.78 (dd, J1=8.0 Hz, J2=0.9 Hz, 1H), 6.69 (td, J1=7.4 Hz, J2=1.1 Hz, 1H), 4.58 (br, 1H), 3.55 (t, J=7.2 Hz, 2H), 2.82 (t, J=7.8 Hz, 2H), 2.65 (t, J=7.2 Hz, 2H), 2.55 (t, J=7.8 Hz, 2H). $^{13}$C NMR (125 MHz, DMSO-d$_6$): δ 170.57, 155.07, 137.20, 134.00, 129.63, 128.94, 127.24, 126.98, 119.01, 118.84, 114.84, 62.27, 38.46, 36.25, 25.59. ESIHRMS: calcd. for C17H19NO3: [M+H]+=m/z 286.1438, found: [M+H]+=m/z 286.1445.

N-[4-(2-Hydroxyethyl)phenyl]-3-(3-hydroxyphenyl)propanamide (16k): The title compound was synthesized from 3-(3-hydroxyphenyl)propanoic acid (0.83 g, 5 mmol) according to general procedure F. Purification by column chromatography (SiO$_2$, 5% MeOH/DCM) afforded the desired product as a clear, viscous oil that solidified on standing overnight to form a white solid (0.67 g, 47%). $^1$H NMR (500 MHz, DMSO-d$_6$): 9.80 (s, 1H), 9.25 (s, 1H), 7.46 (d, J=8.3 Hz, 2H), 7.12 (d, J=8.3 Hz, 2H), 7.05 (t, J=7.8 Hz, 1H), 6.64 (m, 2H), 6.57 (dt, J1=8.0 Hz, J2=1.2 Hz, 1H), 4.59 (t, J=5.3 Hz, 1H), 3.55 (td, J1=7.1 Hz, J2=5.3 Hz, 2H), 2.80 (t, J=7.7 Hz, 2H), 2.65 (t, J=7.1 Hz, 2H), 2.55 (t, J=7.7 Hz, 2H). $^{13}$C NMR (125 MHz, DMSO-d$_6$): δ 170.15, 157.28, 142.61, 137.16, 134.08, 129.19, 128.96, 119.01, 118.80, 115.24, 112.88, 62.27, 38.47, 37.86, 30.86. ESI-HRMS: calcd. for C17H19NO3: [M+H]+=m/z 286.1438, found: [M+H]+=m/z 286.1449.

N-[4-(2-Hydrazinylethyl)phenyl]-3-phenylpropanamide sulfate (12c): The title compound was synthesized from N-[4-(2-hydroxyethyl)phenyl]-3-phenylpropanamide 16c (0.28 g, 1 mmol) according to general procedure G and the sulfate salt was prepared according to general procedure H. The desired product was isolated as a white solid (0.25 g, 67%). $^1$H NMR (500 MHz, MeOD): δ 7.47 (d, J=8.2 Hz, 2H), 7.22 (m, 7H), 3.25 (t, J=7.8 Hz, 2H), 2.99 (t, J=7.6 Hz, 2H), 2.91 (t, J=7.8 Hz, 2H), 2.66 (t, J=7.6 Hz, 2H). $^{13}$C NMR (125 MHz, MeOD): δ 173.91, 142.23, 138.76, 134.18, 130.23, 129.62, 129.54, 127.38, 122.03, 53.71, 39.87, 32.93, 32.12. ESI-HRMS: calcd. for C17H21N3O: [M+H]+=m/z 284.1757, found: [M+H]+=m/z 284.1770.

N-[4-(2-Hydrazinylethyl)phenyl]-5-phenylpentanamide oxalate (12e): The title compound was synthesized from N-[4-(2-Hydroxyethyl)phenyl]-5-phenylpentanamide 16e (0.30 g, 1 mmol) according to general procedure G and the oxalate salt was prepared according to general procedure I. The desired product was isolated as a white solid (0.32 g, 80%). $^1$H NMR (500 MHz, MeOD): δ 7.51 (d, J=8.5 Hz, 2H), 7.20 (m, 7H), 3.24 (m, 2H), 2.91 (t, J=7.7 Hz, 2H), 2.66 (t, J=7.2 Hz, 2H), 2.39 (t, J=7.2 Hz, 2H), 1.71 (m, 4H). $^{13}$C NMR (125 MHz, DMSO-d$_6$): δ 171.02, 163.93, 142.04, 137.77, 132.34, 128.74, 128.25, 128.23, 125.63, 119.21, 51.48, 36.19, 34.89, 30.78, 30.63, 24.80. ESI-HRMS: calcd. for C19H25N3O: [M+H]+=m/z 312.2070, found: [M+H]+=m/z 312.2081.

4-(4-Chlorophenyl)-N-[4-(2-hydrazinylethyl)phenyl]butanamide sulfate (12f): The title compound was synthesized from 4-(4-chlorophenyl)-N-[4-(2-hydroxyethyl)phenyl]butanamide (16f) (0.32 g, 1 mmol) according to general procedure G and the sulfate salt was prepared according to general procedure H. The desired product was isolated as a white solid (0.31 g, 73%). $^1$H NMR (500 MHz, MeOD): δ 7.50 (d, J=8.6 Hz, 2H), 7.23 (m, 6H), 3.25 (m, 2H), 2.92 (t, J=7.8 Hz, 2H), 2.68 (t, J=7.7 Hz, 2H), 2.38 (t, J=7.4 Hz, 2H), 1.99 (quin, J=7.5 Hz, 2H). $^{13}$C NMR (125 MHz, DMSO-d$_6$):

δ 170.73, 140.67, 137.77, 132.29, 130.39, 130.22, 128.76, 128.21, 119.27, 51.48, 35.54, 33.82, 30.81, 26.57. ESI-HRMS: calcd. for C18H22ClN3O: [M+H]+=m/z 332.1524, found: [M+H]+=m/z 332.1537.

4-(4-Fluorophenyl)-N-[4-(2-hydrazinylethyl)phenyl]butanamide sulfate (12g): The title compound was synthesized from 4-(4-fluorophenyl)-N-[4-(2-hydroxyethyl)phenyl]butanamide 16g (0.30 g, 1 mmol) according to general procedure G and the sulfate salt was prepared according to general procedure H. The desired product was isolated as a white solid (0.24 g, 58%). $^1$H NMR (500 MHz, MeOD): δ 7.51 (d, J=8.5 Hz, 2H), 7.21 (m, 4H), 6.99 (t, J=8.8 Hz, 2H), 3.25 (m, 2H), 2.92 (t, J=7.4 Hz, 2H), 2.37 (t, J=7.7 Hz, 2H), 2.38 (t, J=7.4 Hz, 2H), 1.98 (quin, J=7.5 Hz, 2H). $^{13}$C NMR (125 MHz, MeOD): δ 174.39, 162.94 (d, J=242.5 Hz), 139.00 (d, J=3.63 Hz), 138.95, 134.11, 131.23 (d, J=7.3 Hz), 130.23, 121.90, 116.08 (d, J=21.8 Hz), 53.72, 37.29, 35.56, 32.20, 28.79. ESI-HRMS: calcd. for C18H22FN3O: [M+H]+=m/z 316.1820, found: [M+H]+=m/z 316.1825.

N-[4-(2-Hydrazinylethyl)phenyl]-4-(4-methoxyphenyl)butanamide sulfate (12h): The title compound was synthesized from N-[4-(2-Hydroxyethyl)phenyl]-4-(4-methoxyphenyl)butanamide 16h (0.63 g, 2 mmol) according to general procedure G and the sulfate salt was prepared according to general procedure H. The desired product was isolated as a white solid (0.57 g, 67%). $^1$H NMR (500 MHz, MeOD): δ 7.51 (d, J=8.5 Hz, 2H), 7.22 (d, J=8.5 Hz, 2H), 7.12 (d, J=8.6 Hz, 2H), 6.83 (d, J=8.6 Hz, 2H), 3.75 (s, 3H), 3.25 (m, 2H), 2.91 (t, J=7.8 Hz, 2H), 2.62 (t, J=7.5 Hz, 2H), 2.36 (t, J=7.5 Hz, 2H), 1.96 (quin, J=7.5 Hz, 2H). $^{13}$C NMR (125 MHz, DMSO-$d_6$): δ 170.93, 157.44, 137.82, 133.51, 132.30, 129.25, 128.78, 119.29, 113.73, 54.98, 51.53, 35.72, 33.74, 30.82, 27.07. ESI-HRMS: calcd. for C19H25N3O2: [M+H]+=m/z 328.2020, found: [M+H]+=m/z 328.2026.

N-[4-(2-Hydrazinylethyl)phenyl]-4-(4-nitrophenyl)butanamide sulfate (12i): The title compound was synthesized from N-[4-(2-Hydroxyethyl)phenyl]-4-(4-nitrophenyl)butanamide 16i (0.33 g, 1 mmol) according to general procedure G and the sulfate salt was prepared according to general procedure H. The desired product was isolated as a white solid (0.29 g, 65%). $^1$H NMR (500 MHz, MeOD): δ 8.15 (d, J=8.8 Hz, 2H), 7.48 (t, J=9.0 Hz, 4H), 7.21 (d, J=8.5 Hz, 2H), 3.25 (m, 2H), 2.92 (t, J=7.9 Hz, 2H), 2.84 (t, J=8.6 Hz, 2H), 2.42 (t, J=7.4 Hz, 2H), 2.06 (quin, J=7.5 Hz, 2H). $^{13}$C NMR (125 MHz, DMSO-$d_6$): δ 170.63, 150.24, 145.90, 137.75, 132.37, 129.71, 128.80, 123.48, 119.31, 51.52, 35.52, 34.36, 30.83, 26.22. ESI-HRMS: calcd. for C18H22N4O3: [M+H]+=m/z 343.1765, found: [M+H]+=m/z 343.1768.

2-(3-{[4-(2-Hydrazinylethyl)phenyl]amino}-3-oxopropyl)phenyl methanesulfonate oxalate (12j): The title compound was synthesized from N-[4-(2-Hydroxyethyl)phenyl]-3-(2-hydroxyphenyl)propanamide 16j (0.29 g, 1 mmol) according to general procedure G and the oxalate salt was prepared according to general procedure I. The desired product was isolated as a white solid (0.16 g, 34%). $^1$H NMR (500 MHz, MeOD): δ 7.49 (d, J=8.5 Hz, 2H), 7.40 (dd, J1=7.0 Hz, J2=2.3 Hz, 1H), 7.36 (dd, J1=7.6 Hz, J2=1.7 Hz, 1H), 7.28 (m, 2H), 7.21 (d, J=8.6 Hz, 2H), 3.34 (s, 3H), 3.24 (m, 2H), 3.11 (t, J=7.8 Hz, 2H), 2.91 (t, J=7.9 Hz, 2H), 2.70 (t, J=7.6 Hz, 2H). $^{13}$C NMR (125 MHz, DMSO-$d_6$): δ 169.97, 163.85, 147.33, 137.64, 134.27, 132.49, 130.55, 128.78, 127.73, 127.22, 122.09, 119.27, 51.46, 38.30, 36.09, 30.80, 25.03. ESI-HRMS: calcd. for C18H23N3O4S: [M+H]+=m/z 378.1482, found: [M+H]+=m/z 378.1499.

3-(3-{[4-(2-Hydrazinylethyl)phenyl]amino}-3-oxopropyl)phenyl methanesulfonate oxalate (12k): The title compound was synthesized from N-[4-(2-Hydroxyethyl)phenyl]-3-(3-hydroxyphenyl)propanamide 16k (0.29 g, 1 mmol) according to general procedure G and the oxalate salt was prepared according to general procedure I. The desired product was isolated as an off-white solid (56 mg, 12%). $^1$H NMR (500 MHz, DMSOd$_6$/MeOD): δ 7.45 (d, J=8.5 Hz, 2), 7.33 (t, J=7.9 Hz, 1H), 7.21 (d, J=7.7 Hz, 1H), 7.18 (m, 1H), 7.11 (m, 3H), 3.19 (s, 3H), 3.08 (t, J=7.7 Hz, 2H), 2.94 (t, J=7.5 Hz, 2H), 2.77 (t, J=7.7 Hz, 2H), 2.60 (t, J=7.7 Hz, 2H). $^{13}$C NMR (125 MHz, DMSO-$d_6$): δ 170.00, 164.09, 149.13, 143.76, 137.61, 132.54, 129.92, 128.79, 127.32, 121.93, 119.77, 119.27, 51.48, 37.43, 37.36, 30.79, 30.40. ESI-HRMS: calcd. for C18H23N3O4S: [M+H]+=m/z 378.1482, found: [M+H]+=m/z 378.1499.

N-[4-(2-Hydroxyethyl)phenyl]-3-(1H-indol-3-yl)propanamide (18a): The title compound was synthesized from 3-(1H-indol-3-yl)propanoic acid (0.57 g, 3 mmol) according to general procedure F and isolated as a white solid (0.82 g, 89%). $^1$H NMR (500 MHz, DMSO-$d_6$): δ 10.75 (s, 1H), 9.82 (s, 1H), 7.56 (d, J=7.9 Hz, 1H), 7.48 (d, J=8.5 Hz, 2H), 7.32 (d, J=8.0 Hz, 1H), 7.12 (m, 3H), 7.06 (td, J1=7.5 Hz, J2=1.0 Hz, 1H), 6.98 (td, J1=7.5 Hz, J2=0.9 Hz, 1H), 4.60 (t, J=5.3 Hz, 1H), 3.56 (td, J1=7.2 Hz, J2=5.3 Hz, 2H), 3.01 (t, J=7.5 Hz, 2H), 2.66 (t, J=7.4 Hz, 4H). $^{13}$C NMR (125 MHz, DMSO-$d_6$): δ 170.71, 137.23, 136.21, 134.02, 128.95, 127.01, 122.13, 120.90, 119.00, 118.34, 118.14, 113.70, 111.31, 62.27, 38.47, 37.22, 20.83. ESI-HRMS: calcd. for C19H20N2O2: [M+H]+=m/z 309.1598, found: [M+H]+=m/z 309.1603.

N-[4-(2-Hydroxyethyl)phenyl]-4-(1H-indol-3-yl)butanamide (18b): The title compound was synthesized from 4-(1H-indol-3-yl)butanoic acid (0.61 g, 3 mmol) according to general procedure F and isolated as a white solid (0.41 g, 43%). $^1$H NMR (500 MHz, DMSO-$d_6$): δ 10.77 (s, 1H), 9.79 (s, 1H), 7.52 (d, J=7.9 HZ, 1H), 7.49 (d, J=8.3 Hz, 2H), 7.33 (d, J=8.2 Hz, 1H), 7.11 (m, 3H), 7.06 (dt, J1=7.1 Hz, J2=0.9 Hz, 1H), 6.97 (dt, J1=7.1 Hz, J2=0.9 Hz, 1H), 4.60 (t, J=5.2 Hz, 1H), 3.56 (td, J1=7.1 Hz, J2=5.3 Hz, 2H), 2.73 (t, J=7.4 Hz, 2H), 2.66 (t, J=7.2 Hz, 2H), 2.35 (t, J=7.5 Hz, 2H), 1.96 (quin, 7.4 Hz, 2H). $^{13}$C NMR (125 MHz, DMSO-$d_6$): δ 170.97, 137.29, 136.31, 133.97, 128.93, 127.17, 122.28, 120.81, 119.01, 118.29, 118.10, 114.01, 111.31, 62.29, 38.48, 36.14, 25.95, 24.31. ESI-HRMS: calcd. for C20H22N2O2: [M+H]+=m/z 323.1754, found: [M+H]+=m/z 323.1759.

N-[4-(2-Hydrazinylethyl)phenyl]-3-(1H-indol-3-yl)propanamide sulfate (15a): The title compound was synthesized from N-[4-(2-Hydroxyethyl)phenyl]-3-(1H-indol-3-yl)propanamide 18a (0.31 g, 1 mmol) according to general procedure G and the sulfate salt was prepared according to general procedure H. The desired product was isolated as a white solid (0.26 g, 62%). $^1$H NMR (500 MHz, DMSO-$d_6$/MeOD): δ 7.53 (d, J=7.9 Hz, 1H), 7.49 (d, J=8.5 Hz, 2H), 7.29 (d, J=8.2 Hz, 1H), 7.12 (d, J=8.5 Hz, 2H), 7.03 (m, 2H), 6.95 (m, 1H), 3.09 (t, J=7.4 Hz, 2H), 3.02 (t, J=7.5 Hz, 2H), 2.78 (t, J=7.8 Hz, 2H), 2.65 (t, J=7.6 Hz, 2H). $^{13}$C NMR (125 MHz, MeOD/DMSO-$d_6$): δ 173.88, 139.09, 138.11, 134.05, 130.30, 128.73, 123.34, 122.56, 121.65, 119.82, 119.68, 115.34, 112.59, 53.55, 39.03, 32.14, 22.48. ESI-HRMS: calcd. for C19H22N4O: [M+H]+=m/z 323.1866, found: [M+H]+=m/z 323.1871.

N-[4-(2-Hydrazinylethyl)phenyl]-4-(1H-indol-3-yl)butanamide sulfate (15b): The title compound was synthesized from N-[4-(2-Hydroxyethyl)phenyl]-4-(1H-indol-3-yl)butanamide 18b (0.32 g, 1 mmol) according to general procedure G and the sulfate salt was prepared according to general procedure H. The desired product was isolated as an off-white solid (84 mg, 19%). $^1$H NMR (500 MHz, MeOD/DMSO-d$_6$): δ 7.63 (d, J=8.3 Hz, 3H), 7.43 (d, J=8.0 Hz, 1H), 7.27 (d, J=8.5 Hz, 2H), 7.17 (m, 3H), 7.08 (m, 1H), 3.25 (t, J=7.4 Hz, 2H), 2.94 (t, J=7.7 Hz, 2H), 2.88 (t, J=7.5 Hz, 2H), 2.48 (t, J=7.5 Hz, 2H), 2.12 (quin, J=7.4 Hz, 2H). $^{13}$C NMR (125 MHz, DMSO-d$_6$): δ 171.12, 137.86, 136.31, 132.20, 128.76, 127.15, 122.28, 120.81, 119.27, 118.27, 118.09, 113.98, 111.33, 51.48, 36.14, 30.82, 25.95, 24.29. ESI-HRMS: calcd. for C20H24N4O: [M+H]+=m/z 337.2023, found: [M+H]+=m/z 337.2025.

(2E)-N-[4-(2-Hydroxyethyl)phenyl]-3-phenylprop-2-enamide (19): The title compound was synthesized from (2E)-3-phenylprop-2-enoic acid (0.74 g, 5 mmol) according to general procedure F and isolated as a white, crystalline solid (1.34 g, 88%). $^1$H NMR (500 MHz, DMSO-d$_6$): δ 10.13 (s, 1H), 7.61 (m, 5H), 7.42 (m, 3H), 7.18 (d, J=8.5 Hz, 2H), 6.85 (d, J=15.6 Hz, 1H), 4.62 (t, J=5.3 Hz, 1H), 3.59 (td, J1=7.1 Hz, J2=5.2 Hz, 2H), 2.69 (t, J=7.1 Hz, 2H). $^{13}$C NMR (125 MHz, DMSO-d$_6$): δ 163.30, 139.90, 137.17, 134.76, 134.54, 129.69, 129.13, 128.99, 127.66, 122.37, 119.15, 62.25, 38.51. ESI-HRMS: calcd. for C17H17NO2: [M+H]+=m/z 268.1332, found: [M+H]+=m/z 268.1342.

(2E)-N-[4-(2-Hydrazinylethyl)phenyl]-3-phenylprop-2-enamide sulfate (13): The title compound was synthesized from (2E)-N-[4-(2-hydroxyethyl)phenyl]-3-phenylprop-2-enamide 19 (0.27 g, 1 mmol) according to general procedure G and the sulfate salt was prepared according to general procedure H. The desired product was isolated as a white solid (0.24 g, 64%). $^1$H NMR (500 MHz, MeOD): δ 7.63 (m, 5H), 7.41 (m, 3H), 7.27 (d, J=8.5 Hz, 2H), 6.80 (d, J=15.6 Hz, 1H), 3.27 (m, 2H), 2.94 (t, J=7.8 Hz, 2H). $^{13}$C NMR (125 MHz, DMSO-d$_6$): δ 163.48, 140.04, 137.80, 134.75, 132.80, 129.75, 129.00, 128.96, 127.76, 122.38, 119.44, 51.49, 30.89. ESI-HRMS: calcd. for C17H19N3O: [M+H]+=m/z 282.1601, found: [M+H]+=m/z 282.1608.

N-[4-(2-{[tert-Butyl(dimethyl)silyl]oxy}ethyl)phenyl]-4-phenylbutanamide (20): N-[4-(2-hydroxyethyl)phenyl]-4-phenylbutanamide 16d (0.99 g, 3.5 mmol) was dissolved in anhydrous DCM (8 mL) and to it was added triethylamine (1.22 mL, 8.75 mmol) and DMAP (43 mg, 0.35 mmol) at RT. Upon dissolution of 16d, tert-butyldimethylsilyl chloride (0.63 g, 4.2 mmol) was dissolved in anhydrous DCM (7 mL) and added to the reaction in one portion. The reaction was then stirred at RT for 2 h after which it was poured into H$_2$O (15 mL) and the organic layer isolated. The aqueous layer was further extracted with DCM (2×15 mL). The combined organic fractions were washed with brine (15 mL), dried with anhydrous Na$_2$SO$_4$, filtered, and concentrated in vacuo. The residue obtained was dissolved in a 1:1 mixture of EtOAc/hexanes and passed through a 3-inch pad of silica gel (60 Å, 200-400 mesh).

The filtrate was concentrated in vacuo which afforded the desired product as a clear, viscous oil (1.29 g, 92%). $^1$H NMR (500 MHz, CDCl$_3$): δ 7.43 (m, 3H), 7.30 (m, 2H), 7.21 (m, 3H), 7.15 (d, J=8.3 Hz, 2H), 3.79 (t, J=7.1 Hz, 2H), 2.80 (t, J=7.1 Hz, 2H), 2.71 (t, J=7.5 Hz, 2H), 2.34 (t, J=7.5 Hz, 2H), 2.07 (quin, J=7.5 Hz, 2H), 0.90 (s, 9H), 0.01 (s, 6H). $^{13}$C NMR (125 MHz, CDCl$_3$): δ 170.95, 141.31, 136.01, 135.08, 129.52, 128.44, 128.36, 125.95, 119.75, 64.43, 38.94, 36.65, 35.02, 26.84, 25.88, 18.27, 5.42. ESI-HRMS: calcd. for C24H35NO2Si: [M+H]+=m/z 398.2510, found: [M+H]+=m/z 398.2526.

N-[4-(2-Hydroxyethyl)phenyl]-N-methyl-4-phenylbutanamide (21a): Sodium hydride (95% by wt., 33 mg, 1.3 mmol) was placed under argon, suspended in anhydrous THF (2 mL), and cooled to 0 °C in an ice bath. Then, N-[4-(2-{[tertbutyl(dimethyl)silyl]oxy}ethyl)phenyl]-4-phenylbutanamide 20 (0.40 g, 1 mmol) was dissolved in anhydrous THF (3 mL) and added slowly to the reaction at 0 °C. Stirring was continued for 5 min and then methyl iodide (2 M solution in THF, 1.0 mL, 2 mmol) was added dropwise to the reaction. The reaction was stirred at 0 °C for 30 min after which it was warmed to RT and stirred for an additional 16 h. The reaction was then partitioned between saturated aqueous ammonium chloride (15 mL) and EtOAc (15 mL). The organic layer was isolated and the aqueous layer was further extracted with EtOAc (2×15 mL). The combined organic extracts were washed with brine (10 mL), dried with anhydrous Na$_2$SO$_4$, filtered, and concentrated in vacuo. Purification by column chromatography (SiO$_2$, 25% EtOAc/hexanes) afforded the desired product as a clear viscous oil (0.34 g, 82%). $^1$H NMR (500 MHz, CDCl$_3$): δ 7.24 (m, 4H), 7.15 (m, 1H), 7.11 (d, J=7.2 Hz, 2H), 7.05 (d, J=8.0 Hz, 2H), 3.84 (t, J=6.6 Hz, 2H), 3.25 (s, 3H), 2.84 (t, J=6.7 Hz, 2H), 2.54 (t, J=7.7 Hz, 2H), 2.11 (t, J=7.4 Hz, 2H), 1.91 (quin, J=7.5 Hz, 2H), 0.87 (s, 9H), −0.02 (s, 6H). $^{13}$C NMR (125 MHz, CDCl$_3$): δ 172.84, 142.16, 141.78, 139.12, 130.44, 128.33, 128.17, 126.88, 125.68, 64.09, 38.96, 37.28, 35.22, 33.42, 26.99, 25.85, 18.27, −5.45. ESI-HRMS: calcd. for C25H37NO2Si: [M+H]+=m/z 412.2666, found: [M+H]+=m/z 412.2676. N-[4-(2-{[tert-butyl(dimethyl)silyl]oxy}ethyl)phenyl]-N-methyl-4-phenylbutanamide (0.32 g, 0.8 mmol) was dissolved in anhydrous THF (5 mL) and to it was added tetra-nbutylammonium fluoride (1 M solution in THF, 2.4 mL, 2.4 mmol) at RT. Stirring was continued until the reaction was complete as evidenced by TLC (approximately 24 h). Then, the reaction was poured into H$_2$O (10 mL) and the organic products were extracted with DCM (3×10 mL). The combined organic fractions were washed with brine (10 mL), dried with anhydrous Na$_2$SO$_4$, filtered, and concentrated in vacuo. Purification by column chromatography (SiO$_2$, 25-50% EtOAc/hexanes) afforded the desired product as a clear, viscous oil that solidified under vacuum (0.22 g, 94%). $^1$H NMR (500 MHz, CDCl$_3$): δ 7.23 (m, 4H), 7.15 (m, 1H), 7.09 (d, J=7.7 Hz, 2H), 7.07 (d, J=8.2 Hz, 2H), 3.90 (t, J=6.6 Hz, 2H), 3.25 (s, 3H), 2.90 (t, J=6.6 Hz, 2H), 2.54 (t, J=7.6 Hz, 2H), 2.10 (t, J=7.3 Hz, 2H), 1.90 (quin, J=7.4 Hz, 2H). $^{13}$C NMR (125 MHz, CDCl$_3$): δ 172.91, 142.30, 141.70, 138.37, 130.20, 128.33, 128.16, 127.19, 125.68, 63.31, 38.62, 37.26, 35.16, 33.35, 26.94. ESI-HRMS: calcd. for C19H23NO2: [M+H]+=m/z 298.1802, found: [M+H]+=m/z 298.1810.

N-Benzyl-N-[4-(2-hydroxyethyl)phenyl]-4-phenylbutanamide (21b): Potassium tertbutoxide (0.14 g, 1.2 mmol) was placed under argon, suspended in 4 mL of a 1:1 mixture of anhydrous DCM/DMF, and cooled to 0° C. in an ice bath. Then, N-[4-(2-{[tertbutyl(dimethyl)silyl]oxy}ethyl)phenyl]-4-phenylbutanamide 20 (0.40 g, 1 mmol) dissolved in an additional 4 mL of a 1:1 mixture of anhydrous DCM/DMF was added slowly at 0° C. The reaction was stirred for 15 min after which benzyl bromide (0.13 mL, 1.1 mmol) dissolved in 2 mL of a 1:1 mixture of anhydrous DCM/DMF was added dropwise to the reaction at 0° C. The reaction was allowed to warm to RT and then heated to 60° C. for 16 h. The reaction was quenched by the addition of H$_2$O (30 mL), then DCM (15 mL) was added and the organic layer isolated. The aqueous layer was further extracted with DCM (2×10 mL) and the combined organic fractions were washed with H$_2$O (3×30 mL), brine (10 mL), dried with anhydrous Na$_2$SO$_4$, filtered, and concentrated in vacuo. Purification by column chromatography (SiO$_2$, 20% EtOAc/hexanes) afforded the desired product as a clear, viscous oil (0.40 g, 82%). $^1$H NMR (500 MHz, CDCl$_3$): δ 7.29 (m, 7H), 7.19 (m, 5H), 6.89 (d, J=8.5 Hz, 2H), 4.92 (s, 2H), 3.86 (t, J=6.6 Hz, 2H), 2.85 (t, J=6.5 Hz, 2H), 2.61 (t, J=7.8 Hz, 2H), 2.16 (t, J=7.4 Hz, 2H), 1.99 (quin, J=7.5 Hz, 2H), 0.91 (s, 9H), 0.00 (s, 6H). $^{13}$C NMR (125 MHz, CDCl$_3$): δ 172.63, 141.75, 140.36, 139.31, 137.72, 130.24, 128.79, 128.34, 128.24, 128.17, 127.95, 127.18, 125.67, 63.97, 52.93, 38.92, 35.17, 33.63, 26.98, 25.84, 18.24, −5.47. N-Benzyl-N-[4-(2-{[tert-butyl(dimethyl)silyl]oxy}ethyl)phenyl]-4-phenylbutanamide (0.35 g, 0.7 mmol) was dissolved in anhydrous THF (5 mL) and to it was added tetra-n-butylammonium fluoride (1 M solution in THF, 2.2 mL, 2.2 mmol) at RT. Stirring was continued until reaction was complete as evidenced by TLC (approximately 24 h). Then, the reaction was poured into H$_2$O (10 mL) and the organic products extracted with DCM (3×10 mL). The combined organic fractions were washed with brine (10 mL), dried with anhydrous Na$_2$SO$_4$, filtered, and concentrated in vacuo. Purification by column chromatography (SiO$_2$, 25-50% EtOAc/hexanes) afforded the desired product as a clear, viscous oil (0.25 g, 92%). $^1$H NMR (500 MHz, CDCl$_3$): δ 7.26 (m, 7H), 7.17 (m, 3H), 7.11 (d, J=7.2 Hz, 2H), 6.89 (d, J=8.0 Hz, 2H), 4.89 (s, 2H), 3.89 (q, J=6.1 Hz, 2H), 2.88 (t, J=6.6 Hz, 2H), 2.58 (t, J=7.6 Hz, 2H), 2.12 (t, J=7.4 Hz, 2H), 1.96 (quin, J=7.5 Hz, 2H). $^{13}$C NMR (125 MHz, CDCl$_3$): δ 172.70, 141.73, 140.72, 138.41, 137.67, 129.99, 128.69, 128.38, 128.31, 128.19, 127.24, 125.71, 63.30, 52.95, 38.64, 35.16, 33.63, 26.95. ESI-HRMS: calcd. for C25H27NO2: [M+H]+=m/z 374.2115, found: [M+H]+=m/z 374.2125.

N-[4-(2-Hydrazinylethyl)phenyl]-N-methyl-4-phenylbutanamide oxalate (12l): The title compound was synthesized from N-[4-(2-Hydroxyethyl)phenyl]-N-methyl-4-phenylbutanamide 21a (0.20 g, 0.68 mmol) according to general procedure G and the oxalate salt was prepared according to general procedure I. The desired product was isolated as a white solid (0.11 g, 40%). $^1$H NMR (500 MHz, MeOD): δ 7.32 (d, J=8.0 Hz, 2H), 7.19 (m, 4H), 7.13 (m, 1H), 7.05 (d, J=6.9 Hz, 2H), 3.27 (t, J=7.8 Hz, 2H), 3.21 (s, 3H), 2.98 (t, J=7.5 Hz, 2H), 2.50 (t, J=6.9 Hz, 2H), 2.08 (t, J=6.8 Hz, 2H), 1.84 (br, 2H). $^{13}$C NMR (125 MHz, MeOD/DMSO-d$_6$): δ 175.16, 165.52, 144.00, 142.98, 138.91, 131.44, 129.57, 129.50, 128.78, 127.05, 53.20, 37.88, 36.19, 34.35, 32.40, 28.41. ESI-HRMS: calcd. for C19H25N3O: [M+H]+=m/z 312.2070, found: [M+H]+=m/z 312.2079.

N-Benzyl-N-[4-(2-hydrazinylethyl)phenyl]-4-phenylbutanamide oxalate (12m): The title compound was synthesized from N-Benzyl-N-[4-(2-hydroxyethyl)phenyl]-4-phenylbutanamide 21b (0.25 g, 0.66 mmol) according to general procedure G and the oxalate salt was prepared according to general procedure I. The desired product was isolated as an off-white solid (0.23 g, 47%). $^1$H NMR (500 MHz, MeOD): δ 7.20 (m, 10H), 7.06 (d, J=7.2 Hz, 2H), 6.95 (d, J=8.0 Hz, 2H), 4.88 (s, 2H), 3.23 (m, 2H), 2.93 (t, J=8.2 Hz, 2H), 2.53 (t, J=7.5 Hz, 2H), 2.10 (t, J=7.4 Hz, 2H), 1.88 (quin, J=7.4 Hz, 2H). $^{13}$C NMR (125 MHz, DMSO-d$_6$): δ 171.61, 164.24, 141.57, 140.53, 137.76, 137.57, 129.54, 128.27, 128.20, 128.18, 128.06, 127.74, 126.97, 125.69, 51.95, 50.95, 34.39, 32.78, 30.92, 26.64. ESI-HRMS: calcd. for C25H29N3O: [M+H]+=m/z 388.2383, found: [M+H]+=m/z 388.2396.

cDNA Cloning of Mouse LSD2. Two ovaries from a C57Black6 mouse (a gift from Josh Mendell's lab) were dissected and snap frozen by Raghu Chivukula. RNA was isolated by adding 200 μL of cold Trizol (Invitrogen) and the samples were homogenized with a handheld homogenizer with disposable tips (Fisher). An additional 800 μL of Trizol was added and mixed, the sample was clarified 1 min at 12,000×g, and the supernatant was transferred to a fresh tube, precipitated with isopropanol, washed with ethanol, air dried, and then resuspended in 20 μL DEPC-treated ddH$_2$O. cDNA was prepared by first digesting with DNase I and then reverse-transcribing using the Superscript III first strand synthesis system (Invitrogen) using Oligo-dT priming according to the manufacturer's instructions. Refseq LSD2 was amplified with primers AGCGCTCTGAGGTTTTC-CAA (SEQ ID NO: 1) and TGAGGGTCAGTGGTTGCAGA (SEQ ID NO: 2), and an approximately 2.7 kB product was gel purified and cloned using the StrataClone Blunt PCR Cloning Kit (Agilent). Clones were fully sequenced and one was identified as fully identical to the coding region of Kdm1b, NM_172262.3.

LSD2 Expression and Purification. To express Mouse LSD2 with a C-terminal His tag, we N-terminally truncated Refseq Mouse LSD2 by 25 amino acids and installed it into pET28b between NcoI and XhoI sites. The cDNA was PCR amplified with primers TCGTCGACATGTCTGGGCGGCAGGCAAAGAA (SEQ ID NO: 3) and AATAATCTCGAGAAAGGCTGCAATCTTGCTTGCTTC (SEQ ID NO: 4), cut with PciI and XhoI, and ligated into pET28b cut between NcoI and XhoI sites. The Δ25 Mouse LSD2 was then subcloned from the Mouse cDNA library into a pET28b vector and was overexpressed in E. coli BL21DE(3) codon plus cells as a C-terminal His6 tagged protein. Cell were grown to an OD600 of 0.6 in LB at 37° C., then induced with 0.25 mM IPTG (final concentration) and grown for 20 h at 16° C. Cell pellets were harvested by centrifugation at 5000 g for 20 min and resuspended in cold lysis buffer [280 mM NaCl, 5.4 mM KCl, 20 mM Na$_2$HPO$_4$, 3.6 mM KH$_2$PO$_4$, 1.3 mM PMSF, 6.8 μg/mL DNase I and 10% glycerol (pH 7.4)] containing cOmplete, EDTA-free Protease Inhibitor Cocktail Tablets (Roche). The cells were then lysed via single pass on a french press (16000-18000 psi), and the lysates were clarified by centrifugation at 25000 g for 30 min. The clarified lysate from 6 L of culture was incubated with 2 mL nickel sepharose fast flow resin that was pre-equilibrated with resin equilibration buffer [280 mM NaCl, 5.4 mM KCl, 20 mM Na$_2$HPO$_4$, 3.6 mM KH$_2$PO$_4$ and 10% glycerol (pH 7.4)] for 2 h at 4° C. The resin was then washed with equilibration buffer (3×20 mL). The resin was then washed with equilibration buffer containing 20 mM imidazole (20 mL). The protein was then eluted with equilibration buffer containing sequential steps of 100 mM, 200 mM and 300 mM imidazole (3×5 mL). The 200 mM imidazole elution contained the purest fraction of LSD2 as gauged by Coomassie-stained SDSPAGE. This fraction was dialyzed against equilibration buffer (3×2 L) containing 1 mM β-mercaptoethanol. The dialyzed LSD2-His6 was then concentrated to 4.3 μM.

LSD2 Enzymatic Assays. Initial velocity measurements were performed using a peroxidase-coupled assay, which monitors hydrogen peroxide production as previously described. Forneris, F., et al. (2005). The time courses of the reaction were measured under aerobic conditions using a Beckman Instruments DU series 600 spectrophotometer equipped with a thermostatted cell holder (T=25° C.). The 100 μL reactions were initiated by addition of enzyme (430 nM LSD2) to reaction mixtures consisting of 50 mM HEPES buffer (pH 7.5), 0.1 mM 4-aminoantipyrine, 1 mM 3,5-dichloro-2-hydroxybenzene-sulfonic acid, 0.76 μM horseradish peroxidase (Worthington Biochemical Corp.), 20 μM phenelzine analog and 100 μM DiMeK4H3-21. Absorbance changes were monitored at 515 nm, and an extinction coefficient of 26,000 M$^{-1}$ cm$^{-1}$ was used to quantify product formation. Progress curves were then fit accordingly to eq 1-3 as previously stated. Each experiment was repeated at least two independent times and repeat measured values were typically within 20% of each other.

MassSQUIRM Assays. MassSQUIRM inhibition experiments were performed in triplicate as described previously. Blair, L. P., et al. (2011). The reaction mixtures containing 13.3 µM H3K4me2-biotin peptide (1ARTKme2QTA RKS TGG KAP RKQ LYKbio), 50 mM HEPES (pH 7.5), and 50 µM phenelzine or 12d, were incubated at 25° C. for 5 min, prior to initiation with 215 nM GST-LSD1. The demethylase reactions were run at 25° C. for 30 min and then analyzed as reported previously.

Antibodies. H3K4Me was detected using a polyclonal rabbit antibody (abcam ab8895). H3K4Me2 was detected using a monoclonal rabbit antibody (abcam ab32356). H3K4Me3 was detected using a polyclonal rabbit antibody (abcam ab8580). H3K4-Unmodified was detected using a monoclonal mouse antibody (Active Motif 39763). H3K9Me2 was detected using a monoclonal mouse antibody (abcam ab1220). H3K36Me3 was detected using a polyclonal rabbit antibody (abcam ab9050). H3K9Ac was detected using a polyclonal rabbit antibody (abcam ab4441). Total H3 was detected using a polyclonal rabbit antibody (abcam ab1791). LSD1 was detected using a polyclonal rabbit antibody (abcam ab17721). Actin was detected using a monoclonal mouse antibody (Sigma A1978).

ChIP-seq Assay. LNCaP cells were seeded in 2, 150×25 mm tissue culture dishes (Corning 430599) per condition. Cells were grown to approximately 70% confluency, and after washing with phosphate-buffered saline (2×10 mL) (PBS, Gibco 10010-023), the cells were treated with either vehicle (DMSO) or 10 µM 12d (bizine) and grown in serum-free media for 48 h. Cells were then cross-linked with 1% formaldehyde for 10 min at 37° C. Cells were then placed on ice and washed with ice cold PBS (2×10 mL), scraped and pelleted. Pellets were then resuspended in PIPES buffer (5 mM PIPES (pH 8.0), 85 mM KCl, 0.5% NP-40, 1×cOmplete, EDTA-free, Protease Inhibitor Cocktail Tablets (Roche)), lysed in lysis buffer (1% SDS, 10 mM EDTA, 50 mM Tris-HCl pH 8.1, 1×cOmplete, EDTA-free, Protease Inhibitor Cocktail Tablets (Roche)), and sonicated to shear cross-linked DNA. Samples were kept in an ice bath at all times. Nucleic acid concentration was then measured using a Nanodrop (Thermo Scientific). The nucleic acid (20-100 µg) was then resuspended in 450-1,000 µL ChIP dilution buffer (0.01% SDS, 1.1% Triton-X 100, 1.2 mM EDTA, 16.7 mM Tris-HCl pH 8.1, 167 mM NaCl, 1×cOmplete, EDTA-free, Protease Inhibitor Cocktail Tablets (Roche)), and pre-cleared by adding 30 µL Protein A Dynabeads (Invitrogen) and rotated for 30 minutes at 4° C. Samples were then incubated overnight at 4° C. with 5 µg of polyclonal rabbit $H_3K_4me2$ (Millipore 07-030) (a no antibody control sample was included). 65 µL Dynabeads were then added to the samples and rotated for 2 h at 4° C. Dynabeads were then washed 2× with a low salt wash (0.1% SDS, 1% Triton X-100, 2 mM EDTA, 20 mM Tris pH 8.1, 150 mM NaCl); 1× with LiCl wash (0.25 M LiCl, 0.5% NP-40, 0.5% Na Deoxycholate, 1 mM EDTA, 10 mM Tris-HCl pH 8.1); and 2× with TE pH 8.0. Elution buffer was then added to the beads (1% SDS, 0.1 M $NaHCO_3$) and samples were vortexed and rotated at RT for 15 minutes and sample transferred to a new tube. This step was repeated 2×. Crosslinking was reversed by the addition of 20 µL 5 M NaCl and heating at 65° C. for 4 h. 10 mM EDTA, 40 mM Tris-HCl pH 6.5, and 40 µg Proteinase K (Thermo Scientific #EO0491) were then added and samples were incubated for 1 h at 45° C. 500 µL phenol:chloroform was then added to the samples and they were rotated overnight at 4° C. Samples were then spun and the top layer (aqueous) was placed in a new tube. An equal volume of chloroform was added and vortexed and spun and the bottom layer discarded again. 50 µg/mL of GlycoBlue (Life Technologies AM9515), 0.5 M NaOAc pH 5.2, and 2 volumes of 100% ethanol was added and samples were placed on ice for 15 minutes. Samples were then spun down and pellet was washed with 1 volume 70% EtOH and let dry. The pellets were then resuspended in TE and DNA concentrations were quantified by Qubit assay HS kit (Invitrogen Q32851).

Next Generation Sequencing/Library Generation. Libraries were prepared from 10-20 ng of IP ChIP DNA and 100 ng of input DNA according to Illumina's instructions along with the ChIP-seq DNA Sample Prep Kit (IP-102-1001). Briefly, samples were checked for quality and concentration from 150-250 bp on a bioanalyzer. DNA was endrepaired using Klenow polymerase in 58 µL of reaction buffer. For IP DNA, Klenow was diluted 1:5. Samples were incubated at 20° C. for 30 minutes and subsequently purified on QIAquick PCR purification columns. A-tails were then added to the DNA with Klenow and dATP in NEB buffer 2 at 37° C. for 30 minutes and cleaned with Qiagen MiniElute PCR purification columns. Sequencing adapters were then ligated onto the DNA for 15 minutes at room temperature followed by cleaning with MiniElute columns. Samples were then run on 2% agarose gels and DNA from 216-366 bp (DNA plus adapters) were cut from the gel and purified with a Qiagen QIAquickGel Extraction kit. Concentrations were then checked on a bioanalyzer and 8 ng were PCR amplified with Phusion polymerase (Fisher) for 15 cycles (10 sec 98° C., 30 sec 65° C., 30 sec 72° C.) followed by 5 minutes at 72° C. Samples were then cleaned with Ampure kits (Illumina) and washed with 80% ethanol. DNA samples were resuspended at the end of the cleanup into 17.5 µL buffer EB (Qiagen) and subjected to next generation sequencing on Illumina HiSeq platform according to manufacturer's instructions.

Peak Calling and Statistical Analysis of ChIP-seq Data. 46 bp paired-end sequencing data were aligned to the reference human genome (hg19) using BWA with default parameters. Li, H., and Durbin, R. (2009). After alignment, duplicate reads were removed and only uniquely aligned reads were kept for further analysis. For narrow H3K4Me2 peaks, MACS2 were used for peak calling with default parameters. Zhang, Y., et al. (2008). For broad H3K4Me2 peaks, peak calling was performed using RSEG, which is based on the hidden Markov model (HMM) and specifically designed for identifying broad histone peaks. Song, Q., and Smith, A. D. (2011). Differential peaks between samples with two biological replicates were identified by diffReps. Shen, L., et al. (2013). Ensemble human genome annotations were used to identify the human genes around identified peak regions. A gene is defined to be around a peak region if the closest distance between its Transcription Start Site (TSS) and the peak region is less than 2000 bp. In total 2432 Ensemble genes were found to be around the identified peak regions. Furthermore, to compare this ChIP-seq data set to the data set generated by Kerenyi et al., where target genes around LSD1(−/−)-specific and wt-specific histone modification peaks in Gr1 dim Mac1+ cells were reported, Kerenyi, M. A., et al. (2013), the Ensemble gene names were translated into official symbol gene names. In this process, microRNA and genes represented by nonstandard gene names were removed. A total of 1767 genes with official symbol names were identified. Utilizing all of the human genes identified with official symbol names for normalization, the overlap significance was computed by cumulative hypergeometric distribution. 146 of the 1587 Lsd1 KO-specific genes were recovered from our data set (p-val=0.0028). As a negative control, only 17 of the wt specific genes (TSG) were recovered (p-val=0.186). Additionally, to identify the number of tumor suppressor genes in the 146 genes identified to be in common, we used two TSG data sets. One data set used was from Vanderbilt University (http://bioinfo.mc.vanderbilt.edu/TSGene/Human_716_TSGs.txt), which contains 716 TSG genes. The other data set used was from Memorial Sloan-Kettering Cancer Center (http://cbio.mskcc.org/CancerGenes/), which contains 873 TSG genes. Utilizing all of the human genes to normalize, we utilized a cumulative hypergeometric distribution to compute the number of TSG in our data set. From the two TSG datasets, 18 and 19 of the 146 recovered genes are TSG genes, with p-val of 3.72E-7 and 1.50E-6 respectively. Combining the two datasets together to define the total TSG genes (covering 1146 distinct TSG genes in total), 26 of the 146 recovered genes were identified as TSG genes, with a p-val of 5.80E-9.

[$^3$H] Thymidine Assay. Cells were seeded in 96 well plates (Corning 3595). Cells were treated at approximately 70% confluency with 12d in serum-free media for 48 h. 6 hours prior to harvesting cells, 10 μL of 0.1 mCi/mL Thymidine [methyl-3H] (ARC ART0178) was added to each well. The cells were then harvested (PerkinElmer) and radioactivity was measured with a liquid scintillation counter (PerkinElmer MicroBeta).

Drug Combination Experiments. The H460 cell line was exposed to drugs alone or in combination. 12d was added at three different fixed concentrations while the concentration of the other drug added was varied. After 48 h of treatment in serum-free media the [$^3$H] Thymidine Assay was performed as described above. The CPM of drug treated wells were compared to the CPM of control wells to calculate each fraction affected (FA), where FA=X means a decrease in growth of X %. Drug synergy was determined by isobologram analysis and derived from the median-effect principle of the Chou-Talalay method. Chou, T. C., and Talalay, P. (1984). The combination index (CI) was calculated using CompuSyn™ (ComboSyn Inc., Paramus, N.J.) and the multiple drug effect equation18 to evaluate drug interactions. A CI greater than, equal to, and less than one, respectively, indicates antagonistic activity, additivity, or synergy between two drugs. Data are presented from one representative experiment. Each experiment was repeated at least two independent times with nearly identical results.

Example 4

Synthesis of Representative Compounds of Formula (II)

Overview. Synthesis of compound 23 was initiated via the Sonogoshira coupling of 3-butyn-1-ol to 4-bromobenzoic acid methyl ester to produce an alkyne intermediate which was subsequently reduced via palladium catalyzed hydrogenation. The resulting alcohol 41 was oxidized to a carboxylic acid in a two-step process using pyridinium chlorochromate to generate the aldehyde followed by treatment with sodium chlorite. The intermediate acid 43 was coupled to 2-(4-aminophenyl)ethanol under standard conditions to yield alcohol 44, which was further converted to the alkyl bromide 45 via the Appel reaction. The bromide was subsequently displaced with excess di-tert-butylhydrazodiformate to provide intermediate ester 46. Saponification with lithium hydroxide followed by coupling to the protected o-phenylenediamine 39 under standard conditions resulted in the penultimate product which was deprotected with trifluoroacetic acid to yield the desired dual inhibitor 23. Dual functional inhibitors 20-22, as well as intermediate 39 used in the synthesis of 23, were prepared from inexpensive, commercially available starting materials as follows. To generate intermediate 39, 2-nitroaniline was protected using di-tert-butyl dicarbonate resulting in 38 which was subsequently reduced to the desired diamine via palladium catalyzed hydrogenation.

Dual inhibitor 22 was prepared from commercially available 3-(4-bromobenzoyl)propionic acid in nine steps. First, the keto acid starting material was reduced under Wolff-Kishner conditions to yield 4-(4-bromophenyl)butyric acid which was subsequently coupled to 2-(4-aminophenyl)ethanol as previously described for 23 to yield the intermediate alcohol 32. Protection of the alcohol as a silyl ether (33) followed by Heck coupling with methyl acrylate yielded unsaturated ester 34. Deprotection of the alcohol with TBAF yielded intermediate 35 which was subjected to the Appel reaction to generate alkyl bromide 36. Nucleophilic substitution with di-tert-butylhydrazodiformate produced the penultimate compound 37 which was converted to the hydroxamic acid with hydroxylamine and subsequently deprotected with TFA to yield the desired final product 22.

Lastly, dual inhibitors 21 and 20 were prepared in seven steps starting with 4-(4-nitrophenyl)butyric acid. 2-(4-Aminophenyl)ethanol was coupled to 4-(4-nitrophenyl)butyric acid using HATU to generate intermediate 16i which was subsequently hydrogenated in the presence of palladium to yield common intermediate amine 25. Standard peptide coupling conditions were again utilized with 25 and either suberic or adipic acid monomethyl ester to generate compounds 27 and 26, respectively. Separately, intermediates 27 and 26 were subjected to the Appel reaction resulting in alkyl bromides 29 and 28. Substitution of the halide by di-tert-butylhydrazodiformate yielded penultimate intermediates 31 and 30 which were converted to their respective hydroxamic acids using hydroxylamine and ultimately deprotected to yield dual inhibitors 21 and 20.

General. $^1$H and $^{13}$C NMR experiments were run using either a Bruker 500 MHz ($^1$H, 500 MHz; $^{13}$C, 125 MHz) spectrometer or a Bruker AC 400 spectrometer ($^1$H, 400 MHz; $^{13}$C, 100 MHz). Chemical shifts (δ) are presented in parts per million (ppm) relative to tetramethylsilane (TMS), which was used as an internal standard, and J-coupling constants (J) are expressed in hertz (Hz). The following designations were used to indicate multiplicity: s (singlet), d (doublet), t (triplet), q (quartet), quin (quintet), m (multiplet), br (broad), dd (doublet of doublets), dt (doublet of triplets), td (triplet of doublets). Processing of NMR spectra was carried out using ACD/NMR Processor Academic Addition, version 12.01 (Advanced Chemistry Development, Inc., Toronto, On, Canada, www.acdlabs.com, 2013). ESI-HRMS data was obtained on a Shimadzu IT-TOF instrument at the Research Resources Center's Mass Spectrometry Facility at the University of Illinois at Chicago. EI-MS spectra were recorded with a Fisons Trio 1000 spectrometer with only molecular ions (M$^+$) and base peaks reported. Melting points were determined on a Buchi 530 melting point apparatus and are uncorrected. Chemicals, reagents, media, antibiotics, and other disposable materials were purchased from commercial vendors and used as received. Solvents were also purchased from commercial vendors and, when necessary, purified and dried using standard techniques. Reaction progress was monitored by thin layer chromatography (TLC) using either pre-coated, glass silica gel plates (Sigma-Aldrich F254, 60 Å pore size, 250 μM thickness) or aluminum-backed silica gel plates (Merck DC, Alufolien Kieselgel 60 F254) with spots visualized by UV light. Preparatory HPLC was carried out using a Varian ProStar 210 with the following specifications: Column: Varian Dynamax (250×21.4 mm, 5 μm particle size) Microsorb 100-5 C18 fitted with a guard column. Flow rate: 10 mL/min, λ monitoring at 254 nm. Gradient: 5% MeCN/$H_2O$, 1 min; 5-60% MeCN/$H_2O$, 50 min; 60-100% MeCN/$H_2O$, 5 min; 100% MeCN, 5 min; 100-5% MeCN/$H_2O$, 5 min; 5% MeCN/$H_2O$, 5 min. Analytical HPLC was carried out using the same instrument but with the following specifications: Column: Agilent Eclipse XD8-C18 (4.6×250 nm, 5 μm particle size). Flow rate: 1 mL/min, λ monitoring at 254 nm. Gradient: 10% MeCN/$H_2O$, 1 min; 10-100% MeCN/$H_2O$, 19 min; 100% MeCN, 3 min; 100-10% MeCN/$H_2O$, 2 min; 10% MeCN/$H_2O$, 5 min. All HPLC solvents were spiked with 0.05% TFA. All compounds tested were determined to be 95% pure as determined by $^1$H NMR, analytical HPLC, and/or elemental analysis. For elemental analysis, analytical results were within ±0.40% of the theoretical values.

Representative compounds of Formula (II) can be prepared as follows:

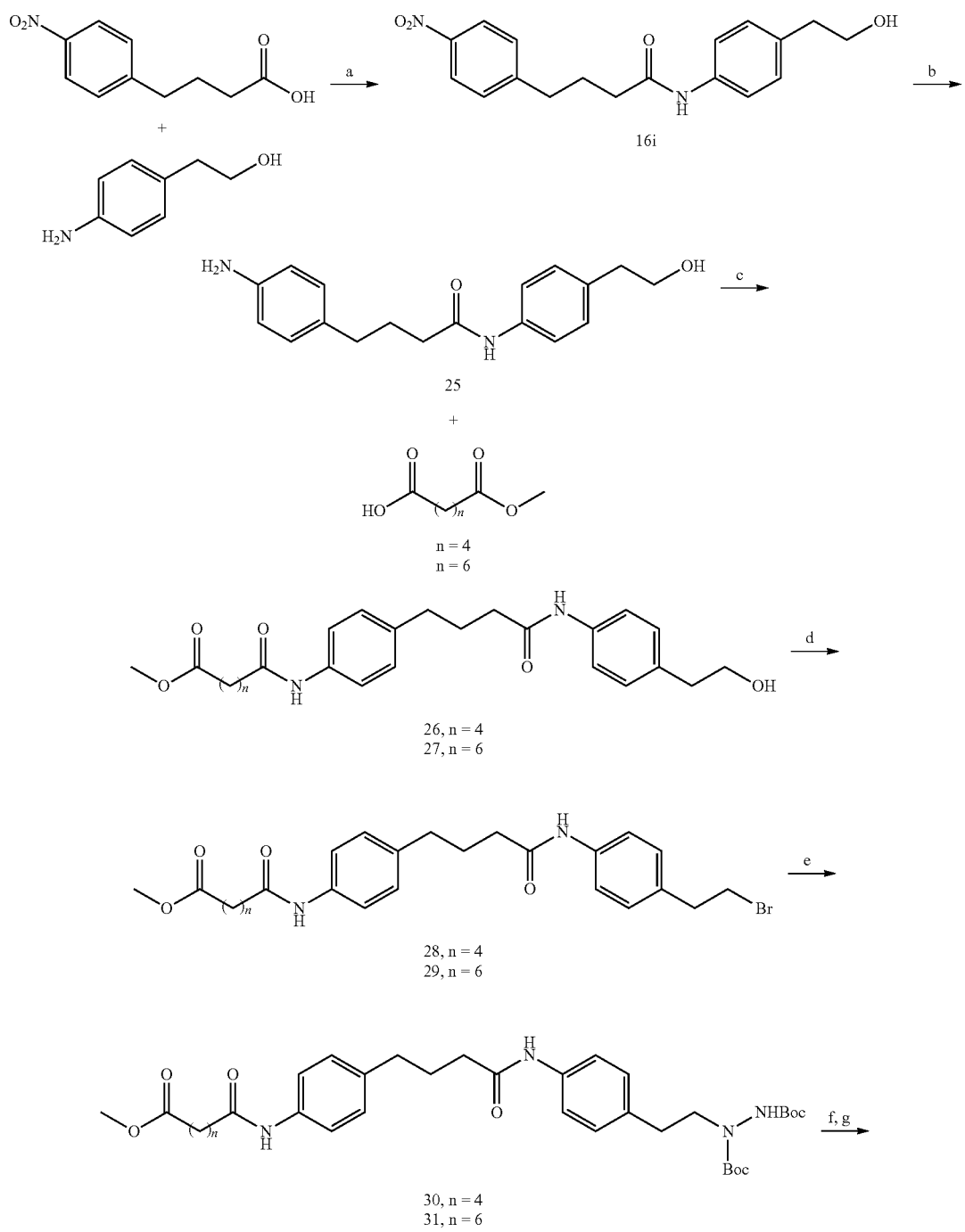

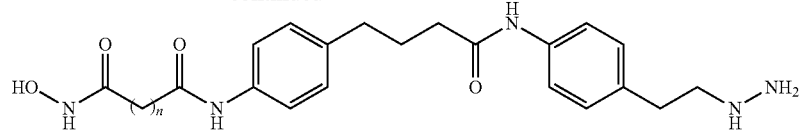
20, n = 4
21, n = 6
Reagents and conditions: a) EDC, DMAP, DCM, RT, 16 h; b) H$_2$, Pd/C, AcOH, EtOH, RT, 16 h; c) EDC, DMAP, DCM/DMF, RT, 16 h; d) PPh$_3$, CBr$_4$, DCM, RT, 30 min; e) BocNHNHBoc, NaH, DMF, RT, 16 h; f) NH$_2$OH (aq), NaOH, THF, MeOH, 0° C. to RT, 30 min; g) TFA, DCM, RT, 16 h.
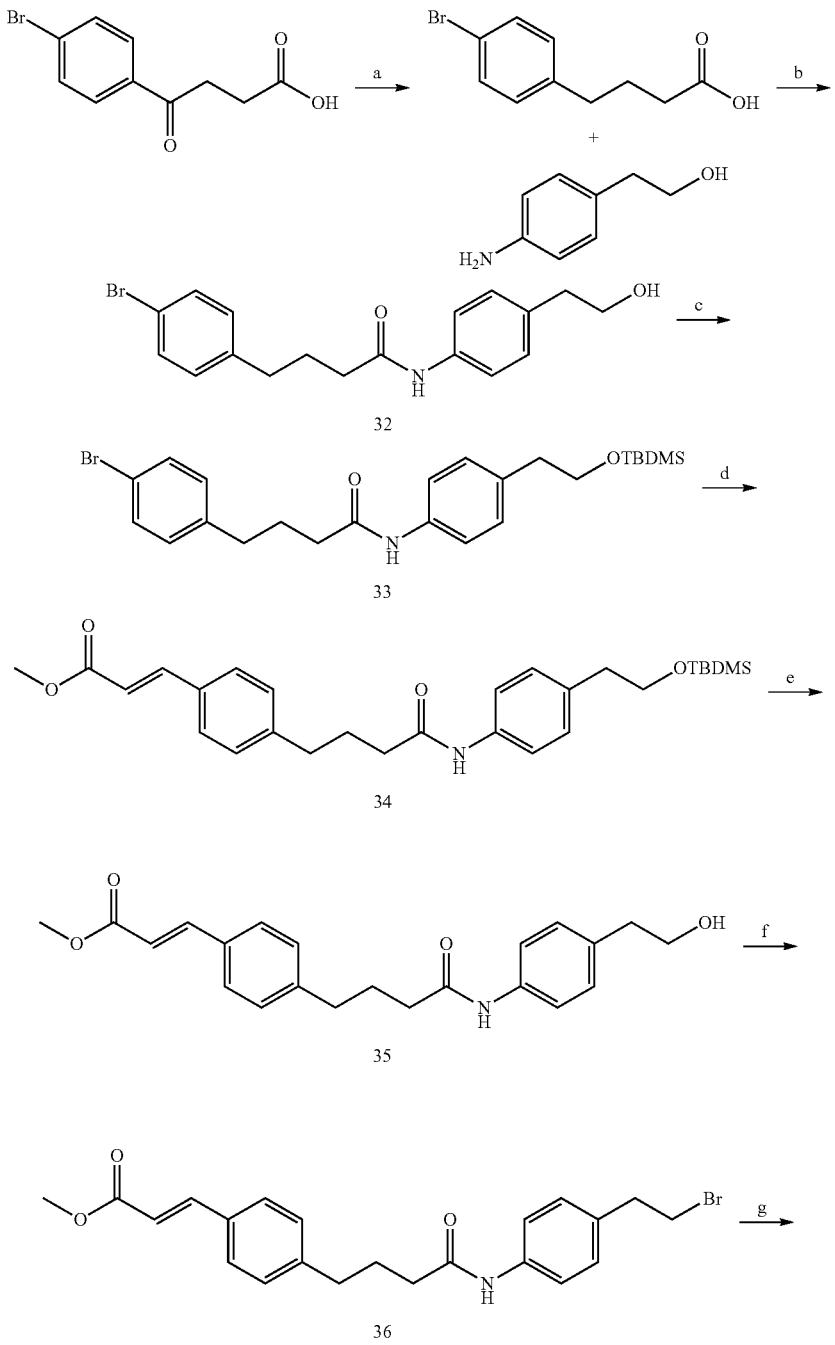

-continued
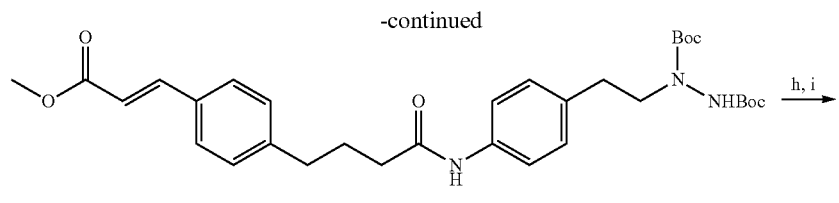
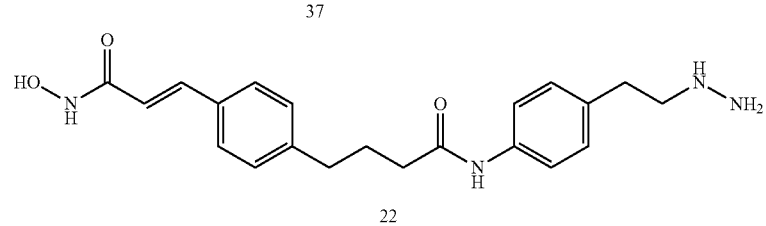
Reagents and conditions: a) N₂H₄.H₂O, KOH, diethylene glycol, 120° C.→200° C., 5 h; b) EDC, DMAP, DCM, RT, 16 h; c) TBDMSCl, DMAP, Et₃N, DCM, RT, 2 h; d) Pd(OAc)₂, PPh₃, TMED, methyl acrylate 135° C., 16 h; e) TBAF, THF, RT, 16 h; f) PPh₃, CBr₄, DCM, RT, 30 min; g) BocNHNHBoc, NaH, DMF, 0° C., 16 h; h) NH₂OH (aq), NaOH, THF, MeOH, 0° C. to RT, 30 min; i) TFA, DCM, RT, 16 h.
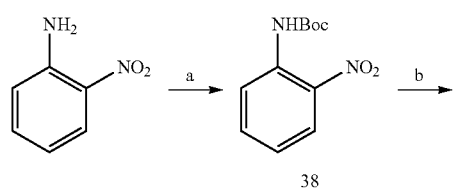
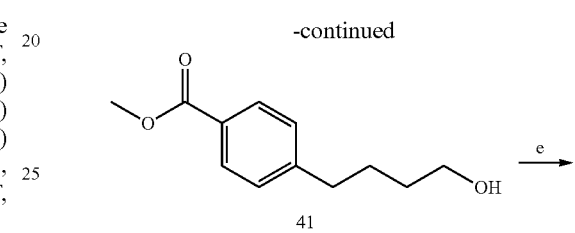
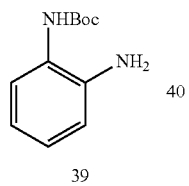
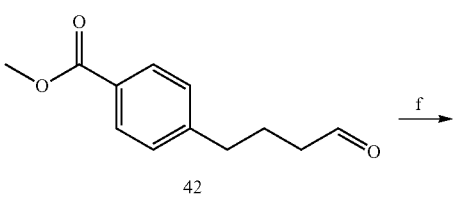
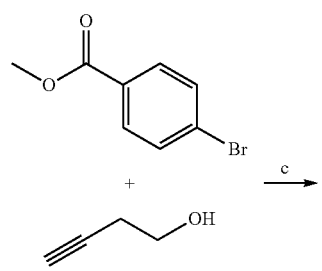
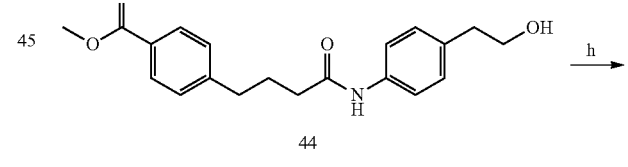
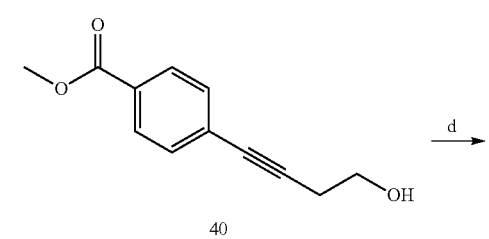
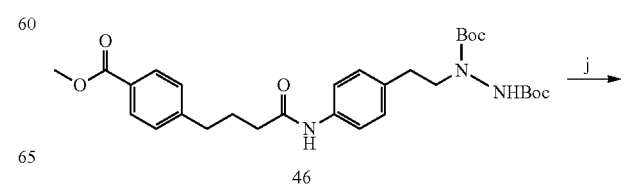

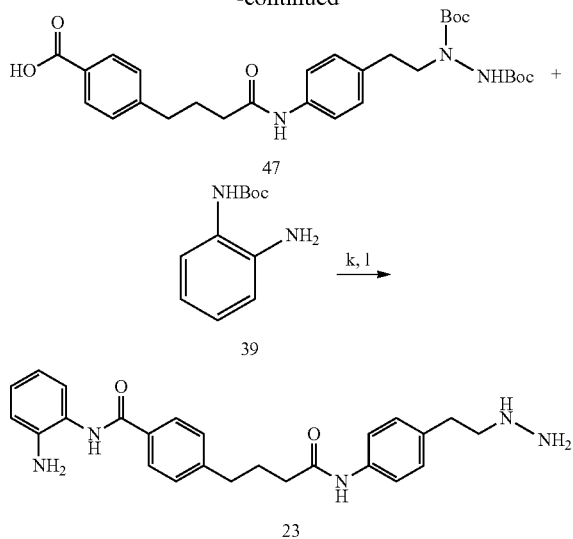

Reagents and conditions: a) Boc₂O, NaHMDS, THF, RT, 2 h; b) H₂, Pd/C, MeOH, RT, 16 h; c) PdCl₂, PPh₃, Et₂NH, CuI, RT, 24 h; d) Pd/C, H₂ (50 psi), EtOH, RT, 12 h; e) PCC, NaOAc, DCM, RT, 12 h; f) NaClO₂, NaH₂PO₄, H₂O, H₂O/MeCN, 0° C., 2 h; g) 2-(4-aminophenyl)ethanol, HATU, Et₃N, DCM, 0° C. to RT, 16 h; h) PPh₃, CBr₄, DCM, RT, 30 min; i) BocNHNHBoc, NaH, DMF, −40° C., 3 h; j) LiOH, THF, MeOH, H₂O, RT, 16 h; k) HATU, Et₃N, DCM, 0° C. to RT, 6 h; l) TFA, DCM, RT, 6 h.

perature and then poured through a 1.5 inch pad of celite which was subsequently washed with methanol (3×30 mL). The combined filtrate and washes were concentrated in vacuo and the solid obtained was purified via recrystallization from ethyl acetate to yield the title compound as a beige solid (2.160 g, 80%). ¹H NMR (500 MHz, DMSO-d₆): δ 9.75 (s, 1H), 7.47 (d, J=8.5 Hz, 2H), 7.11 (d, J=8.5 Hz, 2H), 6.84 (d, J=8.3 Hz, 2H), 6.49 (d, J=8.3 Hz, 2H), 4.81 (s, 2H), 4.59 (t, J=5.0 Hz, 1H), 3.55 (m, 2H), 2.65 (t, J=7.2 Hz, 2H), 2.43 (t, J=7.5 Hz, 2H), 2.25 (t, J=7.5 Hz, 2H), 1.79 (quin, J=7.5 Hz, 2H). ¹³C NMR (125 MHz, DMSO-d₆): δ 170.88, 146.47, 137.27, 133.95, 128.92, 128.66, 128.56, 118.99, 114.00, 62.29, 38.47, 35.79, 33.88, 27.29. ESI-HRMS: calcd. for C₁₈H₂₂N₂O₂: [M+H]⁺=m/z 299.1754, found: [M+H]⁺=m/z 299.1765.

Methyl 6-{[4-(4-{[4-(2-hydroxyethyl)phenyl]amino}-4-oxobutyl)phenyl]amino}-6-oxohexanoate (26):

The title compound was synthesized from 4-(4-aminophenyl)-N-[4-(2-hydroxyethyl)phenyl]butanamide 25 (500 mg, 1.68 mmol) and adipic acid monomethyl ester (248 μL, 1.68 mmol) using a procedure similar to that used to prepare 27. Purification by column chromatography (2-5% MeOH/DCM) yielded the desired product as a white solid (517 mg, 70%). ¹H NMR (500 MHz, MeOD): δ 7.45 (m, 4H), 7.16 (m, 4H), 3.72 (t, J=7.1 Hz, 2H), 3.65 (s, 3H), 2.77 (t, J=7.1 Hz, 2H), 2.65 (t, J=7.5 Hz, 2H), 2.37 (m, 6H), 1.98 (quin, J=7.5 Hz, 2H), 1.69 (m, 4H). ¹³C NMR (125 MHz, MeOD): δ 175.78, 174.33, 174.21, 138.99, 138.12, 137.93, 136.34, 130.40, 129.96, 121.62, 121.54, 64.36, 52.17, 39.80, 37.62, 37.33, 35.83, 34.60, 28.74, 26.47, 25.71. ESI-HRMS: calcd. for C₂₅H₃₂N₂O₅: [M+H]⁺=m/z 441.2384, found: [M+H]⁺=m/z 441.2405.

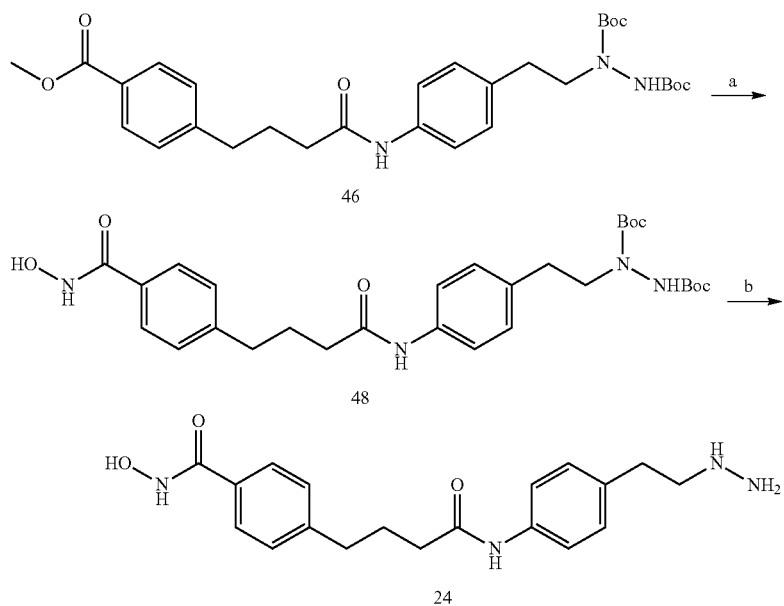

4-(4-Aminophenyl)-N-[4-(2-hydroxyethyl)phenyl]butanamide (25):

N-[4-(2-Hydroxyethyl)phenyl]-4-(4-nitrophenyl)butanamide 16i (2.978 g, 9.07 mmol) and 10% palladium on carbon (300 mg, 20% wt. equivalent) were placed in a two-necked round-bottomed flask under a hydrogen atmosphere. Ethanol (50 mL) was added followed by acetic acid (300 μL). The reaction was stirred overnight at room tem- Methyl 6-{[4-(4-{[4-(2-bromoethyl)phenyl]amino}-4-oxobutyl)phenyl]amino}-6-oxohexanoate (28):

The title compound was synthesized from methyl 6-{[4-(4-{[4-(2-hydroxyethyl)phenyl]amino}-4-oxobutyl)phenyl]amino}-6-oxohexanoate 26 (515 mg, 1.17 mmol) using a procedure similar to that used to prepare 29. Purification by trituration in methanol yielded the desired product as a white solid (401 mg, 68%). ¹H NMR (500 MHz, DMSO-d₆): δ

9.82 (s, 1H), 9.79 (s, 1H), 7.50 (t, J=8.9 Hz, 4H), 7.17 (d, J=8.5 Hz, 2H), 7.12 (d, J=8.3 Hz, 2H), 3.67 (t, J=7.3 Hz, 2H), 3.58 (s, 3H), 3.05 (t, J=7.2 Hz, 2H), 2.56 (t, J=7.5 Hz, 2H), 2.33 (t, J=7.1 Hz, 2H), 2.28 (m, 4H), 1.85 (quin, J=7.5 Hz, 2H), 1.57 (m, 4H). $^{13}$C NMR (125 MHz, DMSO-$d_6$): δ 173.23, 170.84, 170.73, 137.90, 137.15, 136.20, 133.40, 128.90, 128.45, 119.14, 119.07, 51.21, 37.87, 35.96, 35.68, 34.65, 34.02, 33.04, 26.83, 24.60, 24.06. ESI-HRMS: calcd. for $C_{25}H_{31}BrN_2O_4$: [M+H]$^+$=m/z 503.1540, found: [M+H]$^+$=m/z 503.1552.

Di-tert-butyl 1-(2-{4-[(4-{4-[(6-methoxy-6-oxohexanoyl)amino]phenyl}butanoyl)amino]phenyl}ethyl)hydrazine-1,2-dicarboxylate (30):

The title compound was prepared from methyl 6-{[4-(4-{[4-(2-bromoethyl)phenyl]amino}-4-oxobutyl)phenyl]amino}-6-oxohexanoate (28) (400 mg, 0.79 mmol) following a procedure similar to that used for 46. Purification by column chromatography (SiO$_2$, 25-75% EtOAC/hexanes) provided the desired product as a white solid (292 mg, 56%). $^1$H NMR (500 MHz, CDCl$_3$): δ 8.21 (br, 1H), 8.14 (s, 1H), 7.45 (br, 2H), 7.33 (d, J=8.3 Hz, 2H), 7.08 (d, J=8.3 Hz, 2H), 7.00 (d, J=8.3 Hz, 2H), 3.65 (s, 3H), 3.63 (br, 2H), 2.81 (t, J=7.5 Hz, 2H), 2.57 (t, J=7.2 Hz, 2H), 2.34 (t, J=6.9 Hz, 4H), 2.19 (t, J=7.5 Hz, 2H), 1.93 (quin, J=7.3 Hz, 2H), 1.69 (m, 4H), 1.46 (s, 9H), 1.42 (br, 9H). ESI-HRMS: calcd. for $C_{35}H_{50}N_4O_8$: [M+H]$^+$=m/z 655.3701, found: [M+H]$^+$=m/z 655.3715.

N-[4-(4-{[4-(2-Hydrazinylethyl)phenyl]amino}-4-oxobutyl)phenyl]-N'-hydroxyhexanediamide (20):

The title compound was synthesized from di-tert-butyl 1-(2-{4-[(4-{4-[(6-methoxy-6-oxohexanoyl)amino]phenyl}butanoyl)aminio]phenyl}ethyl)hydrazine-1,2-dicarboxylate (30) (275 mg, 0.42 mmol) using a procedure similar to that used to prepare 21. Purification by preparatory HPLC provided the ditrifluoracetic acid salt as a white solid (86 mg, 30%). $^1$H NMR (500 MHz, MeOD): δ 7.49 (d, J=8.5 Hz, 2H), 7.45 (d, J=8.5 Hz, 2H), 7.21 (d, J=8.5 Hz, 2H), 7.16 (d, J=8.3 Hz, 2H), 3.24 (t, J=7.8 Hz, 2H), 2.90 (t, J=7.8 Hz, 2H), 2.66 (t, J=7.5 Hz, 2H), 2.37 (m, 4H), 2.14 (t, J=6.8 Hz, 2H), 1.99 (quin, J=7.4 Hz, 2H), 1.70 (m, 4H). $^{13}$C NMR (125 MHz, MeOD/DMSO-$d_6$): δ 173.94, 173.78, 172.37, 139.08, 138.74, 138.19, 134.15, 130.29, 130.03, 121.67, 121.41, 53.66, 37.69, 37.33, 35.80, 33.71, 32.28, 28.66, 26.52, 26.50. ESI-HRMS: calcd. for $C_{24}H_{33}N_5O_4$: [M+H]$^+$=m/z 426.2605, found: [M+H]$^+$=m/z 426.2621.

Methyl 8-{[4-(4-{[4-(2-hydroxyethyl)phenyl]amino}-4-oxobutyl)phenyl]amino}-8-oxooctanoate (27):

4-(4-Aminophenyl)-N-[4-(2-hydroxyethyl)phenyl]butanamide 16i (1.492, 5 mmol), suberic acid monomethyl ester (941 mg, 5 mmol), and HATU (2.282 g, 6 mmol) were dissolved in a 4:1 mixture of anhydrous methylene chloride (40 mL) and anhydrous N,N-dimethylformamide (10 mL) and cooled to 0° C. in an ice bath. Triethylamine (1.53 mL, 11 mmol) was added and then the reaction was allowed to warm to room temperature with stirring for 4 h. Then, the reaction was poured into a 1 N hydrochloric acid solution (20 mL) and the organic products were extracted with methylene chloride (4×30 mL). The combined organic extracts were washed with 1 N hydrochloric acid (3×15 mL), brine (15 mL), dried with anhydrous sodium sulfate, filtered, and concentrated in vacuo. Purification by trituration in methanol yielded the desired product as a white solid (1.616 g, 69%). $^1$H NMR (500 MHz, DMSO-$d_6$): δ 9.77 (s, 2H), 7.49 (dd, J=11.5, 8.5 Hz, 4H), 7.11 (dd, J=8.5 Hz, 1.7 Hz, 4H), 4.59 (t, J=5.2 Hz, 1H), 3.57 (s, 3H), 3.56 (m, 2H), 2.65 (, d, J=7.2 Hz, 2H), 2.55 (d, J=7.5 Hz, 2H), 2.27 (m, 6H), 1.85 (quin, J=7.5 Hz, 2H), 1.55 (m, 4H), 1.29 (dt, J=6.9 Hz, 3.6 Hz, 4H). $^{13}$C NMR (125 MHz, DMSO-$d_6$): δ 173.33, 170.96, 170.70, 137.23, 137.19, 136.15, 133.99, 128.92, 128.43, 119.12, 119.00, 62.28, 51.15, 38.47, 36.28, 35.67, 34.02, 33.22, 28.30, 28.22, 26.86, 24.98, 24.31. ESI-HRMS: calcd. for $C_{27}H_{36}N_2O_5$: [M+H]$^+$=m/z 469.2697, found: [M+H]$^+$=m/z 469.2712.

Methyl 8-{[4-(4-{[4-(2-bromoethyl)phenyl]amino}-4-oxobutyl)phenyl]amino}-8-oxooctanoate (29):

Methyl 8-{[4-(4-{[4-(2-hydroxyethyl)phenyl]amino}-4-oxobutyl)phenyl]amino}-8-oxooctanoate 27 (469 mg, 1 mmol) and triphenylphosphine (394 mg, 1.5 mmol) were placed in a round-bottomed flask under argon at room temperature. Anhydrous methylene chloride (1.5 mL) was added followed by tetrabromomethane (498 mg, 1.5 mmol) dropwise as a solution in anhydrous methylene chloride (0.5 mL). Stirring was continued for 30 min at room temperature after which the reaction was poured into water (15 mL) and the organic products extracted with methylene chloride (3×15 mL). The combined organic extracts were washed with brine, dried with anhydrous sodium sulfate, filtered, and concentrated in vacuo. Purification by trituration in methanol yielded the title compound as a white solid (383 mg, 72%). $^1$H NMR (500 MHz, DMSO-$d_6$): δ 9.79 (s, 1H), 9.78 (s, 1H), 7.50 (t, J=8.9 Hz, 4H), 7.17 (d, J=8.3 Hz, 2H), 7.11 (d, J=8.5 Hz, 2H), 3.68 (t, J=7.3 Hz, 2H), 3.57 (s, 3H), 3.05 (t, J=7.2 Hz, 2H), 2.55 (t, J=7.5 Hz, 2H), 2.28 (m, 6H), 1.85 (quin, J=7.5 Hz, 2H), 1.54 (m, 4H), 1.29 (m, 4H). $^{13}$C NMR (125 MHz, DMSO-$d_6$): δ 173.33, 170.96, 170.83, 137.90, 137.20, 136.13, 133.39, 128.89, 128.43, 119.12, 119.06, 51.15, 37.86, 36.28, 35.68, 34.65, 34.01, 33.22, 28.30, 28.22, 26.83, 24.98, 24.31. ESI-HRMS: calcd. for $C_{27}H_{35}BrN_2O_4$: [M+H]$^+$=m/z 531.1853, found: [M+H]$^+$=m/z 531.1876.

Di-tert-butyl 1-(2-{4-[(4-{4-[(8-methoxy-8-oxooctanoyl)amino]phenyl}butanoyl)amino]phenyl}ethyl)hydrazine-1,2-dicarboxylate (31):

The title compound was prepared from methyl 8-{[4-(4-{[4-(2-bromoethyl)phenyl]amino}-4-oxobutyl)phenyl]amino}-8-oxooctanoate 29 (266 mg, 0.5 mmol) following a procedure similar to that used for 46. Purification by column chromatography (SiO$_2$, 10-50% EtOAC/hexanes) provided the desired product as a white solid (83 mg, 24%). $^1$H NMR (500 MHz, CDCl$_3$): δ 7.54 (br, 1H), 7.45 (m, 3H), 7.38 (d, J=8.3 Hz, 2H), 7.12 (d, J=7.9 Hz, 2H), 7.09 (d, J=8.2 Hz, 2H), 3.67 (s, 3H), 3.66 (br, 2H), 2.84 (t, J=7.3 Hz, 2H), 2.65 (t, J=7.2 Hz, 2H), 2.33 (m, 4H), 2.25 (t, J=7.5 Hz, 2H), 2.00 (quin, J=7.3 Hz, 2H), 1.73 (quin, J=7.3 Hz, 2H), 1.64 (m, 2H), 1.48 (s, 9H), 1.44 (br, 9H), 1.38 (m, 4H). ESI-HRMS: calcd. for $C_{37}H_{54}N_4O_8$: [M+H]$^+$=m/z 683.4014, found: [M+H]$^+$=m/z 683.3999.

N-[4-(4-{[4-(2-hydrazinylethyl)phenyl]amino}-4-oxobutyl)phenyl]-N'-hydroxyoctanediamide (21):

An aqueous solution of hydroxylamine (50 wt %, 1 mL) was placed on ice and to it was added sodium hydroxide (38 mg, 0.96 mmol). The solution was stirred until the sodium hydroxide was completely dissolved after which di-tert-butyl 1-(2-{4-[(4-{4-[(8-methoxy-8-oxooctanoyl)amino]phenyl}butanoyl)amino]phenyl}ethyl)hydrazine-1,2-dicarboxylate 31 (83 mg, 0.12 mmol) was dissolved in a 1:1 solution of tetrahydrofuran/methanol (4 mL) and added dropwise to the reaction at 0° C. The reaction was then allowed to warm to room temperature and stirring was continued for an additional 30 min. After completion, the reaction was quenched with glacial acetic acid (55 µL, 0.96 mmols) and further acidified with a 10% citric acid solution (10 mL). The organic products were extracted with ethyl acetate (3×10 mL) and the combined organic extracts were washed with brine (10 mL), dried over anhydrous sodium sulfate, filtered, and concentrated in vacuo. Di-tert-butyl 1-[2-(4-{[4-(4-{[8-(hydroxyamino)-8-oxooctanoyl]amino}phenyl)butanoyl]amino}phenyl)ethyl]-hydrazine-1,2-dicarboxylate was obtained as a viscous, yellow oil and used without further purification.

The hydroxamic acid intermediate was taken up in methylene chloride (9.5 mL) and to it was added trifluoroacetic acid (0.5 mL). The reaction was stirred at room temperature for 16 h after which it was complete as evidenced by TLC. Then, the reaction was concentrated in vacuo and the residue obtained was taken up in N,N-dimethylformamide and purified by preparatory HPLC. The ditrifluoroacetic acid salt was isolated as a white solid (30 mg, 35%). $^1$H NMR (500 MHz, DMSO-d$_6$): δ 10.33 (s, 1H), 9.84 (s, 1H), 9.78 (s, 1H), 8.65 (br, 1H), 7.52 (d, J=8.5 Hz, 2H), 7.49 (d, J=8.5 Hz, 2H), 7.14 (d, J=8.5 Hz, 2H), 7.11 (d, J=8.5 Hz, 2H), 3.07 (br, 2H), 2.76 (br, 2H), 2.55 (t, J=7.5 Hz, 2H), 2.27 (m, 4H), 1.93 (t, J=7.4 Hz, 2H), 1.84 (quin, J=7.5 Hz, 2H), 1.56 (m, 2H), 1.48 (m, 2H), 1.26 (m, 4H). $^{13}$C NMR (125 MHz, MeOD/DMSO-d$_6$): δ 174.07, 173.85, 172.58, 139.13, 138.68, 138.23, 130.29, 130.00, 121.61, 121.40, 53.51, 37.96, 37.32, 35.78, 33.84, 32.25, 30.06, 30.00, 28.66, 26.85, 26.71. ESI-HRMS: calcd. for C$_{26}$H$_{37}$N$_5$O$_4$: [M+H]$^+$=m/z 484.2918, found: [M+H]$^+$=m/z 484.2941.

4-(4-Bromophenyl)butanoic acid:

3-(4-Bromobenzoyl)propionic acid (5.142 g, 20 mmols) and potassium hydroxide (2.693 g, 48 mmols) were placed in a round-bottomed flask fitted with a condenser and a Dean-Stark apparatus and suspended in diethylene glycol (50 mL) at room temperature. Hydrazine (1.508 mL, 48 mmol) was slowly added to the reaction which was subsequently heated to 120-130° C. for 2 h upon which the reaction became homogenous. After 2 h, the temperature was increased to 180-200° C. and stirring was continued for 3 h in order to distill off the remaining hydrazine and water byproduct via the Dean-Stark trap. Then, the reaction was allowed to cool to room temperature, diluted with water (20 mL), and carefully poured into 2.5 M hydrochloric acid (40 mL). The precipitate that formed was collected by filtration and residual diethylene glycol was removed by dissolving the precipitate in a saturated, aqueous solution of potassium carbonate (40 mL). This solution was diluted with water (40 mL) and carefully poured into 2.5 M hydrochloric acid (40 mL). A white precipitate formed which was collected by filtration, washed with water (2×30 mL), and dried under vacuum to yield the desired product as a white solid (886 mg, 89%). $^1$H NMR (500 MHz, DMSO-d$_6$): δ 12.07 (br, 1H), 7.46 (m, 2H), 7.16 (m, 2H), 2.56 (m, 2H), 2.20 (t, J=7.4 Hz, 2H), 1.77 (quin, J=7.5 Hz, 2H). $^{13}$C NMR (125 MHz, DMSO-d$_6$): δ 174.15, 140.99, 131.11, 130.59, 118.82, 33.68, 32.94, 26.05. ESI-HRMS: calcd. for C$_{11}$H$_{11}$BrO$_2$: [M−H]$^-$=m/z 240.9870, found: [M−H]$^-$=m/z 240.9882.

4-(4-bromophenyl)-N-[4-(2-hydroxyethyl)phenyl]butanamide (32):

4-(4-Bromophenyl)butanoic acid (1.702 g, 7.00 mmol), 2-(4-aminophenyl)ethanol (0.960 g, 7.00 mmol), and HATU (3.194 g, 8.40 mmol) were placed in a round-bottomed flask under argon and dissolved in anhydrous methylene chloride (30 mL). The reaction was cooled to 0° C. in an ice bath and triethylamine (1.179 mL, 15.4 mmol) was added after which the reaction became homogenous. The reaction was allowed to warm to room temperature and stirring was continued for 4 h. After completion, the reaction was poured into 1 N hydrochloric acid (15 mL) and the organic products were extracted with methylene chloride (3×30 mL). The combined organic extracts were washed with brine, dried with anhydrous sodium sulfate, filtered, and concentrated in vacuo. Purification by recrystallization from ethyl acetate facilitated by the dropwise addition of hexanes provided the desired product as an off-white solid (2.272 g, 90%). $^1$H NMR (500 MHz, DMSO-d$_6$): δ 9.77 (s, 1H), 7.47 (d, J=8.2 Hz, 4H), 7.18 (d, J=8.5 Hz, 2H), 7.11 (d, J=8.5 Hz, 2H), 3.55 (t, J=7.2 Hz, 2H), 2.65 (t, J=7.2 Hz, 2H), 2.59 (t, J=7.5 Hz, 2H), 2.28 (t, J=7.4 Hz, 2H), 1.86 (quin, J=7.5 Hz, 2H). $^{13}$C NMR (125 MHz, DMSO-d$_6$): δ 170.55, 141.10, 137.18, 134.02, 131.10, 130.64, 128.92, 119.01, 118.80, 62.27, 38.46, 35.51, 33.87, 26.50. ESI-HRMS: calcd. for C$_{18}$H$_{20}$BrNO$_2$: [M−H]$^-$=m/z 360.0605, found: [M−H]$^-$=m/z 360.0608.

4-(4-Bromophenyl)-N-[4-(2-{[tert-butyl(dimethyl)silyl]oxy}ethyl)phenyl]butanamide (33):

4-(4-Bromophenyl)-N-[4-(2-hydroxyethyl)phenyl]butanamide 32 (2.174 g, 6.00 mmol) was dissolved in anhydrous methylene chloride (20 mL) and to it was added 4-dimethylaminopyridine (73 mg, 0.6 mmol) and triethylamine (2.091 mL, 15 mmol). The reaction was stirred until all solids were dissolved after which tert-butyldimethylsilyl chloride (1.085 g, 7.2 mmol) was dissolved in anhydrous methylene chloride (10 mL) and added to the reaction in one portion. The reaction was stirred at room temperature for 2 h and then poured into water (30 mL). The organic layer was isolated and the aqueous layer was further extracted with methylene chloride (2×20 mL). The combined organic extracts were washed with brine (20 mL), dried with anhydrous sodium sulfate, filtered, and concentrated in vacuo. Purification by column chromatography (SiO$_2$, 10% EtOAc/hexanes) yielded the desired product as a slightly yellow, viscous oil (2.288 g, 80%). $^1$H NMR (500 MHz, CDCl$_3$): δ 7.40 (m, 4H), 7.26 (br, 1H), 7.15 (d, J=8.3 Hz, 2H), 7.06 (d, J=8.2 Hz, 2H), 3.78 (t, J=7.1 Hz, 2H), 2.79 (t, J=7.0 Hz, 2H), 2.66 (t, J=7.5 Hz, 2H), 2.32 (t, J=7.4 Hz, 2H), 2.03 (quin, J=7.4 Hz, 2H), 0.88 (s, 9H), 0.00 (s, 6H). $^{13}$C NMR (125 MHz, CDCl$_3$): δ 170.58, 140.30, 135.90, 135.24, 131.43, 130.21, 129.59, 119.73, 119.71, 64.42, 38.95, 36.46, 34.41, 26.62, 25.90, 18.29, −5.41. ESI-HRMS: calcd. for C$_{24}$H$_{34}$BrNO$_2$Si: [M+H]$^+$=m/z 476.1615, found: [M+H]$^+$=m/z 476.1633.

Methyl (2E)-3-[4-(4-{[4-(2-{[tert-butyl(dimethyl)silyl]oxy}ethyl)phenyl]amino}-4-oxobutyl)phenyl]prop-2-enoate (34):

4-(4-Bromophenyl)-N-[4-(2-{[tert-butyl(dimethyl)silyl]oxy}ethyl)phenyl]butanamide 33 (1.430 g, 3 mmol), methyl prop-2-enoate (544 μL, 6 mmols), palladium(II) acetate (67 mg, 0.3 mmol), triphenylphosphene (157 mg, 0.6 mmol), and N,N,N',N'-tetramethylethane-1,2-diamine (449 μL, 3 mmol) were placed in a sealed tube and dissolved in toluene (5 mL) under argon. The reaction was heated to 130° C. and stirred for 48 h after which it was cooled to room temperature and diluted with methylene chloride (50 mL). Then, the organic layer was washed with water (3×20 mL), brine (15 mL), dried with anhydrous sodium sulfate, filtered through a 1.5 inch pad of celite, and the celite pad was washed with methylene chloride (3×20 mL). The combined filtrate and washes were concentrated in vacuo and the brown residue obtained was purified by column chromatography (SiO$_2$, 10-25% EtOAc/hexanes) to yield the desired product as a light yellow solid (834 mg, 58%). $^1$H NMR (500 MHz, CDCl$_3$): δ 7.68 (d, J=16.0 Hz, 1H), 7.46 (d, J=8.2 Hz, 2H), 7.41 (d, J=8.3 Hz, 2H), 7.23 (d, J=8.0 Hz, 2H), 7.16 (d, J=8.5 Hz, 2H), 7.10 (s, 1H), 6.41 (d, J=15.9 Hz, 1H), 3.81 (s, 3H), 3.78 (t, J=7.1 Hz, 2H), 2.78 (t, J=7.1 Hz, 2H), 2.74 (t, J=7.5 Hz, 2H), 2.35 (t, J=7.4 Hz, 2H), 2.08 (quin, J=7.5 Hz, 2H), 0.88 (s, 9H), 0.01 (s, 6H). $^{13}$C NMR (125 MHz, CDCl$_3$): δ

170.49, 167.55, 144.67, 144.13, 135.89, 135.27, 132.30, 129.63, 129.08, 128.23, 119.66, 117.05, 64.44, 51.66, 38.97, 36.58, 34.92, 26.55, 25.91, 18.31, −5.40. ESI-HRMS: calcd. for $C_{28}H_{39}NO_4Si$: $[M+H]^+$=m/z 482.2721, found: $[M+H]^+$=m/z 482.2725.

Methyl (2E)-3-[4-(4-{[4-(2-hydroxyethyl)phenyl]amino}-4-oxobutyl)phenyl]prop-2-enoate (35):

Methyl (2E)-3-[4-(4-{[4-(2-{[tert-butyl(dimethyl)silyl]oxy}ethyl)phenyl]amino}-4-oxobutyl)phenyl]prop-2-enoate 34 (834 mg, 1.73 mmol) was dissolved in anhydrous tetrahydrofuran (5 mL) and to it was added a 1 M solution of tetra-n-butylammonium fluoride (5.19 mL, 5.19 mmol). The reaction was stirred for 16 h after which it was complete as evidenced by TLC. The reaction was then poured into a mixture of water (15 mL) and methylene chloride (15 mL). The organic layer was isolated and the aqueous layer was further extracted with methylene chloride (2×15 mL). The combined organic extracts were washed with brine (15 mL), dried with anhydrous sodium sulfate, filtered, and concentrated in vacuo. Purification by column chromatography ($SiO_2$, 25-100% EtOAc/hexanes) afforded the desired product as a white solid (555 mg, 87%). $^1$H NMR (500 MHz, $CDCl_3$): δ 7.68 (d, J=16.0 Hz, 1H), 7.46 (d, J=8.2 Hz, 2H), 7.43 (d, J=8.5 Hz, 2H), 7.23 (d, J=8.0 Hz, 2H), 7.19 (d, J=8.3 Hz, 2H), 7.12 (br, 1H), 6.41 (d, J=16.0 Hz, 1H), 3.84 (t, J=6.4 Hz, 2H), 3.81 (s, 3H), 2.84 (t, J=6.5 Hz, 2H), 2.74 (t, J=7.5 Hz, 2H), 2.35 (t, J=7.4 Hz, 2H), 2.08 (quin, J=7.4 Hz, 2H). $^{13}$C NMR (125 MHz, $CDCl_3$): δ 170.60, 167.56, 144.67, 144.08, 136.21, 134.51, 132.33, 129.55, 129.09, 128.24, 120.11, 117.07, 63.62, 51.68, 38.56, 36.56, 34.92, 26.55. ESI-HRMS: calcd. for $C_{22}H_{25}NO_4$: $[M+H]^+$=m/z 368.1856, found: $[M+H]^+$=m/z 368.1863.

Methyl (2E)-3-[4-(4{[4-(2-bromoethyl)phenyl]amino}-4-oxobutyl)phenyl]prop-2-enoate (36):

Methyl (2E)-3-[4-(4-{[4-(2-hydroxyethyl)phenyl]amino}-4-oxobutyl)phenyl]prop-2-enoate 35 (555 mg, 1.51 mmol) and triphenylphosphine (595 mg, 2.27 mmol) were placed in a round-bottomed flask under argon and dissolved in anhydrous methylene chloride (3 mL). Then, tetrabromomethane (753 mg, 2.27 mmol) was dissolved in anhydrous methylene chloride (2 mL) and added dropwise to the reaction at room temperature after which the reaction turned from an opaque mixture to a homogenous, yellow solution. The reaction was stirred for 30 min and after completion, it was poured into water (15 mL) and the organic products were extracted with methylene chloride (3×10 mL). The combined organic extracts were washed with brine (10 mL), dried with anhydrous sodium sulfate, filtered, and concentrated in vacuo. Purification by column chromatography ($SiO_2$, 25% EtOAC/hexanes) afforded the desired product as a white solid (474 mg, 73%). $^1$H NMR (500 MHz, $CDCl_3$): δ 7.66 (d, J=16.0 Hz, 1H), 7.44 (m, 5H), 7.20 (d, J=8.2 Hz, 2H), 7.15 (d, J=8.5 Hz, 2H), 6.40 (d, J=16.0 Hz, 1H), 3.81 (s, 3H), 3.53 (t, J=7.5 Hz, 2H), 3.12 (t, J=7.5 Hz, 2H), 2.72 (t, J=7.5 Hz, 2H), 2.35 (t, J=7.3 Hz, 2H), 2.06 (quin, J=7.4 Hz, 2H). $^{13}$C NMR (125 MHz, $CDCl_3$): δ 170.74, 167.55, 144.65, 144.07, 136.65, 134.73, 132.22, 129.15, 129.02, 128.18, 119.98, 116.98, 51.65, 38.68, 36.53, 34.89, 32.98, 26.52. ESI-HRMS: calcd. for $C_{22}H_{24}BrNO_3$: $[M+H]^+$=m/z 430.1012, found: $[M+H]^+$=m/z 430.1031.

Di-tert-butyl 1-(2-{4-[(4-{4-[(1E)-3-methoxy-3-oxoprop-1-en-1-yl]phenyl}butanoyl)amino]phenyl}ethyl)hydrazine-1,2-dicarboxylate (37):

The title compound was prepared from methyl (2E)-3-[4-(4-{[4-(2-bromoethyl)phenyl]amino}-4-oxobutyl)pheny]prop-2-enoate 36 (1.871 g, 4.35 mmol) following a procedure similar to that used for 46. Purification by column chromatography (25-50% EtOAc/hexanes) yielded the desired product as viscous oil that solidified to a white solid on standing overnight (1.818 g, 72%). $^1$H NMR (500 MHz, $CDCl_3$): δ 7.68 (d, J=16.0 Hz, 1H), 7.46 (d, J=8.0 Hz, 2H), 7.42 (d, J=8.2 Hz, 2H), 7.23 (d, J=7.9 Hz, 2H), 7.15 (br, 2H), 7.10 (s, 1H), 6.41 (d, J=16.0 Hz, 1H), 3.81 (s, 3H), 3.66 (br, 2H), 2.85 (br, 2H), 2.74 (t, J=7.5 Hz, 2H), 2.35 (t, J=7.3 Hz, 2H), 2.08 (quin, J=7.4 Hz, 2H), 1.48 (s, 9H), 1.44 (s, 9H). ESI-HRMS: calcd. for $C_{32}H_{43}N_3O_7$: $[M-H]^-$=m/z 580.3028, found: $[M-H]^-$=m/z 580.3048.

N-[4-(2-Hydrazinylethyl)phenyl]-4-{4-[(1E)-3-(hydroxyamino)-3-oxoprop-1-en-1-yl]phenyl}butanamide (22):

An aqueous solution of hydroxylamine (50 wt %, 10 mL) was placed on ice and to it was added sodium hydroxide (1.002 g, 25.04 mmol). The solution was stirred until the sodium hydroxide was completely dissolved after which di-tert-butyl 1-(2-{4-[(4-{4-[(1E)-3-methoxy-3-oxoprop-1-en-1-yl]phenyl}butanoyl)amino]phenyl}ethyl)-hydrazine-1,2-dicarboxylate 37 (1.818 g, 3.13 mmol) was dissolved in a 1:1 solution of tetrahydrofuran/methanol (20 mL) and added dropwise to the reaction at 0° C. The reaction was then allowed to warm to room temperature and stirring was continued for an additional 30 min. After completion, the reaction was quenched with glacial acetic acid (1.433 mL, 25.04 mmols) and further acidified with a 10% citric acid solution (30 mL). The organic products were extracted with ethyl acetate (3×30 mL) and the combined organic extracts were washed with brine (30 mL), dried over anhydrous sodium sulfate, filtered, and concentrated in vacuo. Di-tert-butyl 1-(2{4-[(4-{4-[(1E)-3-(hydroxyamino)-3-oxoprop-1-en-1-yl]phenyl}butanoyl)amino]-phenyl}ethyl)hydrazine-1,2-dicarboxylate was obtained as a viscous, yellow oil and used without further purification.

The hydroxamic acid was then taken up in methylene chloride (19 mL) and to it was added trifluoroacetic acid (1 mL). The reaction was stirred at room temperature for 16 h after which it was complete as evidenced by TLC. Then, the reaction was concentrated in vacuo and the residue obtained was taken up in N,N-dimethylformamide and purified by preparatory HPLC. The ditrifluoracetic acid salt was isolated as a white solid (0.932 g, 49%). To prepare the dihydrochloride salt, anhydrous methanol (20 mL) was cooled to 0° C. in an ice bath under argon and to it was added acetyl chloride (1.570 mL, 21.96 mmol) dropwise to generate hydrochloric acid in situ. The reaction was stirred for 15 min after which the ditrifluoracetic acid salt was taken up in anhydrous methanol (10 mL) and added dropwise at 0° C. The reaction was stirred for an additional 30 min and then concentrated to approximately one third of the original volume. The reaction was the placed on ice and the desired dihydrochloride salt was precipitated by the dropwise addition of diethyl ether and isolated by filtration as a white solid (0.556 g, 80%). $^1$H NMR (500 MHz, MeOD/DMSO-$d_6$): δ 7.53 (m, 5H), 7.29 (d, J=8.0 Hz, 2H), 7.23 (d, J=8.5 Hz, 2H), 6.45 (d, J=15.9 Hz, 1H), 3.25 (t, J=7.9 Hz, 2H), 2.92 (t, J=7.8 Hz, 2H), 2.73 (d, J=7.5 Hz, 2H), 2.40 (t, J=7.4 Hz, 2H), 2.02 (quin, J=7.5 Hz, 2H). $^{13}$C NMR (125 MHz, MeOD/DMSO-$d_6$): δ 173.77, 166.12, 145.46, 141.55, 139.09, 134.11, 134.03, 130.42, 130.29, 129.18, 121.59, 117.94, 53.54, 37.33, 36.21, 32.18, 28.37. ESI-HRMS: calcd. for $C_{21}H_{26}N_4O_3$: $[M+H]^+$=m/z 383.2078, found: $[M+H]^+$=m/z 383.2096.

tert-Butyl (2-nitrophenyl)carbamate (38):

2-Nitroaniline (1.519 g, 11 mmols) was placed in a round-bottomed flask under argon and dissolved in anhydrous tetrahydrofuran (10 mL). Then, a 1 M solution of sodium bis(trimethylsilyl)amide in tetrahydrofuran (22 mL, 22 mmols) was added rapidly to the reaction at room temperature and stirring was continued for 15 min. The reaction was deep red in color and a precipitate formed upon addition of base but dissolved with continued stirring. Di-tert-butyl dicarbonate (2.183 g, 10 mmols) was dissolved in anhydrous tetrahydrofuran (20 mL) and added rapidly to the reaction at room temperature. Stirring was continued for 2 h after which the solvent was removed in vacuo and the residue obtained was cautiously partitioned between ethyl acetate (50 mL) and 0.1 N hydrochloric acid (50 mL). The organic layer was isolated and the aqueous layer was further extracted with ethyl acetate (2×25 mL). The combined organic extracts were washed with brine (20 mL), dried with anhydrous sodium sulfate, filtered, and concentrated in vacuo. Purification by column chromatography ($SiO_2$, 15-25% EtOAC/hexanes) provided the desired product as a light yellow solid (2.004 g, 84%). $^1$H NMR (500 MHz, $CDCl_3$): δ 9.66 (br, 1H), 8.55 (dd, J=8.6 Hz, 1.2 Hz, 1H), 8.18 (dd, J=8.5 Hz, 1.6 Hz, 1H), 7.60 (ddd, J=8.5 Hz, 7.3 Hz, 1.3 Hz, 1H), 7.08 (ddd, J=8.5 Hz, 7.2 Hz, 1.3 Hz, 1H), 1.55 (s, 9H). $^{13}$C NMR (125 MHz, $CDCl_3$): δ 152.14, 135.92, 135.89, 135.67, 125.76, 121.77, 120.62, 81.76, 28.15.

tert-Butyl (2-aminophenyl)carbamate (39):

tert-Butyl (2-nitrophenyl)carbamate 38 (2.000 g, 8.39 mmol) and 10% palladium on carbon (200 mg, 10% wt. equivalent) were placed in a two-necked round-bottomed flask under hydrogen at atmospheric pressure. Methanol (20 mL) was added and the reaction was stirred for 16 h at room temperature. After completion, the reaction was poured through a 1.5 inch pad of celite to remove the palladium catalyst. The celite plug was washed with methanol (3×50 mL) and then the combined filtrate and washes were concentrated in vacuo. The desired product was isolated as a reddish orange solid and used directly in the next step without further purification (1.730 g, 99%). $^1$H NMR (500 MHz, $CDCl_3$): δ 7.28 (d, J=7.9 Hz, 1H), 7.01 (td, J=7.6 Hz, 1.4 Hz, 1H), 6.79 (m, 2H), 6.25 (br, 1H), 3.74 (br, 2H), 1.52 (s, 9H). $^{13}$C NMR (125 MHz, $CDCl_3$): δ 153.79, 139.89, 126.12, 124.77, 124.65, 119.62, 117.60, 80.51, 28.32. ESI-HRMS: calcd. for $C_{11}H_{16}N_2O_2$: [M+H]$^+$=m/z 209.1285, found: [M+H]$^+$=m/z 209.1293.

Methyl 4-(4-hydroxybut-1-yn-1-yl)benzoate (40):

4-Bromobenzoic acid methyl ester (2.15 g, 10 mmols), palladium(II) chloride (89 mg, 0.5 mmols), triphenylphosphine (262 mg, 0.1 mmols), and copper(I) iodide (190 mg, 1 mmol) were placed in a round-bottomed flask under argon and suspended in diethylamine (30 mL) at room temperature. 3-Butyn-1-ol (757 μL, 10 mmols) was added and the reaction was stirred for 18 h during which time the reaction mixture turned from light yellow to black. After completion as evidenced by TLC, diethylamine was removed under reduced pressure. Water (50 mL) was added to the resulting residue and the organic products were extracted with methylene chloride (3×30 mL). The combined organic extracts were washed with brine (20 mL), dried with anhydrous sodium sulfate, and poured through a 1.5 inch pad of celite to remove residual catalyst. The celite plug was washed with methylene chloride (3×30 mL) and the combined filtrate and washes were concentrated in vacuo to yield a crude orange solid. Purification by column chromatography ($SiO_2$, 25% EtOAc/hexanes) afforded methyl 4-(4-hydroxybut-1-yn-1-yl)benzoate as a beige, crystalline solid (1.745 g, 85%). $^1$H NMR (500 MHz, $CDCl_3$): δ 7.96 (d, J=8.6 Hz, 2H), 7.46 (d, J=8.5 Hz, 2H), 3.91 (s, 3H), 3.83 (t, J=6.3 Hz, 2H), 2.71 (t, J=6.3 Hz, 2H), 2.08 (br, 1H). $^{13}$C NMR (125 MHz, $CDCl_3$): δ 166.56, 131.54, 129.38, 129.17, 128.11, 89.85, 81.70, 60.97, 52.16, 23.83. ESI-HRMS: calcd. for $C_{12}H_{12}O_3$: [M+H]$^+$=m/z 205.0859, found: [M+H]$^+$=m/z 205.0864.

Methyl 4-(4-hydroxybutyl)benzoate (41):

Methyl 4-(4-hydroxybut-1-yn-1-yl)benzoate 40 (3.320 g, 16.26 mmols) and 10% palladium on carbon (664 mg, 20% wt. equivalent) were suspended in 95% ethanol (125 mL) and placed under a hydrogen atmosphere (60 psi) at room temperature. The suspension was agitated for 12 h after which it was complete as evidenced by TLC. The reaction mixture was filtered through a 1.5 inch celite plug and the filter cake was washed with methanol (3×30 mL). The combined filtrate and washes were concentrated in vacuo to yield the desired product as a viscous, yellow oil (3.159 g, 93%). $^1$H NMR (500 MHz, MeOD): δ 7.90 (m, 2H), 7.28 (d, J=8.5 Hz, 2H), 3.86 (s, 3H), 3.56 (t, J=6.5 Hz, 2H), 2.68 (t, J=7.7 Hz, 2H), 1.69 (m, 2H), 1.55 (m, 2H). $^{13}$C NMR (125 MHz, MeOD): δ 168.70, 149.86, 130.73, 129.75, 128.97, 62.76, 52.59, 36.72, 33.28, 28.66. ESI-HRMS: calcd. for $C_{12}H_{16}O_3$: [M+H]$^+$=m/z 209.1172, found: [M+H]$^+$=m/z 209.1181.

Methyl 4-(4-oxobutyl)benzoate (42):

A two-necked round-bottomed flask fitted with a condenser was charged with pyridinium chlorochromate (1.658 g, 7.69 mmol) and sodium acetate (1.658 g, 7.69 mmol) and placed under argon. Anhydrous methylene chloride (40 mL) was added and stirring was initiated. Methyl 4-(4-hydroxybutyl)benzoate 41 (1.068 g, 5.13 mmol) was dissolved in anhydrous methylene chloride (20 mL) and added to the reaction. The reaction turned from dark orange to black over approximately 15 min and stirring was continued for 12 h. After completion, it was poured through a 1.5 inch silica gel pad which was subsequently washed with methylene chloride (3×30 mL). The combined filtrate and washes were concentrated in vacuo and the resulting residue was purified by column chromatography ($SiO_2$, 10-25% EtOAC/hexanes) to yield methyl 4-(4-oxobutyl)benzoate as a clear, viscous oil (2.126 g, 68%). Of note, some over oxidation to the acid was observed. $^1$H NMR (500 MHz, $CDCl_3$): δ 9.77 (t, J=1.4 Hz, 2H), 7.97 (d, J=8.3 Hz, 2H), 7.25 (d, J=8.3 Hz, 2H), 3.91 (s, 3H), 2.72 (t, J=7.6 Hz, 2H), 2.47 (td, J=7.3 Hz, 1.4 Hz, 2H), 1.98 (m, 2H). $^{13}$C NMR (125 MHz, $CDCl_3$): δ 201.83, 167.00, 146.68, 129.78, 128.44, 128.12, 51.98, 42.99, 34.95, 23.21. ESI-HRMS: calcd. for $C_{12}H_{14}O_3$: [M+H]$^+$=m/z 207.1016, found: [M+H]$^+$=m/z 207.1014.

4-[4-(Methoxycarbonyl)phenyl]butanoic acid (43):

Methyl 4-(4-oxobutyl)benzoate 42 (2.126 g, 10.31 mmols) was dissolved in acetonitrile (10 mL) and cooled to 0° C. in and ice bath. Sodium dihydrogen phosphate monohydrate (356 mg, 2.58 mmols) was dissolved in water (5 mL) and added to the reaction after which a 30% hydrogen peroxide solution (1.228 mL, 10.83 mmol) was slowly added at 0° C. Then, sodium chlorite (1.305 g, 14.43 mmol) was dissolved in water (15 mL) and added dropwise via an addition funnel to the reaction over 1 h with the temperature being maintained at 0° C. Oxygen evolved from the reaction upon addition of the oxidant and the reaction turned from pale yellow to bright yellow. The yellow color faded as the reaction proceeded and stirring was continued for 1 h after addition of the sodium chlorite. After completion, sodium sulfite (100 mg) was added to degrade hypochlorous acid and residual hydrogen peroxide. The pH was adjusted to 2 with 1 N hydrochloric acid after which the organic products were extracted with ethyl acetate (3×20 mL), washed with brine (20 mL), dried with anhydrous sodium sulfate, filtered, and concentrated in vacuo. Purification by column chromatography ($SiO_2$, 25-50% EtOAC/hexanes) yielded the desired product as a white, crystalline solid (2.103 g, 92%).

¹H NMR (500 MHz, CDCl₃): δ 7.97 (d, J=8.3 Hz, 2H), 7.26 (d, J=8.3 Hz, 2H), 3.91 (s, 3H), 2.73 (t, J=7.4 Hz, 2H), 2.39 (t, J=7.4 Hz, 2H), 1.99 (quin, J=7.5 Hz, 2H). ¹³C NMR (125 MHz, CDCl₃): δ 179.45, 167.08, 146.66, 129.76, 128.46, 128.04, 51.99, 34.93, 33.17, 25.78. ESI-HRMS: calcd. for $C_{12}H_{14}O_4$: [M−H]⁻=m/z 221.0819, found: [M−H]⁻=m/z 221.0823.

Methyl 4-(4-{[4-(2-hydroxyethyl)phenyl]amino}-4-oxobutyl)benzoate (44):

4-[4-(Methoxycarbonyl)phenyl]butanoic acid 43 (2.030 g, 9.13 mmol), 2-(4-aminophenyl)ethanol (1.253 g, 9.13 mmol), and HATU (4.166 g, 10.96 mmol) were placed in a round-bottomed flask under argon and dissolved in anhydrous methylene chloride (30 mL). The reaction was cooled to 0° C. in an ice bath and then triethylamine (2.800 mL, 20.09 mmol) was added causing the reaction to become homogenous. The reaction was allowed to warm to room temperature and stirring was continued for 4 h. After completion, the reaction was poured into 1 N hydrochloric acid (15 mL) and the organic products were extracted with methylene chloride (3×30 mL). The combined organic extracts were washed with brine, dried with anhydrous sodium sulfate, filtered, and concentrated in vacuo. Purification by recrystallization from ethyl acetate facilitated by the dropwise addition of hexanes provided the desired product as a white solid (2.936 g, 94%). ¹H NMR (500 MHz, DMSO-d₆): δ 9.78 (s, 1H), 7.89 (d, J=8.2 Hz, 2H), 7.46 (d, J=8.5 Hz, 2H), 7.37 (d, J=8.2 Hz, 2H), 7.11 (d, J=8.3 Hz, 2H), 4.60 (t, J=5.2 Hz, 1H), 3.83 (s, 3H), 3.55 (td, J=7.1 Hz, 5.3 Hz, 2H), 2.69 (t, J=7.6 Hz, 2H), 2.65 (t, J=7.2 Hz, 2H), 2.30 (t, J=7.5 Hz, 2H), 1.90 (quin, J=7.5 Hz, 2H). ¹³C NMR (125 MHz, DMSO-d₆): δ 170.55, 166.21, 147.63, 137.18, 134.06, 129.27, 128.94, 128.76, 127.32, 119.04, 62.29, 51.99, 38.47, 35.59, 34.53, 26.35. ESI-HRMS: calcd. for $C_{20}H_{23}NO_4$: [M+H]⁺=m/z 342.1700, found: [M+H]⁺=m/z 342.1708.

Methyl 4-(4-{[4-(2-bromoethyl)phenyl]amino}-4-oxobutyl)benzoate (45):

Methyl 4-(4-{[4-(2-hydroxyethyl)phenyl]amino}-4-oxobutyl)benzoate 44 (1.932 g, 5.66 mmol) and triphenylphosphine (2.227 g, 8.49 mmol) were placed in a round-bottomed flask under argon and dissolved in anhydrous methylene chloride (7 mL). Then, tetrabromomethane (2.816 g, 8.49 mmol) was dissolved in anhydrous methylene chloride (3 mL) and added dropwise to the reaction at room temperature after which the reaction turned from an opaque mixture to a homogenous, yellow solution. The reaction was stirred for 30 min and after completion, it was poured into water (30 mL) and the organic products extracted with methylene chloride (3×15 mL). The combined organic extracts were washed with brine (15 mL), dried with anhydrous sodium sulfate, filtered, and concentrated in vacuo. Purification by column chromatography (SiO₂, 25-50% EtOAC/hexanes) afforded methyl 4-(4-{[4-(2-bromoethyl)phenyl]amino}-4-oxobutyl)benzoate as a white solid (1.473 g, 64%). ¹H NMR (500 MHz, CDCl₃): δ 7.95 (d, J=8.3 Hz, 2H), 7.46 (d, J=8.5 Hz, 2H), 7.37 (br, 1H), 7.25 (d, J=8.2 Hz, 2H), 7.15 (d, J=8.3 Hz, 2H), 3.91 (s, 3H), 3.53 (t, J=7.5 Hz, 2H), 3.12 (t, J=7.5 Hz, 2H), 2.75 (t, J=7.5 Hz, 2H), 2.34 (t, J=7.3 Hz, 2H), 2.07 (quin, J=7.5 Hz, 2H). ¹³C NMR (125 MHz, CDCl₃): δ 170.64, 167.07, 146.88, 136.62, 134.77, 129.74, 129.17, 128.49, 128.00, 119.99, 52.00, 38.69, 36.48, 35.01, 32.98, 26.43. ESI-HRMS: calcd. for $C_{20}H_{22}BrNO_3$: [M−H]⁻=m/z 402.0710, found: [M−H]⁻=m/z 402.0722.

Di-tert-butyl 1-{2-[4-({4-[4-(methoxycarbonyl)phenyl]butanoyl}amino)phenyl]ethyl}hydrazine-1,2-dicarboxylate (46):

Di-tert-butylhydrazodiformate (2.539 g, 10.93 mmol) was placed in a round-bottomed flask under argon, dissolved in anhydrous N,N-dimethylformamide (5 mL), and cooled to −40° C. in an acetonitrile/CO₂ bath. A 60% dispersion of sodium hydride in mineral oil (32 mg, 0.79 mmol) was suspended in anhydrous N,N-dimethylformamide (10 mL) and added dropwise to the reaction. The reaction was stirred at −40° C. for 10 min and then methyl 4-(4-{[4-(2-bromoethyl)phenyl]amino}-4-oxobutyl)benzoate 45 (1.473 g, 3.64 mmol) was dissolved in N,N-dimethylformamide (5 mL) and added dropwise to the reaction. Stirring was continued at −40° C. for 4 h after which the reaction was allowed to warm to room temperature and then poured into water (50 mL). The organic products were extracted with ethyl acetate (3×20 mL) and the combined organic extracts were washed with brine (20 mL), dried with anhydrous sodium sulfate, filtered, and concentrated in vacuo. Purification by column chromatography (30% EtOAc/hexanes) yielded the desired product as a clear, viscous oil (1.658 g, 82%). ¹H NMR (500 MHz, CDCl₃): δ 8.05 (br, 1H), 7.90 (m, 2H), 7.42 (br, 2H), 7.21 (br, 2H), 7.08 (br, 2H), 6.49 (br, 1H), 3.22 (br, 3H), 3.61 (br, 2H), 2.80 (t, J=6.8 Hz, 2H), 2.69 (br, 2H), 2.32 (t, J=7.3 Hz, 2H), 2.01 (br, 2H), 1.43 (br, 18H). ¹³C NMR (125 MHz, CDCl₃): δ 170.88, 167.00, 155.71, 155.04, 147.05, 136.43, 134.51, 129.58, 128.97, 128.39, 127.75, 119.90, 81.21, 80.95, 51.86, 51.53, 36.27, 34.99, 33.35, 28.06, 28.03, 26.44. ESI-HRMS: calcd. for $C_{30}H_{41}N_3O_7$: [M−H]⁻=m/z 554.2872, found: [M−H]⁻=m/z 554.2894.

4-{4-[(4-{2-[1,2-Bis(tert-butoxycarbonyl)hydrazinyl]ethyl}phenyl)amino]-4-oxobutyl}benzoic acid (47):

Di-tert-butyl 1-{2-[4-({4-[4-(methoxycarbonyl)phenyl]butanoyl}amino)phenyl]-ethyl}hydrazine-1,2-dicarboxylate 46 (1.00 g, 1.80 mmol) was placed in a round-bottomed flask and dissolved in a 3:1:1 mixture of tetrahydrofuran/methanol/water (5 mL) at room temperature. Lithium hydroxide (10 mg, 0.42 mmol) was added as one portion and stirring was continued for 4 h. After completion, the reaction was poured into 1 N hydrochloric acid (15 mL) and the organic products were extracted with ethyl acetate (3×20 mL). The combined organic extracts were washed with brine (15 ml), dried with anhydrous sodium sulfate, filtered, and concentrated in vacuo. 4-{4-[(4-{2-[1,2-Bis(tert-butoxycarbonyl)hydrazinyl]ethyl}phenyl)amino]-4-oxobutyl}benzoic acid was a viscous, yellow oil that solidified under reduced pressure and was used in the next step without further purification (918 mg, 94%). ¹H NMR (500 MHz, CDCl₃): δ 8.01 (d, J=7.9 Hz, 2H), 7.41 (d, J=8.2 Hz, 2H), 7.32 (br, 1H), 7.29 (d, J=8.0 Hz, 2H), 7.14 (d, J=6.9 Hz, 2H), 3.66 (br, 2H), 2.85 (t, J=6.4 Hz, 2H), 2.78 (t, J=7.3 Hz, 2H), 2.34 (t, J=7.2 Hz, 2H), 2.09 (m, 2H), 1.47 (br, 9H), 1.44 (br, 9H). ESI-HRMS: calcd. for $C_{29}H_{39}N_3O_7$: [M+H]⁺=m/z 540.2715, found: [M+H]⁺=m/z 540.2733.

Di-tert-butyl 1-{2-[4-({4-[4-({2-[(tert-butoxycarbonyl)amino]phenyl}carbamoyl)phenyl]butanoyl}amino)phenyl]ethyl}hydrazine-1,2-dicarboxylate:

4-{4-[(4-{2-[1,2-Bis(tert-butoxycarbonyl)hydrazinyl]ethyl}phenyl)amino]-4-oxobutyl}benzoic acid 47 (918 mg, 1.7 mmol), tert-butyl (2-aminophenyl)carbamate 39 (354 mg, 1.7 mmol), and HATU (776 mg, 2.04 mmol) were placed in a round-bottomed flask and dissolved in anhydrous methylene chloride (20 mL) under argon. The reaction was cooled to 0° C. with an ice bath followed by the addition of triethylamine (521 μL, 3.74 mmol). The reaction was allowed to warm to room temperature and stirring was continued for an additional 6 h. After reaction was complete as evidenced by TLC, the reaction was poured into 1 N hydrochloric acid (15 mL) and the organic products were extracted with methylene chloride (3×30 mL). The combined organic extracts were washed with brine, dried with anhydrous sodium sulfate, filtered, and concentrated in vacuo. Purification by column chromatography (SiO$_2$, 15-75% EtOAC/hexanes) yielded di-tert-butyl 1-{2-[4-({4-[4-({2-[(tert-butoxy carbonyl)amino]phenyl}carbamoyl)phenyl]butanoyl}amino)-phenyl]ethyl}hydrazine-1,2-dicarboxylate as a slightly yellow, crystalline solid (684 mg, 55%). $^1$H NMR (500 MHz,): δ 9.18 (br, 1H), 7.86 (d, J=8.0 Hz, 2H), 7.75 (d, J=7.5 Hz, 1H), 7.57 (br, 1H), 7.42 (d, J=6.4 Hz, 2H), 7.30 (dd, J=7.8 Hz, 1.3 Hz, 1H), 7.24 (d, J=8.2 Hz, 2H), 7.18 (m, 2H), 7.12 (d, J=7.7 Hz, 2H), 7.03 (br, 1H), 6.33 (br, 1H), 3.65 (br, 2H), 2.84 (t, J=7.2 Hz, 2H), 2.74 (t, J=7.5 Hz, 2H), 2.30 (t, J=7.4 Hz, 2H), 2.05 (quin, J=7.4 Hz, 2H), 1.51 (s, 9H), 1.48 (s, 9H), 1.43 (br, 9H). ESI-HRMS: calcd. for C$_{40}$H$_{53}$N$_5$O$_8$: [M−H]$^-$=m/z 730.3821, found: [M−H]$^-$=m/z 730.3826.

N-(2-Aminophenyl)-4-(4-{[4-(2-hydrazinylethyl)phenyl]amino}-4-oxobutyl)benzamide (23):

Di-tert-butyl 1-{2-[4-({4-[4-({2-[(tert-butoxycarbonyl)amino]phenyl}carbamoyl)-phenyl]butanoyl}amino)phenyl]ethyl}hydrazine-1,2-dicarboxylate (250 mg, 0.34 mmol) was dissolved in methylene chloride (9 mL) and to it was added trifluoroacetic acid (1 mL). The reaction was stirred at room temperature for 6 h after which it was complete as evidenced by TLC. Then, the reaction was concentrated in vacuo and the residue obtained was taken up in N,N-dimethylformamide and purified by preparatory HPLC. The desired product, a ditrifluoracetic acid salt, was isolated as a white solid (141 mg, 63%). $^1$H NMR (500 MHz, MeOD): δ 7.97 (d, J=8.2 Hz, 2H), 7.52 (d, J=8.5 Hz, 2H), 7.35 (m, 6H), 7.22 (d, J=8.6 Hz, 2H), 3.24 (t, J=7.8 Hz, 2H), 2.91 (t, J=7.8 Hz, 2H), 2.80 (t, J=7.7 Hz, 2H), 2.43 (t, J=7.4 Hz, 2H), 2.05 (quin, 7.6 Hz, 2H). $^{13}$C NMR (125 MHz, MeOD): δ 174.24, 169.24, 148.32, 138.94, 134.15, 132.52, 131.08, 130.22, 130.00, 129.44, 128.83, 127.77, 127.67, 123.55, 121.89, 53.64, 37.34, 36.33, 32.21, 28.41. ESI-HRMS: calcd. for C$_{25}$H$_{29}$N$_5$O$_2$: [M−H]$^-$=m/z 430.2248, found: [M−H]$^-$=m/z 430.2268.

4-(4-{[4-(2-Hydrazinylethyl)phenyl]amino}-4-oxobutyl)-N-hydroxybenzamide (24):

The title compound was prepared from di-tert-butyl 1-{2-[4-({4-[4-(methoxycarbonyl)phenyl]butanoyl}amino)phenyl]ethyl}hydrazine-1,2-dicarboxylate 46 using procedures similar to those described for the preparation of 21. Purification by preparatory HPLC yielded the ditrifluoracetic acid salt as a white solid. $^1$H-NMR (500 MHz, MeOD): δ 7.66 (d, J=8.0 Hz, 2H), 7.49 (d, J=8.3 Hz, 2H), 7.32 (d, J=8.0 Hz, 2H), 7.20 (d, J=8.3 Hz, 2H), 3.25 (br, 2H), 2.91 (br, 2H), 2.76 (t, J=7.5 Hz, 2H), 2.39 (t, J=7.3 Hz, 2H), 2.03 (quin, J=7.5 Hz, 2H). $^{13}$C-NMR (125 MHz, MeOD): δ 174.25, 147.38, 138.94, 130.29, 130.19, 129.98, 128.42, 121.83, 53.66, 37.30, 36.27, 32.21, 28.28. ESI-HRMS: calcd. for C$_{19}$H$_{24}$N$_4$O$_3$: [M+H]$^+$=m/z 357.1921, found: [M+H]$^+$=m/z 357.1927.

Example 5

Tranylcypromine Derivatives of Formula (II)

Tranylcypromine derivatives of the compounds of Formula (II) can be prepared as follows:

Reagents and conditions: a) NH$_2$OH (aq), NaOH, THF, MeOH, 0° C. to RT, 30 min; b) TFA, DCM, RT, 16 h.

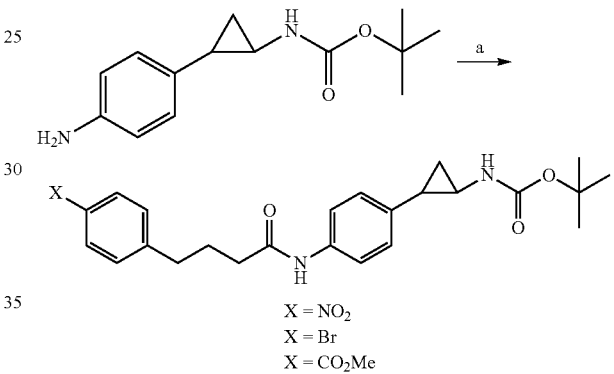

Reagents and conditions: a) 4-(4-nitrophenyl)butanoic acid or 4-(4-bromophenyl)butanoic acid or 43, EDC, DMAP, DCM, RT, 16 h.

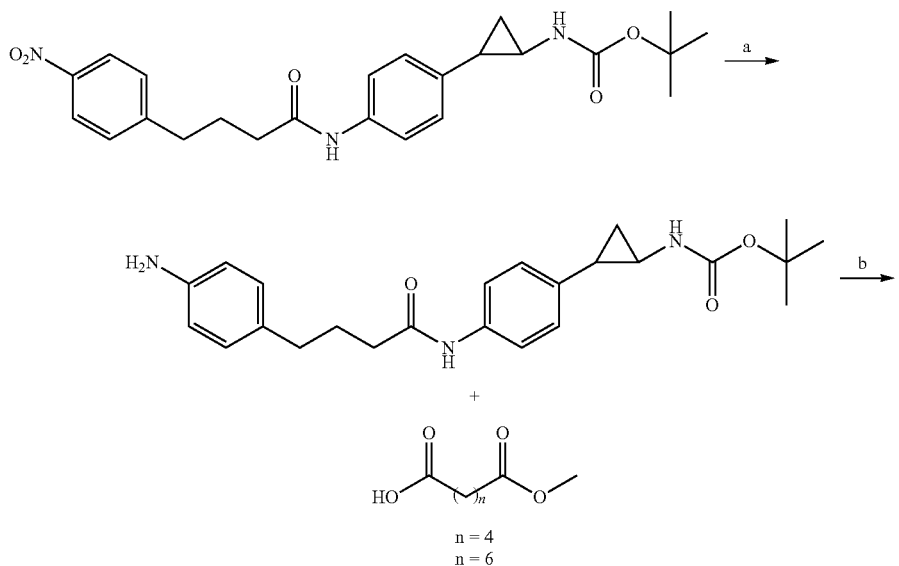

-continued
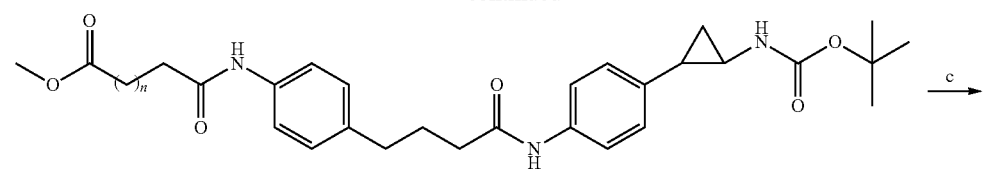
n = 3
n = 5
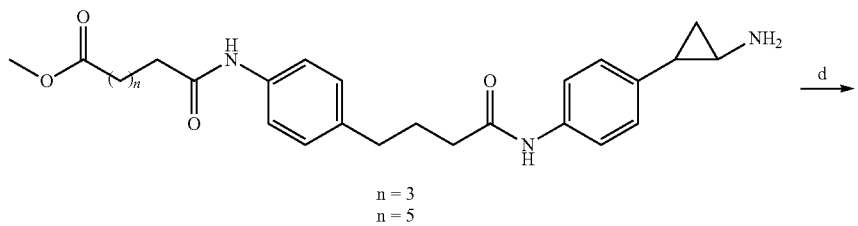
n = 3
n = 5
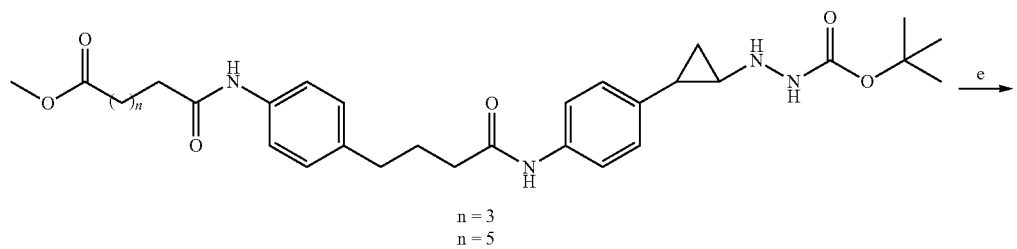
n = 3
n = 5
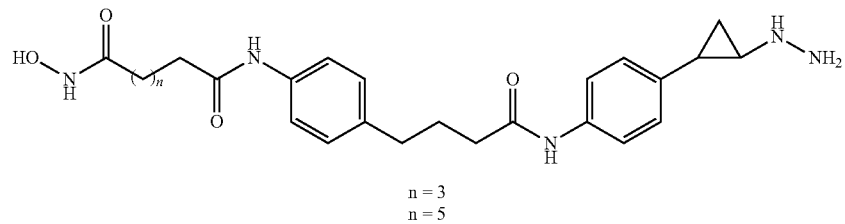
n = 3
n = 5
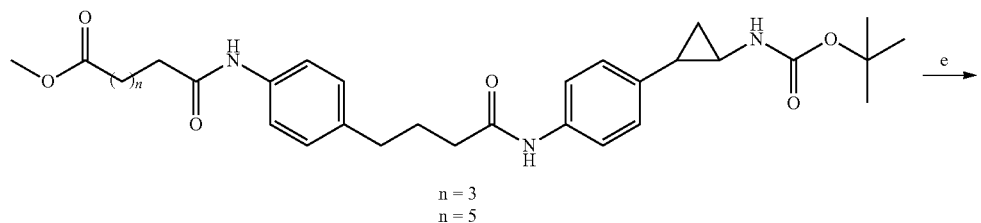
n = 3
n = 5
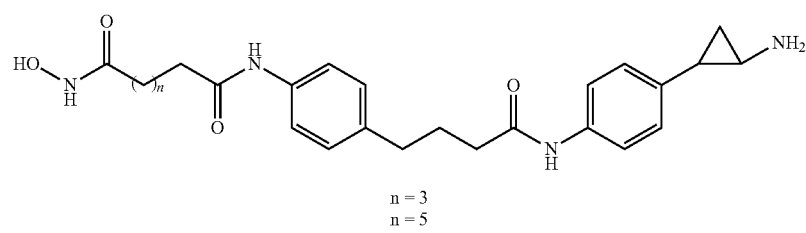
n = 3
n = 5

Reagents and conditions: a) H$_2$, Pd/C, AcOH, EtOH, RT, 16 h; b) EDC, DMAP, DCM/DMF, RT, 16 h; c) TFA, DCM, RT, 16 h; d) BocNHOTs, DMF, K$_2$CO$_3$, 0° C. to RT, 2 h; e) i) NH$_2$OH (aq), NaOH, THF, MeOH, 0° C. to RT, 30 min; ii) TFA, DCM, RT, 16 h.
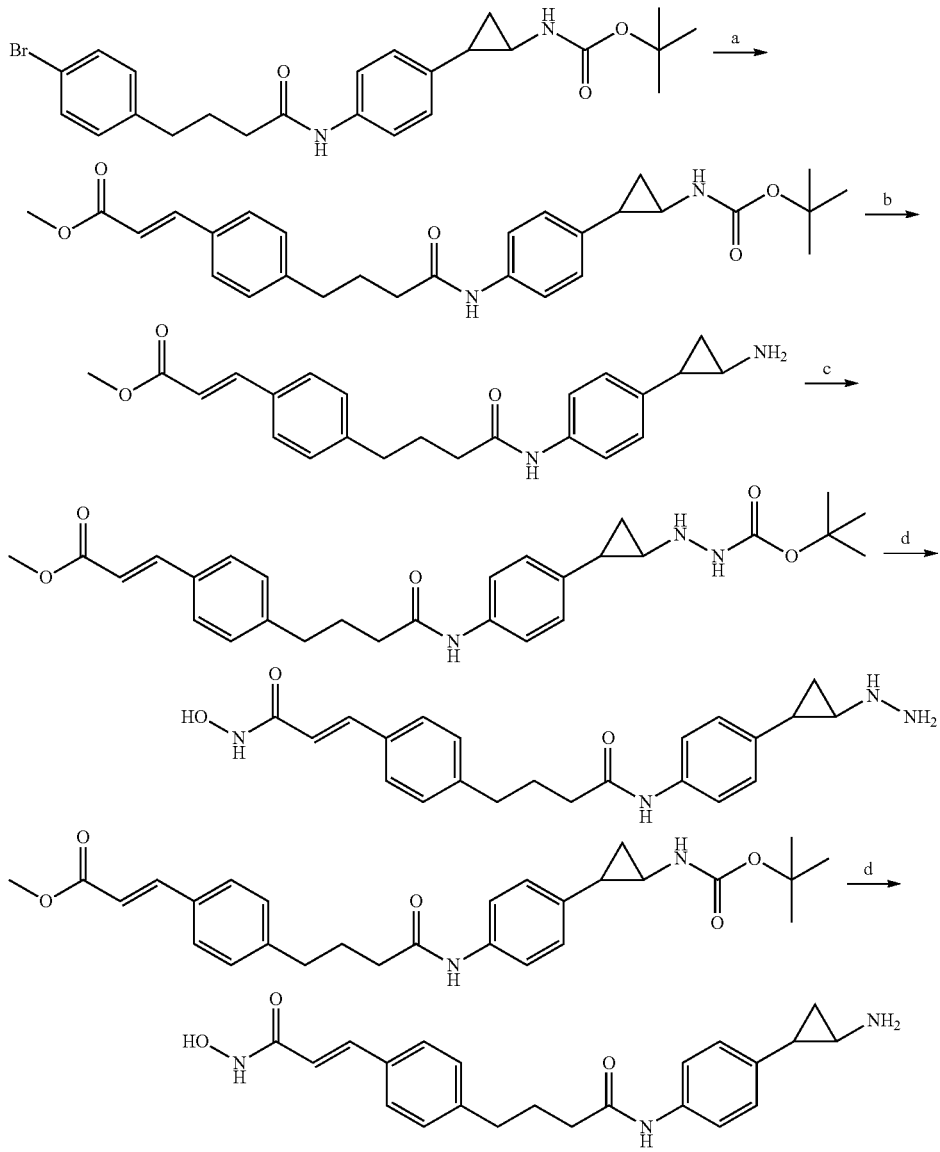
Reagents and conditions: a) Pd(OAc)$_2$, PPh$_3$, TMED, methyl acrylate 135° C., 16 h; b) TFA, DCM, RT, 16 h; c) BocNHOTs, DMF, K$_2$CO$_3$, 0° C. to RT, 2 h; d) i) NH$_2$OH (aq), NaOH, THF, MeOH, 0° C. to RT, 30 min; ii) TFA, DCM, RT, 16 h.
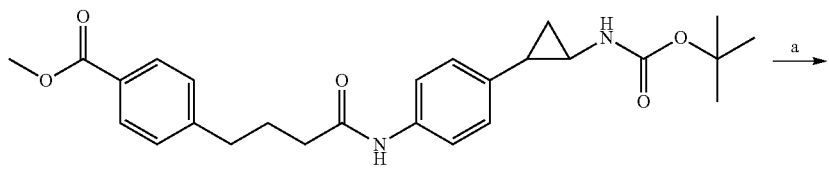

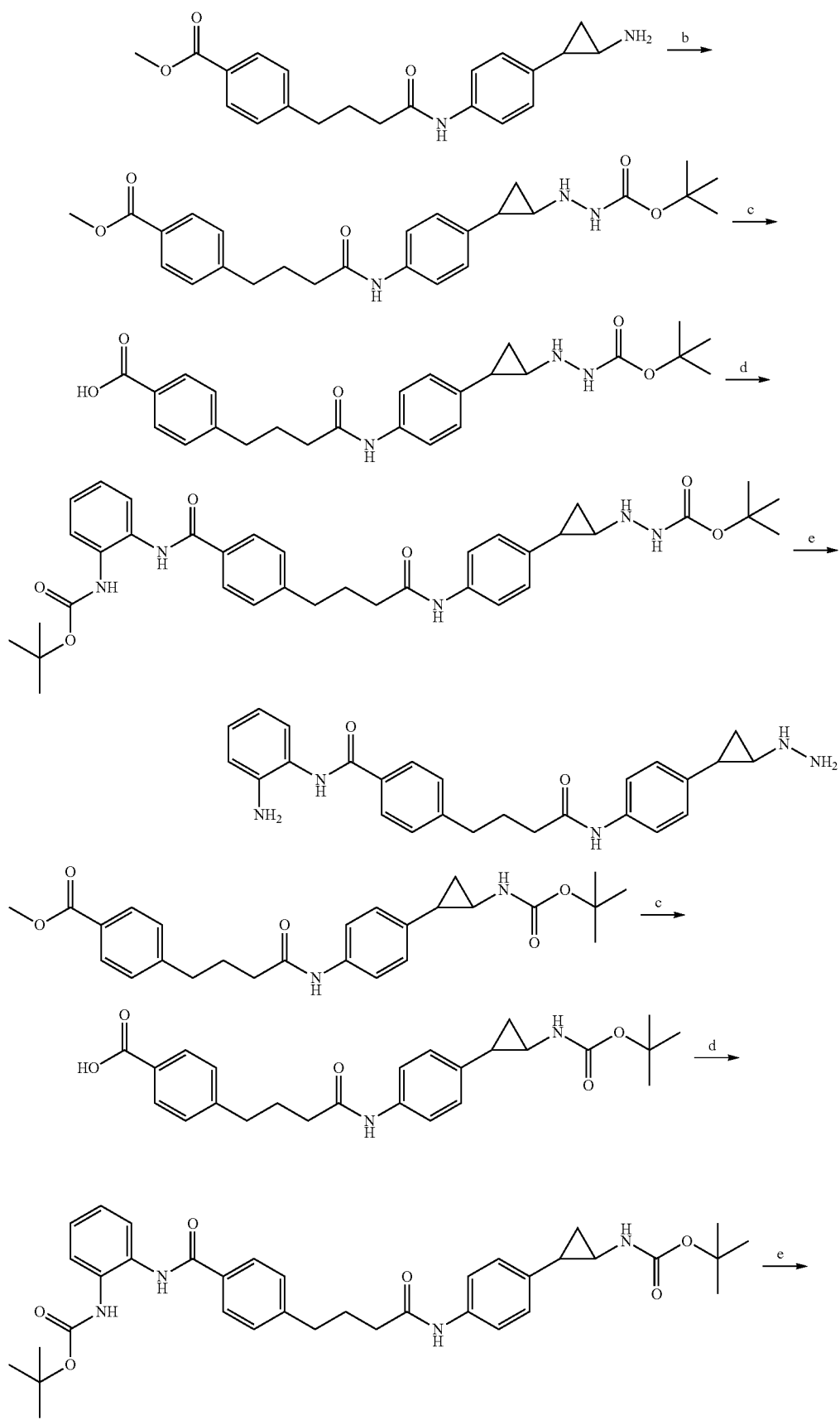

-continued

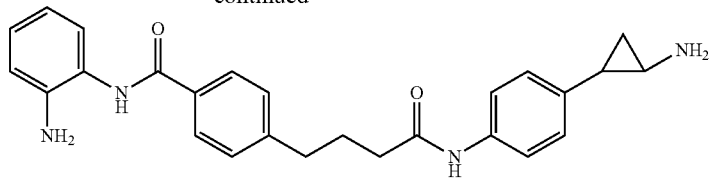

Reagents and conditions: a) TFA, DCM, RT, 16 h; b) BocNHOTs, DMF, K$_2$CO$_3$, 0° C. to RT, 2 h; c) LiOH, THF, MeOH, H$_2$O, RT, 16 h; d) 39, HATU, Et$_3$N, DCM, 0° C. to RT, 6 h; e) TFA, DCM, RT, 6 h.

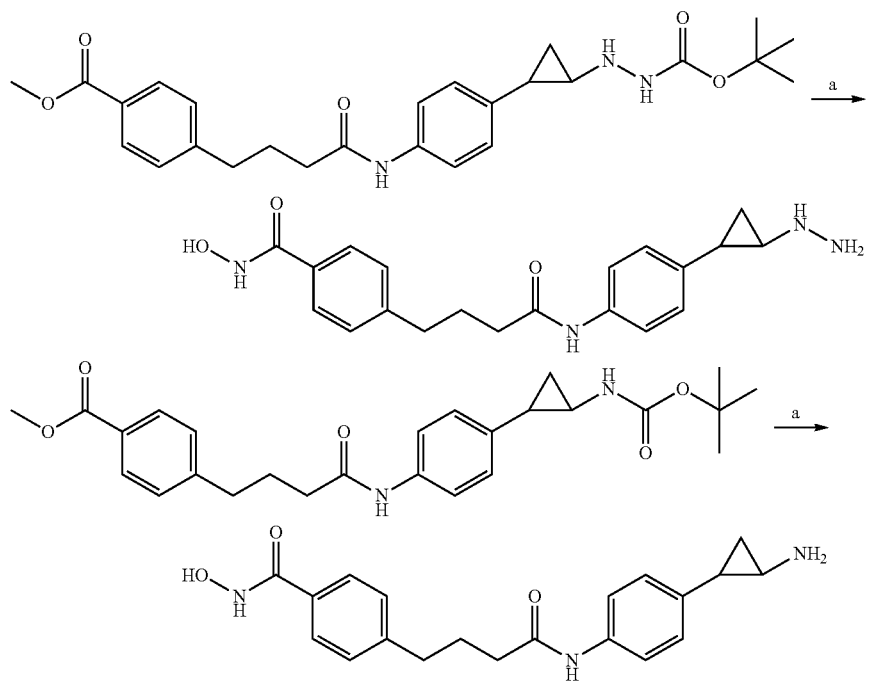

Reagents and conditions: a) i) NH$_2$OH (aq), NaOH, THF, MeOH, 0° C. to RT, 30 min; ii) TFA, DCM, RT, 16 h.

Example 6

Phenylcyclopropylamine Derivatives Selective for LSD1 Over LSD2 and MAO A/B In other embodiments, the presently disclosed subject matter also provides phenylcyclopropylamine derivatives designed to be selective for LSD1 over LSD2 and MAO A/B. These compounds include a similar scaffold in which two pharmacophores are combined into one chemical structure to simultaneously target LSD1 and the histone deacetylases. Again, the presence of ring A and linker L appear to be essential to impart the desired selectivity. The presently disclosed compounds include the trans configuration of the phenylcyclopropylamine portion of the molecule, as well as derivatives containing the cis configuration. The presently disclosed subject matter also includes phenylcyclopropyl-hydrazine derivatives of similar structure.

Examples of trans derivatives

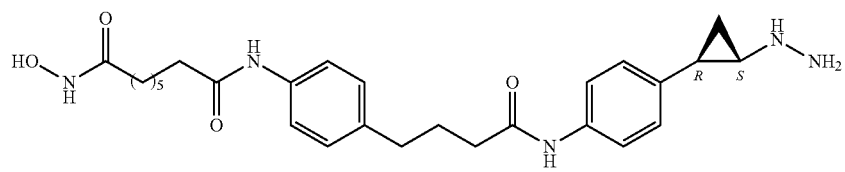

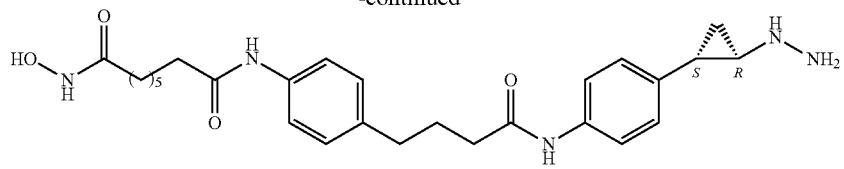
Examples of cis derivatives
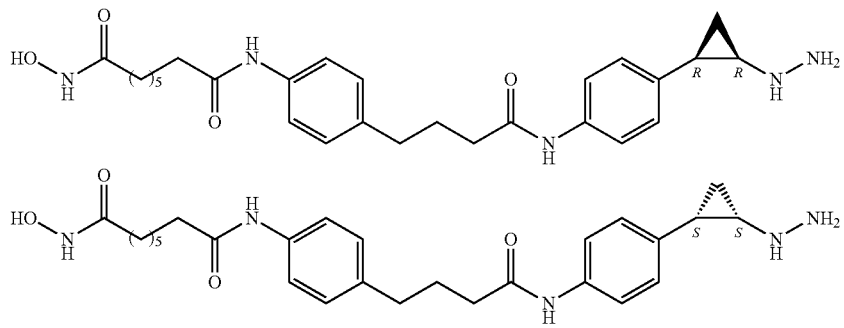
Combinations of the structures provided immediately herein below are representative examples of the presently disclosed compounds:
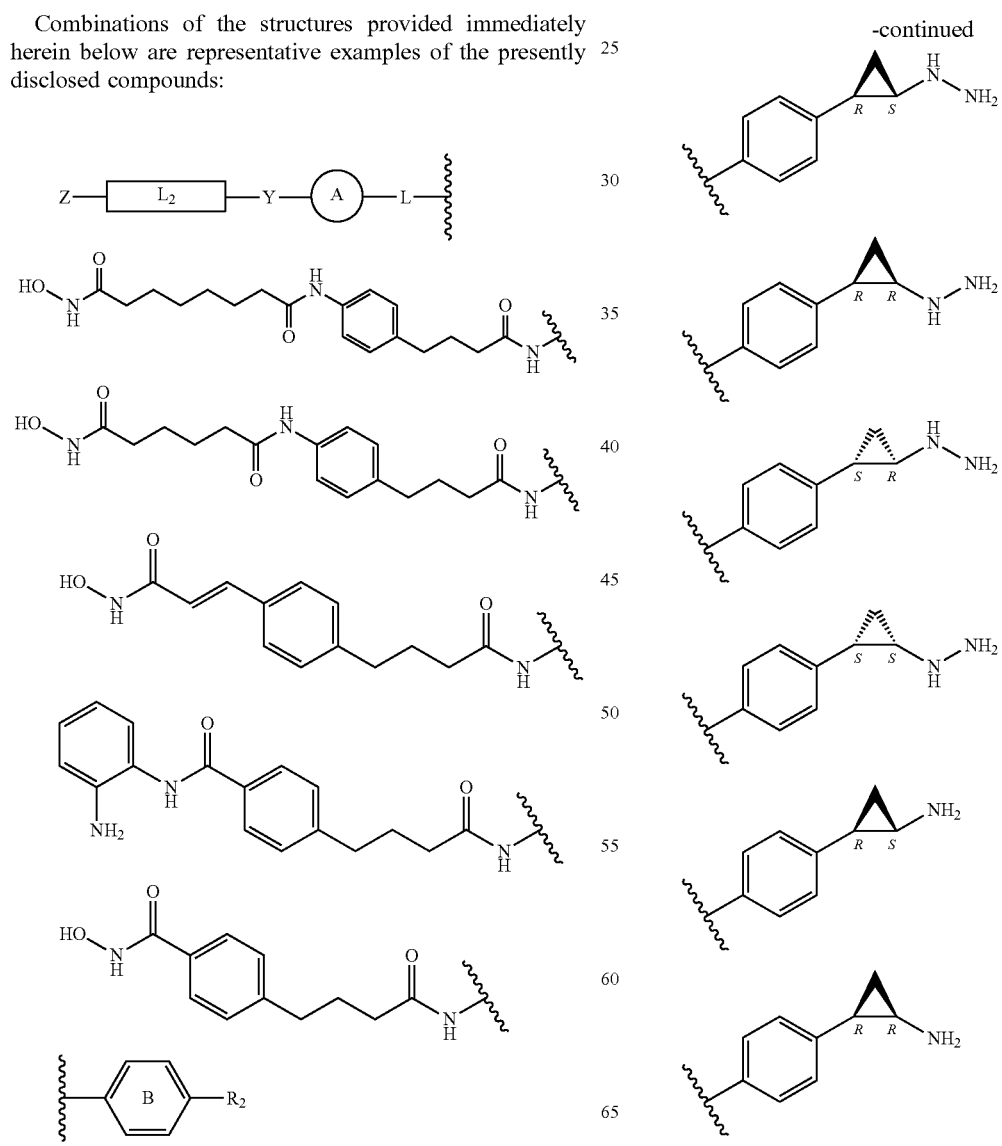

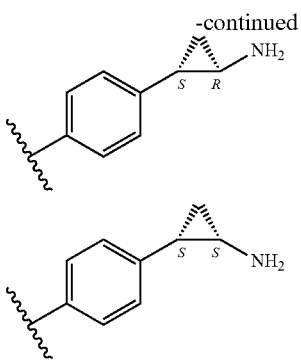

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Culhane, J. C., and Cole, P. A. (2007) LSD1 and the chemistry of histone demethylation. Curr. Opin. Chem. Biol. 11, 561-568.

Yang, M., Culhane, J. C., Szewczuk, L. M., Gocke, C. B., Brautigam, C. A., Tomchick, D. R., Machius, M., Cole, P. A., and Yu, H. (2007) Structural basis of histone demethylation by LSD1 revealed by suicide inactivation. Nat. Struct. Mol. Biol. 14, 535-539.

Forneris, F., Binda, C., Battaglioli, E., and Mattevi, A. (2008) LSD1: oxidative chemistry for multifaceted functions in chromatin regulation. Trends Biochem. Sci. 33,181-189.

Forneris, F., Binda, C., Adamo, A., Battaglioli, E., and Mattevi, A. (2007) Structural basis of LSD1-CoREST selectivity in histone H3 recognition. J. Biol. Chem. 282, 20070-20074.

Forneris, F., Binda, C., Dall'Aglio, A., Fraaije, M. W., Battaglioli, E., and Mattevi, A. (2006) A highly specific mechanism of histone H3-K4 recognition by histone demethylase LSD1. J. Biol. Chem. 281, 35289-35295.

Forneris, F., Binda, C., Vanoni, M. A., Battaglioli, E., and Mattevi, A. (2005) Human histone demethylase LSD1 reads the histone code. J. Biol. Chem. 280, 41360-41365.

Shi, Y., Lan, F., Matson, C., Mulligan, P., Whetstine, J. R., Cole, P. A., Casero, R. A., and Shi, Y. (2004) Histone Demethylation Mediated by the Nuclear Amine Oxidase Homolog LSD1. Cell 119, 941-953.

Liang, G., Lin, J. C. Y., Wei, V., Yoo, C., Cheng, J. C., Nguyen, C. T., Weisenberger, D. J., Egger, G., Takai, D., Gonzales, F. A., and Jones, P. A. (2004) Distinct localization of histone H3 acetylation and H3-K4 methylation to the transcription start sites in the human genome. Proc. Natl. Acad. Sci. U.S.A. 101, 7357-7362.

Heintzman, N. D., Stuart, R. K., Hon, G., Fu, Y., Ching, C. W., Hawkins, R. D., Barrera, L. O., Van Calcar, S., Qu, C., Ching, K. A., Wang, W., Weng, Z., Green, R. D., Crawford, G. E., and Ren, B. (2007) Distinct and predictive chromatin signatures of transcriptional promoters and enhancers in the human genome. Nat. Genet. 39, 311-318.

Lv, T., Yuan, D., Miao, X., Lv, Y., Zhan, P., Shen, X., and Song, Y. (2012) Over-Expression of LSD1 Promotes Proliferation, Migration and Invasion in Non-Small Cell Lung Cancer. PLoS One 7, e35065.

Lim, S., Janzer, A., Becker, A., Zimmer, A., Schule, R., Buettner, R., and Kirfel, J. (2010) Lysine-specific demethylase 1 (LSD1) is highly expressed in ERnegative breast cancers and a biomarker predicting aggressive biology. Carcinogenesis 31, 512-520.

Metzger, E., Wissmann, M., Yin, N., Muller, J. M., Schneider, R., Peters, A. H. F. M., Gunther, T., Buettner, R., and Schule, R. (2005) LSD1 demethylates repressive histone marks to promote androgen-receptor-dependent transcription. Nature 437, 436-439.

Murray-Stewart, T., Woster, P. M., and Casero, R. A., Jr. The re-expression of the epigenetically silenced e-cadherin gene by a polyamine analogue lysine-specific demethylase-1 (LSD1) inhibitor in human acute myeloid leukemia cell lines. Amino Acids 1-10.

Huang, Y., Greene, E., Murray Stewart, T., Goodwin, A. C., Baylin, S. B., Woster, P. M., and Casero, R. A., Jr. (2007) Inhibition of lysine-specific demethylase 1 by polyamine analogues results in reexpression of aberrantly silenced genes. Proc. Natl. Acad. Sci. U.S.A. 104, 8023-8028.

Huang, Y., Stewart, T. M., Wu, Y., Baylin, S. B., Marton, L. J., Perkins, B., Jones, R. J., Woster, P. M., and Casero, R. A., Jr. (2009) Novel oligoamine analogues inhibit lysine-specific demethylase 1 and induce reexpression of epigenetically silenced genes. Clin. Cancer Res. 15, 7217-7228.

Jin, L., Hanigan, C. L., Wu, Y., Wang, W., Park, B. H., Woster, P. M., and Casero, R. A. (2013) Loss of LSD1 (lysine-specific demethylase 1) suppresses growth and alters gene expression of human colon cancer cells in a p53- and DNMT1(DNA methyltransferase 1)-independent manner. Biochem. J. 449, 459-468.

Takai, N., and Narahara, H. (2008) Array-Based Approaches for the Identification of Epigenetic Silenced Tumor Suppressor Genes. Curr. Genomics 9, 22-24.

Gaweska, H., Henderson Pozzi, M., Schmidt, D. M. Z., McCafferty, D. G., and Fitzpatrick, P. F. (2009) Use of pH and kinetic isotope effects to establish chemistry as rate-limiting in oxidation of a peptide substrate by LSD1. Biochemistry 48, 5440-5445.

Forneris, F., Binda, C., Vanoni, M. A., Mattevi, A., and Battaglioli, E. (2005) Histone demethylation catalysed by LSD1 is a flavin-dependent oxidative process. FEBS Lett 579, 2203-2207.

Tsukada, Y., Fang, J., Erdjument-Bromage, H., Warren, M. E., Borchers, C. H., Tempst, P., and Zhang, Y. (2005) Histone demethylation by a family of JmjC domain-containing proteins. Nature 439, 811-816.

Hakimi, M.-A., Dong, Y., Lane, W. S., Speicher, D. W., and Shiekhattar, R. (2003) A candidate X-linked mental retardation gene is a component of a new family of histone deacetylase-containing complexes. J. Biol. Chem. 278, 7234-7239.

Klose, R. J., and Zhang, Y. (2007) Regulation of histone methylation by demethylimination and demethylation. Nat. Rev. Mol. Cell Biol. 8, 307-318.

Hwang, S., Schmitt, A. A., Luteran, A. E., Toone, E. J., and McCafferty, D. G. (2011) Thermodynamic characterization of the binding interaction between the histone demethylase LSD1/KDM1 and CoREST. Biochemistry 50, 546-557.

Baron, R., Binda, C., Tortorici, M., McCammon, J. A., and Mattevi, A. (2011) Molecular mimicry and ligand recognition in binding and catalysis by the histone demethylase LSD1-CoREST complex. *Struct. Lond. Engl. 1993* 19, 212-220.

Forneris, F., Battaglioli, E., Mattevi, A., and Binda, C. (2009) New roles of flavoproteins in molecular cell biology: histone demethylase LSD1 and chromatin. *FEBS J.* 276, 4304-4312.

Zhang, Q., Qi, S., Xu, M., Yu, L., Tao, Y., Deng, Z., Wu, W., Li, J., Chen, Z., and Wong, J. (2013) Structure-function analysis reveals a novel mechanism for regulation of histone demethylase LSD2/AOF1/KDM1b. *Cell Res.* 23, 225-241.

Karytinos, A., Forneris, F., Profumo, A., Ciossani, G., Battaglioli, E., Binda, C., and Mattevi, A. (2009) A novel mammalian flavin-dependent histone demethylase. *J. Biol. Chem.* 284, 17775-17782.

Wang, Y., Murray-Stewart, T., Devereux, W., Hacker, A., Frydman, B., Woster, P. M., and Casero, R. A., Jr. (2003) Properties of purified recombinant human polyamine oxidase, PAOh1/SMO. *Biochem. Biophys. Res. Commun.* 304, 605-611.

Culhane, J. C., Wang, D., Yen, P. M., and Cole, P. A. (2010) Comparative analysis of small molecules and histone substrate analogues as LSD1 lysine demethylase inhibitors. *J. Am. Chem. Soc.* 132, 3164-3176.

Dancy, B. C. R., Ming, S. A., Papazyan, R., Jelinek, C. A., Majumdar, A., Sun, Y., Dancy, B. M., Drury, W. J., 3rd, Cotter, R. J., Taverna, S. D., and Cole, P. A. (2012) Azalysine analogues as probes for protein lysine deacetylation and demethylation. *J. Am. Chem. Soc.* 134, 5138-5148.

Tortorici, M., Borrello, M. T., Tardugno, M., Chiarelli, L. R., Pilotto, S.,

Ciossani, G., Vellore, N. A., Bailey, S. G., Cowan, J., O'Connell, M., Crabb, S. J., Packham, G., Mai, A., Baron, R., Ganesan, A., and Mattevi, A. (2013) Protein recognition by short peptide reversible inhibitors of the chromatin-modifying LSD1/CoREST lysine demethylase. *ACS Chem. Biol.* 8, 1677-1682.

Binda, C., Valente, S., Romanenghi, M., Pilotto, S., Cirilli, R., Karytinos, A., Ciossani, G., Botrugno, O. A., Forneris, F., Tardugno, M., Edmondson, D. E., Minucci, S., Mattevi, A., and Mai, A. (2010) Biochemical, structural, and biological evaluation of tranylcypromine derivatives as inhibitors of histone demethylases LSD1 and LSD2. *J. Am. Chem. Soc.* 132, 6827-6833.

Mimasu, S, Umezawa, N., Sato, S., Higuchi, T., Umehara, T., and Yokoyama, S. (2010) Structurally designed trans-2-phenylcyclopropylamine derivatives potently inhibit histone demethylase LSD1/KDM1. *Biochemistry* 49, 6494-6503.

Zhu, Q., Huang, Y., Marton, L. J., Woster, P. M., Davidson, N. E., and Casero, R. A., Jr. (2012) Polyamine analogs modulate gene expression by inhibiting lysine-specific demethylase 1 (LSD1) and altering chromatin structure in human breast cancer cells. *Amino Acids* 42, 887-898.

Wang, J., Lu, F., Ren, Q., Sun, H., Xu, Z., Lan, R., Liu, Y., Ward, D., Quan, J., Ye, T., and Zhang, H. (2011) Novel histone demethylase LSD1 inhibitors selectively target cancer cells with pluripotent stem cell properties. *Cancer Res.* 71, 7238-7249.

Culhane, J. C., Szewczuk, L. M., Liu, X., Da, G., Marmorstein, R., and Cole, P. A. (2006) A mechanism-based inactivator for histone demethylase LSD1. *J. Am. Chem. Soc.* 128, 4536-4537.

Pollock, J. A., Larrea, M. D., Jasper, J. S., McDonnell, D. P., and McCafferty, D. G. (2012) Lysine-specific histone demethylase 1 inhibitors control breast cancer proliferation in ERα-dependent and-independent manners. *ACS Chem. Biol.* 7, 1221-1231.

Gooden, D. M., Schmidt, D. M. Z., Pollock, J. A., Kabadi, A. M., and McCafferty, D. G. (2008) Facile synthesis of substituted trans-2-arylcyclopropylamine inhibitors of the human histone demethylase LSD1 and monoamine oxidases A and B. *Bioorg. Med. Chem. Lett.* 18, 3047-3051.

Dulla, B., Kirla, K. T., Rathore, V., Deora, G. S., Kavela, S., Maddika, S., Chatti, K., Reiser, O., Iqbal, J., and Pal, M. (2013) Synthesis and evaluation of 3-amino/guanidine substituted phenyl oxazoles as a novel class of LSD1 inhibitors with anti-proliferative properties. *Org. Biomol. Chem.* 11, 3103-3107.

Hazeldine, S., Pachaiyappan, B., Steinbergs, N., Nowotarski, S., Hanson, A. S., Casero, R. A., Jr, and Woster, P. M. (2012) Low molecular weight amidoximes that act as potent inhibitors of lysine-specific demethylase 1. *J. Med. Chem.* 55, 7378-7391.

Yang, M., Culhane, J. C., Szewczuk, L. M., Jalili, P., Ball, H. L., Machius, M., Cole, P. A., and Yu, H. (2007) Structural basis for the inhibition of the LSD1 histone demethylase by the antidepressant trans-2-phenylcyclopropylamine. *Biochemistry* 46, 8058-8065.

Schmidt, D. M. Z., and McCafferty, D. G. (2007) trans-2-Phenylcyclopropylamine is a mechanism-based inactivator of the histone demethylase LSD1. *Biochemistry* 46, 4408-4416.

Lee, M. G., Wynder, C., Schmidt, D. M., McCafferty, D. G., and Shiekhattar, R. (2006) Histone H3 lysine 4 demethylation is a target of nonselective antidepressive medications. *Chem. Biol.* 13, 563-567.

Holt, A., Sharman, D. F., Baker, G. B., and Palcic, M. M. (1997) A continuous spectrophotometric assay for monoamine oxidase and related enzymes in tissue homogenates. *Anal. Biochem.* 244, 384-392.

Blair, L. P., Avaritt, N. L., Huang, R., Cole, P. A., Taverna, S. D., and Tackett, A. J. (2011) MassSQUIRM: An assay for quantitative measurement of lysine demethylase activity. *Epigenetics* 6, 490-499.

Su, X., Zhang, L., Lucas, D. M., Davis, M. E., Knapp, A. R., Green-Church, K. B., Marcucci, G., Parthun, M. R., Byrd, J. C., and Freitas, M. A. (2007) Histone H4 acetylation dynamics determined by stable isotope labeling with amino acids in cell culture and mass spectrometry. *Anal. Biochem.* 363, 22-34.

Shen, L., Shao, N.-Y., Liu, X., Maze, I., Feng, J., and Nestler, E. J. (2013) diffReps: detecting differential chromatin modification sites from ChIP-seq data with biological replicates. *PloS One* 8, e65598.

Kerenyi, M. A., Shao, Z., Hsu, Y.-J., Guo, G., Luc, S., O'Brien, K., Fujiwara, Y., Peng, C., Nguyen, M., and Orkin, S. H. (2013) Histone demethylase Lsd1 represses hematopoietic stem and progenitor cell signatures during blood cell maturation. *eLife* 2, e00633.

Han, H., Yang, X., Pandiyan, K., and Liang, G. (2013) Synergistic reactivation of epigenetically silenced genes by combinatorial inhibition of DNMTs and LSD1 in cancer cells. *PloS One* 8, e75136.

Huang, Y., Vasilatos, S. N., Boric, L., Shaw, P. G., and Davidson, N. E. (2012) Inhibitors of histone demethylation and histone deacetylation cooperate in regulating gene expression and inhibiting growth in human breast cancer cells. *Breast Cancer Res. Treat.* 131, 777-789.

Chou, T. C., and Talalay, P. (1984) Quantitative analysis of dose-effect relationships: the combined effects of multiple drugs or enzyme inhibitors. *Adv. Enzyme Regul.* 22, 27-55.

Langley, B., D'Annibale, M. A., Suh, K., Ayoub, I., Tolhurst, A., Bastan, B., Yang, L., Ko, B., Fisher, M., Cho, S., Beal, M. F., and Ratan, R. R. (2008) Pulse inhibition of histone deacetylases induces complete resistance to oxidative death in cortical neurons without toxicity and reveals a role for cytoplasmic p21(waf1/cip1) in cell cycle-independent neuroprotection. *J. Neurosci.* 28, 163-176.

Kozikowski, A. P., Chen, Y., Subhasish, T., Lewin, N. E., Blumberg, P. M., Zhong, Z., D'Annibale, M. A., Wang, W.-L., Shen, Y., and Langley, B. (2009) Searching for disease modifiers-PKC activation and HDAC inhibition—a dual drug approach to Alzheimer's disease that decreases Abeta production while blocking oxidative stress. *ChemMedChem* 4, 1095-1105.

Neelamegam, R., Ricq, E. L., Malvaez, M., Patnaik, D., Norton, S., Carlin, S. M., Hill, I. T., Wood, M. A., Haggarty, S. J., and Hooker, J. M. (2012) Brain-Penetrant LSD1 Inhibitors Can Block Memory Consolidation. *ACS Chem. Neurosci.* 3, 120-128.

Zhang, Y.-Z., Zhang, Q.-H., Ye, H., Zhang, Y., Luo, Y.-M., Ji, X.-M., and Su, Y.-Y. (2010) Distribution of lysine-specific demethylase 1 in the brain of rat and its response in transient global cerebral ischemia. *Neurosci. Res.* 68, 66-72.

Szewczuk, L. M., Culhane, J. C., Yang, M., Majumdar, A., Yu, H., and Cole, P. A. (2007) Mechanistic Analysis of a Suicide Inactivator of Histone Demethylase LSD1. *Biochemistry* 46, 6892-6902.

Shechter, D., Dormann, H. L., Allis, C. D., and Hake, S. B. (2007) Extraction, purification and analysis of histones. *Nat. Protoc.* 2, 1445-1457.

Ratan, R. R., Murphy, T. H., and Baraban, J. M. (1994) Oxidative stress induces apoptosis in embryonic cortical neurons. *J. Neurochem.* 62, 376-379.

Mosmann, T. (1983) Rapid colorimetric assay for cellular growth and survival: application to proliferation and cytotoxicity assays. *J. Immunol. Methods* 65, 55-63.

Robinson, J. T., Thorvaldsdóttir, H., Winckler, W., Guttman, M., Lander, E. S., Getz, G., and Mesirov, J. P. (2011) Integrative genomics viewer. *Nat. Biotechnol.* 29, 24-26.

Thoryaldsdóttir, H., Robinson, J. T., and Mesirov, J. P. (2013) Integrative Genomics Viewer (IGV): high-performance genomics data visualization and exploration. *Brief. Bioinform.* 14, 178-192.

Calabretta, R., Gallina, C., and Giordano, C. (1991) Sodium Cyanoborohydride Reduction of (Benzyloxycarbonyl)- and (tert-Butoxycarbonyl)hydrazones. *Synthesis* 1991, 536-539.

Lee, Y., Jeon, H. B., Huang, H., and Sayre, L. M. (2001) Temporary inactivation of plasma amine oxidase by alkylhydrazines. A combined enzyme/model study implicates cofactor reduction/reoxidation but cofactor deoxygenation and subsequent reoxygenation in the case of hydrazine itself. *J. Org. Chem.* 66, 1925-1937.

Baraldi, P. G., Cacciari, B., Spalluto, G., Bergonzoni, M., Dionisotti, S., Ongini, E., Varani, K., and Borea, P. A. (1998) Design, synthesis, and biological evaluation of a second generation of pyrazolo[4,3-e]-1,2,4-triazolo[1,5-c]pyrimidines as potent and selective A2A adenosine receptor antagonists. *J. Med. Chem.* 41, 2126-2133.

Carroll, F. I., Blough, B. E., Abraham, P., Mills, A. C., Holleman, J. A., Wolckenhauer, S. A., Decker, A. M., Landavazo, A., McElroy, K. T., Navarro, H. A., Gatch, M. B., and Forster, M. J. (2009) Synthesis and biological evaluation of bupropion analogues as potential pharmacotherapies for cocaine addiction. *J. Med. Chem.* 52, 6768-6781.

Romeiro, L. A. S., da Silva Ferreira, M., da Silva, L. L., Castro, H. C., Miranda, A. L. P., Silva, C. L. M., Noël, F., Nascimento, J. B., Araújo, C. V., Tibiricá, E., Barreiro, E. J., and Fraga, C. A. M. (2011) Discovery of LASSBio-772, a 1,3-benzodioxole N-phenylpiperazine derivative with potent alpha 1A/D-adrenergic receptor blocking properties. *Eur. J. Med. Chem.* 46, 3000-3012.

Walsh, T., Ujjainwalla, F., Goulet, M., and Bugianesi, R. (1999, October 14) Antagonists of Gonadotropin Releasing Hormone.

Peng, Y., Liu, H., Tang, M., Cai, L., and Pike, V. (2009) Highly Efficient NMonomethylation of Primary Aryl Amines. *Chin. J. Chem.* 27, 1339-1344.

Davies, S., Moffat, D., and Testar, R. (2008, May 8) 2-(hetero-)aryl,4-Carbonyl Substituted Pyrazole Derivatives as Inhibitors of P38 Mitogen-Activated Protein Kinase.

Li, H., and Durbin, R. (2009) Fast and accurate short read alignment with Burrows-Wheeler transform. *Bioinforma. Oxf. Engl.* 25, 1754-1760.

Zhang, Y., Liu, T., Meyer, C. A., Eeckhoute, J., Johnson, D. S., Bernstein, B. E., Nusbaum, C., Myers, R. M., Brown, M., Li, W., and Liu, X. S. (2008) Model-based analysis of ChIP-Seq (MACS). *Genome Biol.* 9, R137.

Song, Q., and Smith, A. D. (2011) Identifying dispersed epigenomic domains from ChIP-Seq data. *Bioinforma. Oxf. Engl.* 27, 870-871.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A compound of Formula (IIb):

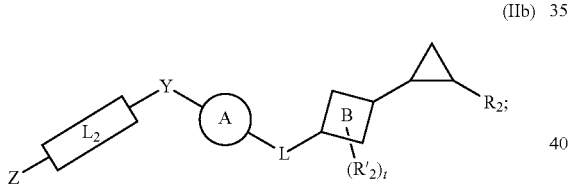

wherein:

t is an integer selected from the group consisting of 0, 1, 2, 3, and 4;

A is substituted or unsubstituted aryl;

B is aryl;

L is $-[X_1-C(=O)-NR_1]_d-$, wherein d is 1;

wherein $X_1$ is $-(CH_2)_n-$, wherein n is 3, wherein the $-(CH_2)_n-$ group can optionally be substituted with a substituent selected from the group consisting of substituted or unsubstituted linear or branched alkyl, hydroxyl, alkoxyl, amino, cyano, halogen, and oxo, and wherein one or more carbon atoms of $-(CH_2)_n-$ can optionally be replaced with one or more heteroatoms selected from the group consisting of O, S, and $NR'_1$, wherein each $-(CH_2)_n-$ group can contain a cycloalkyl or cycloheteroalkyl unit;

$L_2$ is selected from the group consisting of aryl, heteroaryl, $-(CH_2)n-$, $-(CH_2)n-CH=CH-(CH_2)_m-$, $-(CH_2)_n-C\equiv C-(CH_2)_m-$, $-(CH_2)_m-O-$, wherein n and m are each independently an integer selected from the group consisting of 0, 1, 2, 3, 4, 5, and 6, wherein the $-(CH_2)n-$, $-(CH_2)_m-$, and $-CH=CH-$ groups can optionally be substituted with a substituent selected from the group consisting of substituted or unsubstituted linear or branched alkyl, hydroxyl, alkoxyl, amino, cyano, halogen, and oxo, and wherein one or more carbon atoms of $-(CH_2)_n-$ and $-(CH_2)_m-$ can optionally be replaced with one or more heteroatoms selected from the group consisting of 0, S, and $NR'_1$;

$R_1$ and $R'_1$ are each independently selected from the group consisting of hydrogen, substituted or unsubstituted linear or branched alkyl, alkoxyl, substituted or unsubstituted cycloalkyl, substituted or unsubstituted cycloheteroalkyl, substituted or unsubstituted aryl, substituted or unsubstituted heteroaryl, substituted or unsubstituted arylalkyl, and substituted or unsubstituted heteroarylalkyl, and $R_1$ can form a ring system with ring B via a substituted or unsubstituted alkylene or heteroalkylene chain;

$R_2$ is selected from the group consisting of $-(CH_2)_p-NR_3-NR_4R_5$, $-(CH_2)_p-X_2$, and $-NH_2$; wherein p is an integer selected from the group consisting of 0, 1, 2, 3, and 4, and wherein the $-(CH_2)_p-$ group can be saturated or unsaturated or contain a cycloalkyl unit and optionally be substituted with a substituent selected from the group consisting of substituted or unsubstituted linear or branched alkyl, hydroxyl, alkoxyl, amino, cyano, halogen, and oxo, and one or more carbon atoms of $-(CH_2)_p-$ can optionally be replaced with one or more heteroatoms selected from the group consisting of 0, S, and $NR'_1$;

each $R'_2$ is independently selected at each occurrence from the group consisting of substituted or unsubstituted alkyl, substituted or unsubstituted cycloalkyl, substituted or unsubstituted cycloheteroalkyl, allyl, hydroxyl, alkoxyl, amino, cyano, carboxyl, halogen, nitro, oxo, $-CF_3$, substituted or unsubstituted aryl, substituted or unsubstituted heteroaryl;

$R_3$, $R_4$, and $R_5$ are each independently selected from the group consisting of hydrogen, substituted or unsubstituted linear or branched alkyl, alkoxyl, substituted or unsubstituted cycloalkyl, substituted or unsubstituted cycloheteroalkyl, substituted or unsubstituted aryl, substituted or unsubstituted heteroaryl, substituted or unsubstituted arylalkyl, and substituted or unsubstituted heteroarylalkyl, and —C(=O)—O—$R_{21}$, or $R_4$ and $R_5$ together can form a substituted or unsubstituted 4- to 6-membered cycloalkyl, and wherein $R_{24}$ is substituted or unsubstituted linear or branched alkyl;

$X_2$ is selected from the group consisting of hydroxyl, halogen, and —O—Si($R_{21}R_{22})_2$-$R_{23}$, wherein $R_{21}$, $R_{22}$, and $R_{23}$ are each independently substituted or unsubstituted linear or branched alkyl;

Y is selected from the group consisting of null, —N($R^{10}$)C(=O)—, —C(=O)N($R^{10}$)—, —N($R^{10}$)C(=S)—, —C(=S)N($R^{10}$)—, —SO$_2$—, —N($R^{10}$)SO$_2$—, —N($R^{10}$SO$_2$N($R^{10}$)—, —SO$_2$N($R^{10}$)—, and —CH=CH—;

Z is selected from the group consisting of:
—C(=O)N($R^{10}$)OH, —C(=O)O$R^{16}$, N($R^{10}$)OH, —N($R^{10}$)C(=O)C($R^{11}$)$_n$S($R^{12}$), —B(O$R^{13}$)$_{m'}$, —S$R^{14}$,

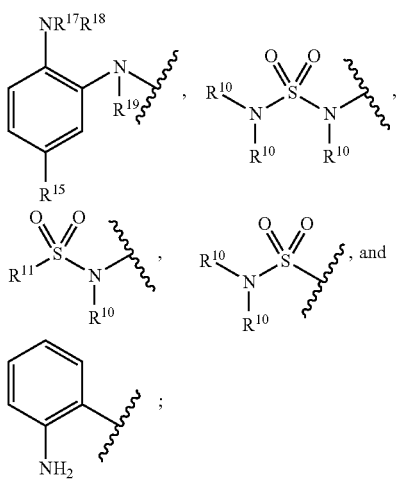

wherein $R^{10}$, $R^{11}$, $R^{12}$, $R^{13}$, $R^{14}$, and $R^{15}$ are each independently selected from the group consisting of hydrogen, substituted or unsubstituted linear or branched alkyl, alkoxyl, substituted or unsubstituted cycloalkyl, substituted or unsubstituted cycloheteroalkyl, substituted or unsubstituted aryl, substituted or unsubstituted heteroaryl, substituted or unsubstituted arylalkyl, and substituted or unsubstituted heteroarylalkyl;

$R^{16}$, $R^{17}$, $R^{18}$, and $R^{19}$ are each independently substituted or unsubstituted linear or branched alkyl;

and n' and m' are integers each independently selected from the group consisting of 0, 1, and 2; or pharmaceutically acceptable salts, hydrates, and solvates thereof.

2. The compound of claim 1, wherein the compound of Formula (IIb) has the following structure:

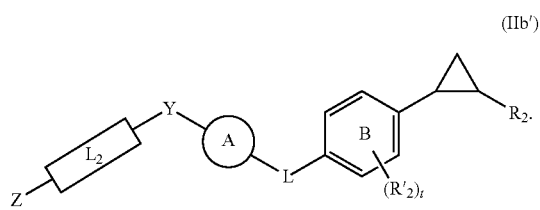

(IIb')

3. The compound of claim 2, wherein:

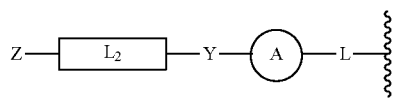

is selected from the group consisting of:

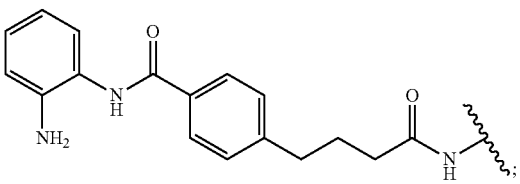

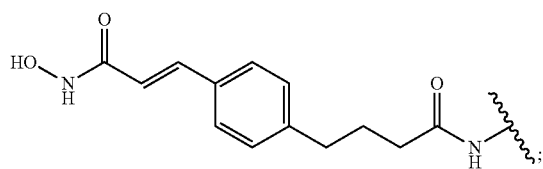

-continued

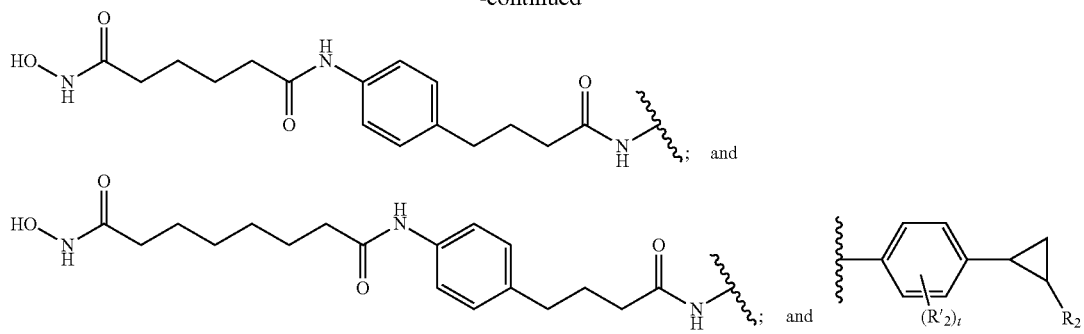

is selected from the group consisting of:

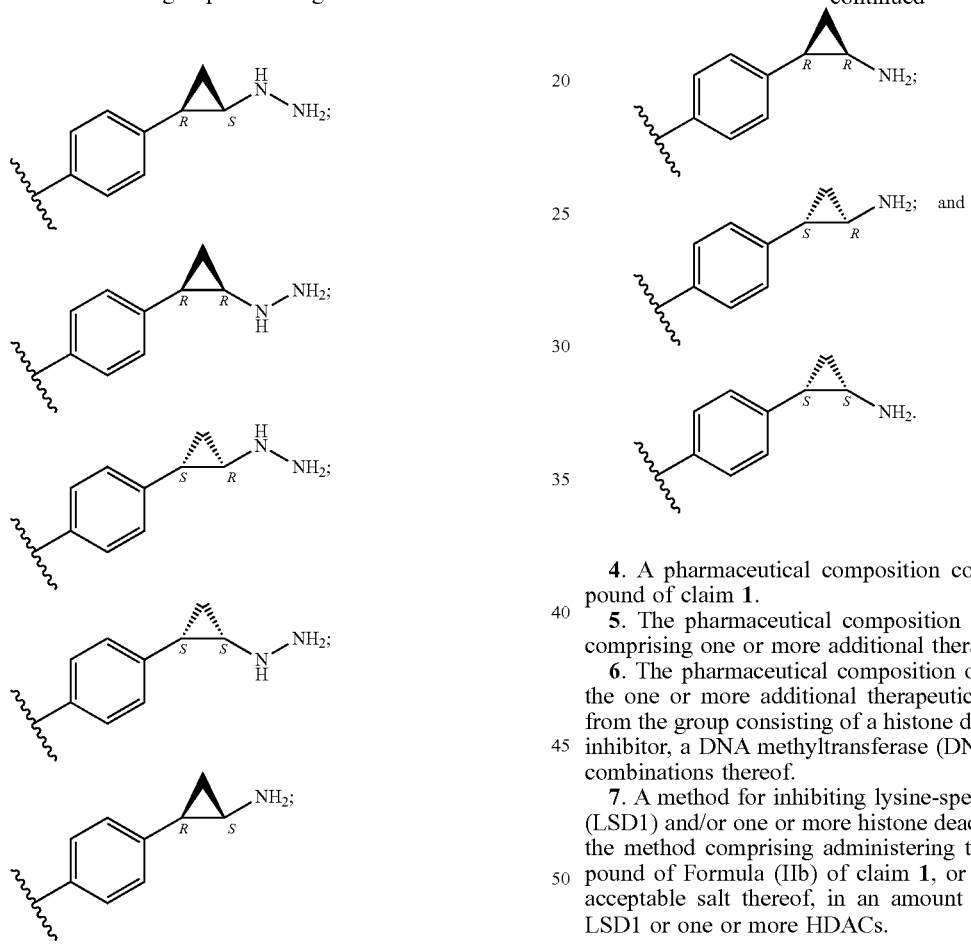

4. A pharmaceutical composition comprising the compound of claim 1.

5. The pharmaceutical composition of claim 4, further comprising one or more additional therapeutic agents.

6. The pharmaceutical composition of claim 5, wherein the one or more additional therapeutic agents is selected from the group consisting of a histone deacetylase (HDAC) inhibitor, a DNA methyltransferase (DNMT) inhibitor, and combinations thereof.

7. A method for inhibiting lysine-specific demethylase 1 (LSD1) and/or one or more histone deacetylases (HDACs), the method comprising administering to a subject a compound of Formula (IIb) of claim 1, or a pharmaceutically acceptable salt thereof, in an amount effective to inhibit LSD1 or one or more HDACs.

* * * * *

SEQUENCE LISTING

<160> NUMBER OF SEQ ID NOS: 4

<210> SEQ ID NO 1
<211> LENGTH: 20
<212> TYPE: DNA
<213> ORGANISM: Artificial sequence
<220> FEATURE:
<223> OTHER INFORMATION: Primer

<400> SEQUENCE: 1
agcgctctga ggttttccaa                                              20

<210> SEQ ID NO 2
<211> LENGTH: 20

```
<212> TYPE: DNA
<213> ORGANISM: Artificial sequence
<220> FEATURE:
<223> OTHER INFORMATION: Primer

<400> SEQUENCE: 2
tgagggtcag tggttgcaga                                          20

<210> SEQ ID NO 3
<211> LENGTH: 31
<212> TYPE: DNA
<213> ORGANISM: Artificial sequence
<220> FEATURE:
<223> OTHER INFORMATION: Primer

<400> SEQUENCE: 3
tcgtcgacat gtctgggcgg caggcaaaga a                             31

<210> SEQ ID NO 4
<211> LENGTH: 35
<212> TYPE: DNA
<213> ORGANISM: Artificial sequence
<220> FEATURE:
<223> OTHER INFORMATION: Primer

<400> SEQUENCE: 4
ataatctcga gaaaggctgc aatcttgctt gcttc                         35
```